(12) United States Patent
Hormann et al.

(10) Patent No.: US 9,102,648 B1
(45) Date of Patent: Aug. 11, 2015

(54) BIOAVAILABLE DIACYLHYDRAZINE LIGANDS FOR MODULATING THE EXPRESSION OF EXOGENOUS GENES VIA AN ECDYSONE RECEPTOR COMPLEX

(75) Inventors: Robert Eugene Hormann, Elkins Park, PA (US); David W. Potter, Allentown, PA (US); Orestes Chortyk, Thompson Station, TN (US); Colin M. Tice, Ambler, PA (US); Glenn Richard Carlson, North Wales, PA (US); Andrew Meyer, Ambler, PA (US); Thomas R. Opie, North Wales, PA (US)

(73) Assignee: Intrexon Corporation, Blacksburg, VA (US)

( * ) Notice: Subject to any disclaimer, the term of this patent is extended or adjusted under 35 U.S.C. 154(b) by 2310 days.

(21) Appl. No.: 11/841,617

(22) Filed: Aug. 20, 2007

Related U.S. Application Data

(63) Continuation of application No. 10/787,906, filed on Feb. 26, 2004, now Pat. No. 7,456,315.

(60) Provisional application No. 60/455,741, filed on Feb. 28, 2003.

(51) Int. Cl.
*C12P 21/06* (2006.01)
*C07D 319/20* (2006.01)
*C12N 9/02* (2006.01)

(52) U.S. Cl.
CPC ............ *C07D 319/20* (2013.01); *C12N 9/0069* (2013.01)

(58) Field of Classification Search
None
See application file for complete search history.

(56) References Cited

U.S. PATENT DOCUMENTS

| | | | |
|---|---|---|---|
| 4,631,211 A | 12/1986 | Houghten | |
| 4,814,349 A | 3/1989 | Addor et al. | |
| 4,859,609 A | 8/1989 | Dull et al. | |
| 4,906,280 A | 3/1990 | Sandler et al. | |
| 4,950,666 A | 8/1990 | Peake et al. | |
| 4,954,655 A | 9/1990 | Kelly | |
| 4,981,784 A | 1/1991 | Evans et al. | |
| 4,985,461 A | 1/1991 | Hsu et al. | |
| 5,010,175 A | 4/1991 | Rutter et al. | |
| 5,071,773 A | 12/1991 | Evans et al. | |
| 5,075,471 A | 12/1991 | Michelotti et al. | |
| 5,117,057 A | 5/1992 | Hsu et al. | |
| 5,171,671 A | 12/1992 | Evans et al. | |
| 5,225,443 A | 7/1993 | Murphy et al. | |
| 5,283,173 A | 2/1994 | Fields et al. | |
| 5,354,762 A | 10/1994 | Hsu et al. | |
| 5,358,966 A | 10/1994 | James, Jr. et al. | |
| 5,378,726 A | 1/1995 | Yanagi et al. | |
| 5,424,333 A | 6/1995 | Wing | |
| 5,429,952 A | 7/1995 | Garner et al. | |
| 5,459,127 A | 10/1995 | Felgner et al. | |
| 5,482,962 A | 1/1996 | Hormann | |
| 5,514,578 A | 5/1996 | Hogness et al. | |
| 5,530,028 A | 6/1996 | Lidert et al. | |
| 5,599,904 A | 2/1997 | Evans et al. | |
| 5,641,652 A | 6/1997 | Oro et al. | |
| 5,668,175 A | 9/1997 | Evans et al. | |
| 5,710,004 A | 1/1998 | Evans et al. | |
| 5,723,329 A | 3/1998 | Mangelsdorf et al. | |
| 5,880,333 A | 3/1999 | Goff et al. | |
| 5,919,667 A | 7/1999 | Gage et al. | |
| 5,945,400 A | 8/1999 | Scherman et al. | |
| 5,989,863 A | 11/1999 | Tang et al. | |
| 6,013,836 A | 1/2000 | Hsu et al. | |
| 6,025,483 A | 2/2000 | Yanofsky | |
| 6,096,787 A | 8/2000 | Evans et al. | |
| 6,107,286 A | 8/2000 | Byk et al. | |
| 6,117,639 A | 9/2000 | Germann et al. | |
| 6,147,282 A | 11/2000 | Goff et al. | |
| 6,245,531 B1 | 6/2001 | Hogness et al. | |
| 6,258,603 B1 | 7/2001 | Carlson et al. | |
| 6,265,173 B1 | 7/2001 | Evans et al. | |
| 6,281,330 B1 | 8/2001 | Evans et al. | |
| 6,300,488 B1 | 10/2001 | Gage et al. | |
| 6,333,318 B1 | 12/2001 | Evans et al. | |

(Continued)

FOREIGN PATENT DOCUMENTS

| | | |
|---|---|---|
| CA | 2103110 | 5/1994 |
| CN | 1245638 | 3/2000 |
| CN | 1313276 | 9/2001 |
| DE | 19837620 | 2/1999 |
| EP | 0234944 | 2/1987 |
| EP | 0236618 | 9/1987 |
| EP | 0286746 | 10/1988 |
| EP | 0339854 | 11/1989 |
| EP | 0347216 | 12/1989 |
| EP | 0361645 | 4/1990 |

(Continued)

OTHER PUBLICATIONS

Nakagawa, Yoshiaki et al., Quantitative structure-activity studies of insect growth regulators. XI. Stimulation and inhibition of N-acetylglucosamine incorporation in a cultured integument system by substituted N-tert-butyl-N,N'-dibenzoylhydrazines. Pesticide Science (1995), 43(4), 339-45. Wiley and Sons England.

(Continued)

*Primary Examiner* — Catherine S Hibbert
(74) *Attorney, Agent, or Firm* — Sterne, Kessler, Goldstein & Fox P.L.L.C.

(57) ABSTRACT

The present invention relates to non-steroidal ligands for use in nuclear receptor-based inducible gene expression system, and a method to modulate exogenous gene expression in which an ecdysone receptor complex comprising: a DNA binding domain; a ligand binding domain; a transactivation domain; and a ligand is contacted with a DNA construct comprising: the exogenous gene and a response element; wherein the exogenous gene is under the control of the response element and binding of the DNA binding domain to the response element in the presence of the ligand results in activation or suppression of the gene.

28 Claims, 1 Drawing Sheet

(56) References Cited

U.S. PATENT DOCUMENTS

| | | |
|---|---|---|
| 6,379,945 B1 | 4/2002 | Jepson et al. |
| 6,458,926 B1 | 10/2002 | Evans et al. |
| 6,723,531 B2 | 4/2004 | Evans et al. |
| 6,756,491 B2 | 6/2004 | Evans et al. |
| 6,875,569 B2 | 4/2005 | Gage et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 | 8/2006 | Palli et al. |
| 7,119,077 B1 | 10/2006 | Evans et al. |
| 7,304,161 B2 | 12/2007 | Hormann et al. |
| 7,456,315 B2 | 11/2008 | Hormann et al. |
| 2002/0110861 A1 | 8/2002 | Dhadialla et al. |
| 2002/0119521 A1 | 8/2002 | Palli et al. |
| 2004/0033600 A1 | 2/2004 | Palli et al. |
| 2004/0096942 A1 | 5/2004 | Kapitskaya et al. |
| 2004/0197861 A1 | 10/2004 | Palli et al. |
| 2004/0235097 A1 | 11/2004 | Zhang et al. |
| 2005/0209283 A1 | 9/2005 | Hormann et al. |
| 2005/0266457 A1 | 12/2005 | Palli et al. |
| 2006/0100416 A1 | 5/2006 | Palli et al. |
| 2007/0161086 A1 | 7/2007 | Palli et al. |
| 2008/0064741 A1 | 3/2008 | Hormann et al. |
| 2008/0103113 A1 | 5/2008 | Hormann et al. |
| 2008/0194521 A1 | 8/2008 | Hormann et al. |
| 2008/0214627 A1 | 9/2008 | Hormann et al. |
| 2012/0046322 A1 | 2/2012 | Hormann et al. |
| 2013/0035487 A1 | 2/2013 | Hormann et al. |

FOREIGN PATENT DOCUMENTS

| | | |
|---|---|---|
| EP | 0395581 | 10/1990 |
| EP | 0 461 809 A1 | 6/1991 |
| EP | 0253468 | 11/1991 |
| EP | 0228564 | 1/1992 |
| EP | 0461809 | 12/1994 |
| EP | 0639559 | 2/1995 |
| EP | 0496342 | 11/1996 |
| EP | 0 798 378 A2 | 1/1997 |
| EP | 0 965 644 A2 | 12/1999 |
| EP | 0965644 | 12/1999 |
| EP | 0984009 A1 | 3/2000 |
| EP | 1266015 B1 | 3/2001 |
| GB | 2231268 | 11/1990 |
| JP | 62209053 | 9/1987 |
| JP | 62293150 | 11/1987 |
| JP | 02207066 | 8/1990 |
| JP | 03141245 | 6/1991 |
| JP | 03145447 | 6/1991 |
| JP | 04089471 | 3/1992 |
| JP | 04178380 A1 | 6/1992 |
| JP | 04235177 | 8/1992 |
| JP | 05039252 | 2/1993 |
| JP | 06172342 | 6/1994 |
| JP | 06184076 | 7/1994 |
| JP | 08231529 | 9/1996 |
| JP | 08231528 | 10/1996 |
| JP | 09100262 | 4/1997 |
| JP | 2000026423 | 1/2000 |
| WO | WO 89/12690 A1 | 12/1989 |
| WO | WO 94/28028 A1 | 12/1994 |
| WO | WO 95/18863 A1 | 7/1995 |
| WO | WO 95/21931 A1 | 8/1995 |
| WO | WO 96/17823 A1 | 6/1996 |
| WO | WO 96/25508 A1 | 8/1996 |
| WO | WO 96/27673 A1 | 9/1996 |
| WO | 9637609 A1 | 11/1996 |
| WO | WO 97/38117 A1 | 10/1997 |
| WO | 9902683 A1 | 1/1999 |
| WO | WO 99/36520 A1 | 7/1999 |
| WO | WO 99/58155 A1 | 11/1999 |
| WO | WO 01/36447 A2 | 5/2001 |
| WO | WO 01/62780 A1 | 8/2001 |
| WO | 0170816 A1 | 9/2001 |
| WO | WO 01/70816 A2 | 9/2001 |
| WO | 0229075 A1 | 4/2002 |
| WO | 02066612 A1 | 8/2002 |
| WO | 02066613 A1 | 8/2002 |
| WO | 02066614 A1 | 8/2002 |
| WO | 02066615 A1 | 8/2002 |
| WO | WO 03/10589 A1 | 12/2003 |
| WO | WO 2004/005478 A2 | 1/2004 |
| WO | 2004072254 A1 | 8/2004 |
| WO | 2004078924 A3 | 9/2004 |
| WO | WO 2005/017126 A2 | 2/2005 |
| WO | 2005108617 A1 | 11/2005 |
| WO | WO 2005/108617 A2 | 11/2005 |
| WO | WO 2006/083253 A1 | 8/2006 |

OTHER PUBLICATIONS

Nakagawa, Yoshiaki et al., Quantitative structure-activity relationships and designed synthesis of larvicidal N,N'-dibenzoyl-N-tert-butylhydrazines against Chila suppressalis. Pesticide Science (1995), 44(1), 102-5. Wiley and Sons England.

Le, D. P. et al., Rh-2485 A new selective insecticide for caterpillar control. Brighton Crop Protection Conference—Pests and Diseases (1996), (vol. 2), 481-486. British Crop Protection Council England.

Carlson, Glenn R. et al., The chemical and biological properties of methoxyfenozide, a new insecticidal ecdysteroid agonist. Pest Management Science (2001), 57(2), 115-119. Wiley England.

El-Abadelah et al. Heterocycles from nitrile oxides. Part V. 4-Amino-•2-1,2,4-oxadiazolines. Heterocycles, 1989, 29(10), 1957-64. Elsevier The Netherlands.

Cao, Song et al., Synthesis of N-tert-butyl-N,N'-aroyl(aryloxyacetyl)hydrazine. Huadong Ligong Daxue Xuebao (2001), 27(3), 316-319. Huodeng Shifan Daxue Chubanshe China.

Zou, Xia-Juan et al., Synthesis and crystal structure of N-tert-butyl-N'-(2,4-dichlorobenzoyl)-N-[1-(4-chlorophenyl)-1,4-dihydro-6-methylpyridazine-4-oxo-3-carbonyl]hydrazine. Jiegou Huaxue (2001), 20(5), 344-348. Zhingguo ke xue Yuan, Fujian wu zhi jie gou yan jiusuo China.

Nie, Kaisheng et al., New type of insect growth regulator-chromafenozide. Nongyao (2001), 40(2), 42-43. Nongyao Biajibu China.

Cao, S. et al., N'-tert-butyl-N'-aroyl-N-(alkoxycarbonylmethyl)-N-aroylhydrazines, a novel nonsteroidal ecdysone agonist: syntheses, insecticidal activity, conformational, and crystal structure analysis. Canadian Journal of Chemistry (2001), 79(3), 272-278. NRC Research Press Canada.

Sawada, Yoshihiro et al., Synthesis and insecticidal activity of 3,5-dimethylbenzoyl moiety modified analogues of N-tert-butyl-N'-(4-ethylbenzoyl)-3,5-dimethylbenzohydrazide. Nippon Noyaku Gakkaishi (2002), 27(4), 365-373. Noyaku Kagaku Kenkyukai Japan.

Nakagawa, Yoshiaki et al., Quantitative structure-activity studies of insect growth regulators: XIX. Effects of substituents on the aromatic moiety of dibenzoylhydrazines on larvicidal activity against the beet armyworm *Spodoptera exigua*. Pest Management Science (2002), 58(2), 131-138. Wiley England.

No, D. et al., "Ecdysone-Inducible Gene Expression in Mammalian Cells and Transgenic Mice," Proc. Natl. Acad. Sci. USA, vol. 93, pp. 3346-3351, 1996. National Academy of Sciences United States.

Zou, Xia-Juan et al. Synthesis of N-benzoyl-N-tert-butyl-N'-[(1,4-dihydro-6-methyl-4-oxo-1-phenyl-3-pyridazinyl) carbonyl]hydrazines. Indian Journal of Chemistry, Section B: Organic Chemistry Including Medicinal Chemistry (2003), 42B(10), 2608-2611. Council of Scientific and Industrial Research India.

Lynn M. Riddiford et al., "Ecdysone Receptors and Their Biological Actions", Vitamins and Hormones, 2000, 60:1-73. Academic Press United States.

Karen S. Christopherson et al., "Ecdysteroid-dependent regulation of genes in mammalian cells by a *Drosophila* ecdysone receptor and chimeric transactivators", Proc. Natl. Acad. Sci. U.S.A., 1992, 89: 6314-6318. National Academy of Sicences United States.

Suhr et al., "High level transactivation by a modified Bombyx ecdysone receptor in mammalian cells without exogenous retinoid X receptor" PNAS, 1998;95: 7999-8004 National Academy of Sciences United States.

(56) References Cited

OTHER PUBLICATIONS

Kakizawa T et al., "Ligand-dependent Heterodimerization of Thyroid Hormone Receptor and Retinoid X Receptor" 1997, JBC, 272: 38; 23799-23804 American Society for Biochemistry and Molecular Biology United States.

Wing, Keith D. et al., RH 5849, a nonsteroidal ecdysone agonist: effects on a *Drosophila* cell line. Science (Washington, DC, United States) (1988), 241(4864), 467-9. American Association for the Advancement of Science.

Sawada, Yoshihiro et al., Synthesis and insecticidal activity of benzoheterocyclic analogues of N'-benzoyl-N-(tert-butyl)benzohydrazide: part 2. Introduction of substituents on the benzene rings of the benzoheterocycle moiety. Pest Management Science (2003), 59(1), 36-48. Wiley England.

Sawada, Yoshihiro et al., Synthesis and insecticidal activity of benzoheterocyclic analogues of N'-benzoyl-N-(tert-butyl)benzohydrazide. Part 3. Modification of N-tert-butylhydrazine moiety. Pest Management Science (2003), 59(1), 49-57. Wiley England.

Koelle MR et al., The *Drosophila* EcR gene encodes an ecdysone receptor, a new member of the steroid receptor superfamily, Cell, 1991, 67: 59-77 Cell Press United States.

Belshaw et al., Rational design of orthogonal receptor-ligand combinations. Angewandte Chemie, International Edition in English (1995), 34(19), 2129-32. Wlley-VCH Germany.

Pierce et al., Computational binding studies of orthogonal cyclosporin-cyclophilin pairs. Angewandte Chemie, International Edition in English (1997), 36(13/14), 1466-1469. Wiley-VCH Germany.

Peet et al., Engineering Novel Specificities for Ligand-Activated Transcription in th enucelar Hormone Receptor RXR. Chemistry & Biology, 1998, 5, 1, 13-21. Current Biology Ltd United States.

Holt et al., Functional Expression of Exogenous Proteins in Mammalian Sensory Hair Cells Infected with Adenoviral Vectors. J Neurophysiol. (1999), 81(4), 1881-8. American Physiological Society United States.

Sawada, Yoshihiro et al., Synthesis and insecticidal activity of benzoheterocyclic analogues of N'-benzoyl-N-(tert-butyl)benzohydrazide. Part 1. Design of benzoheterocyclic analogues. Pest Management Science (2003), 59(1), 25-35. Wiley England.

Hoppe et al., Adenovirus-Mediated Inducible Gene Expression in Vivo by a Hybrid Ecdysone Receptor. Molecular Therapy (2000) 1(2), 159-164. Academic Press United States.

Zhang, Xiangning et al., Study on synthesis and bioactivity of new diacylhydrazine IGR JS118. Nongyao (2003), 42(12), 18-20. Nongyao Biajibu China.

Preliminary Amendment in U.S. Appl. No. 11/934,666, inventors Hormann, R., et al., filed Nov. 2, 2007, U.S. Patent and Trademark Office, Alexandria, Virginia (Nov. 2, 2007).

Restriction Requirement in U.S. Appl. No. 11/934,666, inventors Hormann, R., et al., filed Nov. 2, 2007, U.S. Patent and Trademark Office, Alexandria, Virginia (Jun. 12, 2008).

Reply to Restriction Requirement in U.S. Appl. No. 11/934,666, inventors Hormann, R., et al., filed Nov. 2, 2007, U.S. Patent and Trademark Office, Alexandria, Virginia (Dec. 5, 2008).

Non-Final Office Action in U.S. Appl. No. 11/934,666, inventors Hormann, R., et al., filed Nov. 2, 2007, U.S. Patent and Trademark Office, Alexandria, Virginia (Mar. 20, 2008).

Preliminary Amendment in U.S. Appl. No. 11/838,044, inventors Hormann, R., et al., filed Aug. 13, 2007, U.S. Patent and Trademark Office, Alexandria, Virginia (Aug. 13, 2007).

Restriction Requirement in U.S. Appl. No. 11/838,044, inventors Hormann, R., et al., filed Aug. 13, 2007, U.S. Patent and Trademark Office, Alexandria, Virginia (Sep. 8, 2008).

Reply to Restriction Requirement in U.S. Appl. No. 11/838,044, inventors Hormann, R., et al., filed Aug. 13, 2007, U.S. Patent and Trademark Office, Alexandria, Virginia (Dec. 5, 2008).

Non-Final Office Action in U.S. Appl. No. 11/838,044, inventors Hormann, R., et al., filed Aug. 13, 2007, U.S. Patent and Trademark Office, Alexandria, Virginia (Mar. 30, 2008).

Preliminary Amendment in U.S. Appl. No. 11/838,043, inventors Hormann, R., et al., filed Aug. 13, 2007, U.S. Patent and Trademark Office, Alexandria, Virginia (Aug. 13, 2007).

Restriction Requirement in U.S. Appl. No. 11/838,043, inventors Hormann, R., et al., filed Aug. 13, 2007, U.S. Patent and Trademark Office, Alexandria, Virginia (Jun. 12, 2009).

Reply to Restriction Requirement in U.S. Appl. No. 10/775,883, inventors Hormann, R., et al., Feb. 9, 2004, U.S. Patent and Trademark Office, Alexandria, Virginia (Aug. 24, 2006).

Response Under 37 C.F.R. §1.111 in U.S. Appl. No. 10/775,883, inventors Hormann et al., filed Feb. 9, 2004, U.S. Patent and Trademark Office, Alexandria, Virginia (Feb. 6, 2007).

Notice of Allowance in U.S. Appl. No. 10/775,883, inventors Hormann et al., filed Feb. 9, 2004, U.S. Patent and Trademark Office, Alexandria, Virginia (Feb. 26, 2007).

Notice of Allowance in U.S. Appl. No. 10/775,883, inventors Hormann et al., filed Feb. 9, 2004, U.S. Patent and Trademark Office, Alexandria, Virginia (Jul. 12, 2007).

Preliminary Amendment in United States Application No. 11/841,568, inventors Hormann, R., et al., filed Aug. 20, 2007, U.S. Patent and Trademark Office, Alexandria, Virginia (Nov. 21, 2007).

Amendment and Reply to Restriction Requirement in U.S. Appl. No. 11/841,568, inventors Hormann, R., et al., filed Aug. 20, 2007, U.S. Patent and Trademark Office, Alexandria, Virginia (Jul. 21, 2008).

Non-Final Office Action in U.S. Appl. No. 11/841,568, inventors Hormann, R., et al., filed Aug. 20, 2007, U.S. Patent and Trademark Office, Alexandria, Virginia (Sep. 12, 2008).

Amendment and Reply Under 37 C.F.R. § 1.111 in U.S. Appl. No. 11/841,568, inventors Hormann, R., et al., filed Aug. 20, 2007, U.S. Patent and Trademark Office, Alexandria, Virginia (Dec. 5, 2008).

Non-Final Office Action in U.S. Appl. No. 11/841,568, inventors Hormann, R., et al., filed Aug. 20, 2007, U.S. Patent and Trademark Office, Alexandria, Virginia (Jan. 5, 2009).

Reply Under 37 C.F.R. § 1.111 in U.S. Appl. No. 11/841,568, inventors Hormann, R., et al., filed Aug. 20, 2007, U.S. Patent and Trademark Office, Alexandria, Virginia (Apr. 6, 2009).

Notice of Allowance in U.S. Appl. No. 11/841,568, inventors Hormann, R., et al., filed Aug. 20, 2007, U.S. Patent and Trademark Office, Alexandria, Virginia (May 8, 2009).

Restriction Requirement in U.S. Appl. No. 10/787,906, inventors Hormann, R., et al., filed Feb. 26, 2004, U.S. Patent and Trademark Office, Alexandria, Virginia (Jun. 28, 2006).

Reply to Restriction Requirement in U.S. Appl. No. 10/787,906, inventors Hormann, R., et al., filed Feb. 26, 2004, U.S. Patent and Trademark Office, Alexandria, Virginia (Aug. 23, 2006).

Non-Final Office Action in U.S. Appl. No. 10/787,906, inventors Hormann, R., et al., filed Feb. 26, 2004, U.S. Patent and Trademark Office, Alexandria, Virginia (Sep. 12, 2006).

Response Under 37 C.F.R. § 1.111 in U.S. Appl. No. 10/787,906, inventors Hormann, R., et al., filed Feb. 26, 2004, U.S. Patent and Trademark Office, Alexandria, Virginia (Dec. 14, 2006).

Final Office Action in U.S. Appl. No. 10/787,906, inventors Hormann, R., et al., filed Feb. 26, 2004, U.S. Patent and Trademark Office, Alexandria, Virginia (Mar. 22, 2007).

Non-Final Office Action in U.S. Appl. No. 10/787,906, inventors Hormann, R., et al., filed Feb. 26, 2004, U.S. Patent and Trademark Office, Alexandria, Virginia (Jul. 27, 2007).

Amendment Under 37 C.F.R. § 1.111 in U.S. Appl. No. 10/787,906, inventors Hormann, R., et al., filed Feb. 26, 2004, U.S. Patent and Trademark Office, Alexandria, Virginia (Sep. 7, 2007).

Office Communication in U.S. Appl. No. 10/787,906, inventors Hormann, R., et al., filed Feb. 26, 2004, U.S. Patent and Trademark Office, Alexandria, Virginia (Sep. 11, 2007).

Response to Notice of Non-Compliant Amendment in U.S. Appl. No. 10/787,906, inventors Hormann, R., et al., filed Feb. 26, 2004, U.S. Patent and Trademark Office, Alexandria, Virginia (Sep. 12, 2007).

Amendment in U.S. Appl. No. 10/787,906, inventors Hormann, R., et al., filed Feb. 26, 2004, U.S. Patent and Trademark Office, Alexandria, Virginia (Nov. 2, 2007).

(56) References Cited

OTHER PUBLICATIONS

Notice of Allowance in U.S. Appl. No. 10/787,906, inventors Hormann, R., et al., filed Feb. 26, 2004, U.S. Patent and Trademark Office, Alexandria, Virginia (Nov. 8, 2007).
Non-Final Office Action in U.S. Appl. No. 10/787,906, inventors Hormann, R., et al., filed Feb. 26, 2004, U.S. Patent and Trademark Office, Alexandria, Virginia (Mar. 6, 2008).
Reply Under 37 C.F.R. § 1.111 in U.S. Appl. No. 10/787,906, inventors Hormann, R., et al., filed Feb. 26, 2004, U.S. Patent and Trademark Office, Alexandria, Virginia (Jun. 6, 2008).
Notice of Allowance in U.S. Appl. No. 10/787,906, inventors Hormann, R., et al., filed Feb. 26, 2004, U.S. Patent and Trademark Office, Alexandria, Virginia (Jul. 8, 2008).
International Search Report for International Application No. PCT/US04/003775, mailed Mar. 23, 2005, International Searching Authority, United States.
Supplementary European Search Report for European Patent Application No. 04 70 9841, completed Apr. 8, 2008, The Hague.
Tice et al. Optimization of alpha Acylaminoketone Ecdysone Agonists for Control of Gene Expression. Bioinorganic & Medicinal Chemistry Letters, 2003, vol. 13, pp. 1883-1886 Elsevier Science Ltd. England.
Kumar, MB et al., A single point mutation in ecdysone receptor leads to increased ligand specificity: implications for gene switch applications, Proceedings of the National Academy of Sciences of the United States of America, (2002), 99(23):14710-14715 National Academy of Sciences United States.
Dhiadalla TS et al., New insecticides with ecdysteroidal and juvenile hormone activity, Annu Rev Entol, (1998), 43:545-69 Annual Reviews, Inc. United States.
Martinez A et al., Creation of ecdysone receptor chimeras in plants for controlled regulation of gene expression, Mol Gen Genet. ,(1999),261(3):546-52 Springer-Verlag Germany.
Antoniewski, C. et al., "The Ecdysone Response Enhancer of the *Fbp 1* Gene of *Drosophila melanogaster* Is a Direct Target for the EcR/USP Nuclear Receptor," *Mol. Cell. Biol.* 14:4465-4474, American Society for Microbiology, United States (1994).
Ashburner, M. et al., "Temporal Control of Puffing Activity in Polytene Chromosomes," *Cold Spring Harb. Symp. Quant. Biol* 38:655-662, Cold Spring Harbor Laboratory Press, United States (1974).
Cherbas, L. et al., "Identification of ecdysone response elements by analysis of the *Drosophila* Eip28/29 gene," *Genes & Dev.* 5:120-131, Cold Spring Harbor Laboratory Press, United States (1991).
Cho, W.-L. et al., "Mosquito Ecdysteroid Receptor: Analysis of the cDNA and Expression During Vitellogenesis," *Insect Biochem. Molec. Biol.* 25:19-27, Pergamon Press Ltd., England (1995).
Christopherson, K.S. et al., "Ecdysteroid-dependent regulation of genes in mammalian cells by a *Drosophila* ecdysone receptor and chimeric transactivators," *Proc. Natl. Acad. Sci. USA* 89:6314-6318, National Academy of Sciences, United States (1992).
Chung, A. C.-K. et al., "Cloning of crustacean ecdysteroid receptor and retinoid-X receptor gene homologs and elevation of retinoid-X receptor mRNA by retinoic acid," *Mol. Cell. Endocrinol.* 139:209-227, North Holland Publishing, Ireland (1998).
D'Avino, P.P. et al., "The moulting hormone ecdysone is able to recognize target elements composed of direct repeats," *Mol. Cell. Endocrinol.* 113:1-9, North Holland Publishing, Ireland (1995).
Dhadialla, T.S. et al., "New Insecticides with Ecdysteroidal and Juvenile Hormone Activity," *Annu. Rev. Entomol.* 43:545-569, Annual Reviews Inc., United States (1998).
Evans, R.M., "The Steroid and Thyroid Hormone Receptor Superfamily," *Science* 240:889-895, American Association for the Advancement of Science, United States (1988).
Fujiwara, H. et al., "Cloning of an Ecdysone Receptor Homolog from *Manduca sexta* and the Developmental Profile of Its mRNA in Wings," *Insect Biochem. Molec. Biol.* 25:845-856, Pergamon Press, Ltd., England (1995).

Godowski, P.J. et al., "Signal Transduction and Transcriptional Regulation by Glucocorticoid Receptor—LexA Fusion Proteins," *Science* 241:812-816, American Association for the Advancement of Science, United States (1988).
Guo, X. et al., "Isolation of a Functional Ecdysteroid Receptor Homologue from the Ixodid Tick *Amblyomma americanum* (L.)," *Insect Biochem. Mol. Biol.* 27:945-962, Pergamon Press, Ltd., England (1998).
Hannan, G.N. and Hill, R.J., "Cloning and Characterization of LcEcR[1]: A Functional Ecdysone Receptor from the Sheep Blowfly *Lucilia cuprina*," *Insect Biochem. Mol. Biol.* 27:479-488, Pergamon Press, Ltd., England (1997).
Hayward, D.C. et al., "The structure of the USP/RXR of *Xenos pecki* indicates that Strepsiptera are not closely related to Diptera," *Dev. Genes Evol.* 215:213-219, Springer-Verlag, Germany (Apr. 2005).
Heberlein, U. et al., "Characterization of *Drosophila* Transcription Factors That Activate the Tandem Promoters of the Alcohol Dehydrogenase Gene," *Cell* 41:965-977, Cell Press, United States (1985).
Imhof, M.O. et al., "Cloning of a *Chironomus tentans* cDNA Encoding a Protein (cEcRH) Homologous to the *Drosophila melanogaster* Ecdysteroid Receptor (dEcR)," *Insect Biochem. Mol. Biol.* 23:115-124, Pergamon Press Ltd., England (1993).
Kakizawa, T. et al., "Ligand-dependent Heterodimerization of Thyroid Hormone Receptor and Retinoid X Receptor," *J. Biol. Chem.* 272:23799-23804, The American Society for Biochemistry and Molecular Biology, Inc., United States (1997).
Koelle, M.R. et al., "The *Drosophila EcR* Gene Encodes an Ecdysone Receptor, a New Member of the Steroid Receptor Superfamily," *Cell* 67:59-77, Cell Press, United States (1991).
Kothapalli, R. et al., "Cloning and Developmental Expression of the Ecdysone Receptor Gene From the Spruce Budworm, *Choristoneura fumiferana*," *Dev. Genet.* 17:319-330, Wiley-Liss, Inc., United States (1995).
Leid, M. et al., "Purification, Cloning, and RXR Identify of the HeLa Cell Factor with Which RAR and TR Heterodimerizes to Bind Target Sequences Efficiently," *Cell* 68:377-395, Cell Press, United States (1992).
Leonhardt, S.A. et al., "Agonist and Antagonists Induce Homodimerization and Mixed Ligand Heterodimerization of Human Progesterone Receptors in Vivo by a Mammalian Two-Hybrid Assay," *Mol. Endocrinol.*, 1914-1930, The Endocrine Society, United States (1998).
Licitra, E.J. and Liu, J.O., "A three-hybrid system for detecting small ligand-protein receptor interactions," *Proc. Natl. Acad. Sci. USA* 93:12817-12821, National Academy of Sciences, United States (1996).
Martinez, A. et al., "Creation of ecdysone receptor chimeras in plants for controlled regulation of gene expression," *Mol. Gen. Genet.* 261:546-552, Springer-Verlag, Germany (1999).
Metzger, D. et al., "The human oestrogen receptor functions in yeast," *Nature* 334:31-36, Nature Publishing Group, England (1988).
Morrison, D.A. et al., "Isolation of Transformation-Deficient *Streptococcus pneumoniae* Mutants Defective in Control of Competence, Using Insertion-Duplication Mutagenesis with the Erythromycin Resistance Determinant of pAMβ1," *J. Bacteriol.* 159:870-876, American Society for Microbiology, United States (1984).
Mouillet, J.-F. et al., "Cloning of two putative ecdysteroid receptor isoforms from *Tenebrio molitor* and their developmental expression in the ipidermis during metamorphosis," *Eur. J. Biochem.* 248:856-863, Blackwell Science Ltd., England (1997).
Nakagawa, Y. et al., "Quantitative structure-activity studies of insect growth regulators: XVI. Substituent effects of dibenzoylhydrazines on the insecticidal activity to Colorado potato beetle *Leptinotarsa decemlineata*," *Pestic. Sci.* 55:909-918, Wiley & Sons, England (1999).
Neuberger, M.S. et al., "Recombinant antibodies possession novel effector functions," *Nature* 312:604-608, Nature Publishing Group, England (1984).
Perera, S.C. et al., "An Analysis of Ecdysone Receptor Domains Required for Heterodimerization With Ultraspiracle," *Arch. Insect Biochem. Physiol.* 41:61-70, Wiley-Liss, Inc., United States (1999).

(56) References Cited

OTHER PUBLICATIONS

Perera, S.C. et al., "Studies on two ecdysone receptor isoforms of the spruce budworm, *Choristoneura fumiferana*," *Mol. Cell. EndocrinoL* 152:73-84, North Holland Publishing, Ireland (1999).

Saleh, D.S. et al., "Cloning and characterization of an ecdysone receptor cDNA from *Locusta migratoria*," *Mol. Cell. Endocrinol.* 143:91-99, North Holland Publishing, Ireland (1998).

Swevers, L. et al., "The Silkmouth Homolog of the *Drosophila* Ecdysone Receptor (B1 Isoform): Cloning and Analysis of Expression During Follicular Cell Differentiation," *Insect Biochem. Mol. Biol.* 25:857-866, Pergamon Press Ltd., England (1995).

Verras, M. et al., "Cloning and characterization of CcEcR: An ecdysone receptor homolog from the Mediterranean fruit fly *Ceratitis capitata*," *Eur. J. Biochem.* 265:798-808, Blackwell Science Ltd., England (1999).

Wilson, J.M. et al., "Hepatocyte-directed Gene Transfer in Vivo Leads to Transient Improvement of Hypercholesterolemia in Low Density Lipoprotein Receptor-deficient Rabbits," *J. Biol. Chem.* 267:963-967, The American Society for Biochemistry and Molecular Biology, Inc., United States (1992).

Yao, T.-P. et al., "*Drosophila* ultraspiracle Modulates Ecdysone Receptor Function via Heterodimer formation," *Cell* 71:63-72, Cell Press, United States (1992).

Yao, T.-P. et al., "Functional ecdysone receptor is the product of EcR and *Ultraspiracle* genes," *Nature* 366:476-479, Nature Publishing Group, England (1993).

Kumar, S., Office Action for U.S. Appl. No. 11/841,568, filed Aug. 20, 2007, U.S. Patent and Trademark Office, Alexandria, Virginia (Mar. 19, 2008).

Davis, B. J., Office Action for U.S. Appl. No. 10/775,883, filed Feb. 9, 2004, U.S. Patent and Trademark Office, Alexandria, Virginia (Nov. 6, 2006).

David, B.J., Office Action for U.S. Appl. No. 10/775,883, filed Feb. 9, 2004, U.S. Patent and Trademark Office, Alexandria, Virginia (Aug. 2, 2006).

Notice of Allowance in U.S. Appl. No. 13/243,210, inventors Hormann, R. et al., filed Sep. 23, 2011, U.S. Patent and Trademark Office, Alexandria, Virginia (May 9, 2013).

Non-Final Office Action in U.S. Appl. No. 13/243,210, inventors Hormann, R. et al., filed Sep. 23, 2011, U.S. Patent and Trademark Office, Alexandria, Virginia (Sep. 13, 2012).

Non-Final Office Action in U.S. Appl. No. 13/243,210, inventors Hormann, R. et al., filed Sep. 23, 2011, U.S. Patent and Trademark Office, Alexandria, Virginia (Jan. 22, 2013).

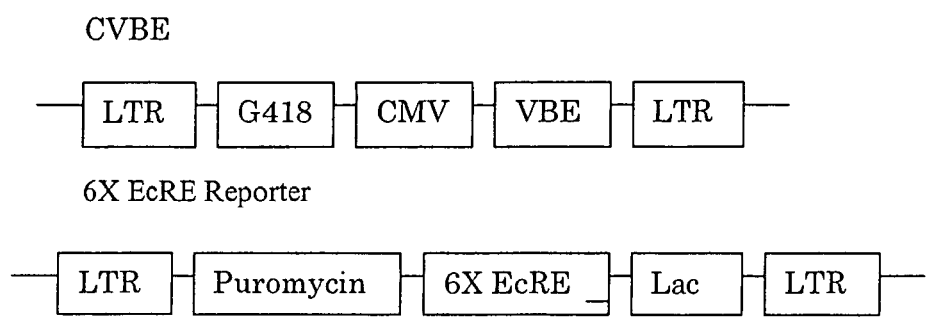

BIOAVAILABLE DIACYLHYDRAZINE LIGANDS FOR MODULATING THE EXPRESSION OF EXOGENOUS GENES VIA AN ECDYSONE RECEPTOR COMPLEX

This is a Divisional of application Ser. No. 10/787,906 filed 26 Feb. 2004, now U.S. Pat. No. 7,456,315 B2, issued 25 Nov. 2008, which claims priority to U.S. Provisional Application No. 60/455,741, filed 28 Feb. 2003, the contents of which are incorporated herein by reference in its entirety.

This application claims priority to U.S. provisional application No. 60/455,741 filed Feb. 28, 2003.

FIELD OF THE INVENTION

This invention relates to the field of biotechnology or genetic engineering. Specifically, this invention relates to the field of gene expression. More specifically, this invention relates to non-steroidal ligands for natural and mutated nuclear receptors and their use in a nuclear receptor-based inducible gene expression system and methods of modulating the expression of a gene within a host cell using these ligands and inducible gene expression system.

BACKGROUND OF THE INVENTION

Various publications are cited herein, the disclosures of which are incorporated by reference in their entireties. However, the citation of any reference herein should not be construed as an admission that such reference is available as "Prior Art" to the instant application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83:5414-5418; Arnheiter et al., 1990 Cell 62:51-61; Filmus et al., 1992 Nucleic Acids Research 20:27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, Science 262:1019-24; Belshaw et al., 1996 *Proc Natl Acad Sci USA* 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998. Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530, 028). Both analogs have exceptional safety profiles to other organisms.

The insect ecdysone receptor (EcR) heterodimerizes with Ultraspiracle (USP), the insect homologue of the mammalian RXR, and binds ecdysteroids and ecdysone receptor response elements and activate transcription of ecdysone responsive genes. The EcR/USP/ligand complexes play important roles during insect development and reproduction. The EcR is a member of the steroid hormone receptor superfamily and has five modular domains, A/B (transactivation), C (DNA binding, heterodimerization)), D (Hinge, heterodimerization), E (ligand binding, heterodimerization and transactivation and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson K. S., Mark M. R., Baja J. V., Godowski P. J. 1992, Proc. Natl. Acad. Sci. U.S.A. 89: 6314-6318; No D., Yao T. P., Evans R. M., 1996, Proc. Natl. Acad. Sci. U.S.A. 93: 3346-3351). Later, Suhr et al. 1998, Proc. Natl. Acad. Sci. 95:7999-8004 showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880, 333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and at the same is insensitive to the natural steroids. Thus, improved systems that are simple, compact, and dependent on ligands that are relatively inexpensive, readily available, and of low toxicity to the host would prove useful for regulating biological systems.

Recently, it has been shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (pending application PCT/US01/09050, incorporated herein in its entirety by reference). This two-hybrid system is a significantly improved inducible gene expression modulation system compared to the two systems disclosed in applications PCT/US97/05330 and PCT/US98/14215. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching systems to obtain maximum transactivation capability for each application. Furthermore, the two-hybrid system avoids some side effects due to overexpression of RXR that often occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell resulting in reduced side effects.

With the improvement in ecdysone receptor-based gene regulation systems there is an increase in their use in various applications resulting in increased demand for ligands with higher activity than those currently exist. U.S. Pat. No. 6,258,603 B1 (and patents cited therein) disclosed dibenzoylhydrazine ligands, however, a need exists for additional ligands with different structures and physicochemical properties. We have discovered novel diacylhydrazine ligands which have not previously been described or shown to have the ability to modulate the expression of transgenes.

SUMMARY OF THE INVENTION

The present invention relates to non-steroidal ligands for use in nuclear receptor-based inducible gene expression system, and methods of modulating the expression of a gene within a host cell using these ligands with nuclear receptor-based inducible gene expression systems.

Applicants' invention also relates to methods of modulating gene expression in a host cell using a gene expression modulation system with a ligand of the present invention. Specifically, Applicants' invention provides a method of modulating the expression of a gene in a host cell comprising the steps of: a) introducing into the host cell a gene expression modulation system according to the invention; b) introducing into the host cell a gene expression cassette comprising i) a response element comprising a domain to which the DNA binding domain from the first hybrid polypeptide of the gene expression modulation system binds; ii) a promoter that is activated by the transactivation domain of the second hybrid polypeptide of the gene expression modulation system; and iii) a gene whose expression is to be modulated; and c) introducing into the host cell a ligand; whereby upon introduction of the ligand into the host cell, expression of the gene is modulated. Applicants' invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

FIG. 1. Schematic of switch construct CVBE, and the reporter construct 6XEcRE Lac Z. Flanking both constructs are long terminal repeats, G418 and puromycin are selectable markers, CMV is the cytomegalovirus promoter, VBE is coding sequence for amino acids 26-546 from Bombyx mori EcR inserted downstream of the VP16 transactivation domain, 6X EcRE is six copies of the ecdysone response element, lacZ encodes for the reporter enzyme β-galactosidase.

DETAILED DESCRIPTION OF THE INVENTION

Applicants' invention provides ligands for use with ecdysone receptor-based inducible gene expression system useful for modulating expression of a gene of interest in a host cell. In a particularly desirable embodiment, Applicants' invention provides an inducible gene expression system that has a reduced level of background gene expression and responds to submicromolar concentrations of non-steroidal ligand. Thus, Applicants' ligands and inducible gene expression system and its use in methods of modulating gene expression in a host cell overcome the limitations of currently available inducible expression systems and provide the skilled artisan with an effective means to control gene expression.

The present invention is useful for applications such as gene therapy, large scale production of proteins and antibodies, cell-based high throughput screening assays, functional genomics, proteomics, metabolomics, and regulation of traits in transgenic organisms, where control of gene expression levels is desirable. An advantage of Applicants' invention is that it provides a means to regulate gene expression and to tailor expression levels to suit the user's requirements.

The present invention pertains to compounds of the general formula:

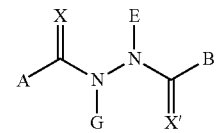

wherein X and X' are independently O or S;

A is unsubstituted or substituted phenyl wherein the substituents are independently 1 to 5H; halo; nitro; cyano; hydroxy; amino (—NR$^a$R$^b$); alkylaminolkyl (—(CH$_2$)$_n$NR$^a$R$^b$); (C$_1$-C$_6$)alkyl; (C$_1$-C$_6$)haloalkyl; (C$_1$-C$_6$)cyanoalkyl; (C$_1$-C$_6$)hydroxyalkyl; (C$_1$-C$_6$)alkoxy; phenoxy; (C$_1$-C$_6$)haloalkoxy; (C$_1$-C$_6$)alkoxy(C$_1$-C$_6$)alkyl; (C$_1$-C$_6$)alkenyloxy(C$_1$-C$_6$)alkyl; (C$_1$-C$_6$)alkoxy(C$_1$-C$_6$)alkoxy; (C$_1$-C$_6$) alkanoyloxy(C$_1$-C$_6$)alkyl; (C$_2$-C$_6$)alkenyl optionally substituted with halo, cyano, (C$_1$-C$_4$)alkyl, or (C$_1$-C$_4$)alkoxy; (C$_2$-C$_6$)alkynyl optionally substituted with halo or (C$_1$-C$_4$)alkyl; formyl; carboxy; (C$_1$-C$_6$)alkylcarbonyl; (C$_1$-C$_6$)haloalkylcarbonyl; benzoyl; (C$_1$-C$_6$)alkoxycarbonyl; (C$_1$-C$_6$)haloalkoxycarbonyl; (C$_1$-C$_6$)alkanoyloxy (—OCOR$^a$); carboxamido (—CONR$^a$R$^b$); amido (—NR$^a$COR$^b$); alkoxycarbonylamino (—NR$^a$CO$_2$R$^b$); alkylaminocarbonylamino (—NR$^a$CONR$^b$R$^c$); mercapto; (C$_1$-C$_6$)alkylthio; (C$_1$-C$_6$)alkylsulfonyl; (C$_1$-C$_6$)alkylsulfonyl(C$_1$-C$_6$)alkyl; (C$_1$-C$_6$)alkylsulfoxido (—S(O)R$^a$); (C$_1$-C$_6$)alkylsulfoxido(C$_1$-C$_6$)alkyl-(CH$_2$)$_n$S(O)R$^a$); sulfamido (—SO$_2$NR$^a$R$^b$); —SO$_3$H; or unsubstituted or substituted phenyl wherein the substituents are independently 1 to 3 halo, nitro, (C$_1$-C$_6$) alkoxy, (C$_1$-C$_6$)alkyl, or amino; or when one or both of two adjacent positions on the phenyl ring are substituted, the attached atoms may form the phenyl-connecting termini of a linkage selected from the group consisting of (—OCH$_2$O—), (—OCH(CH$_3$)O—), (—OCH$_2$CH$_2$O—), (—OCH(CH$_3$)CH$_2$O—), (—S—CH═N—), (—CH$_2$OCH$_2$O—), (—O(CH$_2$)$_3$—), (═N—O—N═), (—C═CH—NH—), (—OCF$_2$O—), (—N—CH═N—), (—CH$_2$CH$_2$O—), and (—(CH$_2$)$_4$—);

B is (a) unsubstituted or substituted phenyl wherein the substituents are independently 1 to 5H; halo; nitro; cyano; hydroxy; amino (—NR$^a$R$^b$); alkylaminolkyl (—(CH$_2$)NR$^a$R$^b$); (C$_1$-C$_6$)alkyl; (C$_1$-C$_6$)haloalkyl; (C$_1$-C$_6$)cyanoalkyl; (C$_1$-C$_6$)hydroxyalkyl; (C$_1$-C$_6$)alkoxy; phenoxy; (C$_1$-C$_6$)haloalkoxy; (C$_1$-C$_6$)alkoxy(C$_1$-C$_6$)alkyl; (C$_1$-C$_6$)alkenyloxy(C$_1$-C$_6$)alkyl; (C$_1$-C$_6$)alkoxy(C$_1$-C$_6$) alkoxy; (C$_1$-C$_6$)alkanoyloxy(C$_1$-C$_6$)alkyl; (C$_2$-C$_6$)alkenyl optionally substituted with halo, cyano, (C$_1$-C$_4$)

alkyl, or (C₁-C₄)alkoxy; (C₂-C₆)alkynyl optionally substituted with halo or (C₁-C₄)alkyl; formyl; carboxy; (C₁-C₆)alkylcarbonyl; (C₁-C₆)haloalkylcarbonyl; benzoyl; (C₁-C₆)alkoxycarbonyl; (C₁-C₆)haloalkoxycarbonyl; (C₁-C₆)alkanoyloxy (—OCOR$^a$); carboxamido (—CONR$^a$R$^b$); amido (—NR$^a$COR$^b$); alkoxycarbonylamino (—NR$^a$CO₂R$^b$); alkylaminocarbonylamino (—NR$^a$CONR$^b$R$^c$); mercapto; (C₁-C₆)alkylthio; (C₁-C₆)alkylsulfonyl; (C₁-C₆)alkylsulfonyl(C₁-C₆)alkyl; (C₁-C₆)alkylsulfoxido (—S(O)R$^a$); (C₁-C₆)alkylsulfoxido(C₁-C₆)alkyl (—CH₂)$_n$S(O)R$^a$); sulfamido (—SO₂NR$^a$R$^b$); —SO₃H; or unsubstituted or substituted phenyl wherein the substituents are independently 1 to 3 halo, nitro, (C₁-C₆)alkoxy, (C₁-C₆)alkyl, or amino; or when one or both of two adjacent positions on the phenyl ring are substituted, the attached atoms may form the phenyl-connecting termini of a linkage selected from the group consisting of (—OCH₂O—), (—OCH(CH₃)O—), (—OCH₂CH₂O—), (—OCH(CH₃)CH₂O—), (—S—CH=N—), (—CH₂OCH₂O—), (—O(CH₂)₃—), (=N—O—N=), (—C=CH—NH—), (—OCF₂O—), (—NH—CH=N—), (—CH₂CH₂O—), and (—(CH₂)₄—);

(b) unsubstituted 6-membered heterocycle or substituted 6-membered heterocycle having 1-3 nitrogen atoms and 3-5 nuclear carbon atoms where the substituents are from one to three of the same or different halo; nitro; hydroxy; (C₁-C₆)alkyl; (C₁-C₆)alkoxy; (C₁-C₆)thioalkoxy; carboxy; (C₁-C₆)alkoxycarbonyl; (C₁-C₆)carboxyalkyl; (C₁-C₆)alkoxycarbonylalkyl having independently the stated number of carbon atoms in each alkyl group; —CONR$^a$R$^b$; amino; (C₁-C₆)alkylamino; (C₁-C₆)dialkylamino having independently the stated number of carbon atoms in each alkyl group; haloalkyl including —CF₃; —C=N—NHC(O)NR$^a$R$^b$; or —C=N—NHC(O)C(O)NR$^a$R$^b$; or (c) 5-benzimidazolyl; 1-trityl-5-benzimidazolyl; 3-trityl-5-benzimidazolyl; 1H-indazole-3-yl; 1-trityl-1H-indazole-3-yl; or 1-(C₁-C₆)alkyl-1H-indole-2-yl;

E is unsubstituted or substituted (C₄-C₁₀) branched alkyl wherein the substituents are independently 1-4 cyano; halo; (C₅-C₆)cycloalkyl; phenyl; (C₂-C₃)alkenyl; hydroxy, (C₁-C₆)alkoxy; carboxy; (C₁-C₆)alkoxycarbonyl; (C₁-C₆)alkanoyloxy (—OCOR$^a$); formyl; (C₁-C₆)trialkylsilyloxy having independently the stated number of carbon atoms in each alkyl group; —C=N—OR$^a$; —C=N—R$^d$; —C=N—NHC(O)NR$^a$R$^b$; or —C=N—NHC(O)C(O)NR$^a$R$^b$;

wherein R$^a$, R$^b$, and R$^c$ are independently H, (C₁-C₆)alkyl, or phenyl; R$^d$ is hydroxy(C₁-C₆)alkyl; and n=1-4; and G is H or CN;

provided that:

1) when E is unsubstituted or substituted (C₄-C₁₀) branched alkyl wherein the substituents are independently 1-4 cyano; halo; (C₂-C₃)alkenyl; carboxy; or (C₁-C₆)alkoxycarbonyl;

then B is
(a) substituted phenyl which bears at least one —C=N—NHC(O)NR$^a$R$^b$ or —C=N—NHC(O)C(O)NR$^a$R$^b$ group;
(b) substituted 6-membered heterocycle having 1-3 nitrogen atoms and 3-5 nuclear carbon atoms which bears at least one haloalkyl group; or
(c) 5-benzimidazolyl; 1-trityl-5-benzimidazolyl; 3-trityl-5-benzimidazolyl; 1H-indazole-3-yl; 1-trityl-1H-indazole-3-yl; or 1-(C₁-C₆)alkyl-1H-indole-2-yl;

wherein R$^a$, R$^b$ are independently H, (C₁-C₆)alkyl, or phenyl; or 2) when E is a substituted (C₄-C₁₀) branched alkyl which bears at least one of phenyl; hydroxy, (C₁-C₆)alkoxy; or formyl;

then B is
(a) substituted phenyl which bears at least one —C=N—NHC(O)NR$^a$R$^b$ or —C=N—NHC(O)C(O)NR$^a$R$^b$ group;
(b) substituted or unsubstituted 6-membered heterocycle having 1-3 nitrogen atoms and 3-5 nuclear carbon atoms; or
(c) 5-benzimidazolyl; 1-trityl-5-benzimidazolyl; 3-trityl-5-benzimidazolyl; 1H-indazole-3-yl; 1-trityl-1H-indazole-3-yl; or 1-(C₁-C₆)alkyl-1H-indole-2-yl;

wherein R$^a$ and R$^b$ are independently H, (C₁-C₆)alkyl, or phenyl.

Compounds of the general formula are preferred when X and X' are O and G is H.

Compounds of the present invention most preferred are the following:

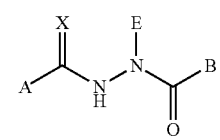

| Compound | A | B | E |
|---|---|---|---|
| RG-100864 | 4-Cl—Ph | Ph | t-Bu |
| RG-101013 | 4-Et—Ph | 2-NO₂—Ph | t-Bu |
| RG-101542 | 4-CH₃—Ph | 3-CH₃, 5-CH₃—Ph | t-Bu |
| RG-102125 | 4-Et—Ph | 3-CH₃, 5-CH₃—Ph | t-Bu |
| RG-100801 | 2,6-di-F—Ph | 3-Cl, 5-Cl—Ph | t-Bu |
| RG-101202 | 2-CH₃, 3-Cl—Ph | 3-Cl—Ph | t-Bu |
| RG-101248 | 2-Cl, 3-OMe—Ph | 2-Cl-5-CH₃—Ph | t-Bu |
| RG-101664 | 2-CH₃, 3-Cl—Ph | 3-CH₃-4-Br—Ph | t-Bu |
| RG-101862 | 4-Et—Ph | 3,5-di-CH₃-4-Cl—Ph | t-Bu |
| RG-101863 | 4-Et—Ph | 3,4-di-CH₃-5-Cl—Ph | t-Bu |
| RG-101057 | 4-OCH₃—Ph | 2-Cl-4-F—Ph | t-Bu |
| RG-101774 | 4-Et—Ph | 3-CH₃, 5-Cl—Ph | t-Bu |
| RG-102592 | 4-Et—Ph | 2-Et—Ph | t-Bu |
| RG-101376 | 4-OCH₃—Ph | 3-Cl, 5-Cl—Ph | t-Bu |
| RG-101398 | 4-Et—Ph | 2-NO₂-5-CH₃—Ph | t-Bu |
| RG-100875 | 4-CH₂CN—Ph | 3-CH₃, 5-CH₃—Ph | t-Bu |
| RG-100694 | 2-CH₃, 3-OMe—Ph | 3-CH₃—Ph | t-Bu |
| RG-101759 | 4-Br—Ph | 3-Cl, 5-Cl—Ph | t-Bu |
| RG-100915 | 2-CH₃, 3-NO₂—Ph | 3-CH₃, 5-CH₃—Ph | t-Bu |

-continued

| Compound | A | B | E |
|---|---|---|---|
| RG-100763 | 2-CH₃, 3-CH₃—Ph | 2,5-di-OCH₃—Ph | t-Bu |
| RG-101178 | 2-CH₃, 3-CH₃—Ph | 2-OCH₃-5-Cl—Ph | t-Bu |
| RG-100568 | 2-NO₂, 3-OMe—Ph | 3-CH₃, 5-CH₃—Ph | t-Bu |
| RG-100764 | 2-CH₃, 3-CH₃—Ph | 3-OMe, 5-OMe—Ph | t-Bu |
| RG-101864 | 3-Cl, 4-Et—Ph | 3-CH₃, 5-CH₃—Ph | t-Bu |
| RG-100342 | 4-CH(OH)CH₃—Ph | 3-F, 5-F—Ph | t-Bu |
| RG-101316 | 2-CH₃, 3-NMe₂—Ph | 3-Cl, 5-Cl—Ph | t-Bu |
| RG-100814 | 2-CH₃, 3-Ac—Ph | 3-CH₃, 5-CH₃—Ph | t-Bu |
| RG-100749 | 2-CH₃, 3-OAc—Ph | 3-CH₃, 5-CH₃—Ph | t-Bu |
| RG-101734 | 2-CH₃, 3-I—Ph | 3-CH₃, 5-CH₃—Ph | t-Bu |
| RG-101408 | 2-CH₃, 3-OMe—Ph | 3-Cl, 5-Br—Ph | t-Bu |
| RG-101670 | 2-CH₃, 3-Oi—Pr—Ph | 3-CH₃, 5-CH₃—Ph | t-Bu |
| RG-100127 | 2-CH₃, 3-OCH₃—Ph | 2-Cl-3-pyridyl | t-Bu |
| RG-100766 | 2-CH₃, 3-OMe—Ph | 2-OCH₃-5-CH₃—Ph | t-Bu |
| RG-100603 | 2-CH₃, 3-OMe—Ph | 2,5-F—Ph | t-Bu |
| RG-101062 | 2-CH₃, 3-OMe—Ph | 2-Et—Ph | t-Bu |
| RG-101353 | 2-CH₃, 3-OMe—Ph | 3-CH₃, 5-Br—Ph | t-Bu |
| RG-100767 | 2-CH₃, 3-OMe—Ph | 3-OMe, 5-CH₃—Ph | t-Bu |
| RG-100848 | 2-CH₃, 3-OMe—Ph | 2-OCH₃-4-Cl—Ph | t-Bu |
| RG-101692 | 2-CH₃, 3-OCF₃—Ph | 3-CH₃, 5-CH₃—Ph | t-Bu |
| RG-100768 | 2-CH₃, 3-OMe—Ph | 3-OCH₃-4-CH₃—Ph | t-Bu |
| RG-101585 | 3-OCH₃, 4-CH₃—Ph | 3-CH₃, 5-CH₃—Ph | t-Bu |
| RG-100769 | 2-CH₃, 3-OMe—Ph | 2-OCH₃-4-CH₃—Ph | t-Bu |
| RG-100394 | 2-CH₃, 3-OCH₃—Ph | 2,6-di-Cl-4-pyridyl | t-Bu |
| RG-100569 | 2-CH₃, 3-OMe—Ph | 2-NO₂-5-CH₃—Ph | t-Bu |
| RG-100929 | 2-CH₃, 3-OMe—Ph | 2-F-4-Cl—Ph | t-Bu |
| RG-101048 | 3,4-OCH₂O—Ph | 2-Cl-4-F—Ph | t-Bu |
| RG-102240 | 2-Et, 3-OMe—Ph | 3-CH₃, 5-CH₃—Ph | t-Bu |
| RG-101691 | 2-CH₃, 3-Et—Ph | 3-CH₃, 5-CH₃—Ph | t-Bu |
| RG-101531 | 3-CH₂CH₂O-4-Ph | 3-CH₃, 5-CH₃—Ph | t-Bu |
| RG-101382 | 2-CH₃, 3-OMe—Ph | 3,5-di-Cl-4-F—Ph | t-Bu |
| RG-100448 | 2-CH₃, 3,4-OCH₂O—Ph | 4-F—Ph | t-Bu |
| RG-100698 | 2-Et, 3,4-OCH₂O—Ph | 2-OCH₃—Ph | t-Bu |
| RG-101889 | 3,4-di-Et—Ph | 3-CH₃, 5-CH₃—Ph | t-Bu |
| RG-100812 | 2-Et, 3-OMe—Ph | 4-F—Ph | t-Bu |
| RG-100725 | 2-Et, 3-OMe—Ph | 2-OCH₃—Ph | t-Bu |
| RG-100524 | 2-CH₃, 3-OMe—Ph | 2-OCH₃-4-F—Ph | t-Bu |
| RG-100667 | 2-Et, 3-OCH₃—Ph | 2-Cl-6-CH₃-4-pyridyl | t-Bu |
| RG-100778 | 2-Et, 3-OMe—Ph | 3-OMe, 5-OMe—Ph | t-Bu |
| RG-101528 | 2-I, 3-OMe—Ph | 3-CH₃, 5-CH₃—Ph | t-Bu |
| RG-100492 | 3,4-ethylenedioxy-Ph | 2-OCH₃—Ph | t-Bu |
| RG-101887 | 3,4-(CH₂)₄—Ph | 3-CH₃, 5-CH₃—Ph | t-Bu |
| RG-115496 | 2-Et, 3-OMe—Ph | 2,3-OCH₂O—Ph | t-Bu |
| RG-100901 | 2-F, 4-Et—Ph | 4-F—Ph | t-Bu |
| RG-100699 | 2-Et, 3-OMe—Ph | 3,4-methylenedioxy-Ph | t-Bu |
| RG-100425 | 2-CH₃, 3,4-ethylenedioxy-Ph | 4-F—Ph | t-Bu |
| RG-101511 | 3,4-OCH(CH₃)O—Ph | 3-CH₃, 5-CH₃—Ph | t-Bu |
| RG-101659 | 2-Et, 3,4-OCH(CH₃)O—Ph | 3-CH₃, 5-CH₃—Ph | t-Bu |
| RG-100360 | 2-CH₃, 3,4-ethylenedioxy-Ph | 3-OCH₃—Ph | t-Bu |
| RG-101509 | 3-OCH(CH₃)CH₂O-4-Ph | 3-CH₃, 5-CH₃—Ph | t-Bu |
| RG-101340 | 2-Br, 3,4-ethylenedioxy-Ph | 3-CH₃, 5-CH₃—Ph | t-Bu |
| RG-101494 | 2-Et, 3,4-ethylenedioxy-Ph | 3-CH₃, 5-Cl—Ph | t-Bu |
| RG-101036 | 2-Et, 3,4-ethylenedioxy-Ph | 3-CH₃—Ph | t-Bu |
| RG-100690 | 2-Et, 3,4-ethylenedioxy-Ph | 2-OCH₃—Ph | t-Bu |
| RG-100691 | 2-Et, 3,4-ethylenedioxy-Ph | 3-OCH₃—Ph | t-Bu |
| RG-101312 | 3-S—C=N-4-Ph | 3-CH₃, 5-CH₃—Ph | t-Bu |
| RG-101218 | 2-Et, 3-OMe—Ph | 2-OCH₃-4-Cl—Ph | t-Bu |
| RG-100779 | 2-Et, 3-OMe—Ph | 2,5-di-OCH₃—Ph | t-Bu |
| RG-101088 | 2-CH₃, 4,5-methylenedioxy-Ph | 3-CH₃, 5-CH₃—Ph | t-Bu |
| RG-101016 | 3-CH₂OCH₂O-4-Ph | 3-CH₃, 5-CH₃—Ph | t-Bu |
| RG-100216 | 2-CH₃, 3-OCH₂OCH₂-4-Ph | 2-OCH₃—Ph | t-Bu |
| RG-100574 | 2-Et, 3-OCH₂OCH₂-4-Ph | 4-F—Ph | t-Bu |
| RG-101171 | 2-Cl 4,5-methylenedioxy-Ph | 3-CH₃, 5-CH₃—Ph | t-Bu |
| RG-100620 | 2,3,6-tri-F—Ph | 2-Cl-4-F—Ph | t-Bu |
| RG-115033 | 2-Et, 3-OMe—Ph | 2,6-F—Ph | t-Bu |
| RG-115515 | 2-Et, 3-OMe—Ph | 3-F—Ph | t-Bu |
| RG-115038 | 2-Et, 3-OMe—Ph | 3-Br—Ph | t-Bu |
| RG-115330 | 2-Et, 3-OMe—Ph | 2-NO₂—Ph | t-Bu |
| RG-115627 | 2-Et, 3-OMe—Ph | 2,3-F—Ph | t-Bu |
| RG-115329 | 2-Et, 3-OMe—Ph | 3,4,5-tri-OCH₃—Ph | t-Bu |
| RG-115088 | 2-Et, 3-OMe—Ph | 3-CF₃, 5-F—Ph | t-Bu |
| RG-115327 | 2-Et, 3-OMe—Ph | 3-CN—Ph | t-Bu |
| RG-115534 | 2-Vinyl, 3-OMe—Ph | 2,4-di-Cl-5-F—Ph | t-Bu |

-continued

| Compound | A | B | E |
|---|---|---|---|
| RG-115046 | 2-Et, 3-OCH$_2$OCH$_2$-4-Ph | Ph | t-Bu |
| RG-115025 | 2-Et, 3-OMe—Ph | 3-CH$_3$, 5-CH$_3$-Ph | —C(CH$_3$)$_2$C(O)OEt |
| RG-115143 | 2-Et, 3-OMe—Ph | 3-CH$_3$, 5-CH$_3$-Ph | —C(CH$_3$)$_2$CH$_2$OH |
| RG-115407 | 2-Et, 3-OMe—Ph | 3-CH$_3$, 5-CH$_3$-Ph | —C(CH$_3$)$_2$CHO |
| RG-115006 | 2-Et, 3-OMe—Ph | 3-CH$_3$, 5-CH$_3$-Ph | —C(CH$_3$)$_2$CH$_2$OCH$_3$ |
| RG-115258 | 2-Et, 3-OMe—Ph | 3-CH$_3$, 5-CH$_3$-Ph | —C(CH$_3$)$_2$CH=NOH |
| RG-115378 | 2-NH$_2$, 3-OMe—Ph | 3-CH$_3$, 5-CH$_3$-Ph | t-Bu |
| RG-115223 | 2-Et, 3-OMe—Ph | 3-CH$_2$OAc, 5-CH$_3$—Ph | t-Bu |
| RG-115310 | 2-Et, 3-OMe—Ph | 3-CH$_3$, 5-CH$_3$-Ph | —C(CH$_3$)$_2$CH$_2$OC(O)CH$_3$ |
| RG-115567 | 2-CH$_3$, 3-OH—Ph | 2,3,4-F—Ph | t-Bu |
| RG-115443 | 2-CH$_3$, 3-OH—Ph | 3-Cl-5-OCH$_3$-4-pyridyl | t-Bu |
| RG-115261 | 2-CH$_3$, 3-OH—Ph | 2,6-di-Cl-4-pyridyl | t-Bu |
| RG-115595 | 2-CH$_3$, 3-OH—Ph | 3-OCH$_3$-4-pyridyl | t-Bu |
| RG-115220 | 2-CH$_3$, 3-OH—Ph | 3,5-di-OCH$_3$-4-CH$_3$—Ph | t-Bu |
| RG-115102 | 2-CH$_3$, 3-CH$_2$CH$_2$CH$_2$O-4-Ph | 2-OCH$_3$—Ph | t-Bu |
| RG-115302 | 2-Et, 3-OMe—Ph | 2,4-di-Cl-5-F—Ph | t-Bu |
| RG-115539 | 2-CH$_3$, 3-CH$_2$CH$_2$CH$_2$O-4-Ph | 2,4-di-Cl-5-F—Ph | t-Bu |
| RG-115499 | 2-CH3, 3-CH$_2$CH$_2$CH$_2$O-4-Ph | 2-F, 5-CH$_3$—Ph | t-Bu |
| RG-115055 | 2-CH$_3$, 3-CH$_2$CH$_2$CH$_2$O-4-Ph | 3,5-di-OCH$_3$-4-CH$_3$—Ph | t-Bu |
| RG-115508 | 2-Et, 3,4-ethylenedioxy-Ph | 2,5-F—Ph | t-Bu |
| RG-115580 | 2-Et, 3,4-ethylenedioxy-Ph | 2,3,4-F—Ph | t-Bu |
| RG-115337 | 2-Et, 3,4-ethylenedioxy-Ph | 2,3,4,5-Ph | t-Bu |
| RG-115280 | 2-Et, 3,4-ethylenedioxy-Ph | 3-CF$_3$-4-F—Ph | t-Bu |
| RG-115297 | 2-Et, 3,4-ethylenedioxy-Ph | 2,6-di-Cl-4-pyridyl | t-Bu |
| RG-115244 | 2-Et, 3,4-ethylenedioxy-Ph | 2-OCH$_3$—Ph | t-Bu |
| RG-115684 | 2-Et, 3,4-ethylenedioxy-Ph | 2,4-di-Cl-5-F—Ph | t-Bu |
| RG-115514 | 2-Et, 3,4-ethylenedioxy-Ph | 2-F, 4-Cl—Ph | t-Bu |
| RG-115557 | 2-CH$_3$, 3-OAc—Ph | 3,5-di-OCH$_3$-4-CH$_3$—Ph | t-Bu |
| RG-115253 | 2-Et, 3-OMe—Ph | 2-OCH$_3$-5-Cl—Ph | t-Bu |
| RG-115085 | 2-Et, 3,4-OCH$_2$O—Ph | 2-OCH$_3$-4-Cl—Ph | t-Bu |
| RG-115551 | 2-CH$_3$, 3-CH$_2$CH$_2$CH$_2$O-4-Ph | 2-OCH$_3$-5-Cl—Ph | t-Bu |
| RG-115162 | 2-Et, 3-OMe—Ph | 2-NO$_2$-5-CH$_3$—Ph | t-Bu |
| RG-115647 | 2-Et, 3-OMe—Ph | 2-NO$_2$-4-Cl—Ph | t-Bu |
| RG-115257 | 2-Et, 3-OMe—Ph | 2-NO$_2$-5-Cl—Ph | t-Bu |
| RG-115664 | 2-CH$_3$, 3-CH$_2$CH$_2$CH$_2$O-4-Ph | 2-NO$_2$-5-CH$_3$—Ph | t-Bu |
| RG-115171 | Benzo[1,2,5]oxadiazole-5-yl | 2-OCH$_3$-4-Cl—Ph | t-Bu |
| RG-115480 | 2-Vinyl, 3-OMe—Ph | 2-Cl, 5-NO$_2$—Ph | t-Bu |
| RG-115095 | 2-Vinyl, 3-OMe—Ph | 2-OCH$_3$-4-Cl—Ph | t-Bu |
| RG-115106 | 2-Et, 3-OCH$_3$—Ph | 1-methyl-1H-indole-2-yl | t-Bu |
| RG-115130 | 2-Et, 3,4-ethylenedioxy—Ph | 3,5-di-OCH$_3$-4-CH$_3$—Ph | t-Bu |
| RG-115532 | 2-Cl, 3-CH$_2$OCH$_2$-4-Ph | 3-CH$_3$, 5-CH$_3$—Ph | t-Bu |
| RG-115167 | 2-F, 4-Et—Ph | 3-NO$_2$—Ph | t-Bu |
| RG-115269 | 2-F, 4-Et—Ph | 3-OCH$_3$—Ph | t-Bu |
| RG-115441 | 2-Cl, 3-CH$_2$OCH$_2$O-4-Ph | 3,5-di-OCH$_3$-4-CH$_3$—Ph | t-Bu |
| RG-115128 | 2-F, 4-Et—Ph | 2,6-di-Cl-4-pyridyl | t-Bu |
| RG-115077 | 2-F, 4-Et—Ph | 3,5-di-OCH$_3$-4-CH$_3$—Ph | t-Bu |
| RG-115259 | 2-F, 4-Et—Ph | 3,4,5-F—Ph | t-Bu |
| RG-115674 | 2-F, 4-Et—Ph | 3-CH$_3$—Ph | t-Bu |
| RG-115422 | 2-F, 4-Et—Ph | 2-OCH$_3$—Ph | t-Bu |
| RG-115086 | 2-F, 4-Et—Ph | 2-NO$_2$-5-F—Ph | t-Bu |
| RG-115592 | 2-F, 4-Et—Ph | 2-OCH$_2$CF$_3$, 5-OCH$_3$—Ph | t-Bu |
| RG-115112 | 2-F, 4-Et—Ph | 2-Cl-6-CH$_3$-4-pyridyl | t-Bu |
| RG-115050 | 2-F, 4-Et—Ph | 2,6-di-OCH$_3$-3-pyridyl | t-Bu |
| RG-115689 | 3-NH—C=C-4-Ph | 3-CH$_3$, 5-CH$_3$—Ph | t-Bu |
| RG-115199 | 2-Et, 3-OMe—Ph | 2-S(O)CH$_3$—Ph | t-Bu |
| RG-115352 | 3,4-OCF2O—Ph | 2-NO$_2$—Ph | t-Bu |
| RG-115256 | 3,4-OCF2O—Ph | 3-CH$_3$, 5-CH$_3$—Ph | t-Bu |
| RG-115683 | 3,4-OCF2O—Ph | 3-OCH$_3$—Ph | t-Bu |
| RG-115648 | 2-Et, 3-OMe—Ph | 3-Br—Ph | —C(CH$_3$)$_2$CN |
| RG-115306 | 2-CH$_2$OMe, 3-OMe—Ph | 3,5-di-Cl—Ph | t-Bu |
| RG-115625 | 2-Et, 3-OMe—Ph | 3-CH=NOH, 5-CH$_3$—Ph | t-Bu |
| RG-115429 | 2-Et, 3-OMe—Ph | 3-CH=NNHCONH$_2$, 5-CH$_3$—Ph | t-Bu |
| RG-115613 | 2-Et, 3-OMe—Ph | 3-CH=NNHCOCONH$_2$, 5-CH$_3$—Ph | t-Bu |
| RG-115043 | 2-Et, 3-OMe—Ph | 3-CH$_3$, 5-CH$_3$—Ph | —C(CH$_3$)$_2$CN |
| RG-115690 | 2-Et, 3-OMe—Ph | 3,5-di-OCH$_3$-4-CH$_3$—Ph | —C(CH$_3$)$_2$CN |
| RG-115065 | 2-Et, 3-OCH$_2$OCH$_2$-4-Ph | 2-OCH$_3$—Ph | t-Bu |
| RG-115229 | 2-CH$_3$, 3-CH$_2$CH$_2$CH$_2$O-4-Ph | 2,4,5-F—Ph | t-Bu |

-continued

| Compound | A | B | E |
|---|---|---|---|
| RG-115575 | 2-CH₃, 3-CH₂CH₂CH₂O-4-Ph | 3,4,5-F—Ph | t-Bu |
| RG-115278 | 2-CH₃, 3-CH₂CH₂CH₂O-4-Ph | 3-F—Ph | t-Bu |
| RG-115260 | 2-Et, 3,4-OCH2O—Ph | 3-CF₃—Ph | t-Bu |
| RG-115118 | 2-CH₃, 3-CH₂CH₂CH₂O-4-Ph | 4-F—Ph | t-Bu |
| RG-115416 | 2-CH₃, 3-CH₂CH₂CH₂O-4-Ph | 3,4-F—Ph | t-Bu |
| RG-115207 | 2-CH₃, 3-CH₂CH₂CH₂O-4-Ph | 3,5-di-F—Ph | t-Bu |
| RG-115518 | 2-CH₃, 3-CH₂CH₂CH₂O-4-Ph | 2,3,4,5-tetra-F—Ph | t-Bu |
| RG-115611 | 2-Et, 3-OCH₂OCH₂-4—Ph | 4-CH₃—Ph | t-Bu |
| RG-115191 | 2-Et, 3-OMe—Ph | 3,5-di-OCH₃-4-OAc—Ph | t-Bu |
| RG-115116 | 2-Et, 3-OMe—Ph | 3,5-di-OCH₃-OH—Ph | t-Bu |
| RG-115637 | 2-CH₃, 3,4-ethylenedioxy-Ph | 3,5-di-OCH₃-4-CH₃—Ph | t-Bu |
| RG-115517 | 2-CH₃, 3,4-ethylenedioxy-Ph | 2,6-di-OCH₃-3-pyridyl | t-Bu |
| RG-115536 | 2-CH₃, 3,4-ethylenedioxy-Ph | 2,6-di-Cl-4-pyridyl | t-Bu |
| RG-115350 | 2-CH₃, 3,4-ethylenedioxy-Ph | 3-F—Ph | t-Bu |
| RG-115169 | 2-CH₃, 3,4-ethylenedioxy-Ph | 3-CF₃, 5-F—Ph | t-Bu |
| RG-115384 | 2-CH₃, 3,4-ethylenedioxy-Ph | 2-NO₂-5-CH₃—Ph | t-Bu |
| RG-115783 | 2-ethyl, 3-methoxy | 4,6-dimethyl-pyridyl | t-Bu |
| RG-115856 | 2-CH₃, 3,4-ethylenedioxy-Ph | 3,5-di-CH₃—Ph | —CH(Et)C(CH₃)₃ |
| RG-115857 | 2-CH₃, 3,4-ethylenedioxy-Ph | 3,5-di-OCH₃-4-CH₃—Ph | —CH(Et)C(CH₃)₃ |
| RG-115864 | 2-CH₃, 3,4-ethylenedioxy-Ph | 3,5-di-CH₃—Ph | —CH(n-Pr)C(CH₃)₃ |
| RG-115865 | 2-CH₃, 3,4-ethylenedioxy-Ph | 3,5-di-OCH₃-4-CH₃—Ph | —CH(n-Pr)C(CH₃)₃ |
| RG-115858 | 2-CH₂CH₃, 3, 4-ethylenedioxy-Ph | 3,5-di-CH₃—Ph | —CH(Et)C(CH₃)₃ |
| RG-115859 | 2-CH₂CH₃, 3, 4-ethylenedioxy-Ph | 3,5-di-OCH₃-4-CH₃—Ph | —CH(Et)C(CH₃)₃ |
| RG-115866 | 2-CH₂CH₃, 3, 4-ethylenedioxy-Ph | 3,5-di-CH₃—Ph | —CH(n-Pr)C(CH₃)₃ |
| RG-115867 | 2-CH₂CH₃, 3, 4-ethylenedioxy-Ph | 3,5-di-OCH₃-4-CH₃—Ph | —CH(n-Pr)C(CH₃)₃ |
| RG-115834 | 2-CH₃, 3-OCH₃—Ph | 2-methoxy-6-trifluoromethyl-3-pyridyl | —C(CH₃)₃ |
| RG-115835 | 2-CH₃, 3-OCH₃—Ph | 1-methyl-2-oxo-6-trifluoromethyl-3-pyridyl | —C(CH₃)₃ |
| RG-115849 | 2-CH₃, 3-OCH₃—Ph | 2,6-dimethoxy-4-pyrimidinyl | —C(CH₃)₃ |
| RG-115850 | 2-CH₃, 3-OCH₃—Ph | 3,6-dimethoxy-4-pyridazinyl | —C(CH₃)₃ |
| RG-115861 | 2-CH₃, 3-OCH₃—Ph | 3,6-dichloro-4-pyridazinyl | —C(CH₃)₃ |
| RG-115862 | 2-CH₃, 3-OCH₃—Ph | 4-pyridazinyl | —C(CH₃)₃ |
| RG-115863 | 2-CH₃, 3-OCH₃—Ph | 3-oxo-6-methoxy-4-pyridazinyl (or regioisomer) | —C(CH₃)₃ |
| RG-115819 | 2-CH₃, 3-OCH₃—Ph | 3,5-di-CH₃—Ph | —CH(Et)C(CH₃)₃ |
| RG-115820 | 2-CH₃, 3-OCH₃—Ph | 3,5-di-OCH₃-4-CH₃—Ph | —CH(Et)C(CH₃)₃ |
| RG-115823 | 2-CH₃, 3-OCH₃—Ph | 3,5-di-CH₃—Ph | —CH(n-Pr)C(CH₃)₃ |
| RG-115824 | 2-CH₃, 3-OCH₃—Ph | 3,5-di-OCH₃-4-CH₃—Ph | —CH(n-Pr)C(CH₃)₃ |
| RG-115832 | 2-CH₂CH₃, 3-OCH₃—Ph | 3,5-di-CH₃—Ph | —CH(Et)C(CH₃)₃ |
| RG-115831 | 2-CH₂CH₃, 3-OCH₃—Ph | 3,5-di-OCH₃-4-CH₃—Ph | —CH(Et)C(CH₃)₃ |
| RG-115830 | 2-CH₂CH₃, 3-OCH₃—Ph | 3,5-di-CH₃—Ph | —CH(n-Pr)C(CH₃)₃ |
| RG-115829 | 2-CH₂CH₃, 3-OCH₃—Ph | 3,5-di-OCH₃-4-CH₃—Ph | —CH(n-Pr)C(CH₃)₃ |
| RG-103309 | 2-CH₃, 3-OCH₃—Ph | 3,5-di-CH₃—Ph | —CH(Et)C(CH₃)₃ |
| RG-115595 | 2-CH₃, 3-OH—Ph | 3-OCH₃-4-pyridyl | —C(CH₃)₃ |
| RG-100021 | 4-CH(OH)CH₃—Ph | 3,5-di(CH₂OH)—Ph | —C(CH₃)₃ |
| RG-115199 | 2-CH₂CH₃, 3-OCH₃—Ph | 2-S(O)CH₃—Ph | —C(CH₃)₃ |
| RG-100150 | 4-C(O)CH₃—Ph | 3,5-di-CO₂H—Ph | —C(CH₃)₃ |
| RG-115517 | 2-CH₃, 3,4-ethylenedioxy-Ph | 2,6-di-OCH₃-3-pyridyl | —C(CH₃)₃ |
| RG-115280 | 2-CH₂CH₃, 3,4-ethylenedioxy-Ph | 3-CF₃-4-F—Phenyl | —C(CH₃)₃ |
| RG-101523 | 2-F, 4-CH₂CH₃—Ph | 3,5-di-CH3—Ph | —C(CH₃)₃ |
| RG-115555 | 2-CH₂CH₃, 3-OCH₃—Ph | 2-SO₃H—Ph | —C(CH₃)₃ |
| RG-102408 | 2-CH₃, 3-CH₂CH₂CH₂O-4-Ph | 3,5-di-CH₃—Ph | —C(CH₃)₃ |

-continued

| Compound | A | B | E |
|---|---|---|---|
| RG-103451 | 4-CH$_2$CH$_3$—Ph | 3,5-di-CH$_3$—Ph | —CH(CH$_3$)C(CH$_3$)$_3$ |
| RG-101036 | 2-CH$_2$CH$_3$, 3,4-ethylenedioxy—Ph | 3-CH$_3$—Ph | —C(CH$_3$)$_3$ |
| RG-103361 | 2,3-di-CH$_3$—Ph | Ph | —CH(Et)(n-Bu) |
| RG-104074 | 2,3-di-CH$_3$—Ph | 3-CH$_3$—Ph | —CH(Et)(t-Bu) |
| RG-115009 | 2-CH$_3$, 3,4-ethylenedioxy-Ph | 3,5-di-OCH$_3$, 4-OH—Ph | —C(CH$_3$)$_3$ |
| RG-115068 | 2-F, 3-CH$_2$OCH$_2$O-4-Ph | 3,5-di-CH$_3$—Ph | —C(CH$_3$)$_3$ |
| RG-115064 | 2-CH$_3$, 3,4-ethylenedioxy-Ph | 2-S(O)CH$_3$—Ph | —C(CH$_3$)$_3$ |
| RG-115092 | 2-CH$_3$, 3,4-ethylenedioxy-Ph | 3,5-di-OCH$_3$, 4-CH$_3$—Ph | —C(CH$_3$)$_2$CN |
| RG-115311 | 2-CH$_2$CH$_3$-3-OCH$_3$—Ph | 6-CH$_3$-2-pyridyl- | —C(CH$_3$)$_3$ |
| RG-115609 | 2-CH$_3$, 3,4-ethylenedioxy-Ph | 2-NO$_2$-3,5-di-OCH$_3$, 4-CH$_3$—Ph | —C(CH$_3$)$_3$ |
| RG-102317 | 2-CH$_3$, 3,4-ethylenedioxy-Ph | 3,5-di-CH$_3$—Ph | —C(CH$_3$)$_3$ |
| RG-102125 | 4-CH$_2$CH$_3$—Ph | 3,5-di-CH$_3$—Ph | —C(CH$_3$)$_3$ |
| RG-102398 | 2-CH$_3$-3-OCH$_3$—Ph | 3,5-di-CH$_3$—Ph | —C(CH$_3$)$_3$ |
| RG-115836 | 4-CH$_2$CH$_3$—Ph | 3,5-di-CH$_3$—Ph | —CH(Et)(t-Bu) |
| RG-115837 | 4-CH$_2$CH$_3$—Ph | 2-OCH$_3$-3-pyridyl | —CH(Et)(t-Bu) |
| RG-115840 | 4-CH$_2$CH$_3$—Ph | 3,5-di-CH$_3$—Ph | —CH(n-Bu)(t-Bu) |
| RG-115841 | 4-CH$_2$CH$_3$—Ph | 3,5-di-OCH$_3$, 4-CH$_3$—Ph | —CH(n-Bu)(t-Bu) |
| RG-115842 | 4-CH$_2$CH$_3$—Ph | 2-OCH$_3$-3-pyridyl | —CH(n-Bu)(t-Bu) |
| RG-115846 | 4-CH$_2$CH$_3$—Ph | 3,5-di-CH$_3$—Ph | —CH(Ph)(t-Bu) |
| RG-115847 | 4-CH$_2$CH$_3$—Ph | 3,5-di-OCH$_3$, 4-CH$_3$—Ph | —CH(Ph)(t-Bu) |
| RG-115848 | 4-CH$_2$CH$_3$—Ph | 2-OCH$_3$-3-pyridyl | —CH(Ph)(t-Bu) |
| RG-115719 | 2-CH$_2$CH$_3$, 3-OCH$_3$—Ph | 5-benzimidazolyl | —C(CH$_3$)$_3$ |
| RG-115718 | 2-CH$_2$CH$_3$, 3-OCH$_3$—Ph | 1- (or 3-)trityl-5-benzimidazolyl | —C(CH$_3$)$_3$ |
| RG-115721 | 2-CH$_2$CH$_3$, 3-OCH$_3$—Ph | 5-methyl-1-phenyl-1H-pyrazole-3-yl | —C(CH$_3$)$_3$ |
| RG-115716 | 2-CH$_2$CH$_3$, 3-OCH3—Ph | 3-chloro-6-methylsulfanyl-pyrazine-2-yl | —C(CH$_3$)$_3$ |
| RG-115723 | 2-CH$_2$CH$_3$, 3-OCH$_3$—Ph | 1H-indazole-3-yl | —C(CH$_3$)$_3$ |
| RG-115722 | 2-CH$_2$CH$_3$, 3-OCH$_3$—Ph | 1-trityl-1H-indazole-3-yl | —C(CH$_3$)$_3$ |
| RG-115717 | 2-CH$_2$CH$_3$, 3-OCH$_3$—Ph | 5-methoxycarbonyl-2-pyridyl | —C(CH$_3$)$_3$ |
| RG-115550 | 2-CH$_2$CH$_3$, 3-OCH$_3$—Ph | pyrazine-2-yl | —C(CH$_3$)$_3$ |
| RG-115665 | 2-CH$_2$CH$_3$, 3-OCH$_3$—Ph | 3,5-di-CH$_3$—Ph | —C(CH$_3$)$_2$CH$_2$OSi(CH$_3$)$_2$tBu |
| RG-115511 | 2-CH$_2$CH$_3$, 3-OCH$_3$—Ph | 3,5-di-CH$_3$—Ph | —C(CH$_3$)$_2$CH═NCH2CH═OH |
| RG-115653 | 2-CH$_2$CH$_3$, 3-OCH$_3$—Ph | 3,5-di-CH$_3$—Ph | —C(CH$_3$)$_2$CH═NNHC(O)NH$_2$ |
| RG-115597 | 2-CH$_2$CH$_3$, 3-OCH$_3$—Ph | 3,5-di-CH$_3$—Ph | —C(CH$_3$)$_2$CH═NNHC(O)C(O)NH$_2$ |
| RG-115044 | 2-CH$_2$CH$_3$, 3-OCH$_3$—Ph | 3,5-di-CH$_3$—Ph | —C(CH$_3$)$_2$COOH |
| RG-115172 | 2-CH$_2$S(O)CH$_3$, 3-OCH$_3$—Ph | 3,5-di-CH$_3$—Ph | —C(CH$_3$)$_3$ |
| RG-115408 | 2-CH$_2$S(O)$_2$CH$_3$, 3-OCH$_3$—Ph | 3,5-di-CH$_3$—Ph | —C(CH$_3$)$_3$ |
| RG-115497 | 2-CH$_2$NMe$_2$, 3-OCH$_3$—Ph | 3,5-di-CH$_3$—Ph | —C(CH$_3$)$_3$ |
| RG-115079 | 2-CH$_2$NHCH$_3$, 3-OCH$_3$—Ph | 3,5-di-CH$_3$—Ph | —C(CH$_3$)$_3$ |
| RG-102021 | 2-CH═CH$_2$, 3-OCH$_3$—Ph— | 3,5-di-CH$_3$—Ph | —C(CH$_3$)$_3$ |
| RG-115117 | 2-CH$_2$OMe, 3-OCH$_3$—Ph— | 3,5-di-CH$_3$—Ph | —C(CH$_3$)$_3$ |
| RG-115358 | 2-CH$_2$SCH$_3$, 3-OCH$_3$—Ph | 3,5-di-CH$_3$—Ph | —C(CH$_3$)$_3$ |
| RG-115003 | 2-CH$_2$OCH$_2$CH═CH$_2$, 3-OCH$_3$—Ph | 3,5-di-CH$_3$—Ph | —C(CH$_3$)$_3$ |
| RG-115490 | 2-CH$_2$Cl, 3-OCH$_3$—Ph— | 3,5-di-CH$_3$—Ph | —C(CH$_3$)$_3$ |
| RG-115371 | 2-CH$_2$OH, 3-OCH$_3$—Ph— | 3,5-di-CH$_3$—Ph | —C(CH$_3$)$_3$ |
| RG-115225 | 2-CH$_2$OAc, 3-OCH$_3$—Ph | 3,5-di-CH$_3$—Ph | —C(CH$_3$)$_3$ |
| RG-115160 | 2-CH$_2$F, 3-OCH$_3$—Ph— | 3,5-di-CH$_3$—Ph | —C(CH$_3$)$_3$ |
| RG-115851 | 2-CH$_3$, 3-OCH$_3$ | 3,5-di-CH$_3$ | —CH(n-Bu)(t-Bu) |
| RG-115852 | 2-CH$_3$, 3-OCH$_3$ | 3,5-di-OCH$_3$, 4-CH$_3$ | —CH(n-Bu)(t-Bu) |
| RG-115091 | 2-CH$_2$CH$_3$, 3-OCH$_3$—Ph | 5-Methyl-pyrazine-2-yl- | —C(CH$_3$)$_3$ |

Because the compounds of the general formula of the present invention may contain a number of stereogenic carbon atoms, the compounds may exist as enantiomers, diastereomers, stereoisomers, or their mixtures, even if a stereogenic center is explicitly specified.

The present invention also pertains to a process for the preparation of a compound of formula (IV) comprising the steps of:

i reacting a compound of formula (I) with a base selected from NaH, KH, or an amide MNR$^a$R$^b$ to produce a product II, wherein M is Li, Na, or K, and R$^a$ and R$^b$ are independently (C$_1$-C$_6$)alkyl or phenyl; and

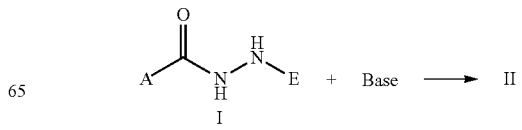

ii reacting the product (II) of step (i) with a compound of formula (III) wherein R is phenyl substituted with three to five of the same or different chloro, fluoro, or trifluoromethyl;

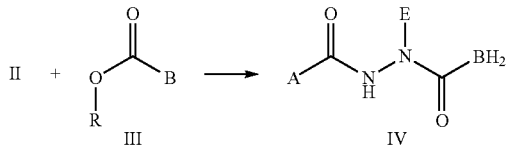

wherein
A and B are independently
(a) unsubstituted or substituted phenyl wherein the substituents are independently 1 to 5H; halo; nitro; cyano; amino (—NR$^a$R$^b$); alkylaminoalkyl (—(CH$_2$)NR$^a$R$^b$); (C$_1$-C$_6$)alkyl; (C$_1$-C$_6$)haloalkyl; (C$_1$-C$_6$)cyanoalkyl; (C$_1$-C$_6$)alkoxy; phenoxy; (C$_1$-C$_6$)haloalkoxy; (C$_1$-C$_6$)alkoxy(C$_1$-C$_6$)alkyl; (C$_1$-C$_6$)alkenyloxy(C$_1$-C$_6$)alkyl; (C$_1$-C$_6$)alkoxy(C$_1$-C$_6$)alkoxy; (C$_2$-C$_6$)alkenyl optionally substituted with halo, cyano, (C$_1$-C$_4$)alkyl, or (C$_1$-C$_4$)alkoxy; (C$_2$-C$_6$)alkynyl optionally substituted with halo or (C$_1$-C$_4$)alkyl; formyl; (C$_1$-C$_6$)haloalkylcarbonyl; benzoyl; (C$_1$-C$_6$)alkoxycarbonyl; (C$_1$-C$_6$)haloalkoxycarbonyl; (C$_1$-C$_6$)alkanoyloxy (—OCOR$^a$); carboxamido (—CONR$^a$R$^b$); amido (—NR$^a$COR$^b$); alkoxycarbonylamino (—N(CH$_2$)$_n$CO$_2$R$^b$); alkylaminocarbonylamino (—N(CH$_2$)$_n$CONR$^b$R); (C$_1$-C$_6$)alkylthio; sulfamido (—SO$_2$NR$^a$R$^b$); or unsubstituted or substituted phenyl wherein the substituents are independently 1 to 3 halo, nitro, (C$_1$-C$_6$)alkoxy, (C$_1$-C$_6$)alkyl, or (—NR$^a$R$^b$); or when one or both of two adjacent positions on the phenyl ring are substituted, the attached atoms may form the phenyl-connecting termini of a linkage selected from the group consisting of (—OCH$_2$O—), (—OCH(CH$_3$)O—), (—OCH$_2$CH$_2$O—), (—OCH(CH$_3$)CH$_2$O—), (—S—CH═N—), (—CH$_2$OCH$_2$O—), (—O(CH$_2$)$_3$—), (═N—O—N═), (—C═CH—NH—), (—OCF$_2$O—), (—NH—CH═N—), (—CH$_2$CH$_2$O—), and (—(CH$_2$)$_4$—); or
(b) unsubstituted 5- or 6-membered heterocycle or substituted 5 or 6-membered heterocycle having 1-3 nitrogen atoms where the substituents are from one to four of the same or different halo; nitro; (C$_1$-C$_6$)alkyl; (C$_1$-C$_6$)alkenyl; (C$_1$-C$_6$)alkoxy; (C$_1$-C$_6$)thioalkoxy; (C$_1$-C$_6$)alkoxycarbonyl; (C$_1$-C$_6$)carboxyalkyl; —CONR$^a$R$^b$; amino (—NR$^a$R$^b$); haloalkyl including —CF$_3$; -trialkylsilyl (—SiR$^a$R$^b$R$^c$); trityl (C(Ph)$_3$); or unsubstituted or substituted phenyl wherein the substituents are independently 1 to 3 halo, nitro, (C$_1$-C$_6$)alkoxy, (C$_1$-C$_6$)alkyl, or (—NR$^a$R$^b$); or when two adjacent positions are substituted, these positions may form a benzo ring fusion; and
E is phenyl, or unsubstituted or substituted (C$_1$-C$_{10}$) straight or branched alkyl wherein the substituents are independently 1-4 cyano; halo; (C$_5$-C$_6$)cycloalkyl; phenyl; (C$_2$-C$_3$)alkenyl; (C$_1$-C$_6$)alkoxy; (C$_1$-C$_6$)alkoxycarbonyl; (C$_1$-C$_6$)alkanoyloxy (—OCOR$^a$); formyl; (C$_1$-C$_6$)trialkylsilyloxy having independently the stated number of carbon atoms in each alkyl group; or —C═N—OR$^a$;
wherein R$^a$, R$^b$, and R$^c$ are independently (C$_1$-C$_6$)alkyl or phenyl, and n=1-4.

DEFINITIONS

When an R$^x$ group is specified, wherein x represents a letter a-g, and the same R$^x$ group is also specified with an alkyl group chain length such as "(C$_1$-C$_3$)", it is understood that the specified chain length refers only to the cases where R$^x$ may be alkyl, and does not pertain to cases where R$^x$ may be a non-alkyl group, such as H or aryl.

The term "alkyl" includes both branched and straight chain alkyl groups. Typical alkyl groups include, for example, methyl, ethyl, n-propyl, isopropyl, n-butyl, sec-butyl, isobutyl, tert-butyl, n-pentyl, isopentyl, n-hexyl, n-heptyl, isooctyl, nonyl, and decyl.

The term "halo" refers to fluoro, chloro, bromo or iodo.

The term "haloalkyl" refers to an alkyl group substituted with one or more halo groups such as, for example, chloromethyl, 2-bromoethyl, 3-iodopropyl, trifluoromethyl, and perfluoropropyl.

The term "cycloalkyl" refers to a cyclic aliphatic ring structure, optionally substituted with alkyl, hydroxy, or halo, such as cyclopropyl, methylcyclopropyl, cyclobutyl, 2-hydroxycyclopentyl, cyclohexyl, and 4-chlorocyclohexyl.

The term "hydroxyalkyl" refers to an alkyl group substituted with one or more hydroxy groups such as, for example, hydroxymethyl and 2,3-dihydroxybutyl.

The term "alkylsulfonyl" refers to a sulfonyl moiety substituted with an alkyl group such as, for example, mesyl, and n-propylsulfonyl.

The term "alkenyl" refers to an ethylenically unsaturated hydrocarbon group, straight or branched chain, having 1 or 2 ethylenic bonds such as, for example, vinyl, allyl, 1-butenyl, 2-butenyl, isopropenyl, and 2-pentenyl.

The term "haloalkenyl" refers to an alkenyl group substituted with one or more halo groups.

The term "alkynyl" refers to an unsaturated hydrocarbon group, straight or branched, having 1 or 2 acetylenic bonds such as, for example, ethynyl and propargyl.

The term "alkylcarbonyl" refers to an alkylketo functionality, for example acetyl, n-butyryl and the like.

The term "heterocyclyl" or "heterocycle" refers to an unsubstituted or substituted; saturated, partially unsaturated, or unsaturated 5 or 6-membered ring containing one, two or three heteroatoms, preferably one or two heteroatoms independently selected from the group consisting of oxygen, nitrogen and sulfur. Examples of heterocyclyls include, for example, pyridyl, thienyl, furyl, pyrimidinyl, pyrazinyl, quinolinyl, isoquinolinyl, pyrrolyl, indolyl, tetrahydrofuryl, pyrrolidinyl, piperidinyl, tetrahydropyranyl, morpholinyl, piperazinyl, dioxolanyl, and dioxanyl.

The term "alkoxy" includes both branched and straight chain alkyl groups attached to a terminal oxygen atom. Typical alkoxy groups include, for example, methoxy, ethoxy, n-propoxy, isopropoxy, and tert-butoxy.

The term "haloalkoxy" refers to an alkoxy group substituted with one or more halo groups such as, for example chloromethoxy, trifluoromethoxy, difluoromethoxy, and perfluoroisobutoxy.

The term "alkylthio" includes both branched and straight chain alkyl groups attached to a terminal sulfur atom such as, for example methylthio.

The term "haloalkylthio" refers to an alkylthio group substituted with one or more halo groups such as, for example tiifluoromethylthio.

The term "alkoxyalkyl" refers to an alkyl group substituted with an alkoxy group such as, for example, isopropoxymethyl.

"Silica gel chromatography" refers to a purification method wherein a chemical substance of interest is applied as a concentrated sample to the top of a vertical column of silica gel or chemically-modified silica gel contained in a glass, plastic, or metal cylinder, and elution from such column with a solvent or mixture of solvents.

"Flash chromatography" refers to silica gel chromatography performed under air, argon, or nitrogen pressure typically in the range of 10 to 50 psi.

"Gradient chromatography" refers to silica gel chromatography in which the chemical substance is eluted from a column with a progressively changing composition of a solvent mixture.

"Rf" is a thin layer chromatography term which refers to the fractional distance of movement of a chemical substance of interest on a thin layer chromatography plate, relative to the distance of movement of the eluting solvent system.

"Parr hydrogenator" and "Parr shaker" refer to apparatus available from Parr Instrument Company, Moline Ill., which are designed to facilitate vigorous mixing of a solution containing a chemical substance of interest with an optional solid suspended catalyst and a pressurized, contained atmosphere of a reactant gas. Typically, the gas is hydrogen and the catalyst is palladium, platinum, or oxides thereof deposited on small charcoal particles. The hydrogen pressure is typically in the range of 30 to 70 psi.

"Dess-Martin reagent" refers to (1,1,1-triacetoxy)-1,1-dihydro-1,2-benziodoxol-3(1H)-one as a solution in dichloromethane available from Acros Organics/Fisher Scientific Company, L.L.C.

"PS-NMM" refers to a $-SO_2NH(CH_2)_3$-morpholine functionalized polystyrene resin available from Argonaut Technologies, San Carlos, Calif.

"AP-NCO" refers to an isocyante-functionalized resin available from ArgonautTechnologies, San Carlos, Calif.

"AP-trisamine" refers to a polystyrene-$CH_2NHCH_2CH_2NH(CH_2CH_2NH_2)_2$ resin available from Argonaut Technologies, San Carlos, Calif.

The term "isolated" for the purposes of the present invention designates a biological material (nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated". The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semisynthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms.

Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment of the invention, polynucleotides are detected by employing hybridization conditions comprising a hybridization step at $T_m$ of 55° C., and utilizing conditions as set forth above. In a preferred embodiment, the $T_m$ is 60° C.; in a more preferred embodiment, the $T_m$ is 63° C.; in an even more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA: RNA, DNA: RNA, DNA: DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In a specific embodiment of the invention, polynucleotides are detected by employing hybridization conditions comprising a hybridization step in less than 500 mM salt and at least 37 degrees Celsius, and a washing step in 2×SSPE at at least 63 degrees Celsius. In a preferred embodiment, the hybridization conditions comprise less than 200 mM salt and at least 37 degrees Celsius for the hybridization step. In a more preferred embodiment, the hybridization conditions comprise 2×SSPE and 63 degrees Celsius for both the hybridization and washing steps.

In one embodiment, the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267: 963-967; Wu and Wu, 1988, J. Biol. Chem. 263: 14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., 1987, PNAS 84:7413; Mackey, et al., 1988. Proc. Natl. Acad. Sci. U.S.A. 85:8027-8031; and Ulmer et al., 1993, Science 259:1745-1748). The use of cationic lipids may promote encapsulation of negatively charged nucleic acids, and also promote fusion with negatively charged cell membranes (Felgner and Ringold, 1989, Science 337: 387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992, Hum. Gene Ther. 3: 147-154; and Wu and Wu, 1987, J. Biol. Chem. 262: 4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 16) (see Cherbas L., et. al., (1991), *Genes Dev.* 5, 120-131); AGGTCAN$_{(n)}$AGGTCA, where N$_{(n)}$ can be one or more spacer nucleotides (SEQ ID NO: 17) (see D'Avino PP., et. al., (1995), *Mol. Cell. Endocrinol,* 113, 1-9); and GGGTTAAGATGAATTT (SEQ ID NO: 18) (see Antoniewski C., et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest- and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TP1, alkaline phosphatase promoters (useful for expression in *Saccharomyces*); AOX1 promoter (useful for expression in *Pichia*); β-lactamase, lac, ara, tet, trp, IP$_L$, IP$_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (Cs-VMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" means a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

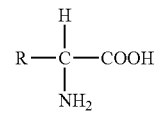

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally occurring polypeptide. According to the invention, a Group H nuclear receptor ligand binding domain polypeptide comprising a substitution mutation comprises a substitution of at least one (1) wild-type or naturally occurring amino acid with a different amino acid relative to the wild-type or naturally occurring Group H nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth (20$^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson, C., et al., 1978, J. Biol. Chem. 253: 6551; Zoller and Smith, 1984, DNA 3: 479-488; Oliphant et al., 1986, Gene 44: 177; Hutchinson et al., 1986, Proc. Natl. Acad. Sci. U.S.A. 83: 710), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667.). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50: 667).

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215: 403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNAS-TAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal". The present invention is useful to search for orthogonal ligands and orthogonal receptor-based gene expression systems such as those described in co-pending U.S. application Ser. No. 09/965,697, which is incorporated herein by reference in its entirety.

The term "modulate" means the ability of a given ligand/receptor complex to induce or suppress the transactivation of an exogenous gene.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. For example, transgenic plants are obtained by regeneration from the transformed cells. Numerous transformation procedures are known from the literature such as agroinfection using *Agrobacterium tumefaciens* or its Ti plasmid, electroporation, microinjection of plant cells and protoplasts, and microprojectile transformation. Complementary techniques are known for transformation of animal cells and regeneration of such transformed cells in transgenic animals. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject. The term "therapeutic gene" means a gene which imparts a beneficial function to the host cell in which such gene is expressed. Therapeutic genes are not naturally found in host cells.

The term "ecdysone receptor complex" generally refers to a heterodimeric protein complex consisting of two members of the steroid receptor family, ecdysone receptor ("EcR") and ultraspiracle ("USP") proteins (see Yao, T. P., et. al. (1993) Nature 366, 476-479; Yao, T.-P., et. al., (1992) Cell 71, 63-72). The functional ecdysteroid receptor complex may also include additional protein(s) such as immunophilins. Additional members of the steroid receptor family of proteins, known as transcriptional factors (such as DHR38, betaF7Z-1 or other insect homologs), may also be ligand dependent or independent partners for EcR and/or USP. The ecdysone receptor complex can also be a heterodimer of ecdysone receptor protein and the vertebrate homolog of ultraspiracle protein, retinoic acid-X-receptor ("RXR") protein. Homodimer complexes of the ecdysone receptor protein or USP may also be functional under some circumstances.

An ecdysteroid receptor complex can be activated by an active ecdysteroid or non-steroidal ligand bound to one of the proteins of the complex, inclusive of EcR, but not excluding other proteins of the complex.

The ecdysone receptor complex includes proteins which are members of the steroid receptor superfamily wherein all members are characterized by the presence of an amino-terminal transactivation domain, a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the ecdysone receptor complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the ecdysone receptor. As a result, they are insensitive to the ligands of this invention. Thus, the ligands of this invention will have negligible physiological or other effects on untransformed cells, or the whole organism.

The term "subject" means an intact plant or animal or a cell from a plant or animal. It is also anticipated that the ligands will work equally well when the subject is a fungus or yeast. When the subject is an intact animal, preferably the animal is a vertebrate, most preferably a mammal.

The ligands of the present invention, when used with the ecdysone receptor complex which in turn is bound to the response element linked to an exogenous gene, provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the ecdysone receptor complex to a specific control, or regulatory, DNA element. The ecdysone receptor protein, like other members of the steroid receptor family, possesses at least three domains, a transactivation domain, a DNA binding domain, and a ligand binding domain. This receptor, like a subset of the steroid receptor family, also possesses less well-defined regions responsible for heterodimerization properties. Binding of the ligand to the ligand binding domain of ecdysone receptor protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). Preferably, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et. al. (1988) Nature, 335, 563-564) or LexA protein from *E. coli* (see Brent and Ptashne (1985), Cell, 43, 729-736) to accommodate chimeric ecdysone receptor complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. The term "promoter" means a specific nucleotide sequence recognized by RNA polymerase. The sequence is the site at which transcription can be specifically initiated under proper conditions. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Another aspect of this invention is a method to modulate the expression of one or more exogenous genes in a subject, comprising administering to the subject an effective amount, that is, the amount required to elicit the desired gene expression or suppression, of a ligand comprising a compound of the present invention and wherein the cells of the subject contain:
   a) an ecdysone receptor complex comprising:
      1) a DNA binding domain;
      2) a binding domain for the ligand; and
      3) a transactivation domain; and
   b) a DNA construct comprising:
      1) the exogenous gene; and
      2) a response element;
wherein the exogenous gene is under the control of the response element; and binding of the DNA binding domain to the response element in the presence of the ligand results in activation or suppression of the gene.

A related aspect of this invention is a method for regulating endogenous or heterologous gene expression in a transgenic subject comprising contacting a ligand comprising a compound of the present invention with an ecdysone receptor within the cells of the subject wherein the cells contain a DNA binding sequence for the ecdysone receptor and wherein formation of an ecdysone receptor-ligand-DNA binding sequence complex induces expression of the gene.

Another aspect of the present invention is a method for producing a polypeptide comprising the steps of:
   a) selecting a cell which is substantially insensitive to exposure to a ligand comprising a compound of the present invention;
   b) introducing into the cell:
      1) a DNA construct comprising:
         i) an exogenous gene encoding the polypeptide; and
         ii) a response element;
wherein the gene is under the control of the response element; and
      2) an ecdysone receptor complex comprising:
         i) a DNA binding domain;
         ii) a binding domain for the ligand; and
         iii) a transactivation domain; and
   c) exposing the cell to the ligand.

As well as the advantage of temporally controlling polypeptide production by the cell, this aspect of the invention provides a further advantage, in those cases when accumulation of such a polypeptide can damage the cell, in that expression of the polypeptide may be limited to short periods. Such control is particularly important when the exogenous gene is a therapeutic gene. Therapeutic genes may be called upon to produce polypeptides which control needed functions, such as the production of insulin in diabetic patients. They may also be used to produce damaging or even lethal proteins, such as those lethal to cancer cells. Such control may also be important when the protein levels produced may constitute a metabolic drain on growth or reproduction, such as in transgenic plants.

Numerous genomic and cDNA nucleic acid sequences coding for a variety of polypeptides are well known in the art. Exogenous genetic material useful with the ligands of this invention include genes that encode biologically active proteins of interest, such as, for example, secretory proteins that can be released from a cell; enzymes that can metabolize a substrate from a toxic substance to a non-toxic substance, or from an inactive substance to an active substance; regulatory proteins; cell surface receptors; and the like. Useful genes also include genes that encode blood clotting factors, hormones such as insulin, parathyroid hormone, luteinizing hormone releasing factor, alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor, colony stimulating factor-1, tumor necrosis factor, and erythropoietin; genes encoding inhibitor substances such as alpha,-antitrypsin, genes encoding substances that function as drugs such as diphtheria and cholera toxins; and the like. Useful genes also include those useful for cancer therapies and to treat genetic disorders. Those skilled in the art have access to nucleic acid sequence information for virtually all known genes and can either obtain the nucleic acid molecule directly from a public depository, the institution that published the sequence, or employ routine methods to prepare the molecule.

For gene therapy use, the ligands described herein may be taken up in pharmaceutically acceptable carriers, such as, for example, solutions, suspensions, tablets, capsules, ointments, elixirs, and injectable compositions. Pharmaceutical preparations may contain from 0.01% to 99% by weight of the ligand. Preparations may be either in single or multiple dose forms. The amount of ligand in any particular pharmaceutical preparation will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

The ligands described herein may also be administered in conjunction with other pharmaceutically active compounds. It will be understood by those skilled in the art that pharmaceutically active compounds to be used in combination with the ligands described herein will be selected in order to avoid adverse effects on the recipient or undesirable interactions between the compounds. Examples of other pharmaceutically active compounds which may be used in combination with the ligands include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, *porphyria* agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases the ligands may be useful as an adjunct to drug therapy, for example, to "turn off" a gene that produces an enzyme that metabolizes a particular drug.

For agricultural applications, in addition to the applications described above, the ligands of this invention may also be used to control the expression of pesticidal proteins such as *Bacillus thuringiensis* (Bt) toxin. Such expression may be tissue or plant specific. In addition, particularly when control of plant pests is also needed, one or more pesticides may be combined with the ligands described herein, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with the ligands described herein include fungicides, herbicides, insecticides, miticides, and microbicides.

The ligands described herein can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials, and McCutcheon's Functional Materials*, all published annually by McCutcheon Division of MC Publishing Company (New Jersey). The ligands can also be mixed with fertilizers or fertilizing materials before their application. The ligands and solid fertilizing material can also be admixed in mixing or blending equipment, or they can be incorporated with fertilizers in granular formulations. Any relative proportion of fertilizer can be used which is suitable for the crops and weeds to be treated. The ligands described herein will commonly comprise from 5% to 50% of the fertilizing composition. These compositions provide fertilizing materials which promote the rapid growth of desired plants, and at the same time control gene expression.

Host Cells and Non-Human Organisms of the Invention

As described above, ligands for modulating gene expression system of the present invention may be used to modulate gene expression in a host cell. Expression in transgenic host cells may be useful for the expression of various genes of interest. The present invention provides ligands for modulation of gene expression in prokaryotic and eukaryotic host cells. Expression in transgenic host cells is useful for the expression of various polypeptides of interest including but not limited to antigens produced in plants as vaccines, enzymes like alpha-amylase, phytase, glucanes, and xylanse, genes for resistance against insects, nematodes, fungi, bacteria, viruses, and abiotic stresses, antigens, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, therapeutic polypeptides, pathway intermediates; for the modulation of pathways already existing in the host for the synthesis of new products heretofore not possible using the host; cell based assays; functional genomics assays, biotherapeutic protein production, proteomics assays, and the like. Additionally the gene products may be useful for conferring higher growth yields of the host or for enabling an alternative growth mode to be utilized.

Thus, the present invention provides ligands for modulating gene expression in an isolated host cell according to the invention. The host cell may be a bacterial cell, a fungal cell, a nematode cell, an insect cell, a fish cell, a plant cell, an avian cell, an animal cell, or a mammalian cell. In still another embodiment, the invention relates to ligands for modulating gene expression in an host cell, wherein the method comprises culturing the host cell as described above in culture medium under conditions permitting expression of a polynucleotide encoding the nuclear receptor ligand binding domain comprising a substitution mutation, and isolating the nuclear receptor ligand binding domain comprising a substitution mutation from the culture.

In a specific embodiment, the isolated host cell is a prokaryotic host cell or a eukaryotic host cell. In another specific embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*; plant species selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In a specific embodiment, the host cell is a yeast cell selected from the group consisting of a *Saccharomyces*, a *Pichia*, and a *Candida* host cell.

In another specific embodiment, the host cell is a *Caenorhabdus elegans* nematode cell.

In another specific embodiment, the host cell is an insect cell.

In another specific embodiment, the host cell is a plant cell selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another specific embodiment, the host cell is a zebrafish cell.

In another specific embodiment, the host cell is a chicken cell.

In another specific embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification [e.g., glycosylation, cleavage (e.g., of signal sequence)] of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent. The present invention also relates to a non-human organism comprising an isolated host cell according to the invention. In a specific embodiment, the non-human organism is a prokaryotic organism or a eukaryotic organism. In another specific embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In a specific embodiment, the non-human organism is a yeast selected from the group consisting of *Saccharomyces, Pichia*, and *Candida*.

In another specific embodiment, the non-human organism is a *Caenorhabdus elegans* nematode.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another specific embodiment, the non-human organism is a *Mus musculus* mouse.

Gene Expression Modulation System of the Invention

The present invention relates to a group of ligands that are useful in an ecdysone receptor-based inducible gene expression system. As presented herein, a novel group of ligands provides an improved inducible gene expression system in both prokaryotic and eukaryotic host cells. Thus, the present invention relates to ligands that are useful to modulate expression of genes. In particular, the present invention relates to ligands having the ability to transactivate a gene expression modulation system comprising at least one gene expression cassette that is capable of being expressed in a host cell comprising a polynucleotide that encodes a polypeptide comprising a Group H nuclear receptor ligand binding domain. Preferably, the Group H nuclear receptor ligand binding is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a famesol receptor. More preferably, the Group H nuclear receptor ligand binding domain is from an ecdysone receptor.

In a specific embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another specific embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In a preferred embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysone receptor ligand binding domain comprising a substitution mutation, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see co-pending applications PCT/US01/09050, PCT/US02/05235, and PCT/US02/05706, incorporated herein by reference in their entirety). The "partner" nuclear receptor ligand binding domain may further comprise a truncation mutation, a deletion mutation, a substitution mutation, or another modification.

Preferably, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

Preferably, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), a ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

Preferably, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In a preferred embodiment, the chimeric RXR ligand binding domain comprises at least one vertebrate species RXR polypeptide fragment and one invertebrate species RXR polypeptide fragment.

In a more preferred embodiment, the chimeric RXR ligand binding domain comprises at least one vertebrate species RXR polypeptide fragment and one non-Dipteran/non-Lepidopteran invertebrate species RXR homolog polypeptide fragment.

In a specific embodiment, the gene whose expression is to be modulated is a homologous gene with respect to the host cell. In another specific embodiment, the gene whose expression is to be modulated is a heterologous gene with respect to the host cell.

The ligands for use in the present invention as described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

In a specific example, binding of the ligand to the ligand binding domain of a Group H nuclear receptor and its nuclear receptor ligand binding domain partner enables expression or suppression of the gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988) Nature, 335: 563-564) or LexA protein from *Escherichia coli* (see Brent and Ptashne (1985), Cell, 43: 729-736), or synthetic response elements specific for targeted interactions with proteins designed, modified, and selected for such specific interactions (see, for example, Kim, et al. (1997), *Proc. Natl. Acad. Sci., USA,* 94: 3616-3620) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The ecdysone receptor is a member of the nuclear receptor superfamily and classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; Cell 97: 161-163). In addition to the ecdysone receptor, other members of this nuclear receptor subfamily 1, group H include: ubiquitous receptor (UR), orphan receptor 1 (OR-1), steroid hormone nuclear receptor 1 (NER-1), retinoid X receptor interacting protein-15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1

In particular, described herein are novel ligands useful in a gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides.

An ecdysone receptor-based gene expression modulation system of the present invention may be either heterodimeric or homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476-479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIPIN-CoA-2, ACTR/AIB1/RAC3/pCIP as well as the promiscuous coactivator C response element B binding protein, CBP/p300 (for review see Glass et al., Curr. Opin. Cell Biol. 9:222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. It has previously been shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Method of Modulating Gene Expression of the Invention

The present invention also relates to methods of modulating gene expression in a host cell using a gene expression modulation system according to the invention. Specifically, the present invention provides a method of modulating the expression of a gene in a host cell comprising the steps of: a) introducing into the host cell a gene expression modulation system according to the invention; and b) introducing into the host cell a ligand; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the ligand into the host cell, expression of the gene is modulated.

The invention also provides a method of modulating the expression of a gene in a host cell comprising the steps of: a) introducing into the host cell a gene expression modulation system according to the invention; b) introducing into the host cell a gene expression cassette according to the invention, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a ligand; whereby upon introduction of the ligand into the host cell, expression of the gene is modulated.

The present invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system according to the invention; and b) introducing into the host cell a ligand; whereby upon introduction of the ligand into the host, expression of the gene is modulated.

Genes of interest for expression in a host cell using methods disclosed herein may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in the methods described herein.

Examples of genes of interest for expression in a host cell using methods set forth herein include, but are not limited to: antigens produced in plants as vaccines, enzymes like alpha-amylase, phytase, glucanes, and xylanse, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products that may be used to treat a condition, a disease, a disorder, a dysfunction, a genetic defect, such as monoclonal antibodies, enzymes, proteases, cytokines, interferons, insulin, erthropoietin, clotting factors, other blood factors or components, viral vectors for gene therapy, virus for vaccines, targets for drug discovery, functional genomics, and proteomics analyses and applications, and the like.

Measuring Gene Expression/Transcription

One useful measurement of the methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of the methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using the present invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybidizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "L" means microliter(s), "mL" means milliliter(s), "L" means liter(s), "μM" means micromolar, "mM" means millimolar, "M" means molar, "mol" means moles, "mmol" means millimoles, "pg" means microgram(s), "mg" means milligram(s), "A" means adenine or adenosine, "T" means thymine or thymidine, "G" means guanine or guanosine, "C" means cytidine or cytosine, "x g" means times gravity, "nt" means nucleotide(s), "aa" means amino acid(s), "bp" means base pair(s), "kb" means kilobase(s), "k" means kilo, "μ" means micro, "° C." means degrees Celsius, "C" in the context of a chemical equation means Celsius, "THF" means tetrahydrofuran, "DME" means dimethoxyethane, "DMF" means dimethylformamide, "NMR" means nuclear magnetic resonance, "psi" refers to pounds per square inch, and "TLC" means thin layer chromatography.

Example 1

Preparation of Compounds

The compounds of the present invention may be made according to the following synthesis routes.

1.1 Preparation of 3,5-Dimethyl-benzoic acid N-tert-butyl-N'-(4-ethyl-2-fluoro-benzoyl)-hydrazide (RG-101523)

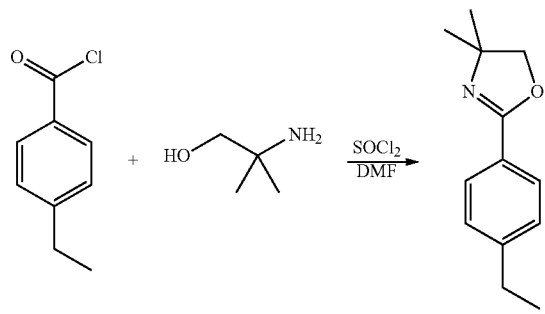

To a 3-neck, 2 L round bottom flask was added 173.71 g (1.0 mol, 97%) of 2-amino-2-methyl-1-propanol in 300 mL of dry methylene chloride. The flask was equipped with a magnetic stir bar and thermometer and was placed into a dry ice/acetone bath and cooled to 0° C. From a separatory funnel, a solution of 4-ethylbenzoyl chloride (168.5 g, 1.0 mol), dissolved in about 300 mL of methylene chloride was slowly added, while maintaining the reaction temperature below 5° C. The mixture was allowed to stir at room temperature overnight. Solid propanol amine-HCl was filtered off and the filter cake was washed with methylene chloride. The combined methylene chloride extracts were concentrated partially on a rotary evaporator and used directly in the next step. The intermediate amide solution generated in the first step was cooled in an ice bath and DMF (0.5 mL) was added. 125 g (1.04 mol) of $SOCl_2$ in 50 mL of methylene chloride from a separatory funnel was added drop-wise at a controlled rate, keeping the reaction temperature at 0-5° C. The reaction was stirred at room temperature for an additional 2-3 hours. The reaction mixture was cooled in an ice bath and 25% NaOH was added to make the aqueous layer basic (pH=11-12). The mixture was transferred to a large separatory funnel, the methylene chloride layer was separated, and the aqueous layer was extracted twice with chloroform. The combined organic phases were dried and evaporated to yield 201 g of 2-(4-ethyl-phenyl)-4,4-dimethyl-4,5-dihydro-oxazole as a yellow viscous oil. $^1$H NMR ($CDCl_3$, 300 MHz), δ (ppm): 7.8 (d, 2H), 7.2 (d, 2H), 4.088 (s, 2H), 2.68 (q, 2H), 1.375 (s, 6H), 1.24 (t, 3H).

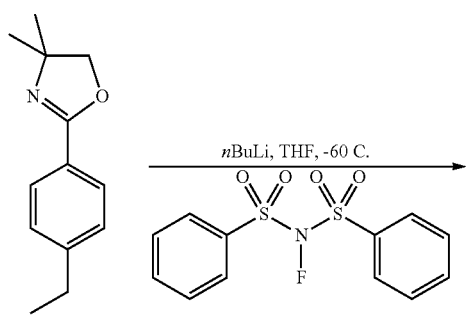

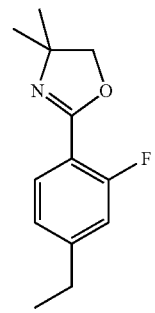

The 4-ethylphenyloxazoline (2.03 g, 10 mmol) was dried in a vacuum oven at 60° C. for 2-3 hours, dissolved in 50 mL of dry THF, and charged to a 300 mL round bottom flask equipped with a thermometer, nitrogen inlet, and magnetic stir bar. The mixture was cooled under nitrogen to −70° C. in a dry ice/acetone bath. Butyl lithium in hexane (7.5 mL, 0.012 mmol) was added in two portions and warmed to −25° C. over 2 hours. The mixture was cooled again to −65° C. and N-fluorobenzenesulfonimide (3.79 g, 0.012 mmol) was added in three portions. The mixture was allowed to warm to room temperature and was stirred overnight. The reaction mixture was quenched with 100 mL of saturated $NH_4Cl$, and transferred to a separatory funnel with ethyl ether washes. 25% NaOH was added slowly and mixed until an aqueous phase with pH=10 was achieved. The aqueous phase was extracted with ether and the ether was washed with a small volume of water. The ether extracts were dried over $MgSO_4$ and evaporated to give 2.51 g of 2-(2-fluoro-4-ethyl-phenyl)-4,4-dimethyl-4,5-dihydro-oxazole as a brown oil. In a second experiment, a rate of 70% fluorination was achieved (highest) with a reactant ratio of 1:1.5:1.5 oxazoline: BuLi: N-fluorobenzenesulfonimide.

$^1$H NMR (300 MHz, $CDCl_3$) δ (ppm): 7.0 (d, 2H), 7.78 (t, 1H), 4.1 (s, 2H), 2.7 (q, 2H), 1.39 (s, 6H), 1.2 (t, 3H).

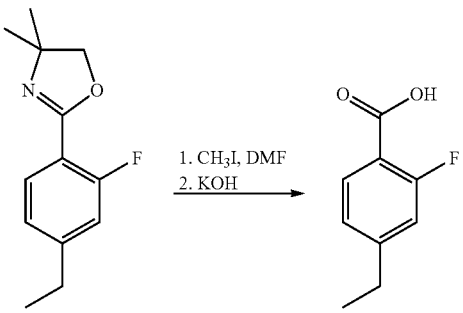

DMSO (4 mL) and $CH_3I$ (2 mL) were added to 2.31 g of oxazoline in a round bottom flask, and the mixture was stirred overnight at room temperature. Methyl iodide was removed in vacuo on a rotary evaporator. Aqueous KOH (4.4 g in 35 mL of water) was added and the mixture was refluxed for 8 hours. The reaction mixture and water washes were transferred to a separatory funnel; the neutral components were removed with a chloroform extraction. The aqueous mixture was acidified with 6N HCl to pH 1-2, and extracted with ether. Ether extracts were dried over $MgSO_4$ and evaporated to yield 1.2 g of a white solid, comprised of both 2-fluoro-4-ethylbenzoic acid and 4-ethylbenzoic acid. The product mixture was dissolved in KOH and the pH was adjusted with 2N HCl to pH=7. With vigorous stirring and careful monitoring with a pH meter, the mixture was acidified to pH=5 with 0.1N HCl. 4-Ethylbenzoic acid precipitated first, which was filtered through Whatman #541 paper, acidification continued with 0.1N HCl to pH=4.9, and at 0.1 unit increments until pH=4.3, each time filtering the solids through Whatman #541 paper. Finally, the mixture was acidified to pH=2.5 and filtered. Precipitates of decreasing pH contain increasing rations of 2-fluoro-4-ethylbenzoic acid, the last two fractions contain 98-100% desired product. Extraction of the remaining aqueous phase with ether recovers more 2-fluoro-4-ethylbenzoic acid. The product was air-dried as drying in a vacuum oven results in substantial product losses due to volatility. $^1$H NMR (300 MHz, CDCl$_3$) δ=7.95 (t, 1H), 7.1 (d, 1H), 7.0 (d, 1H), 2.71 (q, 2H), 1.27 (t, 3H). 4-Ethylbenzoic acid: $^1$H NMR (CDCl$_3$) δ (ppm): 8.1 (d, 2H), 7.3 (t, 2H), 2.71 (q, 2H), 1.27 (t, 3H).

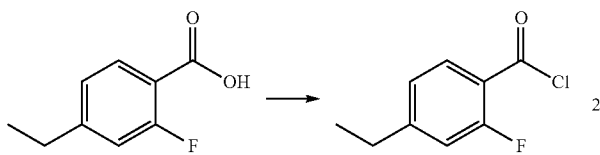

1.31 g (1.3 mmol) of thionyl chloride, 1 drop of DMF and 1.0 g (5.95 mmol) of acid were added to 30 mL of toluene with stirring. The mixture was refluxed for 4 hours. After this period, the toluene and unreacted thionyl chloride were removed by distillation. The resulting 2-fluoro-4-ethylbenzoyl chloride was used without further purification.

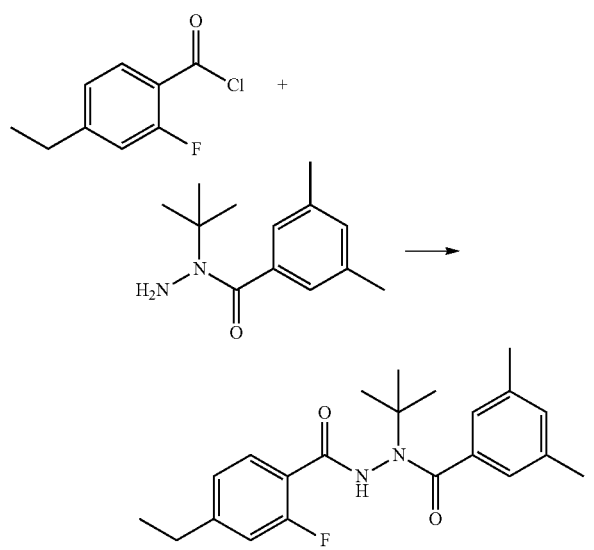

0.150 g of 3,5-dimethyl-benzoic acid N-tert-butyl-hydrazide (1 eq, 0.68 mmol) and 0.110 mL (1.2 eq, 0.77 mmol) of 2-fluoro-4-ethyl benzoyl chloride were weighed into a 1 oz. vial. A small stirbar was added followed by 2 mL of methylene chloride. The mixture was stirred until the hydrazone dissolved. The stirring was stopped and 2 mL of a 1 M potassium carbonate (K$_2$CO$_3$) solution was added. The mixture was allowed to stir overnight. At the end of this period, 1 mL of water and 1 mL of methylene chloride were added. The aqueous phase was removed and the organic phase was washed twice with 1 M potassium carbonate solution. The organic phase was removed and dried over magnesium sulfate. The organic phase was filtered thru a pad of basic alumina and the solvent removed. The product, 3,5-dimethyl-benzoic acid N-tert-butyl-N'-(2-fluoro-4-ethylbenzoyl)-hydrazide, was purified by trituration with 1:1 ether:hexane.

$^1$H NMR (300 MHz, CDCl$_3$) δ (ppm): 7.7 (m, 2H), 7.6 (t, 1H), 7.0 (m, 3H), 2.6 (q, 2H), 2.3 (s, 3H), 2.1 (s, 6H), 1.5 (s, 9H), 1.1 (t, 3H).

1.2 Preparation of 5-chloro-4H-benzo[1,3]dioxine-6-carboxylic acid

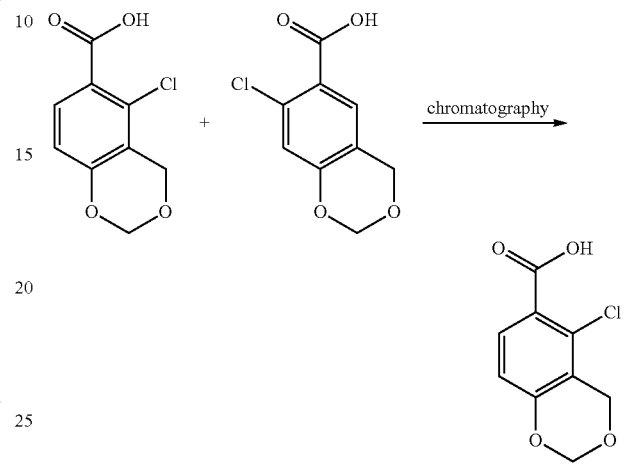

5-chloro and 7-chloro isomers were separated by silica gel cartridge chromatography. The mixture was dissolved in CHCl$_3$/CH$_3$OH and added to the top of a large cartridge. The 5-chloro isomer eluted with 2:3 ether:hexane and the 7-chloroisomer began to elute with 3:2 ether:hexane and completed elution with neat ether. $^1$H NMR (DMSO-d$_6$, 300 MHz) δ (ppm): 7.75 (d, 1H), 6.95 (d, 1H), 5.3 (s, 2H), 4.9 (s, 2H).

1.3 Preparation of 2-fluoro-4-hydroxy-benzoic acid

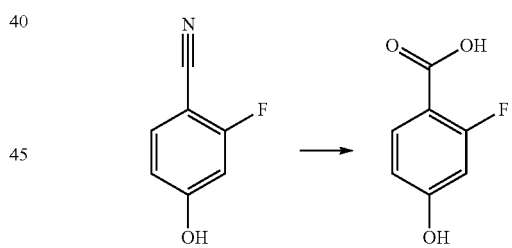

To a stirred solution of 2-fluoro-4-hydroxybenzonitrile (20.00 g, 145.9 mmol) in 160 mL of water, was added 50% aqueous sodium hydroxide (40.00 g, 500.0 mmol). The mixture was heated to reflux for 4 hours, cooled to room temperature, poured into iced concentrated hydrochloric acid, and extracted with ether. The product was extracted into saturated aqueous sodium bicarbonate and the ether layer discarded. This aqueous extract was acidified with concentrated hydrochloric acid and extracted with ether. The organic extract was dried over magnesium sulfate, filtered, and evaporated to give a white solid (22.90 g) of 2-fluoro-4-hydroxybenzoic acid in 100% yield. $^1$H NMR (300 MHz, CD$_3$COCD$_3$) δ (ppm): 9.80 (b, 1H), 7.87 (t, 1H), 6.77 (dd, 1H), 6.66 (dd, 1H). $^{19}$F-NMR (300 MHz, CD$_3$COCD$_3$) δ (ppm): −108.13 (s, decoupled). 2-Fluoro-4-hydroxybenzonitrile: $^1$H-NMR (300 MHz, CD$_3$COCD$_3$) δ (ppm): 7.61 (t, 1H), 6.81 (m, 2H), 5.80 (b, 1H). $^{19}$F-NMR (300 MHz, CD$_3$COCD$_3$) δ (ppm): −108.82 (s, decoupled)

1.4 Preparation of of 5-fluoro-4H-benzo{1,3}dioxine-6-carboxylic acid, methyl ester and 6-fluoro-4H-benzo{1,3}dioxine-7-carboxylic acid, methyl ester

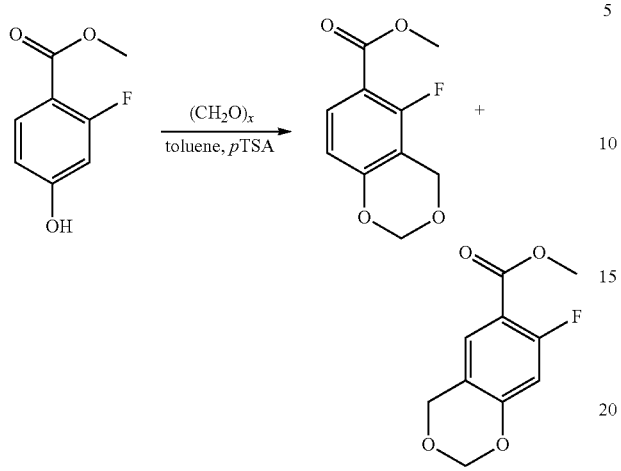

1.6 g methyl 2-fluoro-4-hydroxy-benzoate (7.54 mmol), 0.157 g of p-toluenesulfonic acid (0.9 mmol), 50 mL of toluene and 1.2 g of paraformaldehyde (40 mmol) were combined and refluxed for 3 hours after which time TLC (1:1 ethyl acetate: $CH_2Cl_2$) showed the absence of the starting material. Occasionally it became necessary to cool the reaction and scrape off unreacted paraformaldehyde from the walls of the reaction flask. The reaction flask was vented to the hood exhaust. After the mixture was filtered to remove the solid paraformaldehyde, the solid was washed twice with 100 mL of toluene. The toluene washes were combined with the filtered liquid. The organic liquid was washed three times with 75 mL of 5% aqueous NaOH. 50 mL of methanol was added to the organic phase and the solvent was removed on the rotary evaporator to yield a thick syrup which gradually formed a somewhat tacky white solid. Proton and $^{19}F$ NMR showed the presence of two isomers in a ratio of approximately 7:3. These isomers could be separated by careful chromatography on silica gel using a hexane to 85% hexane-15% ether gradient. The desired 3,4-methylenedioxy-2-fluoro benzoic acid, methyl ester eluted first as a white solid. $^1H$ NMR ($CDCl_3$, 300 MHz) δ (ppm): 3.85 (s, 3H), 4.85 (s, 2H), 5.20 (s, 2H), 6.60 (d, 1H), 7.80 (t, 1H). $^{19}F$ NMR (ppm, $CDCl_3$) −115 (s); Rf=0.4 (1:1 $CH_2Cl_2$: EtOAc).

The 4,5-methylenedioxy isomer eluted shortly thereafter, also as a white solid. $^1H$ NMR ($CDCl_3$, 300 MHz) δ (ppm): 3.90 (s, 3H), 4.85 (s, 2H), 5.25 (s, 2H), 6.65 (d, 1H), 7.60 (d, 1H). $^{19}F$ NMR (ppm, $CDCl_3$) −108 (s).); Rf=0.32 (1:1 $CH_2Cl_2$: EtOAc).

1.5 Preparation of 5-fluoro-4H-benzo{1.3}dioxin-6-carboxylic acid and 6-fluoro-4H-benzo{1,3}dioxin-7-carboxylic acid

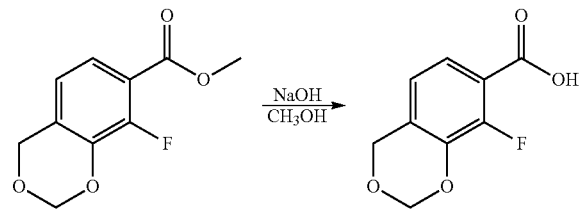

5-Fluoro-4H-benzo[1,3]dioxine-6-carboxylic acid methyl ester (2.02 g), water (1 mL), methanol (20 mL) and sodium hydroxide (1 mL of a 50% NaOH solution) were added to a flask equipped with a condenser and magnetic stirbar. The stirring was started and the mixture was refluxed for 2 hours. At this point, the TLC (1:1: $CH_2Cl_2$/ethyl acetate) showed no starting ester was present. The solvent was removed, leaving a white solid. The solid was taken up in water and the aqueous layer was washed three times with 50 mL of ether. The aqueous layer was then acidified with dilute hydrochloric acid causing the formation of a white precipitate. This white solid was collected on a sintered glass filter funnel and washed well with de-ionized water. The solid was dried under vacuum at 60° C. overnight and used in the following reaction without further purification.

1.6 Preparation of 5-fluoro-4H-benzo{1,3}dioxine-6-carboxylic acid N'-tert-butyl-hydrazide and 5-fluoro-4H-[1,3]dioxine-6-carboxylic acid N-tert-butyl-N'-(5-fluoro-4H-benzo[1,3]dioxine-6-carbonyl)-hydrazide

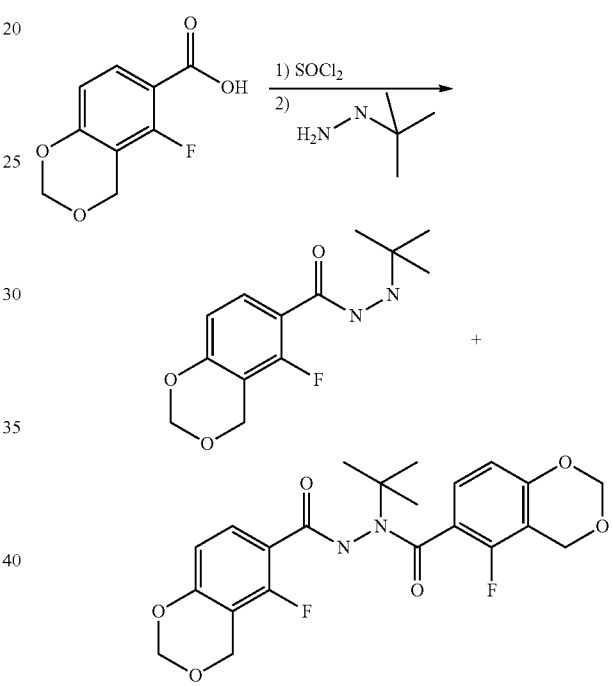

1.6 g of 5-fluoro-4H-benzo{1.3}dioxin-6-carboxylic acid (8.1 mmol), 30 mL of toluene and 1 drop of DMF were combined in a 100 mL flask equipped with magnetic stirbar, scrubber and condenser. 0.59 mL of thionyl chloride (0.96 g, 9.7 mmol) was added and the mixture was heated to reflux and held at reflux for 4 hours. After this period, the mixture was cooled slightly and the condenser was replaced with a distillation head. The excess thionyl chloride was distilled off. The mixture was cooled to 20° C. and the toluene was removed using a rotary evaporator. NOTE: It is advisable to use care during the toluene removal. The 5-fluoro-4H-benzo[1,3]dioxine-6-carbonyl chloride starts to distill under vacuum if the temperature exceeds 27° C.

50% NaOH (0.648 g, 8.1 mmol) of was dissolved in 3 mL of water and added to a reaction flask containing a magnetic stirbar and rubber septum for reagent addition. 1.00 (8.1 mmol) g of tert-butyl hydrazine hydrochloride was added. The mixture was stirred for 5 min at room temperature and then cooled to −5° C. 5-Fluoro-4H-benzo[1,3]dioxine-6-carbonyl chloride (8.1 mmol) was dissolved in 25 mL of dichloromethane and was added simultaneously with a second portion of 0.648 g (8.1 mmol) of 50% NaOH in 3 mL of water.

The reaction temperature was kept below −2° C. during the addition. The mixture was stirred at −5° C. to −2° C. for 30 min. After this time, the mixture was allowed to warm to room temperature and stirred for 30 min. 50 mL of dichloromethane and 50 mL of water were added to the reaction mixture. The layers were separated and the organic layer was washed three times with 50 mL of water. The organic layer was then dried over MgSO$_4$ and filtered. Removal of the solvent yielded 2.4 g of a yellow syrup, which appeared to be approximately 85% of the desired product by NMR analysis. The pure product, 5-fluoro-4H-benzo[1,3]dioxine-6-carboxylic acid N'-tert-butyl-hydrazide, was isolated as a pale, yellow solid by careful column chromatography on silica gel using a dichloromethane to 4:1 dichloromethane/ethyl acetate gradient. $^1$H NMR (CDCl$_3$, 300 MHz) δ (ppm): 0.85 (s, 9H), 4.58, (s, 2H), 4.90 (s, 2H), 6.40 (d, 1H), 7.50 (t, 1H) and 7.70 (br s, 1H). $^{19}$F NMR (CDCl3), δ ppm: (s, −190, s). Rf=0.35 (1:1 CH$_2$Cl$_2$: ethyl acetate).

1.7 Preparation of 2-Bromomethyl-3-methoxy-benzoic acid methyl ester

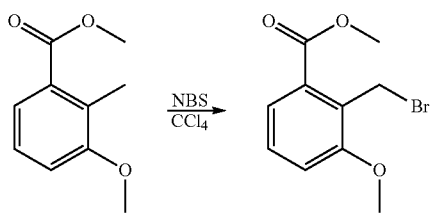

Into a 2 L 3-neck round bottom flask was added 75 g (0.42 mol) of 2-methyl-3-methoxy methyl benzoate, 500 mL of CCl$_4$, 80.1 g (0.45 mol) of NBS, and 1 g of AIBN. The mixture was stirred and refluxed gently for 2 hours. The reaction mixture was cooled and ca. 600 mL of CH$_2$Cl$_2$ and 500 mL of water were added. The mixture was stirred to dissolve floating solids, transferred to a 2 L separatory funnel, and then shaken. The organic layer was separated and the water extracted with CH$_2$Cl$_2$. The aqueous fractions were discarded and the organic phase extracted with 400-500 mL of water to remove the NBS (note: solubility of succinimide is 1 g/3 g water, solubility of NBS is 1.47 g/100 mL water). The water extractions were repeated, the organic phase dried with MgSO$_4$ and charcoal, and the solvent evaporated in 2 portions, to yield methyl-3-methoxy-2-bromomethylbenzoate. TLC: Rf=0.58, single spot (1:1 ethyl acetate:hexane). $^1$H NMR (CDCl$_3$, 300 MHz) δ (ppm): 7.5 (d, 1H), 7.3 (t, 1H), 7.05 (d, 1H), 5.06 (s, 2H), 3.94 (s, 3H), 3.93 (s, 3H).

1.8 Preparation of 4-methoxy-3H-isobenzofuran-1-one

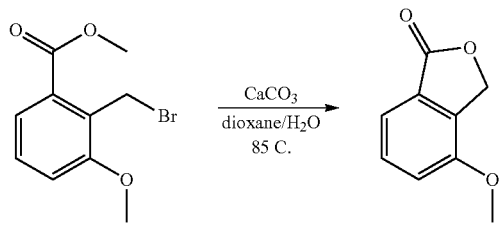

In a 500 mL round bottom flask was added 15.15 g (0.0585 mol) of 2-bromomethyl, 3-methoxy methyl benzoate, 29.3 g (0.293 mol) of CaCO$_3$, 150 mL of dioxane and 150 mL of water. The flask was placed into an oil bath and the mixture heated with stirring at 85° C. for 3.5 to 4 hours. The CaCO$_3$ was filtered off and washed with ethyl acetate and water. To the filtrate was added ethyl acetate (200 mL) and water (50 mL) and the mixture then shaken in separatory funnel. The water phase was extracted twice with ethyl acetate (50 mL). The ethyl acetate extracts were combined, extracted once with water, dried over MgSO$_4$, and evaporated. This yielded 9.2 g of white crystals of 7-methoxybenzolactone (95% yield). $^1$H NMR (CDCl$_3$, 300 MHz) δ (ppm): 7.5 (m, 2H), 7.1 (m, 1H), 5.26 (s, 2H), 3.93 (s, 3H). TLC: Rf=0.46 (1:1 EtOAC: hexane).

1.9 Preparation of 2-cyanomethyl-3-methoxybenzoic acid

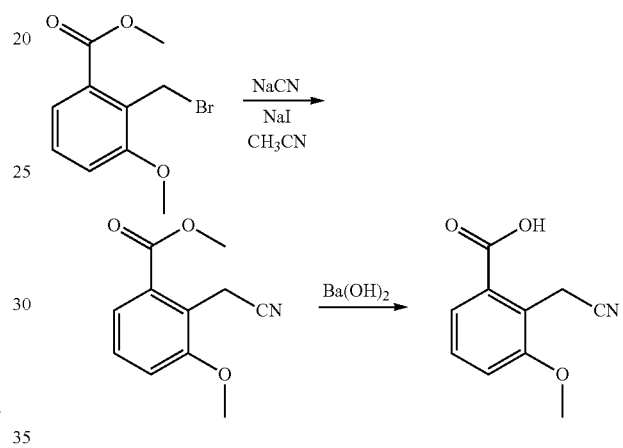

Into a 500 mL 3-neck round bottom flask was added 10 g (61.75 mmol) of 2-bromomethyl, 3-methoxy methyl benzoate, 4.0 g (81.6 mmol) of NaCN, 0.30 g (2 mmol) of NaI, 100 mL of CH$_3$CN, and 50 mL of DMF. The reaction mixture was heated and refluxed for 10 hours. The precipitate (NaBr) was filtered off, and the solution was concentrated on an evaporator. 300 mL of water and 200 mL of ether were added and then shaken in a separatory funnel. The water was extracted twice with 100 mL of ether. The ether fractions were dried over MgSO$_4$, and concentrated to yield methyl 3-methoxy-2-cyanomethylbenzoate (95-100% yield). This ester (0.053 mmol, 10.51 g) was stirred vigorously in 100 mL of CH$_3$OH. Ba(OH)$_2$H2O (0.079 mmol, 14.97 g) was added and the mixture stirred at room temperature overnight. The CH$_3$OH was removed on a rotary evaporator. 150 mL of water, 200 mL of CH$_2$Cl$_2$, and 50 mL of 6N HCl were added, and then stirred in a flask to dissolve all residues. The mixture was transferred to a separatory funnel, acidified with 6N HCl to pH 1-2. The CH$_2$Cl$_2$ phase was separated and the aqueous phase extracted twice with 50 mL of CH$_2$Cl$_2$. The CH$_2$Cl$_2$ extracts were combined, dried over MgSO$_4$ and charcoal, filtered, and evaporated to yield 8.8 g of a white solid, 2-cyanomethyl-3-methoxybenzoic acid, (87%).

Methyl 3-methoxy-2-cyanomethylbenzoate: $^1$H NMR (CDCl$_3$, 300 MHz) δ (ppm): 7.6 (d, 1H), 7.4 (t, 1H), 7.1 (d, 1H), 4.18 (s, 2H), 3.94 (s, 3H), 3.926 (s, 3H). TLC (1:1 ethyl acetate:hexane) 0.55.

2-Cyanomethyl-3-methoxybenzoic acid: $^1$H NMR (300 Mhz, CDCl$_3$) δ (ppm): 7.55 (d, 1H), 7.45 (t, 1H), 7.3 (d, 1H), 4.121 (d, 2H), 3.91, (s, 3H). TLC (1:1 ethyl acetate:hexane), Rf 0.36 streak.

1.10 Preparation of 3-methoxy-2-methylsulfanylmethyl-benzoic acid and pentafluorophenyl 2-(methylthiomethyl 3-methoxybenzoate

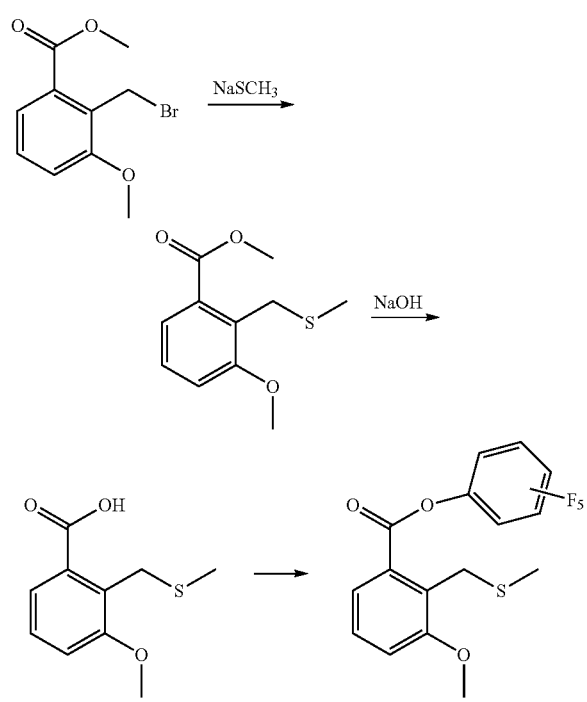

Methyl 2-bromomethyl-3-methoxy benzoate was stirred in methanol at room temperature with 1.02 eq. of sodium methylmercaptide. After 30 min the reaction was complete based on GC analysis. The mixture was poured into water and extracted twice with ethyl acetate. The combined organic layers were stripped under vacuum leaving methyl 2-(methylthiomethyl)-3-methoxybenzoate as a pale yellow oil in about 86% yield. GC: DB-5, 30 m, film: 0.25 um, $t_{init}$=1.00 T=120-280 C@20 C/min; Rt=6:30 area %=98. $^1$H NMR (CDCl$_3$, 300 MHz) δ (ppm): 7.46 (d, 1H), 7.26 (t, 1H), 7.03 (d, 1H), 4.18 (s, 1H), 3.90 (s, 2H), 3.89 (s, 3H), 2.04 (s, 3H).

Methyl 2-(methylthiomethyl)-3-methoxy benzoate was heated to reflux with 1.5 eq of NaOH in 10% aqueous methanol for 1.5 hr. The solution was added drop-wise to excess 10% sulfuric acid. The precipitate was filtered and dried in air giving ca. 92% yield of 2-(methylthiomethyl)-3-methoxybenzoic acid. TLC (2:1 ethyl acetate:hexane) indicated one spot, Rf 0.50.

2-(Methylthiomethyl)-3-methoxybenzoic acid was dissolved in ethyl acetate and added to a solution of 1.1 eq. of pentafluorophenol and 1.1 eq. of dicyclohexycarbodiimide in ethyl acetate. After 1 hr the mixture was filtered and the mother liquors were stripped under vacuum. The yellow oily residue was crystallized from hexane to give the product, pentafluorophenyl 2-(methylthiomethyl 3-methoxybenzoate, in 100% yield. TLC (1:2 ethyl acetate:hexane) indicated one spot, Rf 0.58.

1.11 Preparation of 3-Methoxy-2-methoxymethyl-benzoic acid

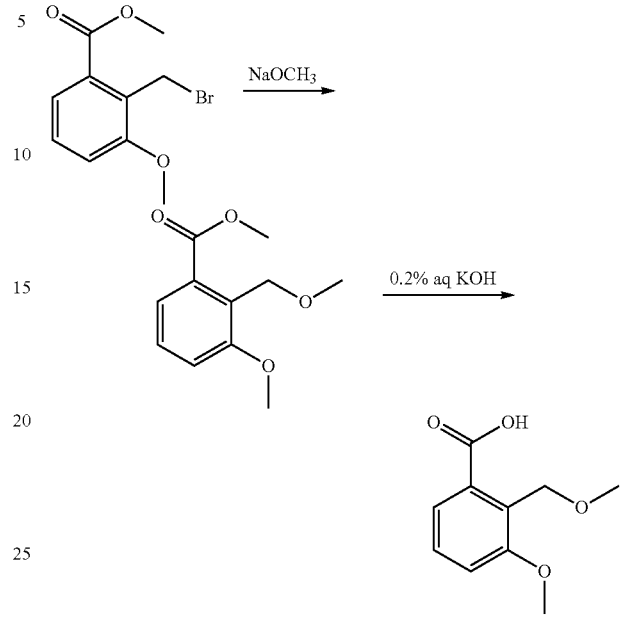

To a 100 mL flask containing 10.1 g (0.039 mol) of methyl 2-bromomethyl-3-methoxybenzoate in 50 mL of CH$_3$OH, were added 19 g of a 25% wt. solution of NaOMe (4.74 g, 0.087 mol). The reaction was stirred at room temperature for 2 hours and then evaporated on a rotary evaporator to remove the CH$_3$OH. About 200 mL of water were added to the residue and the resulting solution was extracted with CHCl$_3$. The CHCl$_3$ extract was dried and evaporated to yield 6.27 g of crude methyl 3-methoxy-2-methoxymethylbenzoate (77% yield). $^1$H NMR (CDCl$_3$, 300 MHz) δ (ppm): 7-7.4 (multiple, 3H), 4.783 (s, 2H), 3.897 (s, 3H), 3.864 (s, 3H), 3.37 (s, 3H). 6.27 g of methyl 3-methoxy-2-methoxymethylbenzoate was stirred with a 20% aqueous KOH solution (6.7 g, 0.12 mol in 34 g of solution) at 50° C. in an oil bath for 4-5 hours, and then at room temperature for 16 hours. The reaction mixture was acidified with 3N HCl to pH 2 and extracted with CH$_2$Cl$_2$. The CH$_2$Cl$_2$ extract was dried and evaporated to yield 5.35 g of 3-methoxy-2-methoxymethylbenzoic acid (92% yield). $^1$H NMR (CDCl$_3$, 300 MHz) δ (ppm): 7.65 (1H, d), 7.40 (t, 1H), 7.10 (d, 1H), 4.83 (s, 2H), 3.88 (s, 3H), 3.46 (s, 3H).

1.12 Preparation of N'-t-butyl-3-methoxy-2-methoxymethylphenylhydrazide

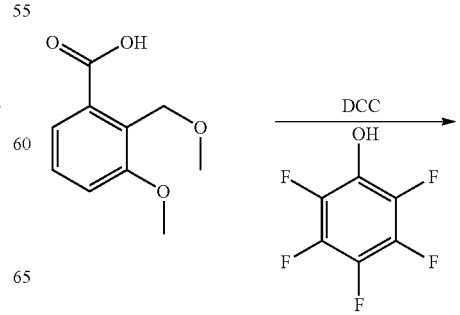

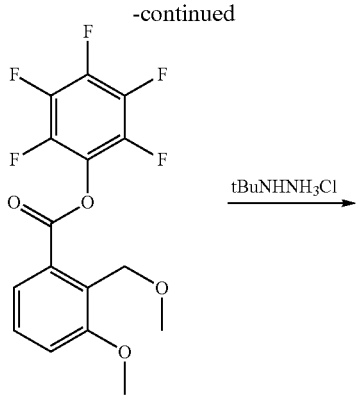

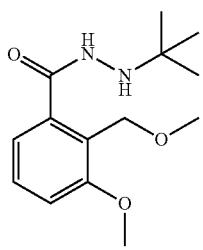

To 4.30 g (0.0219 m) of 3-methoxy-2-methoxymethylbenzoic acid in 50 mL of ethyl acetate in a round bottom flask, was added 8.88 g of a 50% wt solution of pentafluorophenyl phenol, followed by 21.91 mL of DCC solution (0.0219 m). After stirring for 2 hr at room temperature, TLC showed a spot for the intended pentafluorophenyl ester product at Rf=0.64 (1:1 ethyl acetate: hexanes), while the starting acid was Rf=0.39.

A small volume of ethyl acetate (30 mL) and a teaspoon of anhydrous MgSO$_4$ was added and then filtered to remove the DCC and DCU. The filtrate was evaporated to yield 9.4 g of product. $^1$H NMR (CDCl$_3$, 300 MHz) δ (ppm): 3.39 (s, 3H), 3.90 (s, 3H), 4.81 (s, 2H). NMR analysis of the starting material indicated the following spectrum: $^1$H NMR (CDCl$_3$, 300 MHz) δ (ppm): 4.83 (s, 2H), 3.88 (s, 3H), 3.4 (s, 3H).

The remaining DCC and DCU were removed by column chromatography on silica gel. The products eluted in the 6 and 8% ethyl acetate/hexane fractions. The yield of 7.08 g, contained some DCC and DCU. 7.08 g (0.02 mol) of the pentafluorophenyl ester in 60 mL of CH$_2$Cl$_2$ was stirred with 3.67 g (0.029 mol) of t-butylhydrazine HCl and 12 g of K$_2$CO$_3$ in 60 mL of water at room temperature overnight. 60 mL of CH$_2$Cl$_2$ and 50 mL of water were added and then shaken in separatory funnel. The organic phase was dried over MgSO$_4$ and then evaporated to yield 5.6 g of t-butyl hydrazide. $^1$H NMR (CDCl$_3$, 300 MHz) δ (ppm): 7.4 (d, 2H). 7.0 (t, 1H), 4.627 (s, 2H), 3.874 (s, 3H), 3.465 (s, 3H), 1.184 (s, 9H). TLC: (1:1 ethyl acetate:hexanes), Rf=0.16. The product can be further purified by trituration with hexanes.

1.13 Preparation of 3-methoxy-2-methoxymethyl-benzoic acid

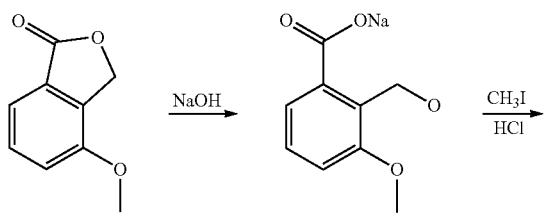

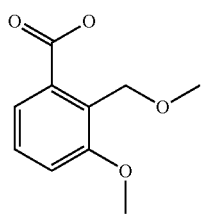

1.0 g (0.0061 mol) of lactone was refluxed with 20 mL of 7.5% NaOH and 20 mL of CH$_3$OH for 7 hours. The methanol was removed on a rotary evaporator, set up a Dean Stark, refluxed in toluene to azeotropically remove water, toluene was removed in vacuo, and the residue was dried in a vacuum oven. $^1$H NMR (DMSO, 300 MHz) δ (ppm): 3.74 (s, 3H), 4.47 (s, 2H), 6.9 (d, 1H), 7.1 (t, 1H), 7.2 (d, 1H).

The sodium carboxylate was dissolved in 15 mL of DMF and then CH$_3$I (0.87 g, 0.0061 mol) was added and the mixture was stirred at room temperature overnight. 50 mL of saturated NH$_4$Cl was added to quench the reaction. 250 mL of water was added (solution is basic at this point), and extracted with ether to remove the neutral and basic substances. The remaining aqueous solution was acidified with 3N HCl to pH=2 and the desired carboxylic acid extracted with ether. The ether extracts were dried and evaporated to yield 0.55 g of 3-methoxy-2-hydroxymethylbenzoate, sodium salt and 3-methoxy-2-methoxymethylbenzoic acid. $^1$H NMR (CDCl$_3$, 300 MHz) δ (ppm): 3.456 (s, 3H), 3.884 (s, 3H), 4.832 (s, 2H), 7.1 (d, 1H), 7.4 (t, 1H), 7.6 (d, 1H).

1.14 Preparation of 2-allyloxymethyl-3-methoxy-benzoic acid

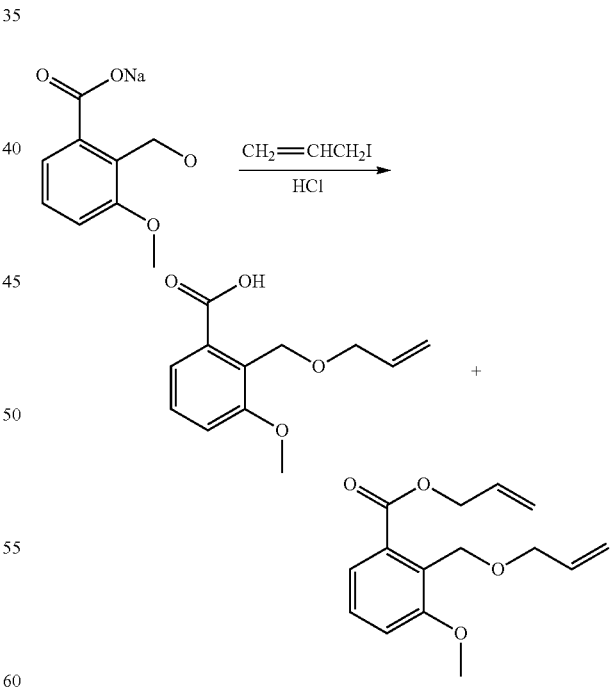

1.0 g (0.005 mol) of sodium 3-methoxy-2-hydroxymethylbenzoate was combined in a 200 mL flask with 1.68 g (0.01 mol) of allyl iodide and 50 mL of dioxane and refluxed for 2 hr. The mixture was stirred at room temperature overnight. The reaction mixture was concentrated on an evaporator. Water were added, and aqueous 5% NaOH to pH=10-11, and the mixture was extracted with ether. The ether was evaporated to give a diallyl product (0.34 g). ¹H NMR indicated complex allyl signals in addition to the aromatic protons. The water solution was acidified with 3N HCl and extracted twice with 100 mL of ether to yield 3-methoxy-2-allyloxybenzoic acid and allyl 3-methoxy-2-allyloxybenzoate (0.34 g). ¹H NMR (CDCl₃, 300 MHz) δ (ppm): 3.879 (s, 3H), 4.11 (d, 2H), 5.3 (q, 2H), 5.9-6.0 (m, 1H). TLC: (1:1 ethyl acetate:hexane): diallyl, Rf 0.60, monoallyl, Rf 0.31, streak.

1.15 Preparation of methyl 3-methoxy-2-allyloxymethyl benzoate

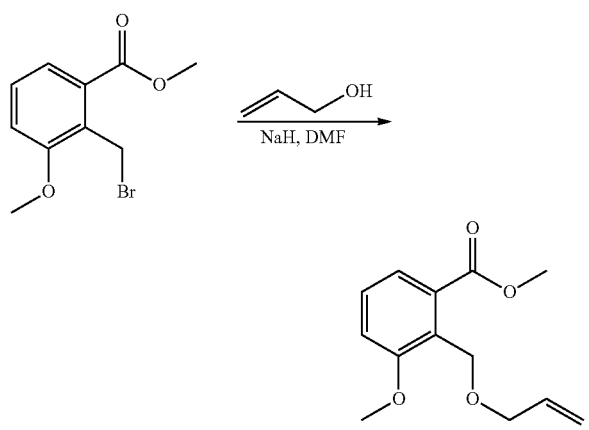

Into a 25 mL round bottom flask, was added 0.96 g (0.0165 m) of allyl alcohol and 3 mL of DMF. While cooling the flask in an ice bath, 0.80 g of a 60% dispersion of NaH (0.020 m, 0.48 g) was added, with magnetic stirring. The reaction mixture was stirred for 45 min at room temperature. The flask was placed in the ice bath and 2 g of DMF and 3.89 g (0.015 m) of methyl 2-bromomethyl-3-methoxy benzoate were added in small portions. The reaction was allowed to stir at room temperature for 4-5 hours. The reaction was transferred to a separatory funnel with 150 mL of ethyl ether and 50 mL of water. The reaction mixture was shaken, the ether phase separated and the water phase again extracted with 50 mL of ether. The ether phase was extracted with water (20 mL), dried with MgSO₄ and concentrated to yield 2.7 g of a pale, yellow oil (76% yield). ¹H NMR (CDCL₃, 300 MHz) δ (ppm): 7.3-7.0 (m, 3H), 5.9-6.0 (m, 1H), 5.1-5.3 (2d, 2H), 4.8 (d, 2H), 4.02 (d, 2H), 3.90 (s, 3H), 3.88 (s, 3H). TLC (1:1 ethyl acetate/hexane), Rf 0.58.

1.16 Preparation of 2-allyloxymethyl-3-methoxybenzoic acid

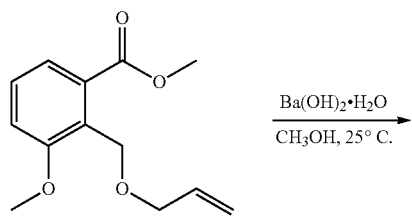

Into a 200 mL round bottom flask containing 5.40 g (0.0229 m) of 3-methoxy-2-allyloxymethyl benzoate, was added 40 mL of methyl-alcohol. With magnetic stirring, 6.50 g (0.034 m) of barium hydroxide monohydrate was added. The reaction was stirred for 4 hours in a 45° C. water bath. The reaction flask was transferred to a rotary evaporator and the methanol was removed under vacuum. H₂O (150 mL) was added to the residue in the flask and the mixture was stirred until most of the residue dissolved. The reaction mixture was transferred with water (50-100 mL) to a large beaker. The mixture was acidified with 6 HCl (to pH=1) and transferred to a separatory funnel. The reaction mixture was extracted three times with 100 mL of ethyl acetate with salting out. Ethyl acetate extract was dried and evaporated to yield 4.38 (g) of viscous product, 2-allyloxymethyl-3-methoxybenzoic acid (98% yield). ¹H NMR (CDCL₃, 300 MHz) δ (ppm): 7.55 (d, 1H), 7.40 (t, 1H), 7.1 (d, 1H), 6.0-5.9 (m, 1H), 5.4-5.2 (2d, 2H), 4.87 (d, 2H), 4.10 (d, 2H), 3.878 (s, 3H). TLC (1:1 ethyl acetate:hexane) Rf 0.38.

1.17 Preparation of pentafluorophenyl 2-allyloxymethyl-3-methoxybenzoate

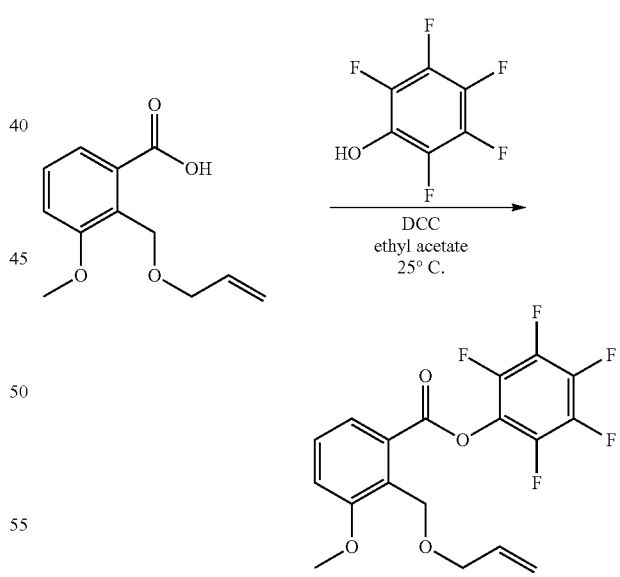

Into a 200 mL round bottom flask was added 6.6 g (0.0297 mol) of 2-allyloxymethyl-3-methoxy benzoic acid and 40 mL of ethyl acetate. 24.05 g of a 25% pentafluorophenol (6.01 g, 0.0327 mol) solution in ethyl acetate was added while stirring. The reaction flask was placed into a water bath and while stirring small portions of DCC (6.2 g, 0.030 mol) were added. The stirring continued overnight at room temperature. The reaction was filtered through two Whatman #541 filters to remove the DCU precipitate. The ethyl acetate solution was concentrated to yield 12.8 g (110% yield), indicating presence of DCC and DCU. This was confirmed by TLC (1:1 ethyl acetate:hexane), which indicated a Rf of 0.72 plus other less polar compounds (I₂ stain indicates about 85% purity). $^1$H NMR (CDCl₃, 300 MHz) δ (ppm): 7.7 (d, 1H), 7.45 (t, 1H), 7.15 (d, 1H), 6.0-5.9 (m, 1H), 5.3-5.1 (2d, 2H), 4.88-4.83 (d, 2H), 4.06 (d, 2H), 3.90 (s, 3H).

1.18 Preparation of 2-allyloxymethyl-3-methoxy-benzoic acid N'-tert-butyl-hydrazide

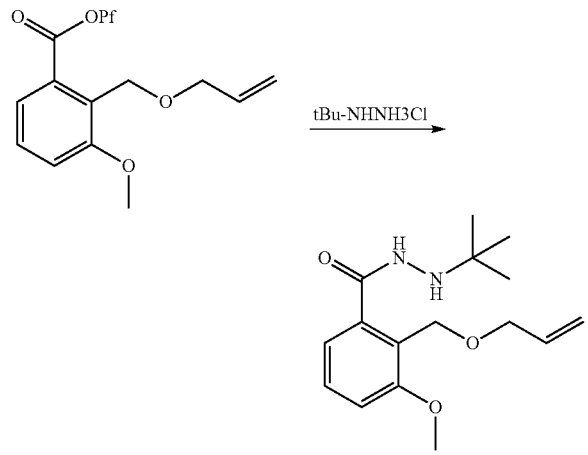

Into a round bottom flask containing 18.9 g (0.048 m) of pentafluorophenyl ester in 50 mL of CH₂Cl₂, was added 9.1 g (0.73 m) of t-butylhydrazine hydrochloride, and then 20.16 g (0.146 m) of K₂CO₃ in 50 mL of H₂O. The mixture was stirred at room temperature for 24 hours. 50 mL of H₂O were added, the CH₂Cl₂ layer was separated, and H₂O phase extracted twice with 100 mL of CH₂C₂. The CH₂Cl₂ fraction was dried with MgSO₄, and concentrated to yield 9.75 g of N-2-allyloxymethyl-3-methoxyphenyl-N'-t-butylhydrazide. $^1$H NMR (CDCl₃, 300 MHz) δ (ppm): 1.151 (s, 9H), 3.87 (s, 3H), 4.12 (d, 2H), 4.68 (s, 2H), 5.15-5.35 (q, 2H), 5.19 (m, 1H), 7.0 (t, 1H), 7.4 (d, 2H). TLC: (1:1, ethyl acetate:hexane) Rf=0.25.

1.19 Preparation of 3,5-dimethyl-benzoic acid N'-(2-allyloxymethyl-3-methoxy-benzoyl)-N-tert-butyl-hydrazide

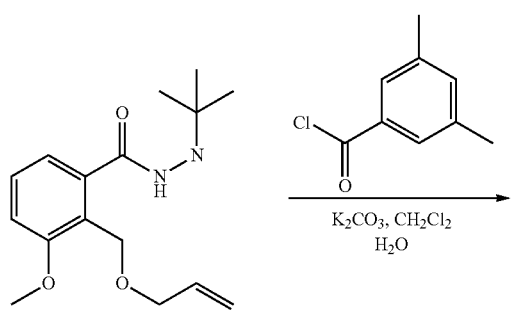

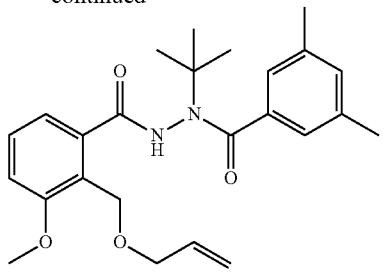

To a flask containing 2.0 g (0.0068 mol) of 2-allyloxymethyl-3-methoxy-benzoic acid N'-tert-butyl-hydrazide dissolved in 15 mL of CH₂Cl₂, was added 1.27 g (0.0075 mol) of 3,5-dimethylbenzoyl chloride in 10 mL of CH₂Cl₂ and 2.84 g of K₂CO₃ (0.02 mol) in 30 mL of H₂O. The mixture was stirred at room temperature for 24 hours. The reaction mixture was diluted and partitioned, and the organic phase was dried and solvent was removed in vacuo. The product was purified by silica gel chromatography; eluting in 25% ethyl acetate:hexane fractions, to yield 2.40 g of pure 3,5-dimethylbenzoic acid N'-(2-allyloxymethyl-3-methoxy-benzoyl)-N-tert-butyl-hydrazide. $^1$H NMR (CDCl₃, 300 MHz) δ (ppm): 7.2 (t, 1H,) 7.1 (s, 1H), 7.05 (d, 2H), 6.95 (m, 2H), 5.9 (m, 1H), 5.2-5.3 (q, 2H), 4.5 (d, 2H), 3.9 (m, 2H), 3.80 (s, 3H), 2.245 (s, 6H), 1.547 (s, 9H).

1.20 Preparation of 3,5-dimethyl-benzoic acid N-tert-butyl-N'-(2-hydroxymethyl-3-methoxy-benzoyl)-hydrazide (RG-115371)

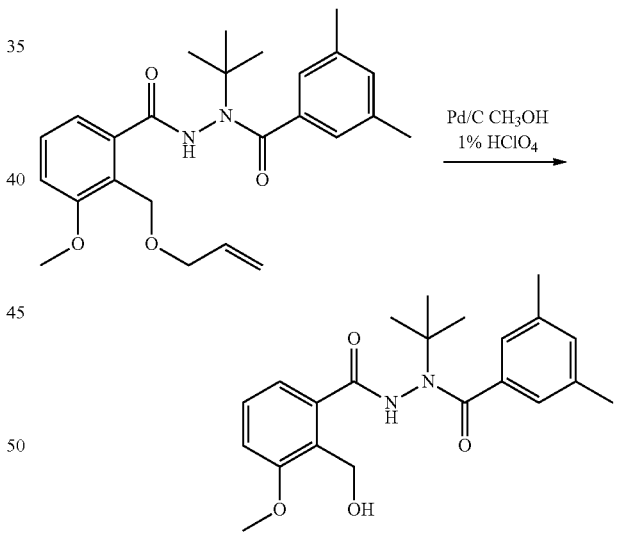

1.57 g of allyl ether were dissolved in 50 mL of CH₃OH. 600 mg of Pd/C and 20 drops of 1% HClO₄/H₂O were added and refluxed for 4 hours. CH₂Cl₂ (70 mL) and a teaspoon of anhydrous MgSO₄ were added and then filtered. The filtrate was evaporated to dryness to yield 1.62 g of crude benzylic alcohol. The product was purified by column chromatography on silica gel and eluted with 50-60% ethyl acetate/hexanes to yield 1.25 g of 3,5-dimethyl-benzoic acid N-tert-butyl-N'-(2-hydroxymethyl-3-methoxy-benzoyl)-hydrazide as a white solid. $^1$H NMR (CDCl₃, 300 MHz) δ (ppm): 7.1 (t, 1H), 7.05 (s, 2H), 6.98 (s, 1H), 6.9 (d, 1H), 6.5 (d, 1H), 4.2 (q, 2H), 3.79 (s, 3H), 2.23 (s, 6H), 1.57 (s, 9H). TLC (1:1 ethyl acetate:hexane) Rf=−0.20.

1.21 Preparation of 3,5-dimethyl-benzoic acid N-tert-butyl-N'-(2-chloromethyl-3-methoxy-benzoyl)-hydrazide (RG-115490)

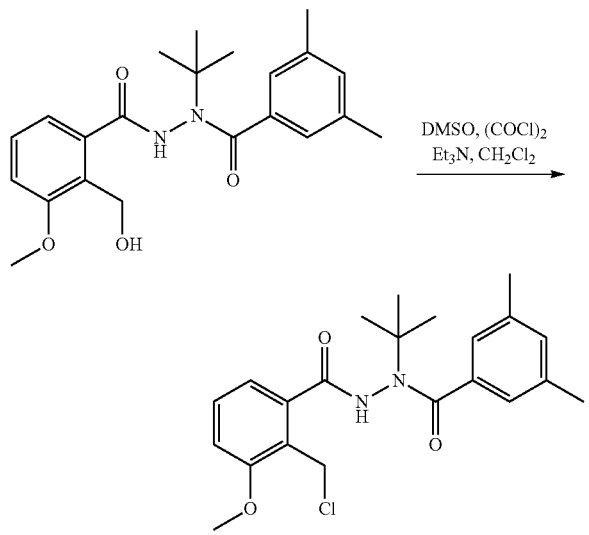

To a 50 mL round bottom flask, was added 400 mg (0.00315 mol) of oxalyl chloride and 5 mL of $CH_2Cl_2$. The mixture was stirred and then cooled in acetone/dry ice bath to $-70°$ C. 616-620 mg (0.0079 mol) of DMSO in 5 mL of $CH_2Cl_2$ was slowly added and stirred for 30 min at $-70°$ C. 405 mg (0.00105 mol) of RG-115371 in 4 mL of $CH_2Cl_2$ was added and stirred for 30 min at $-70°$ C. The dry ice bath was removed and the mixture was allowed to warm to room temperature over 30 min. The mixture was cool again to $-70°$ C. and then 1.60 g (0.158 mol) of triethylamine was added and the mixture was allowed to warm to room temperature. 6 mL of water was added to quench the reaction. $CH_2Cl_2$ was added to the flask and transferred to a separatory funnel with a total of 100 mL of $CH_2Cl_2$. 50 mL of water were added and the aqueous layer was again extracted with $CH_2Cl_2$. The $CH_2Cl_2$ extract was extracted with dilute (0.05-0.1 N) $HCl/H_2O$ to remove the $Et_3N$ and DMSO. The $CH_2Cl_2$ extract was dried and concentrated to yield about 0.44 g of product. TLC: Rf=0.47. The product can be purified by silica gel column chromatography, eluting with 35-40% ethyl acetate in hexanes. $^1H$ NMR ($CDCl_3$, 300 MHz) δ (ppm): 8.0 (s, 1H), 6.9-7.2 (t,s,s,d, 5H), 6.35 (d, 1H), 4.5 (d, 1H), 4.1 (d, 1H), 3.85 (s, 3H), 2.28 (s, 6H), 1.59 (s, 9H).

1.22 Preparation of 3,5-dimethyl-benzoic acid N-tert-butyl-N'-(2-iodomethyl-3-methoxy-benzoyl)-hydrazide

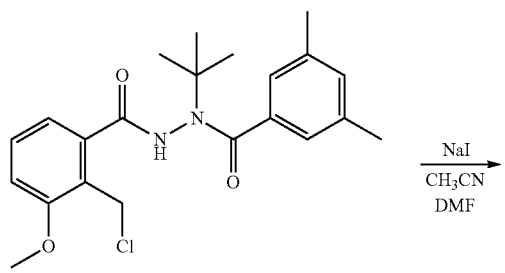

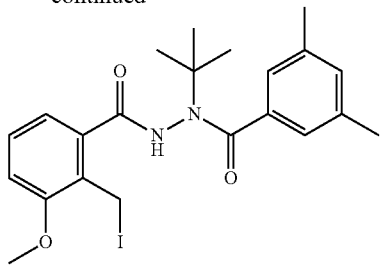

To a 50 mL flask containing 400 mg of the RG-115490, was added 10 mL of $CH_3CN$, 1 mL of DMF, and 100 mg of NaI. The mixture was refluxed for 4 hours. The reaction was poured into 250 mL of ether and 75 mL of water in a separatory funnel. The mixture was shaken vigorously and the ether layer extracted with ca. 50 mL of water. The ether extracts were dried over $MgSO_4$ and charcoal, filtered, and the solvent removed to yield 250 mg of a yellow solid. TLC Rf=0.50 (1:1 ethyl acetate:hexane). $^1H$ NMR ($CDCl_3$, 300 MHz) δ (ppm): 6.9-7.3 (m, 6H), 6.3 (d, 1H), 4.3 (d, 1H), 4.2 (d, 1H), 3.88 (s, 3H), 2.28 (s, 6H), 1.62 (s, 9H).

1.23 Preparation of 3,5-dimethyl-benzoic acid N-tert-butyl-N'-(2-methylaminomethyl-3-methoxy-benzoyl)-hydrazide (RG-115079)

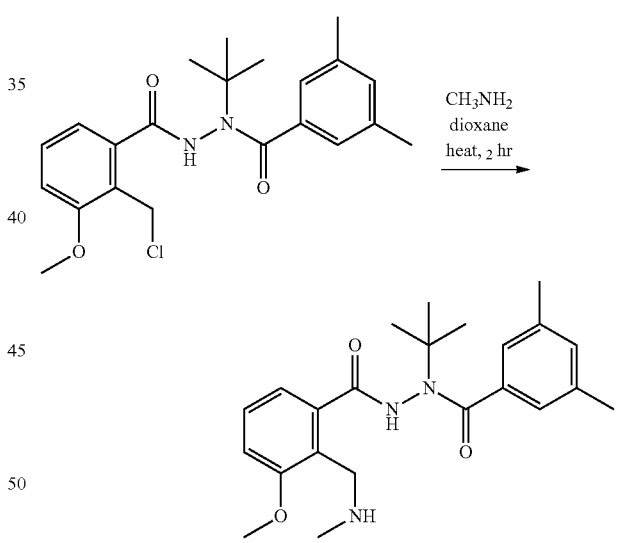

Into a small flask, containing 300 mg of the RG-15490 dissolved in 15 mL of dioxane (99.8% anhydrous, Aldrich), was added $CH_3NH_2$ in dioxane (4 eq). The reaction was refluxed for 2 hours. The solvent was removed on a rotovap, redissolved in $CH_2Cl_2$, filtered, and the $CH_2Cl_2$ solubles were concentrated. The methylamine was obtained after column chromatography by elution with ethyl acetate, then 9:1 ethyl acetate: methanol with about 0.2% triethylamine, after having run the column with 4:1 ethyl acetate:hexane, 0.2% triethylamine. The total yield of the product was 183 mg. TLC: Rf 0.23 (1:1 ethyl acetate:hexane+triethylamine). $^1H$ NMR ($CDCl_3$, 300 MHz), δ (ppm): 7.3-6.9 (m, 6H), 3.80 (s, 3H), 3.6 (d, 1H), 2.8 (d, 1H), 2.4 (s, 3H), 2.28 (s, 6H), 1.59 (s, 9H).

1.24 Preparation of 3,5-dimethyl-benzoic acid N-tert-butyl-N'-(2-dimethylaminomethyl-3-methoxy-benzoyl)-hydrazide (RG-115079)

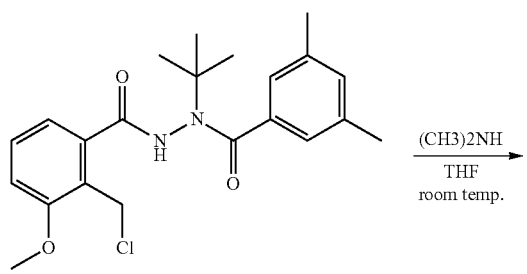

250 mg (0.0006 mol) of the RG-115490 was added to a 20 mL vial. 3 mL of THF and 0.31 mL of a 2 M dimethylamine/THF solution (Aldrich) was then added. The mixture was stirred for 4 hr at room temperature. The solvent was removed on a rotovap and the solid was triturated with hexane while stirring at room temperature. 3,5-Dimethyl-benzoic acid N-tert-butyl-N'-(2-dimethylaminomethyl-3-methoxy-benzoyl)-hydrazide: $^1$H NMR (CDCl$_3$, 300 MHz) δ (ppm): 7.1-6.9 (m, 6H), 3.93 (s, 3H), 2.68 (s, 3H), 2.54 (s, 3H), 2.24 (s, 6H), 1.61 (s, 9H).

1.25 Preparation of 3,5-dimethyl-benzoic acid N-tert-butyl-N'-(2-acetoxymethyl-3-methoxy-benzoyl)-hydrazide (RG-115225)

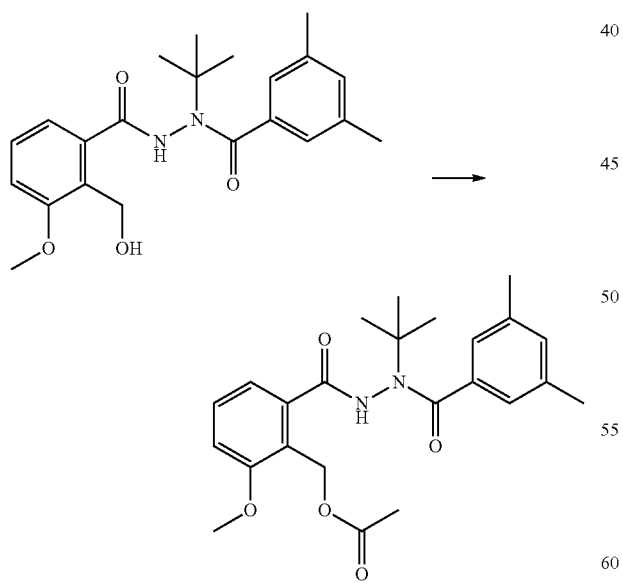

In a 20 mL vial containing 200 mg of RG-115371 in 4 mL of anhydrous CH$_2$Cl$_2$, was added 200 mg of Et$_3$N and 10 mg of CH$_3$COCl. The mixture was stirred at room temperature overnight. TLC indicated an incomplete reaction. 100 mg of acetyl chloride and some pyridine were added and refluxed for 1 hour. The reaction mixture was poured into CH$_2$Cl$_2$ and extracted with aqueous, dilute K$_2$CO$_3$, then dilute aqueous HCl. The CH$_2$Cl$_2$ extract was dried and concentrated, to yield a crude acetate. The material was purified by silica gel column chromatography, eluting with 1:1 ethyl acetate:hexane. $^1$H NMR (CDCl$_3$, 300 MHz) δ (ppm): 7.3-6.9 (m, 6H), 6.4 (d, 1H), 4.8 (d, 1H), 4.6 (d, 1H), 3.795 (s, 3H), 2.3 (s, 6H), 2.03 (s, 3H), 1.58 (s, 9H).

1.26 Preparation of 2-methanesulfonylmethyl-3-methoxy-benzoic acid N'-tert-butyl-N'-(3,5-dimethyl-benzoyl)-hydrazide (RG-115172)

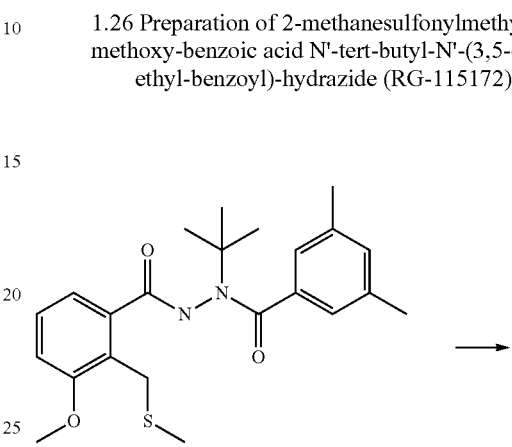

3-Methoxy-2-methylsulfanylmethyl-benzoic acid N'-tert-butyl-N'-(3,5-dimethyl-benzoyl)-hydrazide in CH$_2$Cl$_2$ was stirred at room temperature with 1.0 eq of m-chloroperbenzoic acid. The reaction was complete within 5 min as indicated by TLC. The reaction mixture was washed with saturated NaHCO$_3$ and the organic layer was stripped under vacuum. The residue was mixed with 1-2 mL of 1:1 ether:hexane and the solution was removed with a pipette, leaving the product which was then dried under vacuum.

1.27 Preparation of 2-methanesulfonylmethyl-3-methoxy-benzoic acid N'-tert-butyl-N'-(3,5-dimethyl-benzoyl)-hydrazide (RG-115408)

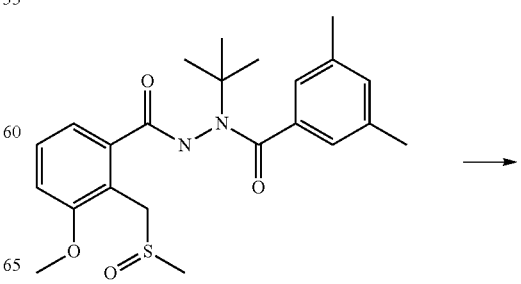

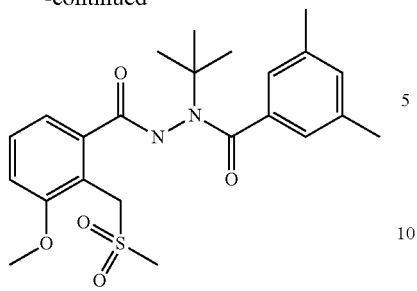

RG-115172 was dissolved in ethylene dichloride. 1.2 eq. of m-chloroperbenzoic acid was added and the mixture was heated to reflux. The reaction was complete by the time the mixture reached reflux. After cooling to ambient temperature, the solution was washed with saturated NaHCO$_3$. The organic layer was stripped under vacuum. The residue was mixed with 1-2 mL of ether and the solution was removed with a pipette, leaving the product which was dried under vacuum.

1.28 Preparation of 2,4,6-trimethyl-pyridine 1-oxide

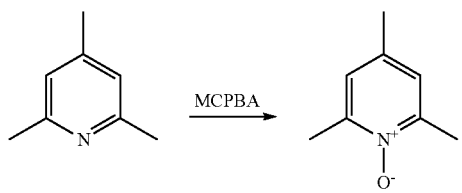

In a 500 mL round bottom flask equipped with a magnetic stirrer and thermometer were added 36.7 g (164 mmol) of 77% 3-chloroperbenzoic acid (Aldrich) and 200 mL of methylene chloride. This slurry was cooled to 5° C. and a solution of 16.6 g (137 mmol) of collidine (Aldrich) in 50 mL of methylene chloride was added over 30 min while maintaining the temperature at 5-10° C. The mixture was then allowed to warm to room temperature over 1 hr and then stirred overnight. The crude reaction mixture was transferred slowly to a beaker containing 200 g of basic alumina, which resulted in a slight warming of the mixture. The mixture was stirred and filtered and the alumina was mixed with 300 mL of 2:1 CHCl$_3$: CH$_3$OH. The solvent was removed on a rotary evaporator at room temperature. The alumina was washed with ether and the solvent was removed to yield 24.7 g of a clear liquid, which solidified to give a white, waxy solid. This yield was slightly high due to the presence of some salt. TLC (silica gel developed with methanol) showed a single major spot (Rf=0.45) along with a minor spot (Rf=0.55). The major spot was the desired N-oxide. $^1$H NMR (CDCl$_3$, 300 MHz) δ (ppm): 6.96 (s), 2.51 9 (s) and 2.28 (s). The minor spot corresponded to the starting collidine. $^1$H NMR (CDCl$_3$, 300 MHz) δ (ppm): 6.78 (s), 2.48 (s) and 2.26 (s).

1.29 Preparation of (4,6-dimethyl-pyridin-2-yl)-methanol

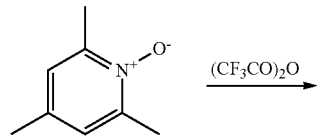

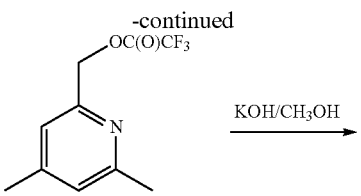

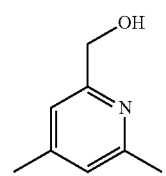

Under an atmosphere of nitrogen, 18.1 g (137 mmol) of the collidine N-oxide was dissolved in 200 mL of methylene chloride dried over molecular sieves. The mixture was cooled to 5° C. Trifluoroacetic anhydride (71.9 g, 49.8 ml, 343 mmol) was added drop-wise in portions to maintain the reaction mixture at 5-10° C. After addition of the trifluoroacetic anhydride, the mixture was allowed to warm to room temperature and then stirred at room temperature overnight. Subsequent TLC (reverse phase, methanol/water, 7:3) showed the absence of the starting N-oxide. The solvent was removed to yield the acetate product as a yellow, waxy solid. $^1$H NMR (CDCl$_3$, 300 MHz) δ (ppm): 2.5 (s, 3H), 2.8 (s, 3H), 5.65 (s, 2H), and 7.45 (m, 2H). The mixture was cooled in an ice bath and 100 mL of a 10% solution of KOH in methanol was added. The pH of the solution was checked, and if the solution was not basic, additional KOH was added to make the solution basic. The solution was then stirred at 10-15° C. for 30 min and then stirred at room temperature for 6 hours. The solvent was removed to yield 7.4 g of a yellow-brown syrup. If desired, the alcohol could be purified by careful chromatography, using silica gel and eluting with ethyl acetate/chloroform (4:1). The alcohol was isolated as a pale, yellow oil. TLC: Rf is 0.55 in silica gel, developed with methanol/ethyl acetate, 1:1. $^1$H NMR (CDCl$_3$, 300 MHz) δ (ppm): 6.67 (s, 2H), 4.67 (s, 2H), 2.50 (s, 3H) and 2.31 (s, 3H). In most cases, the crude alcohol was sufficiently pure to be used for the subsequent oxidation reaction.

1.30 Preparation of 4,6-dimethyl-2-pyridinecarboxylic acid

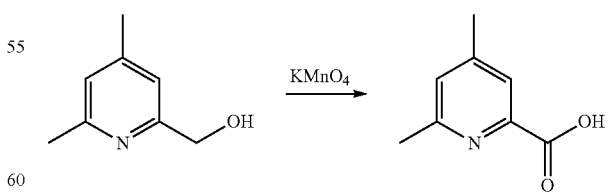

4,6-Dimethyl-2-pyridinemethanol (7.5 g, 29.2 mmol) was added to 100 mL of water and stirred at 0-5° C. A solution of 5.3 g (32.1 mmol) of potassium permanganate in 100 mL of water was added portion-wise over 30 min while maintaining the temperature at 5-10° C. This resulted in the formation of a black solid. The mixture was stirred at 5-10° C. for an additional 30 min and then allowed to stir at room temperature for 30 min. The mixture was filtered and the manganese dioxide washed with methanol. The methanol washings were combined with the water extracts and the solvent was removed. The resulting tan solid was redissolved in water and washed with chloroform. The water layer was separated and the water removed to yield 5.4 g of 4,6-dimethyl-2-pyridinecarboxylic acid. The product was characterized by HPLC/MS.

1.31 Preparation of pyrazine-2-carboxylic acid N-tert-butyl-N'-(2-ethyl-3-methoxy-benzoyl)-hydrazide (RG-115550)

Into a 20 mL vial, containing a stirred mixture of 0.120 g (0.003 mol) of NaH in 6 mL of DMF, was slowly added 0.238 g (0.001 mol) of 2-ethyl-3-methoxy-benzoic acid N'-tert-butyl-hydrazide. The reaction was stirred for 1 hr at room temperature. 0.278 g (0.001 mol) of pentafluorophenyl ester pyrazine-2-carboxylic acid pentafluorophenyl ester in 2 mL of DMF was slowly added. The reaction was stirred for 24 hours. The reaction was washed out with ethyl acetate into a separatory funnel containing 100 mL of water and 100 mL of ethyl ether. The reaction mixture was shaken and the organic phase was dried over $MgSO_4$ and concentrated to dryness to yield pyrazine-2-carboxylic acid N-tert-butyl-N'-(2-ethyl-3-methoxy-benzoyl)-hydrazide: $^1$H NMR ($CDCl_3$, 300 MHz) δ (ppm): (note—a 1:3 reaction ratio of hydrazide to NaH gave highest yield of product (100%), lesser ratios, such as 1:2, only yielded 70%; DMF was a better solvent than DMSO). The progress of the reaction was monitored by following the intensity of —$OCH_3$ signals in $^1$H NMR. $^1$H NMR (300 MHz, CDCl3) δ ppm: 9.05 (, 1H), 8.6 (s, 1H), 8.45 (s, 1H), 8.4 (s, 1H), 7.1 (t, 1H), 6.9 (d, 1H), 6.45 (d, 1H), 3.8 (s, 3H), 2.4 (m, 1H), 1.95 (m, 1H), 1.62 (s, 9H), 0.95 (t, 3H). Pyrazine-2-carboxylic acid pentafluorophenyl ester:. $^1$H NMR (300 MHz, CDCl3) δ ppm: 9.49 (s, 1H), 8.95 (d, 1H), 8.87 (d, 1H).

TABLE 1

Optimization of the preparation of RG-115550

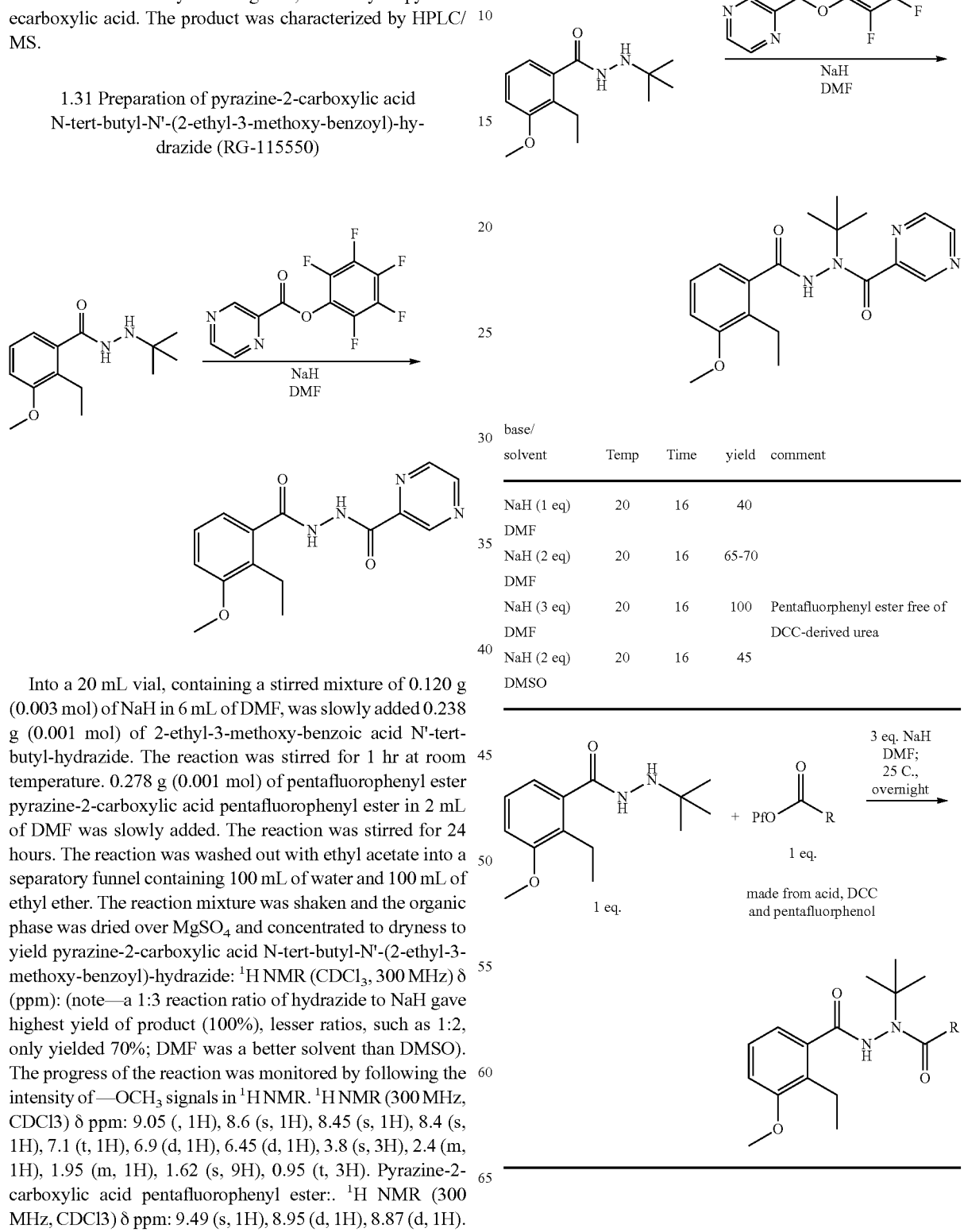

| base/solvent | Temp | Time | yield | comment |
|---|---|---|---|---|
| NaH (1 eq) DMF | 20 | 16 | 40 | |
| NaH (2 eq) DMF | 20 | 16 | 65-70 | |
| NaH (3 eq) DMF | 20 | 16 | 100 | Pentafluorphenyl ester free of DCC-derived urea |
| NaH (2 eq) DMSO | 20 | 16 | 45 | |

TABLE 2

Preparation of heterocyclic diacylhydrazines by the pentafluorophenyl ester method.

| R | NMR yield | $^1$H NMR (300 MHz, CDCl$_3$) |
|---|---|---|
| (6-methoxycarbonyl-pyridin-3-yl) | ca. 30% | Diacylhydrazine: 9.1 (s, 1H), 8.4 (d, 1H), 7.85 (d, 1H), 7.1 (t, 1H), 6.9 (d, 1H), 6.3 (d, 1H), 4.0 (s, 3H), 3.82 (s, 3H), 2.4 (m 1H), 2.1 (m 1H), 1.7 (s, 9H), 0.95 (t, 3H)<br>R-pentafluorophenyl ester: 9.45 (s, 1H), 8.6 (d, 1H), 8.4 (d, 1H), 4.04 (s, 3H) |
| (1-trityl-benzimidazol-5-yl) | ca. 20% | Diacylhydrazine: Isomer 1: 9.4 (br, 1H), 7.95 (s, 1H), 7.7 (s, 1H), 7.3 (m, 10H), 7.1 (m, 5H), 6.85 (t, 1H), 6.75 (d, 1H), 6.5 (d, 1H), 6.05 (d, 1H), 3.75 (s, 3H), 2.1 (m, 1H), 1.9 (m, 1H), 1.57 (s, 9H), 0.8 (t, 3H).<br>Isomer 2: 8.6 (br, 1H), 7.9 (s, 1H), 7.8 (s, 1H), 7.3 (m, 10H), 7.1 (m, 5H), 6.9 (t, 1H), 6.75 (d, 1H), 6.5 (d, 1H), 6.05 (d, 1H), 3.75 (s, 3H), 2.1 (m, 1H), 1.9 (m, 1H), 1.57 (s, 9H), 0.85 (t, 3H)<br>R-pentafluorophenyl ester: 8.15 (s, 1H), 8.05 (d, 1H), 7.9 (d, 1H), 7.1-7.5 (m, 15H) |
| (1-methyl-indol-2-yl) | 100% | Diacylhydrazine: 7.75 (s, 1H), 7.55 (d, 1H), 7.35 (d, 1H), 7.3 (m, 1H), 7.15 (t, 1H), 7.0 (t, 1H), 6.8 (d, 1H), 6.6 (s, 1H), 6.4 (d, 1H), 3.9 (s, 3H), 3.75 (s, 3H), 2.2 (m, 1H), 1.9 (m, 1H), 1.62 (s, 9H), 0.85 (t, 3H)<br>R-pentafluorophenyl ester: 7.75 (d, 1H), 7.65 (s, 1H), 7.5 (br s, 2H), 7.2 (m, 1H), 4.09 (s, 3H) |
| (5-methyl-1-phenyl-pyrazol-4-yl) | 100% | Diacylhydrazine: 7.85 (s, 1H), 7.65 (s, 1H), 7.5 (m, 3H), 7.4 (m, 2H), 7.15 (t, 1H), 6.9 (d, 1H), 6.65 (d, 1H), 3.81 (s, 3H), 2.6 (m, 1H), 2.5 (s, 3H), 2.2 (m 1H), 1.6 (s, 9H), 1.1 (t, 3H)<br>R-pentafluorophenyl ester: 8.25 (s, 1H), 7.6 (m, 3H), 7.5 (m, 2H), 2.62 (s, 3H) |
| (5-chloro-2-methylthio-pyrazin-3-yl) | 100% | Diacylhydrazine: 8.5 (s, 1H), 7.95 (s, 1H [NH]), 7.1 (t, 1H), 6.87 (d, 1H), 6.3 (d, 1H), 3.85 (s, 3H), 2.55 (s, 3H), 2.5 (m, 1H), 2.3 (m, 1H), 1.64 (s, 9H), 1.05 (t, 3H).<br>R-pentafluorophenyl ester: 8.8 (s, 1H), 2.62 (s, 3H) |

Procedure for pentafluorophenyl ester formation: Heterocyclic carboxylic acid and pentafluorphenol are dissolved in anhydrous dioxane, ethyl acetate, dimethoxyethane, or THF under an N$_2$ atmosphere. One equivalent of dicyclohexylcarbodiimide (DCC) is added. The reaction is stirred at room temperature overnight. A trace of water is then added to quench any remaining DCC. The DCC-derived urea (DCU) is removed by filtration on Celite, the filtrate is washed with dilute NaHCO$_3$ to remove remaining pentafluorophenol,
and the filtrate is evaporated to dryness. The product is purified by trituration or chromatography on silica gel. It is thought that the level of trace DCC or urea in the pentafluorophenyl ester may be critically detrimental to the success of the NaH amide coupling reaction.

1.32 Preparation of 1H-Indazole-3-carboxylic acid N-tert-butyl-N'-(2-ethyl-3-methoxy-benzoyl)-hydrazide (RG-115723)

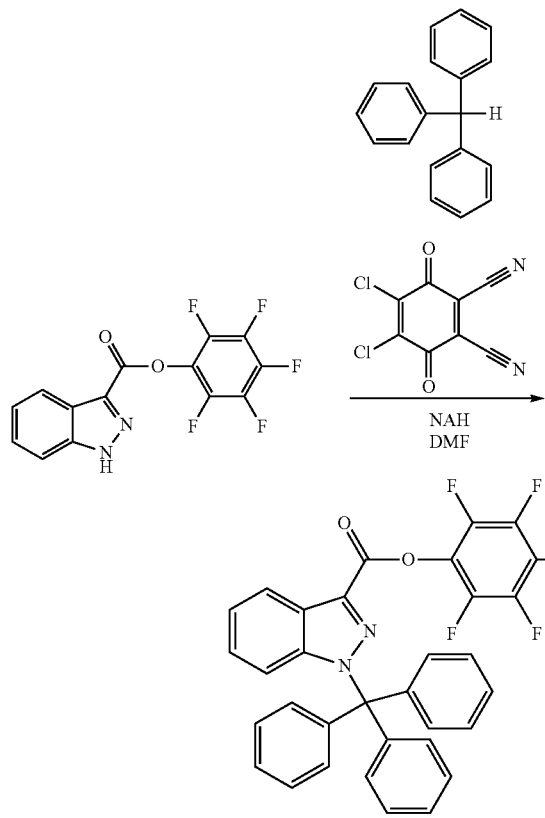

Into a 10 mL round bottom flask, was added 0.328 g (0.001 mol) of pentafluorophenyl ester of indazole-3-carboxylic acid, 0.244 g (0.001 mol) of triphenylmethane, 0.227 g (0.001 mol) of 2,3-dichloro, 5,6-dicyano, 1,4-benzoquinone and 4 mL of dry toluene. The reaction mixture was refluxed for 7-8 hours. The reaction mixture was washed out with ethyl acetate (60 mL) into a separatory funnel and extracted with water (20 mL). The organic phase was dried and concentrated to yield 0.45 g of 1-trityl-1H-indazole-3-carboxylic acid pentafluorophenyl ester. NMR indicated the presence of the product, but TLC also showed the presence of the starting pentafluorophenyl ester (Rf 57) and product (Rf 70). The product was purified by column chromatography on silica gel, eluted with 5% ethyl acetate/hexane to yield 0.30 g of pure product. $^1$H NMR (CDCl$_3$, 300 MHz) δ (ppm): 8.2 (d, 1H), 7.4-7.0 (m, 17H), 6.52 (d, 1H).

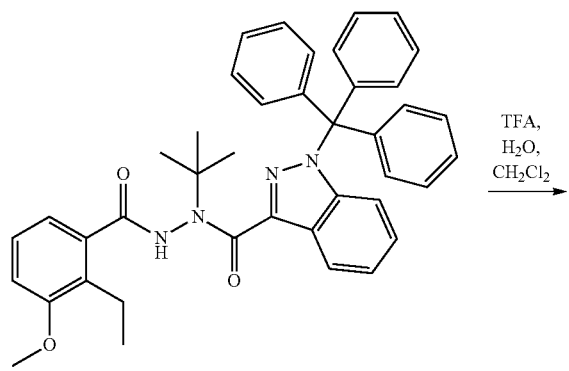

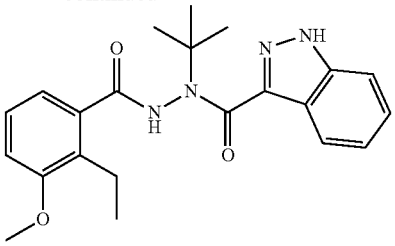

0.17 g (0.16 mmol) of 1-trityl-1H-indazole-3-carboxylic acid pentafluorophenyl ester in 3 mL of CH$_2$Cl$_2$ was added to a 100 mL flask with 20 mL of CH$_2$Cl$_2$, containing 2% TFA and 1% H$_2$O. The reaction was stirred at room temperature for 90 min. TLC indicated 50% reaction. An additional 15 mL of the TFA-H$_2$O—CH$_2$Cl$_2$ was added and stirring continued for 1 hr. The reaction was transferred to a separatory funnel and washed with ca. 0.5 M K$_2$CO$_3$/H$_2$O. The CH$_2$Cl$_2$ phase was dried and concentrated to give crude 1H-indazole-3-carboxylic acid N-tert-butyl-N'-(2-ethyl-3-methoxy-benzoyl)-hydrazide (0.15 g). TLC: product, Rf 0.33; starting material, Rf=0.68. The product was purified by column chromatography, eluting with 45% ethyl acetate/hexane. $^1$H NMR (CDCl$_3$, 300 MHz) δ (ppm): 8.6 (s, 1H), 8.2 (s, 1H), 7.4-7.2 (m, 3H), 7.1 (t, 1H), 6.9 (d, 1H), 6.7 (d, 1H), 3.80 (s, 3H), 2.4 (m, 1H), 2.0 (m, 1H), 1.652 (s, 9H), 0.85 (t, 3H).

1.33 Preparation of 3H-benzoimidazole-5-carboxylic acid N-tert-butyl-N'-(2-ethyl-3-methoxy-benzoyl)-hydrazide (RG-115718)

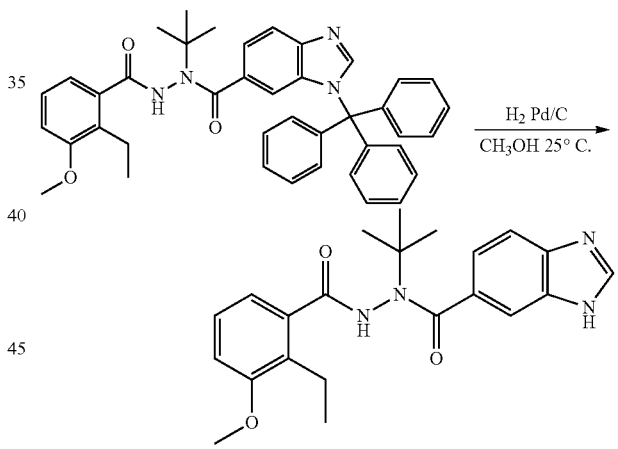

About 120 mg of 3-trityl-3H-benzoimidazole-5-carboxylic acid N-tert-butyl-N'-(2-ethyl-3-methoxy-benzoyl)-hydrazide were dissolved in 35 mL of CH$_3$OH and added into a hydrogenation bottle, together with 2 drops of glacial acid and 0.20 g Pd/C. Hydrogenation was conducted by shaking the bottle for 6 hours and then remaining under H$_2$ pressure for 16 hours. The Pd/C was removed by filtration and the methanol removed by an evaporator. The residue was stirred with CH$_2$Cl$_2$ and the CH$_2$Cl$_2$ was decanted. Evaporation of the CH$_2$Cl$_2$ yielded a solid product identified by NMR, as triphenylmethane. The residue was stirred with dilute KOH/H$_2$O and extracted with ethyl acetate. The ethyl acetate was dried and concentrated on a rotary evaporator to yield the product 3H-benzoimidazole-5-carboxylic acid N-tert-butyl-N'-(2-ethyl-3-methoxy-benzoyl)-hydrazide. NMR analysis of the product indicated the absorbances for the methoxy and t-Butyl groups occurred at 3.69 and 1.61 vs. 3.77 and 1.59 for the starting material.

1.34 Preparation of N'-2-Ethyl-3-methoxybenzoyl-N-t-butyl-N-(N-methylindole-2-carbonyl) hydrazide N'-2-Ethyl-3-methoxybenzoyl-N-t-butyl hydrazide (150 mg, 0.6 mmol) was dissolved in 2 mL of DMF. Potassium t-butoxide (80 mg, 0.7 mmol) was added and magnetically stirred for about 5 min. N-Methylindole-2-carboxylic acid pentafluorophenyl ester was added and the mixture was heated to 100° C. After 3 hours the reaction was complete as indicated by TLC. The mixture was cooled to ambient temperature and poured into 10 mL of water. Two extractions with methylene chloride were combined and evaporated. The residue was mixed with about 2 mL of 1:1 ethyl ether:hexane. The mother liquors were removed by pipette and the residue dried under vacuum. The product was a tan solid weighing 140 mg. LC MS analysis confirmed the structure and estimated the purity (UV detection) at 91%. (Yield=52%).

1.35 Preparation of 2,6-dimethoxy-nicotinic acid N-tert-butyl-N'-(5-methyl-2,3-dihydro-benzo[1,4]dioxine-6-carbonyl)-hydrazide (RG-115517)

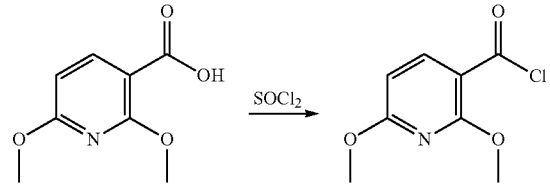

2.0 g (10.92 mmol) of 2,6-dimethoxyisonicotinic acid was dissolved in 100 mL of toluene and then 1 drop of dimethyl formamide was added. 1.55 g (13.1 mmol, 0.98 mL) of thionyl chloride was added and the solution was refluxed for 4 hours. The toluene and excess thionyl chloride were removed under vacuum and 2,6-dimethoxyisonicotinoyl chloride was used without further purification.

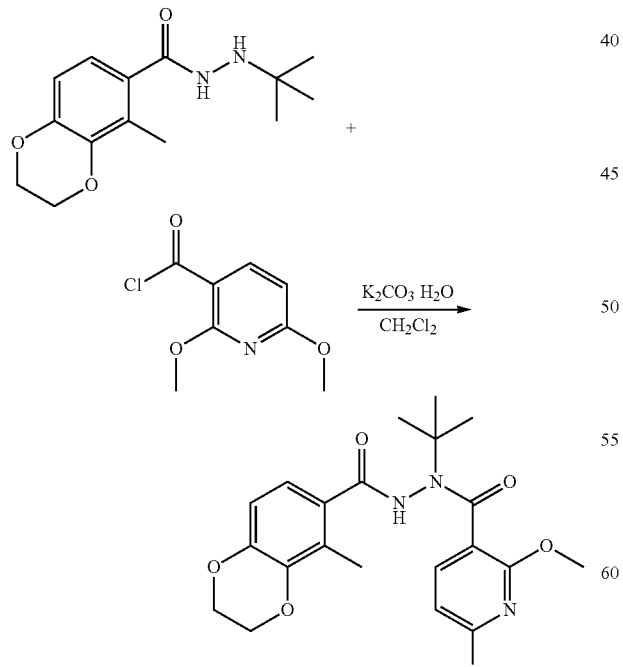

In a 1 oz vial, with a stirbar, 1 mL of 1 M $K_2CO_3$ was added. 0.250 g (1.2 mmol) of 5-methyl-2,3-dihydro-benzo[1,4]dioxine-6-carboxylic acid N'-tert-butyl-hydrazide was dissolved in 2 mL of methylene chloride and added to the aqueous solution. 2,6-dimethyl-isonicotinoyl chloride was then added and the mixture was allowed to stir at room temperature overnight. The aqueous layer was removed and the organic layer was washed twice with 2 mL of a 1 M $K_2CO_3$ solution followed by 2 mL of water. The water layer was removed and the organic layer was dried over $MgSO_4$. The organic layer was filtered and then removed. The product, 2,6-dimethoxy-nicotinic acid N-tert-butyl-N'-(5-methyl-2,3-dihydro-benzo[1,4]dioxine-6-carbonyl)-hydrazide, was purified by trituration with 1:1 ether:hexane or chromatography. $^1$H NMR (CDCl$_3$, 300 MHz) δ (ppm): 1.6 (s, 9H), 1.9 (s, 3H), 3.9 (s s, 6H), 4.2 (m, 4H), 6.2 (m, 1H), 6.7 (d, 1H), 7.7 (d, 1H), 8.3 (m, 1H).

1.36 Preparation of 4-Hydroxy-3,5-dimethoxy-benzoic acid N-tert-butyl-N'-(5-methyl-2,3-dihydro-benzo[1,4]dioxine-6-carbonyl)-hydrazide (RG-115009)

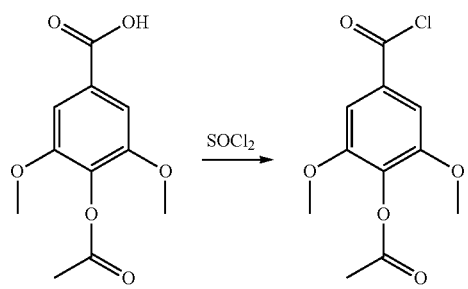

4-Acetoxy-3,5-dimethoxy-benzoic acid (1.45 g) was heated with thionyl chloride (0.86 g) in 3 mL of dimethoxyethane. After 1.5 hours the mixture was stripped under vacuum leaving 1.60 g of 4-acetoxy-3,5-dimethoxy-benzoyl chloride as an oil. $^1$H NMR (CDCl$_3$, 300 MHz) δ (ppm): 2.26 (s, 3H), 3.89 (s, 9H), 7.34 (s, 2H).

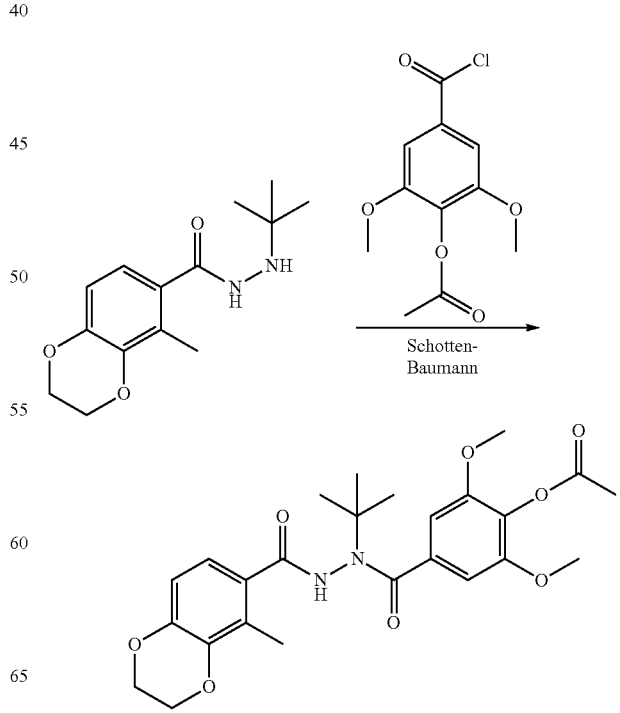

4-Acetoxy-3,5-dimethoxy-benzoyl chloride (250 mg) and 5-methyl-2,3-dihydro-benzo[1,4]dioxine-6-carboxylic acid N'-tert-butyl-hydrazide (204 mg) were dissolved in 3 mL of dichloromethane and stirred at ambient temperature with 1.5 mL of a 1 M aqueous sodium carbonate solution. After two hours the phases were separated and the organic phase was evaporated. The solid residue was washed with 1:1 ether:hexane leaving 360 mg of acetic acid 4-[N-tert-butyl-N'-(5-methyl-2,3-dihydro-benzo[1,4]dioxine-6-carbonyl)-hydrazinocarbonyl]-2,6-dimethoxy-phenyl ester. $^1$H NMR (CDCl$_3$, 300 MHz) δ (ppm): 1.60 (m, 15H), 2.06 (s, 3H), 2.32 (s, 3H), 3.77 (s, 6H), 4.2 (m, 4H), 6.08 (d, 1H), 6.63 (d, 1H), 6.74 (s, 2H).

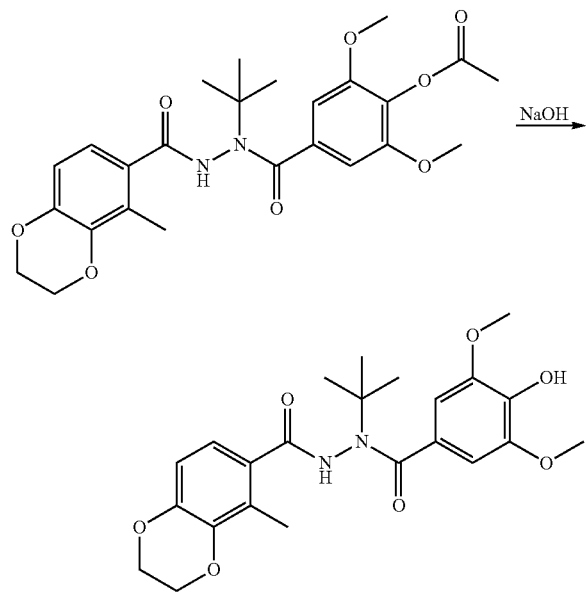

Acetic acid 4-[N-tert-butyl-N'-(5-methyl-2,3-dihydro-benzo[1,4]dioxine-6-carbonyl)-hydrazinocarbonyl]-2,6-dimethoxy-phenyl ester (300 mg) was dissolved in methanol with 28% aqueous ammonia (750 mg). The mixture was stirred at ambient temperature over the weekend. The precipitate was filtered to provide 110 mg of white solid 4-hydroxy-3,5-dimethoxy-benzoic acid N-tert-butyl-N'-(5-methyl-2,3-dihydro-benzo[1,4]dioxine-6-carbonyl)-hydrazide. $^1$H NMR (CDCl$_3$, 300 MHz) δ (ppm): 1.59 (s, 15H), 2.02 (s, 3H), 3.85 (s, 6H), 4.21 (m, 4H), 5.6-5.7 (broad s, 1H), 6.22 (d, 1H), 6.58 (d, 1H), 6.81 (s, 2H).

1.37 Preparation of Compounds RG-115613 and RG-115429

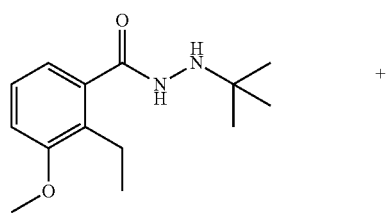 +

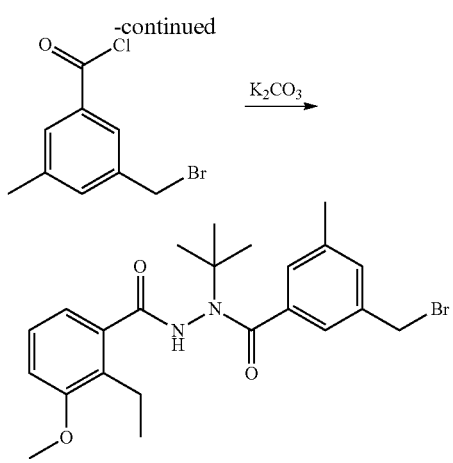

Into a 100 mL round bottom flask containing 2.50 g (10 mmol) of 2-ethyl-3-methoxy-benzoyl-N'-tert-butyl-hydrazide was added 15 mL of methylene chloride, 2.60 g (10.5 mmol) of 3-bromomethyl-5-methylbenzoyl chloride in 5 mL of methylene chloride and a solution of 2.76 g (20 mmol) of potassium carbonate in 15 mL of water. The reaction mixture was stirred overnight at room temperature, then diluted with 20 mL of methylene chloride and transferred to a separatory funnel. The methylene chloride layer was separated and dried, and the solvent was removed in vacuo. The crude product was purified by column chromatography to yield 4.01 g of N-(3-bromomethyl-5-methyl-benzoyl)-N-tert-butyl-N'-(2-ethyl-3-methoxy-benzoyl) hydrazide (87% yield). $^1$H NMR (CDCL$_3$, 300 MHz) δ (ppm): 7.41 (s, 1H), 7.1 (m, 3H), 7.02 (t, 1H), 6082 (d, 1H), 6.08 (d, 1H), 4.41 (s, 2H), 3.78 (s, 3H), 2.4 (m, 1H), 2.31 (s, 3H), 2.25 (m, 1H), 1.60 (s, 9H), 1.01 (t, 3H).

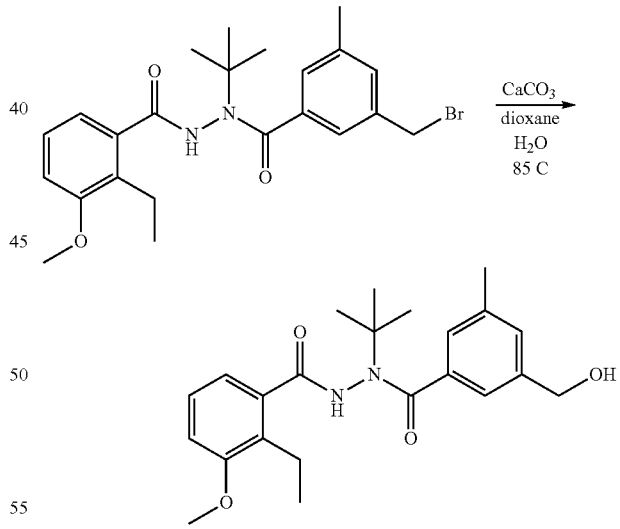

To 4.00 g (8.68 mmol) of N-(3-bromomethyl-5-methyl-benzoyl)-N-tert-butyl-N'-(2-ethyl-3-methoxy-benzoyl) hydrazide, contained in a 250 mL round bottom flask, were added 40 mL of dioxane, 40 mL of water, and 4.34 g of calcium carbonate. The reaction flask was placed into an 85° C. oil bath and the reaction was stirred and heated for 18 hours. The reaction mixture was cooled, transferred to a larger flask with ethyl acetate and most of the dioxane was evaporated. The reaction mixture was shaken with about 100 mL of ethyl acetate and filtered. The ethyl acetate layer was separated and the aqueous layer extracted twice with ethyl acetate. Ethyl acetate extract was dried and evaporated to yield 2.07 g of N-(3-hydroxymethyl-5-methyl-benzoyl)-N-tert-butyl-N'-(2-ethyl-3-methoxy-benzyl) hydrazide (60% yield). $^1$H NMR (300 MHz, CDCl$_3$) δ (ppm): 7.78 (s, 1H), 7.1-7.4 (3s, 3H), 6.96 (t, 1H), 6.8 (d, 1H), 6.08 (d, 1H), 4.53 (s, 2H), 3.77 (s, 3H), 2.35 (m, 1H), 2.32 (s, 3H), 2.2 (m, 1H), 1.60 (s, 9H), 0.96 (t, 3H).

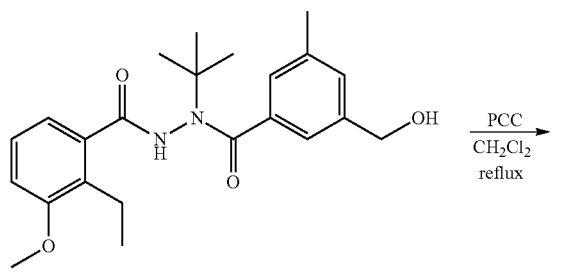

To 2.00 g (5.02 mmole) of N-(3-hydroxymethyl-5-methyl-benzoyl)-N-tert-butyl-N'-(2-ethyl-3-methoxy-benzyl)hydrazide placed in a 250 mL round bottom flask, were added 100 mL of methylene chloride and 1.16 g of pyridinium chlorochromate. The reaction mixture was refluxed for about 1 hour, at which time TLC (1:1 ethyl acetate:hexane) indicated the formation of the product (R$_f$=0.5). The reaction mixture was concentrated to about 20 mL and then chromatographed on silica gel. Elution with 30-35% ethyl acetate in hexane yielded 1.75 g (88%) 3-formyl-5-methyl-benzoic acid N-tert-butyl-N'-(2-ethyl-3-methoxy-benzoyl)-hydrazide as a white solid. $^1$H NMR (300 MHz, CDCl$_3$) δ (ppm): 9.93 (s, 1H), 7.6-7.8 (3s, 3H), 7.0 (t, 1H), 6.82 (d, 1H), 6.19 (d, 1H), 3.77 (s, 3H), 2.42 (s, 3H), 2.3 (m, 1H), 2.0 (m, 1H), 1.62 (s, 9H), 0.90 (t, 3H).

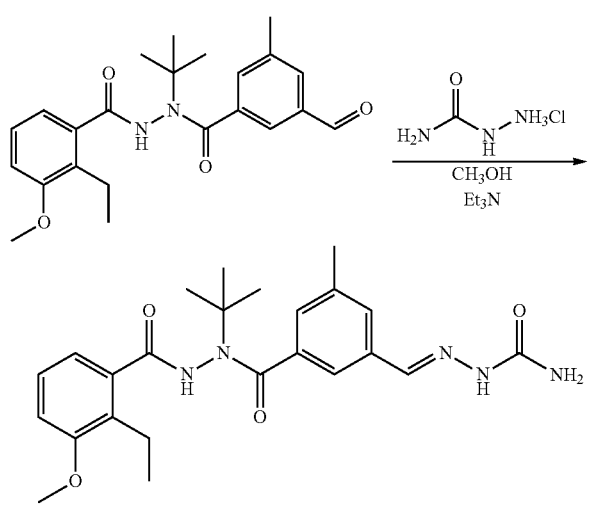

RG-115429

To 100 mg (0.25 mmoles) of N-(3-formyl-5-methyl-benzoyl)-N-tert-butyl-N'-(2-ethyl-3-methoxy-benzoyl)hydrazide placed in a 20 mL vial, were added 2 mL of methanol, 112 mg of semicarbazide hydrochloride, 0.2 g triethylamine and a drop of glacial acetic acid. The reaction mixture was magnetically stirred on a hot plate adjusted to 50° C. for about 3 hours, then at room temperature for 48 hours. The solvent was evaporated with a stream of nitrogen and the resulting residue was dissolved in 20 mL of chloroform and extracted with dilute HCl. The chloroform extract was dried, the solvent was removed in vacuo, and the residue was dried in a vacuum oven at 60° C. The residue was cooled and triturated with hexane to yield 81 mg of semicarbazide of N-(3-formyl-5-methyl-benzoyl)-N-tert-butyl-N'-(2-ethyl-3-methoxy-benzoyl) hydrazide. $^1$H NMR (300 MHz, CDCl$_3$) δ (ppm): 8.9 (broad s, 1H), 8.6 (broad s, 1H), 7.3-7.5 (3s, 3H), 7.03 (t, 1H), 6.8 (d, 1H), 6.38 (d, 1H), 3.76 (s, 3H), 3.26 (d, 1H), 2.4 (s, 3H), 1.95 (m, 1H), 1.57 (s, 9H), 0.95 (t, 3H).

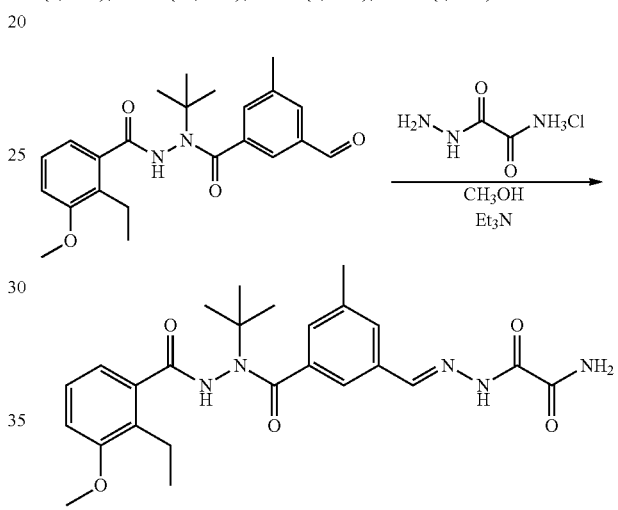

To 100 mg (0.25 mmol) of N-(3-formyl-5-methyl-benzoyl)-N-tert-butyl-N'-(2-ethyl-3-methoxy-benzoyl)hydrazide placed in a 20 mL vial, was added 2 mL of methanol, 103 mg of oxamic hydrazide hydrochloride, and a drop of glacial acetic acid. The reaction mixture was magnetically stirred on a hot plate adjusted to 50° C. for about 3 hours, then at room temperature for 48 hours. The solvent was evaporated with a stream of nitrogen and the resulting residue was dried in a vacuum oven at 60° C. The residue was cooled and triturated with hexane to yield 70 mg of oxamic hydrazone of N-(3-formyl-5-methyl-benzoyl)-N-tert-butyl-N'-(2-ethyl-3-methoxy-benzoyl) hydrazide. $^1$H NMR (300 MHz, DMSO-d$_6$) δ (ppm): 8.5 (s, 1H), 8.6 (d, 1H), 7.9 (d, 1H), 7.55 (s, 1H), 7.5 (s, 1H), 7.3 (s, 1H), 7.0 (t, 1H), 6.95 (d, 1H), 3.73 (s, 3H), 2.2 (m, 1H), 2.35 (s, 3H), 1.95 (m, 1H), 1.51 (s, 9H), 0.80 (t, 3H).

1.38 Preparation of 3,5-dichloro-4-fluorobenzoic acid (N-(3-methoxy-2-methylbenzoyl)-N'-(3,5-dichloro-4-fluorobenzoyl)-N'-tert-butylhydrazine can be prepared according to U.S. Pat. No. 5,530,028. Briefly, the product of Example 8 and 3,5-dichloro-4-fluorobenzoyl chloride can be prepared in accordance with Example 9 to yield (N-(3-methoxy-2-methylbenzoyl)-N'-(3,5-dichloro-4-fluorobenzoyl)-N'-tert-butylhydrazine.

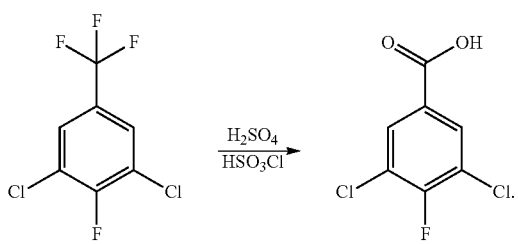

3,5-dichloro-4-fluorobenzoyl chloride can be prepared as follows: To a round bottom flask with nitrogen purge through a 10% aqueous NaOH trap, was added 3,5-dichloro-4-flurobenzotriflouride (5.00 g, 21.46 mmol, Aldrich), concentrated sulfuric acid (4.30 g, 42.92 mmol), and finally chlorosulfonic acid (5.15 g, 43.78 mmol). The reaction began to bubble immediately. After the bubbling subsided, the mixture was heated to 80° C. for 1 hr, cooled to room temperature, and added cautiously to stirred ice water. This was extracted twice with methylene chloride. The combined extracts were washed with water and brine, dried over magnesium sulfate, filtered, and evaporated to give a white solid (2.19 g) of 3,5-dichloro-4-fluorobenzoic acid in 49% yield. $^1$H-NMR (CD$_3$COCD$_3$, 300 MHz) δ (ppm): 7.95 (d, 2H).

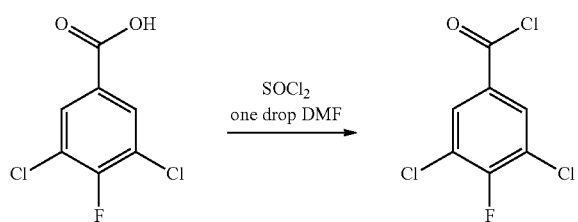 [SMILES: O=C(O)c1cc(Cl)c(F)c(Cl)c1 ; O=C(Cl)c1cc(Cl)c(F)c(Cl)c1]

3,5-dichloro-4-fluorobenzoic acid was refluxed with >1 equivalent of thionyl chloride and one drop of DMF neat or as a solution in CHCl$_3$. The solvent and volatile by-products were removed in vacuo to provide 3,5-dichloro-4-fluorobenzoyl chloride.

1.39 Preparation of 3,5-dimethoxy-4-methyl-2-nitrobenzoic acid N-t-butyl-N'-(5-methy-1benzo-1,4-dioxan-6-carbonyl)-hydrazide (RG-115609)

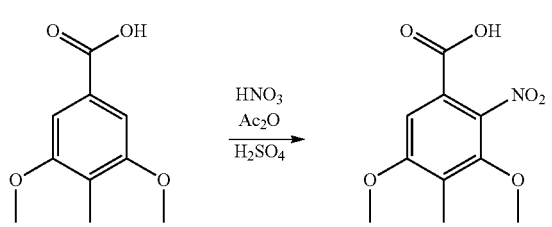 [SMILES: COc1cc(C(=O)O)cc(OC)c1C ; "H2SO4" ; COc1cc(C(=O)O)c([N+](=O)[O-])c(OC)c1C]

3,5-Dimethoxy-4-methylbenzoic acid was slurried with 2.7 eq. Of acetic anhydride and 0.05 molar equivalents of concentrated sulfuric acid in dichloromethane. After cooling to 10° C., 1.05 eq. Of 70% nitric acid was added drop-wise while the temperature was maintained below 15 θC. After 30 min the mixture was poured into water and extracted twice with ethyl acetate. The combined organic extracts were concentrated until a thick slurry was present. The slurry was filtered and the solid washed with ice-cold dichloromethane. Further concentration of the mother liquors gave a second crop. The total yield of 3,5-dimethoxy-4-methyl-2nitrobenzoic acid was about 80%. $^1$H NMR: (acetone-d6, 300 MHz) δ (ppm): 7.34 (s, 1H), 4.00 (s, 3H), 3.85 (s, 3H), 2.23 (s, 3H).

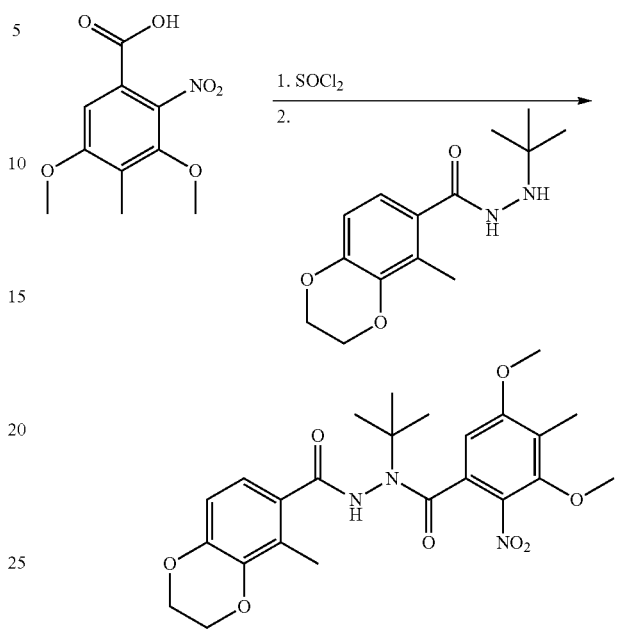

3,5-Dimethoxy-4-methyl-2nitrobenzoic acid was stirred with 1.1 eq. Of thionyl chloride at ambient temperature in dimethoxyethane until the reaction was complete. The solvent and excess thionyl chloride were distilled at atmospheric pressure and the residue dissolved in dichloromethane. This solution was added to a mixture of 1 M aqueous potassium carbonate and 5-methylbenzo-1,4-dioxan-6-benzoic acid-N'-t-butyl-hydrazide in dichloromethane. After 3 hr, water and dichloromethane were added. The organic phase was removed and stripped under vacuum. The residue was triturated with 1:1 (wt: wt) ether:hexane to provide 3,5-dimethoxy-4-methyl-2-nitrobenzoic acid N-t-butyl-N'-(5-methy-1benzo-1,4-dioxan-6-carbonyl)-hydrazide (ca 94% yield). TLC (1:1 ethyl acetate:hexane) indicated one spot, Rf 0.53. $^1$H NMR: (CDCl$_3$, 300 MHz) δ (ppm): 7.84 (s, 1H), 7.02 (t, 1H), 6.86 (d, 1H), 6.82 (s, 1H), 6.11 (s, 1H), 3.90 (m, 4H), 3.79 (s, 6H), 2.16 (s, 3H), 1.60 (s, 9H).

1.40 Preparation of 3,5-dimethyl-benzoic acid N'-(2,3-dimethyl-benzoyl)-N-(1-ethyl-2,2-dimethyl-propyl)-hydrazide (RG-103309)

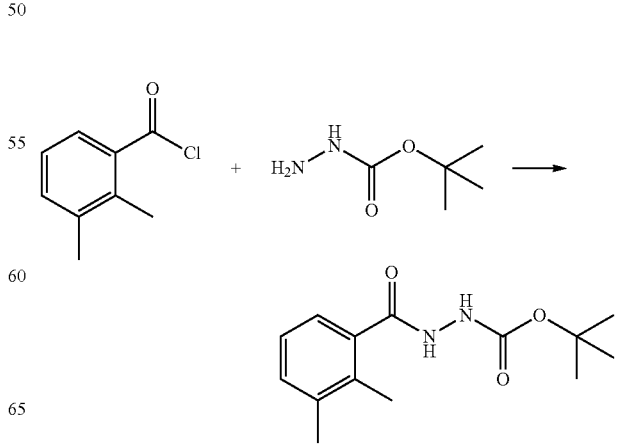

T-butylcarbazate (35.15 g, 266 mmol) and 200 mL of CH₂Cl₂ were added to a round bottom flask. Potassium carbonate (55.2 g, 0.4 moles) dissolved in 350 mL of water was added to the flask, and the mixture was stirred for 15 minutes with ice chilling. 2,3 dimethylbenzoyl chloride (44.9 g, 266 mmol) in ca. 200 mL of CH₂Cl₂ was added drop-wise from a 500 mL separatory funnel over 30 minutes. The reaction was allowed to stir overnight and then the reaction mixture was poured into a 1 L separatory funnel and the CH₂Cl₂ phase was separated. Then ca. 150 mL of water was added, and the mixture was extracted twice with 150 mL of CHCl₃. The combined organic phase was back-extracted with 100 mL of water, then with 1N HCl (250 mL), to remove the hydrazide. The organic phase was dried, stirred with charcoal, and the solvent removed in vacuo to yield a light tan solid (71.5 g) of N'-(2,3-dimethyl-benzoyl)-hydrazinecarboxylic acid, tert-butyl ester. $^1$H NMR (300 MHz, CHCl₃) δ (ppm): 7.7 (br, 1H), 7.22 (m, 2H), 7.1 (t, 1H), 7.85 (br, 1H), 2.35 (s, 3H), 2.3 (s, 3H), 1.5 (s, 9H).

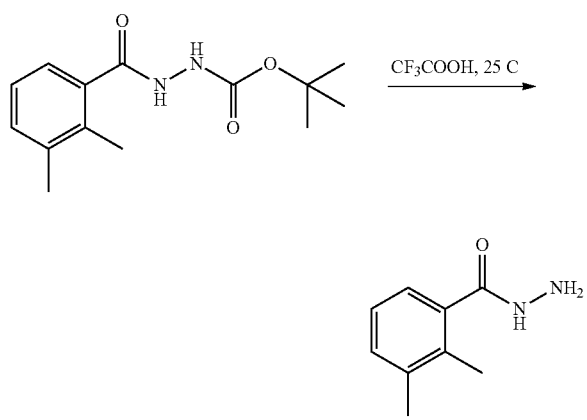

N'-(2,3-Dimethyl-benzoyl)-hydrazinecarboxylic acid, tert-butyl ester (70.3 g, 266 moles) was placed in to a 500 mL round bottom flask. With gentle stirring, 200 mL of trifluoroacetic acid (296 g, 2.6 moles) was slowly added, resulting in a vigorous evolution of gas. The reaction mixture was then stirred at room temperature for 2 hours. Water (ca. 100 mL) was then added slowly to the mixture. The mixture was slowly added to 1 L of a cold 2 M K₂CO₃ solution, contained in a 2 L beaker, while stirring slowly (evolution of gas). About 200 mL of a 10% NaOH solution and 250 mL of CH₂Cl₂ were added. The reaction mixture was transferred to a large separatory funnel and gently shaken (gas evolution). The aqueous phase was extracted with CHCl₃ and the extracts dried and evaporated to yield a white solid, which was dried in a 50° C. vacuum oven to yield 31.72 g (73% yield) of 2,3-dimethyl-benzoic acid hydrazide. $^1$H NMR (CDCl₃, 300 MHz) δ (ppm): 7-7.3 (m, 4H), 4.00 (br s, 2H), 2.271 (s, 6H).

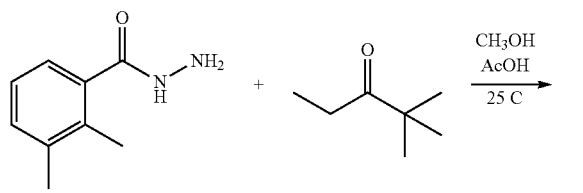

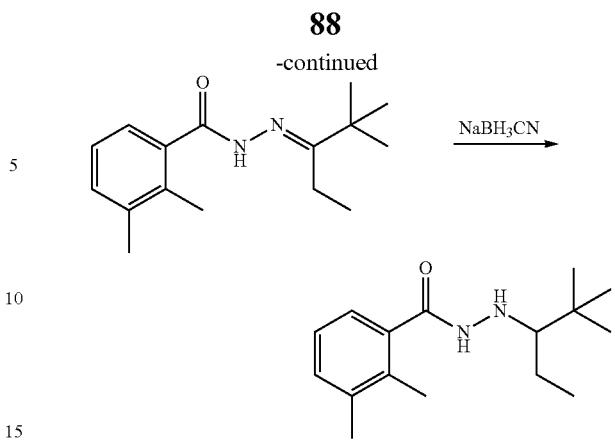

In a 200 mL round bottom flask, 7.90 g (48 mmol) of 2,3-dimethyl-benzoic acid hydrazide was dissolved in 60 mL of methanol and 3 drops of glacial acetic acid were then added. To the reaction mixture was added 6.00 g (52.6 mmol) of 2,2-dimethylpentan-3-one, and the reaction was stirred at room temperature for 24 hours. The product hydrazone was not isolated, but subjected directly to reduction. Glacial acetic acid (10 mL) and sodium cyanoborohydride (3.2 g, 50.95 mmol) were added to the reaction mixture, which was then stirred at room temperature for 24 hours. About 50 mL of 10% aqueous NaOH solution was added and most of the CH₃OH was removed on a rotary evaporator. The reaction was diluted with water (100 mL) and the product was extracted with CH₂Cl₂. The organic extract was dried and evaporated to yield 11.87 g (94%) of 2,3-dimethyl-benzoic acid N'-(1-ethyl-2,2-dimethyl-propyl)-hydrazide. $^1$H NMR (500 MHz, CDCl₃) δ (ppm): 7.0-7.3 (m, 4H), 2.32 (s, 3H), 2.296 (s, 3H), 1.7 (m, 1H), 1.3 (m, 1H), 1.16 (t, 3H), 0.979 (s, 9H). TLC: Rf=0.57 (1:1 ethyl acetate:hexane), indicated >90% purity. Further purification can be achieved by silica gel chromatography and elution of product with 20% ethyl acetate in hexanes.

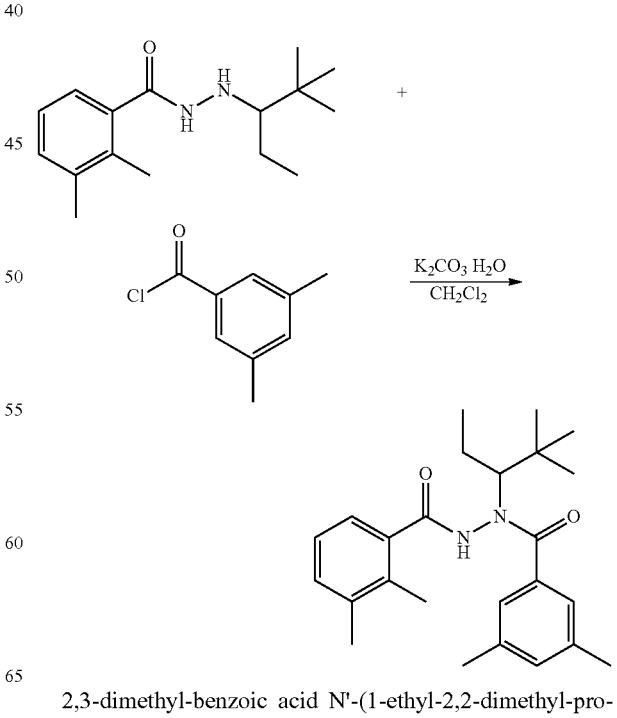

2,3-dimethyl-benzoic acid N'-(1-ethyl-2,2-dimethyl-propyl)-hydrazide (0.59 g, 2.25 mmol) was dissolved in 15 mL of CH$_2$Cl$_2$ in a small round-bottom flask. Aqueous K$_2$CO$_3$ solution (0.70 g in 150 mL of H$_2$O) was added. 3,5-dimethylbenzoyl chloride (0.45 g, 2.7 mmol) dissolved in 10 mL of CH$_2$Cl$_2$ was added and the reaction mixture was stirred at room temperature for 24 hours. The reaction mixture was transferred to a separatory funnel and extracted with CH$_2$Cl$_2$. (In another experiment, this was washed with weak NaOH to get rid of excess acid and acid chloride). The extract was dried and evaporated to give about 1 g of a white solid, which was purified by silica gel chromatography. Elution with 15% ethyl acetate in hexane yielded pure product of 3,5-dimethyl-benzoic acid N'-(2,3-dimethyl-benzoyl)-N-(1-ethyl-2,2-dimethyl-propyl)-hydrazide (0.62 g, 70%). $^1$H NMR (500 MHz, CDCl$_3$) δ=(ppm): 6.95-7.4 (m, 7H), 4.61 (m, 1H), 2.2-2.4 (multiple s, 9H), 1.81 (s, 3H), 1.6-1.8 (m, 2H), 1.3 (br t, 3H), 1.08 (multiple br s, 9H).

1.41 Preparation of 3,5-dimethyl-benzoic acid N-(1-ethyl-2,2-dimethyl-propyl)-N'-(3-methoxy-2-methyl-benzoyl)-hydrazide (RG-115819)

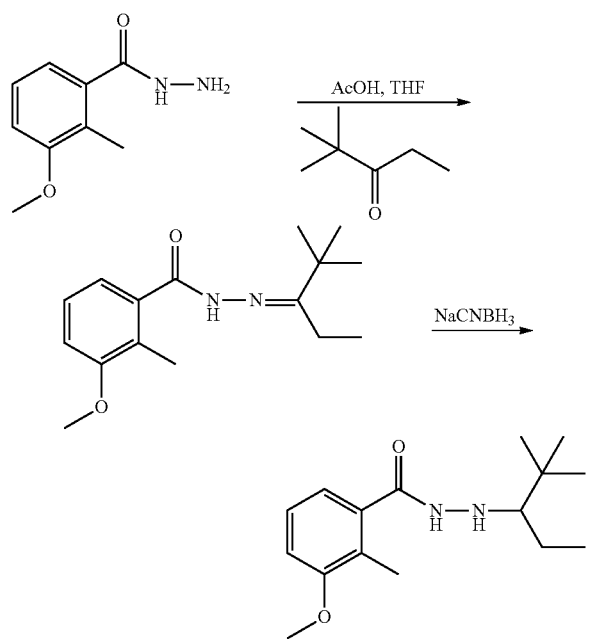

10.34 g (57.5 mmol) of 3-methoxy-2-methyl-benzoic acid hydrazide (lot CPO 10925) was dissolved in 100 mL of methanol and stirred. 9.80 g (86.3 mmol) of 2,2-dimethyl-3-pentanone was added followed by 3 drops of glacial acetic acid. The mixture was allowed to stir for 48 hours. The crude mixture was then brought to pH=3. 3.84 g (61.2 mmol) of NaCNBH$_3$ was then added. The slurry was allowed to stir at room temperature overnight, and then the methanol was removed. 100 mL of 10% NaOH and 100 mL methylene chloride were added. The mixture was shaken and the methylene chloride layer removed. The aqueous layer was washed twice with 75 mL of methylene chloride. The methylene chloride layers were combined and dried. Removal of the solvent yielded the desired product as a pale, yellow liquid. The product could also be obtained by reduction of the hydrazide with 10% Pd on carbon. Purification was accomplished by column chromatography on silica gel, eluting with 3:2 hexane:ether. $^1$H NMR (CDCl$_3$, 300 MHz) δ (ppm): 1.0 (s, 9H), 1.1 (t, 3H) 1.2 (m, 1H), 1.5 (m 2H), 2.1 (s, 3H), 3.8, (s, 3H), 4.9 (br s, 1H), 6.6 (d, 1H), 7.0-7.2 (m, 2H). TLC: Rf=0.45 (1:1 hexane:ether).

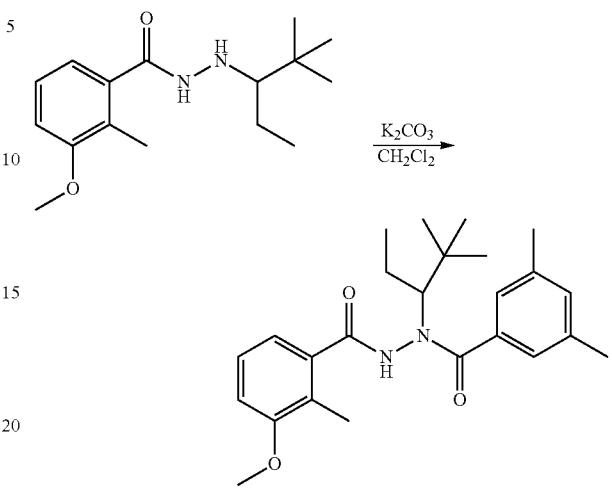

6.2 g (22.1 mmol) of 3-methoxy-2-methyl-benzoic acid (1-ethyl-2,2-dimethyl-propyl)-hydrazide was dissolved in 35 mL of ethyl acetate and cooled to 0° C. 74 mL of a 1N aqueous K$_2$CO$_3$ was added and the mixtures stirred. 5.6 g (33.6 mmol) of 3,5-dimethylbenzoyl chloride was dissolved in 40 mL ethyl acetate and this solution was added to the hydrazide mixture over 15 min. The mixture was allowed to warm to room temperature and stirred overnight. The aqueous layer was then removed and the organic layer was washed with 75 mL of a 1N aqueous K$_2$CO$_3$ solution and then with 100 mL of water. The water layer was removed and the organic layer was dried and removed to yield an off-white solid. This material was triturated three times with 25 mL of 1:1 hexane:ether to yield the final product in 98.7% purity. $^1$H NMR (CDCl$_3$, 300 MHz) δ (ppm): 0.7-1.5 (m, 15H), 2.1 (s, 9H), 3.7 (s, 3H), 6.8-7.1, (m, 6H).; TLC: Rf=0.62 (1:1 hexane:ether).

1.42 Preparation of 3,5-dimethoxy-4-methyl-benzoic acid N-(1-ethyl-2,2-dimethyl-propyl)-N'-(3-methoxy-2-methyl-benzoyl)-hydrazide (RG-115820)

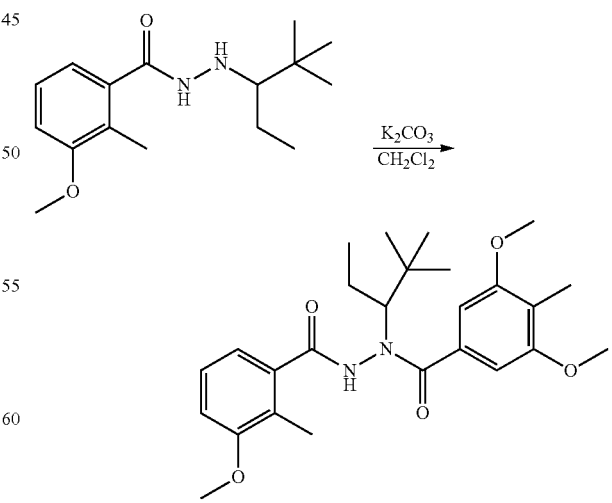

RG-115820

Into a 20 mL vial was added 161 mg (0.75 mmol) of 3,5 dimethoxy, 4-methyl benzoyl chloride, a 5 mL solution of 3-methoxy-2-methyl-benzoic acid N'-(1-ethyl-2,2-dimethyl-propyl)-hydrazide, and 1.5 mL of aqueous 25% K₂CO₃. The reaction mixture was stirred at room temperature for 24 hours. The reaction mixture was transferred to a separatory funnel with CH₂Cl₂ and shaken with dilute aqueous NaHCO₃. The organic phase was dried, concentrated and chromatographed on silica. 100 mg of pure product, 3,5-dimethoxy-4-methyl-benzoic acid N-(1-ethyl-2,2-dimethyl-propyl)-N'-(3-methoxy-2-methyl-benzoyl)-hydrazide, was eluted with 25% ethyl acetate/hexane. TLC: Rf=0.54 (1:1 ethyl acetate:hexane); ¹H NMR (CDCl₃, 300 MHz) δ (ppm): 6.6-7.2 (m, 4H), 6.25 (d, 1H), 4.6 (d, 1H), 3.8-3.95 (br s, 9H), 2.1 (br s, 3H), 1.9 (s, 3H), 1.6 (br, 2H), 1.3 (m, 3H), 0.9-1.2 (br d, 9H).

1.43 Preparation of 2,2-dimethyl-heptan-3-ol

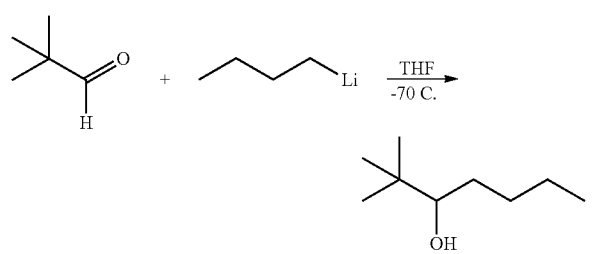

20 g (0.232 mol) of pivaldehyde dissolved in 600 mL of THF was added to a 2 L 3-neck round bottom flask equipped with a magnetic stir bar, thermometer and rubber stopper. The vessel was maintained under N₂. The reaction mixture was cooled to -65° C. in a dry ice/acetone bath. 112 mL (0.279 mol) of a 2.5 M BuLi solution in hexane was slowly added in 5 mL portions with a 20 mL glass syringe, maintaining the temperature below -55° C. The reaction was stirred at -60° C. for one hour, then allowed to warm to -5° C. over one hour. The reaction was cooled again to -60° C. and slowly quenched with NH₄Cl/H₂O solution, maintaining the temperature below -50° C. 100 mL of water were added and the reaction was allowed to warm to room temperature. The THF was removed on a rotary evaporator with a bath temperature of 25° C. until an oil was observed. The product was extracted with ethyl ether, and the ether was dried and evaporated carefully to yield 31.0 g of 2,2-dimethyl-heptan-3-ol that was used directly in a subsequent oxidation reaction. ¹H NMR (CDCl₃, 500 MHz) δ (ppm): 3.2 (m, 1H), 1.2-1.7 (m, 3H), 0.93 (m, 3H), 0.89 (s, 9H).

1.44 Preparation of 2,2-dimethyl-heptan-3-one

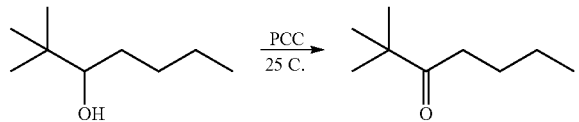

2,2-Dimethyl-heptan-3-ol (0.23 mol) was dissolved in 350 mL of CH₂Cl₂ in a 500 mL round bottom flask with a magnetic stirbar. The flask was partially cooled with ice. 76.6 g (0.355 mol) of pyridinium chlorochromate was added, while vigorously stirring. The reaction turned black and warmed up slightly. The reaction mixture was stirred at room temperature for 24 hours. The solution was decanted away from the black sludge, which was rinsed with hexane. The organic extracts were combined and chromatographed directly on silica gel. (Note: only silica has been found to trap and remove the reduced non-reacted chromium compounds). The product, 2,2-dimethyl-heptan-3-one, eluted with CH₂Cl₂/hexane and in a subsequent 10% ethyl acetate/hexane fraction to yield 29.19 g of product at 88% yield. ¹H NMR (CDCl₃, 500 MHz) δ (ppm): 2.48 (t, 2H), 1.54 (m, 2H), 1.28 (m, 2H), 1.13 (s, 9H), 0.90 (m, 3H).

1.45 Preparation of 3-methoxy-2-methyl-benzoic acid N'-(1-tert-butyl-pentyl)-hydrazide 2.84 g (20 mmol) of 2,2-dimethyl-heptan-3-one, 3.60 g (20 mmol) of 2-methyl, 3-methoxy benzoic acid hydrazide, 20 drops of glacial acetic acid and 40 mL of 100% ethyl alcohol were refluxed for 4 hours and then stirred at room temperature for 24 hours. TLC indicated only a 35% reaction. Accordingly, the reaction mixture was refluxed for an additional 6 hours. TLC indicated ca. 80% reaction (TLC Rf=0.57, starting hydrazide, Rf=0.08, 1:1 ethyl acetate:hexane). To the reaction mixture was added, 3.5 mL of glacial acetic acid and 1.89 g (30 mmol) of NaCNBH₃. The mixture was stirred at room temperature for 2 hours and refluxed for 1 hour. 50 mL of water was added and 15% NaOH was added until the reaction mixture was basic. Most of the alcohol was removed on a rotary evaporator and the product was extracted with CHCl₃, to yield 4.28 g of crude material. TLC indicated the product hydrazide at Rf 0.54 (1:1 ethyl acetate:hexane). Purification by gradient chromatography on silica yielded 3.03 g of product, which eluted in a 25-40% ethyl acetate/hexane fraction. Drying in a vacuum oven at 55° C. eliminated volatile materials, yielding 2.69 g of 3-methoxy-2-methyl-benzoic acid N'-(1-tert-butyl-pentyl)-hydrazide. $^1$H NMR (CDCl$_3$, 500 MHz) δ (ppm): 7.2 (t, 1H), 7.05 (br, 1H[NH]), 6.9 (m, 2H), 4.9 (br, 1H), 3.84 (s, 3H), 2.5 (m, 1H), 2.3 (s, 3H), 1.2-1.8 (m, 6H), 0.97 (s, 9H), 0.92 (t, 3H).

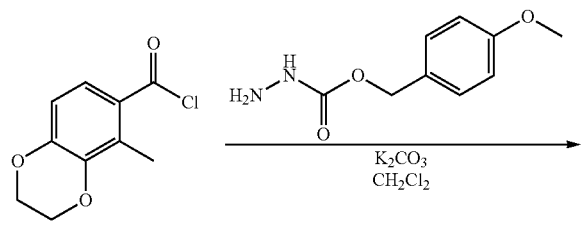

17.8 5 g (90.98 mmol) of 4-methoxybenzyl carbazate was dissolved in 50 mL of CH$_2$Cl$_2$ in a 250 mL flask and then cooled in ice water. 21.42 g (155 mmol) of potassium carbonate dissolved in 80 mL of water was added. While the reaction mixture was being stirred in the ice bath, 17.0 g (79.95 mmol) of 5-methyl-2,3-dihydro-benzo[1,4]dioxine-6-carbonyl chloride in 60 mL of CH$_2$Cl$_2$ were slowly added. The reaction mixture was stirred at room temperature overnight and then transferred to a separatory funnel with 200 mL of CH$_2$Cl$_2$ and 200 mL of H$_2$O. After shaking, a floating white precipitate was filtered off, washed with water, dried in a vacuum oven to give 29.1 g of N'-(5-methyl-2,3-dihydro-benzo[1,4]dioxine-6-carbonyl)hydrazinecarboxylic acid 4-methoxy-benzyl ester. The CH$_2$Cl$_2$ solution was dried and concentrated to give 5.19 g of a residue consisting of the original acid chloride, 4-methoxybenzyl carbazate, and some product. TLC Rf=0.38 (streak 1:1 ethyl acetate:hexane). $^1$H NMR (CDCl$_3$, 300 MHz) δ (ppm): 7.4-6.7 (m, 6H), 5.139 (s 2H), 4.279 (s 4H), 3.81 (s, 3H), 2.303 (s, 3H).

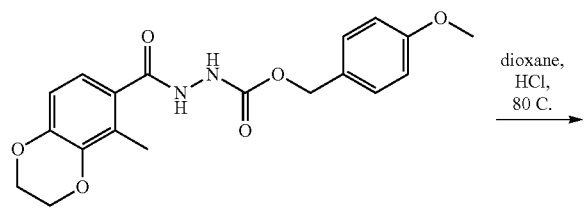

In a 500 mL volume flask, was combined 18.6 g (0.0499 moles) of N'-(5-methyl-2,3-dihydro-benzo[1,4]dioxine-6-carbonyl)-hydrazinecarboxylic acid 4-methoxy-benzyl ester, 72 mL of concentrated HCl, and 108 mL of dioxane. The flask was placed into an 80° C. oil bath and mechanically stirred for 2 hours. The reaction mixture was cooled with ice water, then poured onto ice water and transferred to a separatory funnel. The reaction mixture—H$_2$O solution was then extracted twice with 150 mL of CH$_2$Cl$_2$ to remove the acids and neutrals (the starting material). The aqueous phase was made basic (pH 12) with a 20% NaOH solution and extracted 4 times with 150 mL of ethyl acetate. The ethyl acetate extract was dried over MgSO$_4$ and concentrated to yield 4.5 g of 5-methyl-2,3-dihydro-benzo[1,4]dioxine-6-carboxylic acid hydrazide. $^1$H NMR (CDCL$_3$, 300 MHz) δ (ppm): 7.0 (s, 1H), 6.85 (d, 1H), 6.74 (d, 1H), 4.28 (m, 4H), 2.781 (s, 3H).

1.46 Preparation of 5-methyl-2,3-dihydro-benzo[1.4]dioxine-6-carboxylic acid N'-(1-ethyl-2,2-dimethyl-propyl)-hydrazide

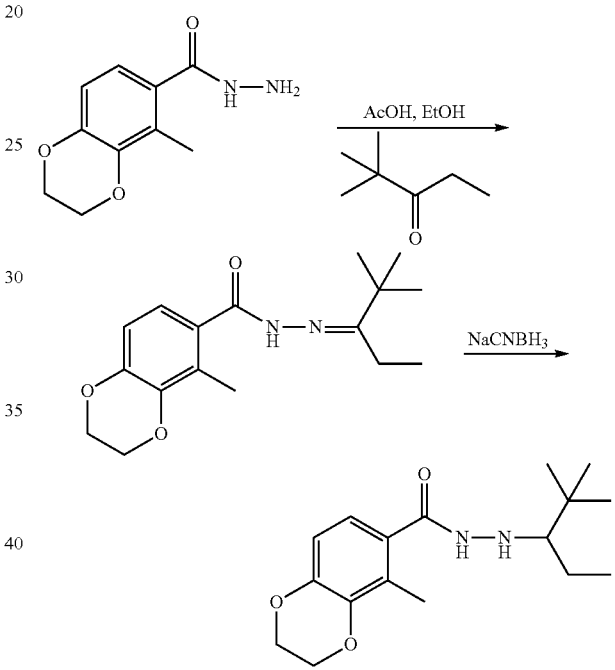

0.86 g (4.1 mmol) of -methyl-2,3-dihydro-benzo[1,4]dioxine-6-carboxylic acid hydrazide and 1.14 g (10 mmol) of 2,2 dimethyl pentan-3-one, 30 mL of ethyl alcohol and 20 drops of glacial acetic acid were refluxed for 6 hours. TLC indicated ca. a 60% conversion to 5-methyl-2,3-dihydro-benzo[1,4] dioxine-6-carboxylic acid (1-ethyl-2,2-dimethyl-propylidene)-hydrazide (Rf=0.40, 1:1 ethyl acetate:hexane). The reaction was cooled, 3 mL of glacial acetic acid followed by 0.63 g (10 mmol) of sodium cyanoborohydride were added, and the reaction was stirred at room temperature for 3 hours. Most of the alcohol was removed on a rotary evaporator. 30 mL of water was added, followed by the addition of 10% NaOH/H$_2$O until the reaction mixture was basic. The mixture was extracted extensively with ethyl acetate. The ethyl acetate extract was dried and evaporated to give 1.2 g of crude material. The product was purified by column chromatography on silica gel, eluting with 20-30% ethyl acetate/hexane. About 0.46 g of pure 5-methyl-2,3-dihydro-benzo[1,4]dioxine-6-carboxylic acid N'-(1-ethyl-2,2-dimethyl-propyl)-hydrazide was obtained. TLC: Rf=0.46 (1:1 ethyl acetate:hexane). $^1$H NMR (CDCl$_3$, 500 MHz) δ (ppm): 7.1 (br, 1H[NH]), 6.85 (d, 1H), 6.71 (d, 1H), 4.8 (br, 1H), 4.29 (m, 2H), 4.25 (m, 2H), 2.4 (m, 1H), 2.29 (s, 3H), 1.7 (m, 1H), 1.3 (m, 1H), 1.15 (t, 3H), 0.98 (s, 9H).

1.47 Preparation of RG-115858, 3,5-dimethyl-benzoic acid N'-(5-ethyl-2,3-dihydro-benzo[1,4]dioxine-6-carbonyl)-N-(1-ethyl-2,2-dimethyl-propyl)-hydrazide

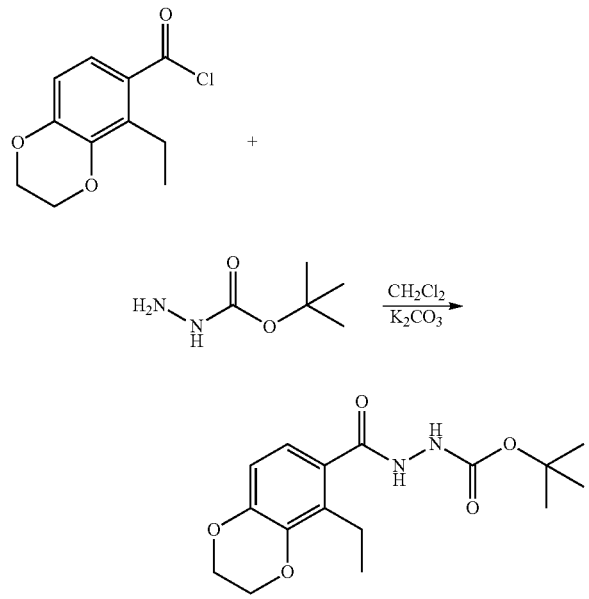

2.38 g (18 mmol) of t-butyl carbazate were dissolved in 50 mL of CH₂Cl₂ in a 250 mL round bottom flask and cooled to 0° C. An aqueous K₂CO₃ solution was prepared (4.15 g K₂CO₃/35 mL H₂O) and added to the reaction mixture which was again cooled to 0° C. 3.63 g (16 mmol) of 5-ethyl-2,3-dihydro-benzo[1,4]dioxine-6-carbonyl chloride were dissolved in 40 mL of CH₂Cl₂ and added from a separatory funnel, drop-wise over 15 min. The reaction mixture was stirred at room temperature for 3 days. The reaction mixture was transferred to a separatory funnel with CH₂Cl₂ and H₂O. The water phase was thoroughly extracted with CH₂Cl₂. The CH₂Cl₂ extract was then extracted with 0.5N HCl, dried, and evaporated. The residue was further dried in a vacuum oven to yield 5.15 g of a tan solid of N'-(5-ethyl-2,3-dihydro-benzo[1,4]dioxine-6-carbonyl)-hydrazinecarboxylic acid tert-butyl ester. TLC (1:1 ethyl acetate:hexane) gave a single spot at Rf=0.43 and NMR indicated a very pure product: ¹H NMR (CDCl₃, 500 MHz) δ (ppm): 7.5 (br, 1H), 7.0 (br, 1H), 6.75 (d, 2H), 4.28 (br, 4H), 2.76 (m, 2H), 1.5 (s, 9H), 1.18 (t, 3H).

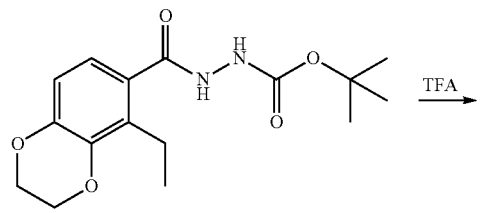

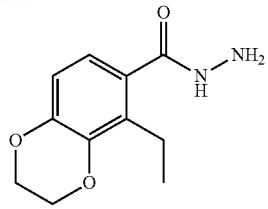

5.15 g (16 mmol) of N'-(5-ethyl-2,3-dihydro-benzo[1,4]dioxine-6-carbonyl)-hydrazinecarboxylic acid tert-butyl ester were added to a 200 mL round bottom flask. About 20 mL of trifluoroacetic acid were added and the reaction mixture was stirred at room temperature for 24 hours. Then about 40 mL of water were added, followed by the slow addition of cold 10% NaOH/H₂O, with stirring, until the acid was neutralized (pH ~14). The reaction mixture was transferred to a separatory funnel and extracted with ethyl acetate by shaking gently (caution: gas evolution). The ethyl acetate extract was dried and evaporated to yield 5.51 g of a pale, viscous yellow semi-solid. The material was then placed in a 50° C. vacuum oven for about 1 hour to yield 4.62 g of 5-ethyl-2,3-dihydro-benzo[1,4]dioxine-6-carboxylic acid hydrazide. The t-Boc cleavage is best accomplished with neat trifluoroacetic acid; use of adjunctive solvents always resulted in much lower yields. ¹H NMR (CDCl₃, 500 MHz) δ (ppm): 7.0 (br, 1H), 6.83 (m, 1H), 6.71 (m, 1H), 4.28 (br s, 4H), 2.76 (m, 2H), 1.6 (br, 2H), 1.17 (t, 3H).

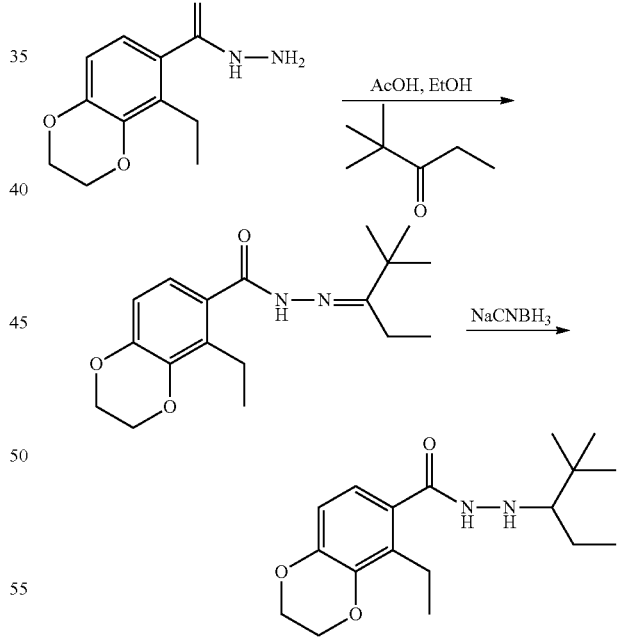

1.12 g (5.1 mmol) of 5-ethyl-2,3-dihydro-benzo[1,4]dioxine-6-carboxylic acid hydrazide, 1.37 g (12 mmol) of 2,2 dimethyl pentanone-3, 30 mL of ethanol, and 20 drops of glacial acetic acid were refluxed for 6 hours to generate 5-ethyl-2,3-dihydro-benzo[1,4]dioxine-6-carboxylic acid (1-ethyl-2,2-dimethyl-propylidene)-hydrazide, which was used in situ. To the cooled reaction mixture, was added 3 mL of glacial acetic acid and 0.63 g (10 mmol) of NaCNBH₃. The reaction was stirred at room temperature for 24 hours. 25 mL of water were added and most of the alcohol was removed on a rotary evaporator. Then 10% NaOH/H$_2$O was added until the reaction mixture was basic. The product was extracted with ethyl acetate, which was then dried and evaporated to give 1.61 g of residue. Pure 5-ethyl-2,3-dihydro-benzo[1,4]dioxine-6-carboxylic acid N'-(1-ethyl-2,2-dimethyl-propyl)-hydrazide was obtained (ca. 0.77 g) by column chromatography on silica gel, eluting with 25% ethyl acetate/hexane. TLC: Rf=0.53, 1:1 ethyl acetate:hexane). $^1$H NMR (CDCl$_3$, 500 MHz) δ (ppm): 7.1 (br s, 1H), 6.8 (d, 1H), 6.7 (d, 1H), 4.27 (m, 4H), 2.8 (m, 2H), 2.4 (m, 1H), 1.7 (m, 1H), 1.3 (m, 1H), 1.2 (t, 3H), 1.15 (t, 3H), 0.97 (s, 9H).

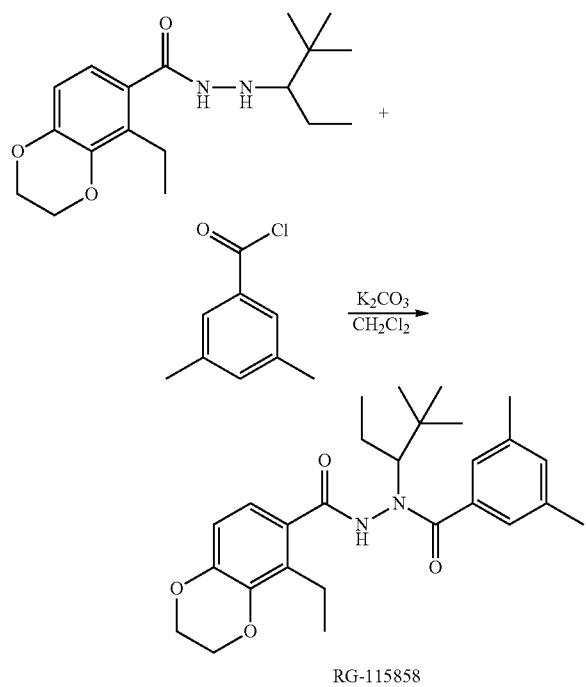

RG-115858

0.214 g (0.70 mmol) of 5-ethyl-2,3-dihydro-benzo[1,4]dioxine-6-carboxylic acid N'-(1-ethyl-2,2-dimethyl-propyl)-hydrazide, 151 mg (0.9 mmol) of 3,5 dimethylbenzoyl chloride, 7 mL of 25% K$_2$CO$_3$/H$_2$O and 7 mL of CH$_2$Cl$_2$ were added to a 20 mL vial and stirred at room temperature for 24 hours. The reaction mixture was transferred to a separatory funnel, and dilute NaHCO$_3$ and CH$_2$Cl$_2$ were added. The CH$_2$Cl$_2$ layer was separated and the water layer extracted twice with CH$_2$Cl$_2$. The CH$_2$Cl$_2$ extracts were dried over MgSO$_4$ and evaporated to yield 0.59 g of a white residue. Purification by column chromatography and elution with 15 mL of 20% ethyl acetate/hexane yielded about 350 mg of 3,5-dimethyl-benzoic acid N'-(5-ethyl-2,3-dihydro-benzo[1,4]dioxine-6-carbonyl)-N-(1-ethyl-2,2-dimethyl-propyl)-hydrazide (95% pure by TLC: Rf=0.56, 1:1 ethyl acetate:hexane). $^1$H NMR (CDCl$_3$, 500 MHz) δ (ppm): 7.05 (s, 1H), 7.0 (s, 2H), 6.6 (d, 1H), 6.27 (d, 1H), 4.65 (d, 1H), 4.25 (s, 4H), 2.9 (m, 1H), 2.3 (s, 6H), 2.0 (m, 1H), 1.55-1.7 (m, 2H), 1.25 (m, 3H), 0.9-1.2 (3s, 9H), 0.9 (t, 3H).

The following compounds were prepared in a similar manner:

3,5-Dimethoxy-4-methyl-benzoic acid N-(1-tert-butyl-butyl)-N'-(2-ethyl-3-methoxy-benzoyl)-hydrazide. TLC: Rf=0.45, 3:2 (hexane: acetone).

RG-115851, 3,5-dimethyl-benzoic acid N-(1-tert-butyl-pentyl)-N'-(3-methoxy-2-methyl-benzoyl)-hydrazide. $^1$H NMR (CDCl$_3$, 500 MHz), δ (ppm): 7.7 (s, 1H), 7.22, 7.1 (2 br s, 1H), 7.08 (s, 2H), 7.0 (s, 1H), 6.87 (m, 1H), 6.28 (m, 1H), 4.7 (m, 1H), 3.78 (s, 3H), 2.28 (s, 6H), 1.8 (s, 3H), 1.3-1.6 (br m, 6H), 1.2, 1.1, 0.95 (3s, 9H), 0.95 (m, 3H); TLC Rf=0.56 (1:1 ethyl acetate:hexane).

RG-115852, 3,5-dimethoxy-4-methyl-benzoic acid N-(1-tert-butyl-pentyl)-N'-(3-methoxy-2-methyl-benzoyl)-hydrazide. $^1$H NMR (CDCl$_3$, 500 MHz), δ (ppm): 7.05 (t, 1H), 7.0 (s, 1H), 6.85 (d, 1H), 6.65 (s, 2H), 6.25 (d, 1H), 4.7 (d, 1H), 3.89 (s, 3H), 3.78 (s, 6H), 2.10 (s, 3H), 1.86 (s, 3H), 1.3-1.6 (br m, 6H), 1.06, 0.99 (2s, 9H), 0.94 (t, 3H); TLC Rf=0.55 (1:1 ethyl acetate:hexane).

3,5-Dimethyl-benzoic acid N-(1-ethyl-2,2-dimethyl-propyl)-N'-(5-methyl-2,3-dihydro-benzo[1,4]dioxine-6-carbonyl)-hydrazide. $^1$H NMR (CDCl$_3$, 500 MHz), δ (ppm): 7.05 (s, 2H), 7.0 (s, 1H), 6.6 (d, 1H), 6.3 (d, 1H), 4.6 (d, 1H), 4.25 (m, 4H), 2.25 (s, 6H), 1.85 (s, 3H), 1.5-1.8 (br, 2H), 1.3 (t, 3H), 1.0-1.2 (2s, 9H); TLC Rf=0.52 (1:1 ethyl acetate:hexane).

3,5-Dimethoxy-4-methyl-benzoic acid N-(1-ethyl-2,2-dimethyl-propyl)-N'-(5-methyl-2,3-dihydro-benzo[1,4]dioxine-6-carbonyl)-hydrazide. $^1$H NMR (CDCl$_3$, 500 MHz), δ (ppm): 6.8 (br s, 1H), 6.62 (s, 1H), 6.6 (d, 1H), 6.27 (d, 1H), 4.6 (d, 1H), 4.25 (m, 4H), 3.84, 3.78 (2s, 6H), 2.1 (s, 3H), 1.87 (s, 3H), 1.6 (br, 2H), 1.3 (t, 3H), 0.9-1.2 (m, 9H); TLC Rf=0.45 (1:1 ethyl acetate:hexane).

3,5-Dimethyl-benzoic acid N-(1-tert-butyl-butyl)-N'-(5-methyl-2,3-dihydro-benzo[1,4]dioxine-6-carbonyl)-hydrazide. $^1$H NMR (CDCl$_3$, 500 MHz), δ (ppm): 7.05 (s, 2H), 7.0 (s, 1H), 6.6 (d, 1H), 6.3 (d, 1H), 4.7 (d, 1H), 4.2 (m, 4H), 2.3 (s, 6H), 1.8 (s, 3H), 1.3-1.7 (br m, 4H), 1.1, 1.15 (2s, 9H), 0.95 (t, 3H).

3,5-Dimethoxy-4-methyl-benzoic acid N-(1-tert-butyl-butyl)-N'-(5-methyl-2,3-dihydrobenzo[1,4]dioxine-6-carbonyl)-hydrazide. $^1$H NMR (CDCl$_3$, 500 MHz), δ (ppm): 6.75 (br s, 1H), 6.62 (s, 1H), 6.6 (d, 1H), 6.25 (d, 1H), 4.7 (t, 1H), 4.25 (m, 4H), 3.78, 3.84 (2s, 6H), 2.85 (br, 1H), 2.37 (m, 1H), 2.07 (s, 3H), 1.86 (s, 3H), 1.3-1.7 (br m, 4H), 3,5-Dimethoxy-4-methyl-benzoic acid N'-(5-ethyl-2,3-dihydro-benzo[1,4]dioxine-6-carbonyl)-N-(1-ethyl-2,2-dimethyl-propyl)-hydrazide. $^1$H NMR (CDCl$_3$, 500 MHz), δ (ppm): 6.8 (br s, 1 h), 6.65 (s, 1H), 6.6 (d, 1H), 6.25 (d, 1H), 4.6 (d, 1H), 4.25 (2s, 4H), 3.79-3.84 (2s, 6H), 2.9 (br, 1H), 2.35 (br, 1H), 2.1 (s, 3H), 1.3-1.9 (br m, 2H), 1.3 (t, 3H), 1.1-1.3 (m, 9H), 0.94 (t, 3H); TLC Rf=0.48 (1:1 ethyl acetate:hexane).

3,5-Dimethyl-benzoic acid N-(1-tert-butyl-butyl)-N'-(5-ethyl-2,3-dihydro-benzo[1,4]dioxine-6-carbonyl)-hydrazide. $^1$H NMR (CDCl$_3$, 500 MHz), δ (ppm): 7.05 (s, 2H), 7.0 (s, 1H), 6.59 (d, 1H), 6.18 (d, 1H), 4.7 (d, 1H), 4.27, 4.25 (s, 4H), 2.85 (m, 1H), 2.3 (s, 6H), 2.1 (m, 1H), 1.3-1.8 (br m, 4H), 1.1, 1.15 (2s, 9H), 0.95 (t, 6H); TLC Rf=0.53 (1:1 ethyl acetate:hexane).

3,5-Dimethoxy-4-methyl-benzoic acid N-(1-tert-butyl-butyl)-N'-(5-ethyl-2,3-dihydro-benzo[1,4]dioxine-6-carbonyl)-hydrazide. $^1$H NMR (CDCl$_3$, 500 MHz), δ (ppm): 6.75 (br s, 1H), 6.62 (s, 1H), 6.6 (d, 1H), 6.2 (d, 1H), 4.7 (m, 1H), 4.25 (br m, 4H), 3.84, 3.78 (2s, 6H), 2.4 (m, 1H), 1.95 (m, 1H), 2.1 (s, 3H), 1.2-1.8 (br m, 4H), 1.1-0.95 (m, 9H), 0.95 (m, 6H). TLC: 0.54 (1:1 ethyl acetate: hexane); TLC Rf=0.54 (1:1 ethyl acetate:hexane).

1.48 Preparation of RG-115665

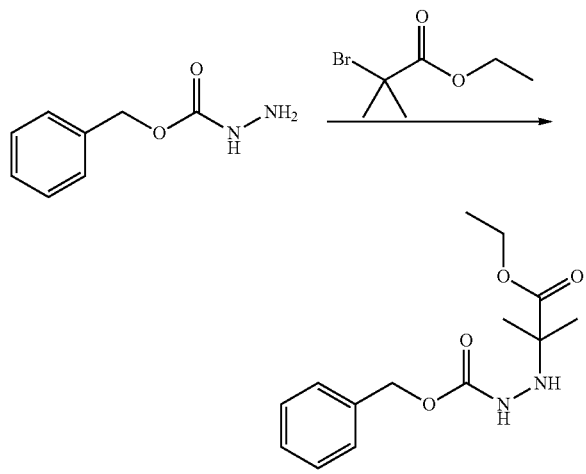

Benzyl carbazate (25 g, 0.15 mol) was dissolved in 50 mL of DMF in a round bottom flask. The solution was heated to 95-100° C. From two separate addition funnels, ethyl 2-bromoisobutyrate (58.5 g, 0.3 mol) and pyridine (29.7 g, 0.375 mol, 30 mL) were added drop-wise separately and simultaneously over 30-120 minutes. Heating was continued if necessary to propel the reaction to completion. The reaction was monitored by TLC (30% ethyl acetate in hexanes, $I_2$ visualization). The mixture was allowed to cool, and then poured onto ice water. The aqueous mixture was extracted with ethyl ether, and the solvent was removed in vacuo. 2-(N'-benzyloxycarbonyl-hydrazino)-2-methyl-propionic acid ethyl ester was isolated, optionally after silica gel chromatography. $^1$H NMR (300 MHz, CDCl$_3$) δ (ppm): 7.36 (br s, 5H), 6.6 (br s, 1H), 5.15 (br s, 2H), 4.2 (q, 2H), 1.3 (s, 6H), 1.25 (t, 3H). $^1$H NMR analysis alone is insufficient to ascertain the extent of the reaction.

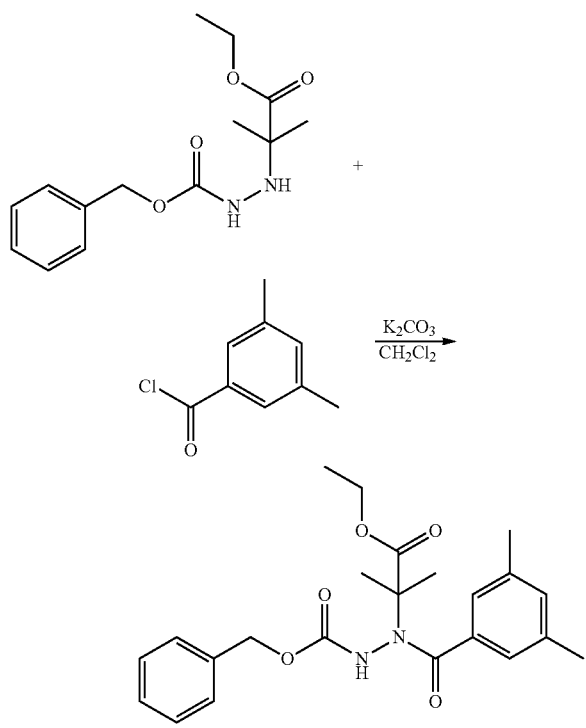

2-(N'-benzyloxycarbonyl-hydrazino)-2-methyl-propionic acid ethyl ester (28 g, 0.1 mol) was dissolved in 50 mL CH$_2$Cl$_2$ and cooled on ice. A solution of 20.7 g K$_2$CO$_3$ in 30 mL of water was added. A solution of 3,5-dimethylbenzoyl chloride (17 g, 0.1 mol) in 50 mL of CH$_2$Cl$_2$ was added drop-wise over a period of 1 hour, maintaining the temperature at 0-5° C. The mixture was stirred for 1 hour on an ice bath, and then at room temperature overnight. TLC indicated the reaction was complete. The aqueous layer was removed in a separatory funnel and the organic phase was washed with water and then brine, and then dried over Na$_2$SO$_4$. The solvent was removed on a rotary evaporator. The residue was slurried in hexane, filtered, and then air-dried. 2-[N'-Benzyloxycarbonyl-N-(3,5-dimethyl-benzoyl)-hydrazino]-2-methyl-propionic acid ethyl ester was obtained as a white solid (35 g), giving a single spot by TLC. $^1$H NMR (300 MHz, CDCl$_3$) δ (ppm): 7.4 (s, 1H), 7.3 (m, 3H), 7.15 (m, 2H), 7.1 (s, 2H), 7.0 (s, 1H), 5.2 (d, 1H), 5.0 (d, 1H), 4.2 (m, 2H), 2.25 (s, 6H), 1.78 (s, 3H), 1.64 (s, 3H), 1.28 (t, 3H).

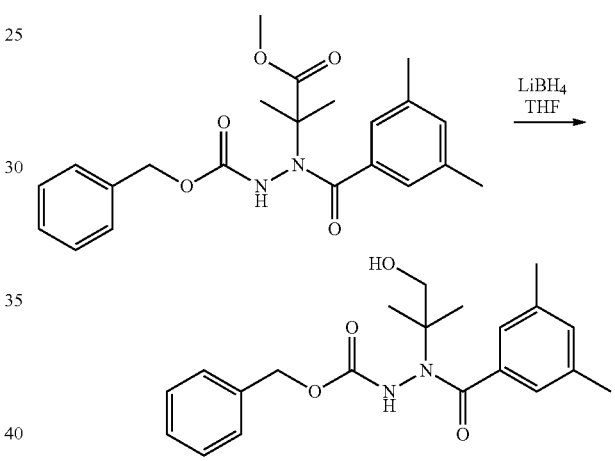

To a 500 mL round bottom flask was added 20.62 g (0.05 mol) of 2-[N'-benzyloxycarbonyl-N-(3,5-dimethyl-benzoyl)-hydrazino]-2-methyl-propionic acid methyl ester and 200 mL of dry THF. The mixture was stirred and the flask was cooled in dry ice, and then 0.87 g (0.04 mol) of LiBH$_4$ was added with stirring at room temperature. The reaction mixture was refrigerated and more LiBH$_4$ was added (1.3 g) and the reaction was refrigerated for 2 days. The reaction mixture was warmed to room temperature, and 100 mL of ether were added and the total mixture was poured slowly into 150 mL of water in a separatory funnel. After the bubbling subsided, the mixture was agitated and then shaken gently. The ether layer was separated and the water extracted twice with 100 mL of et2o. The total ether extract was extracted with water, washed with brine, and evaporated to yield 20.04 g of product. The product was purified by chromatography. The product eluted with 30-35% ethyl acetate:hexane to yield 11.6 g of N'-(3,5-dimethyl-benzoyl)-N'-(2-hydroxy-1,1-dimethyl-ethyl)-hydrazinecarboxylic acid benzyl ester, $^1$H NMR (CDCl$_3$, 300 MHz) δ (ppm): 7.3-6.9 (3s, 8H), 5.1 (d, 1H), 4.9 (d, 1H), 4.1 (d, 1H), 4.1 (d, 1H), 3.6 (d, 1H), 2.25 (s, 6H), 1.48 (s, 3H), 1.41 (s, 3H), as well as 4 g of unreacted starting material.

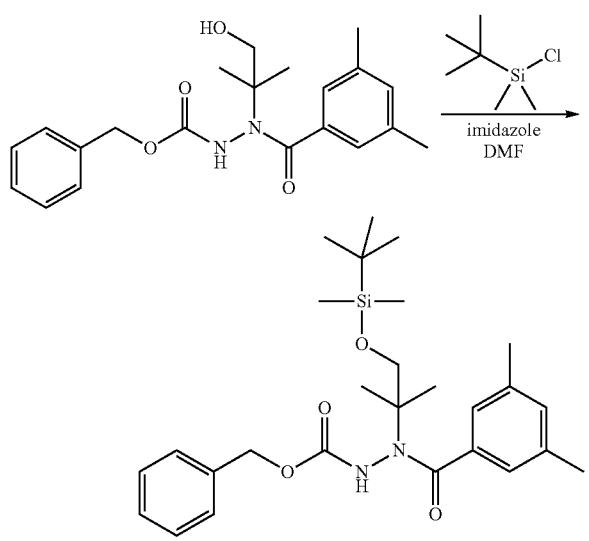

To a round bottom flask was added 4.00 g (0.0108 mol) of N'-(3,5-dimethyl-benzoyl)-N'-(2-hydroxy-1,1-dimethyl-ethyl)-hydrazinecarboxylic acid benzyl ester, 3.27 g (0.048 mol) of imidazole and 20 mL of DMF. The flask was cooled in an ice bath and then 4.08 g (0.027 mol) of t-butyl, dimethylsilyl chloride was slowly added as the temperature was maintained below 25° C. The ice bath was removed and the reaction stirred overnight at room temperature. The reaction mixture was then poured into 200 mL of water and extracted three times with 100 mL of ether. The ether extract was washed with water, dried over MgSO$_4$, and concentrated to yield 7.12 g of product. The product was cleaned up by column chromatography. Unreacted t-butyl, dimethylsilyl chloride was eluted with hexane and 10% CH$_2$Cl$_2$/hexane. The product eluted with 20-100% CH$_2$Cl$_2$/hexane to yield 5.13 g of N'-[2-(tert-butyl-dimethyl-silanyloxy)-1,1-dimethyl-ethyl]-N'-(3,5-dimethyl-benzoyl)-hydrazinecarboxylic acid benzyl ester. $^1$H NMR (CDCl$_3$, 300 MHz) δ (ppm): 7.3-6.7 (m, 8H), 5.0 (s, 2H), 4.1 (d, 1H), 3.4 (d, 1H), 2.15 (d, 6H), 1.54 (d, 3H), 1.25 (d, 3H), 0.82 (s, 9H), 0.01 (s, 6H).

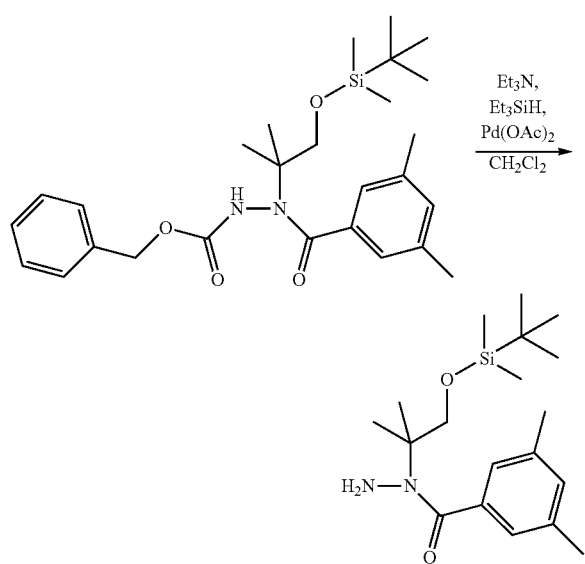

Into a 200 mL round bottom flask, was added 4.62 g (0.0095 mol) of N'-[2-(tert-butyl-dimethyl-silanyloxy)-1,1-dimethyl-ethyl]-N'-(3,5-dimethyl-benzoyl)-hydrazinecarboxylic acid benzyl ester, 100 mL of dry CH$_2$Cl$_2$, 2.5 g of Et$_3$N, and 1.66 g (0.0143 mol) of Et$_3$Si H. The reaction mixture was cooled in an ice bath, and then 100 mg of palladium acetate was added in 3 portions over 30 min. The reaction was then allowed to warm to room temperature. As TLC indicated no product, only the starting material (20% ethyl acetate/hexane, Rf 4.3), the reaction was warmed gently with a heat gun and then stirred at room temperature for 30 min. TLC indicated the product (20% ethyl acetate/hexane, Rf 0.43).

The reaction mixture was stirred with some MgSO$_4$ and then filtered. The filter cake was then washed with CH$_2$Cl$_2$. The total CH$_2$Cl$_2$ fraction was shaken with saturated NH$_4$Cl, then with H$_2$O. The CH$_2$Cl$_2$ was dried and evaporated to yield 3.78 g of 3,5-Dimethyl-benzoic acid N-[2-(tert-butyl-dimethyl-silanyloxy)-1,1-dimethyl-ethyl]-hydrazide. The product was purified by column chromatography, eluted with 5-10% ethyl acetate/hexane. The product fractions were combined, concentrated, and placed in warm (50° C.) vacuum oven to yield 2.96 g of solid 3,5-Dimethyl-benzoic acid N-[2-(tert-butyl-dimethyl-silanyloxy)-1,1-dimethyl-ethyl]-hydrazide. $^1$H NMR (CDCl$_3$, 300 MHz) δ (ppm): 7.0 (s, 2H), 6.9 (s, 1H), 3.80 (s, 2H), 2.23 (s, 6H), 1.40 (s, 6H), 0.82 (s, 9H), 0.08 (s, 6H).

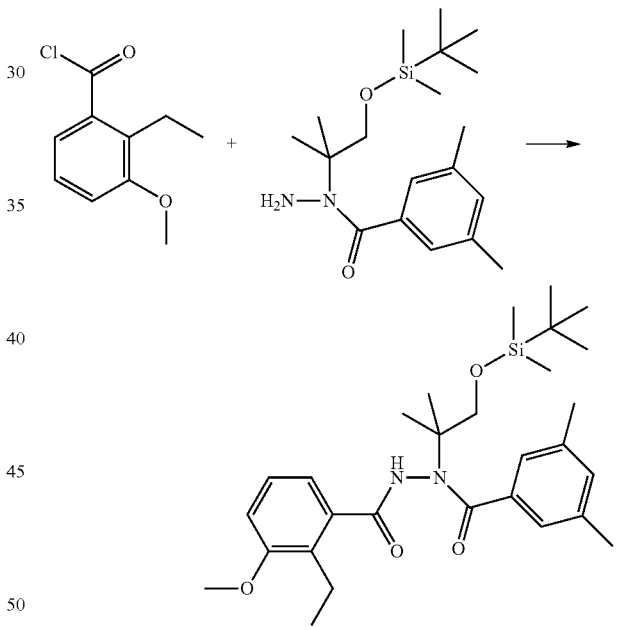

Into a 250 mL round bottom flask, was added 3.71 g (0.010 mol) of 3,5-dimethyl-benzoic acid N-[2-(tert-butyl-dimethyl-silanyloxy)-1,1-dimethyl-ethyl]-hydrazide and 50 mL of CH$_2$Cl$_2$. 2.11 g (0.106 mol) of 2-ethyl-3-methoxybenzoyl chloride and a K$_2$CO$_3$ solution (4.15 g in 20 mL of H$_2$O) were added. The reaction mixture was stirred at room temperature overnight. The reaction mixture was transferred to a separatory funnel and the aqueous layer extracted twice with 50 mL of CH$_2$Cl$_2$. The organic phase was dried and concentrated to give 5.52 g of a syrupy product. The product was purified by column chromatography, eluting in 10% ethyl acetate in hexane. Further purification was achieved by triturating the product with heptane, placing the mixture into the freezer, and then either decanting the yellow solution or the more preferred method of rapidly filtering through a cold Buchner filter for 1-2 hours to obtain a white solid product, 2-ethyl-3-methoxy-benzoic acid N'-[2-(tert-butyl-dimethyl-silanyloxy)-1,1-dimethyl-ethyl]-N'-(3,5-dimethyl-benzoyl)-hydrazide (2.9 g). $^1$H NMR (CDCl$_3$, 300 MHz) δ (ppm): 7.0-6.8 (m, 5H), 6.2 (d, 1H), 4.1 (d, 1H), 3.69 (s, 3H), 3.5 (d, 1H), 2.19 (s, 6H), 1.62 (s, 3H), 1.40 (s, 3H), 0.9 (t, 3H), 0.76 (s, 9H).

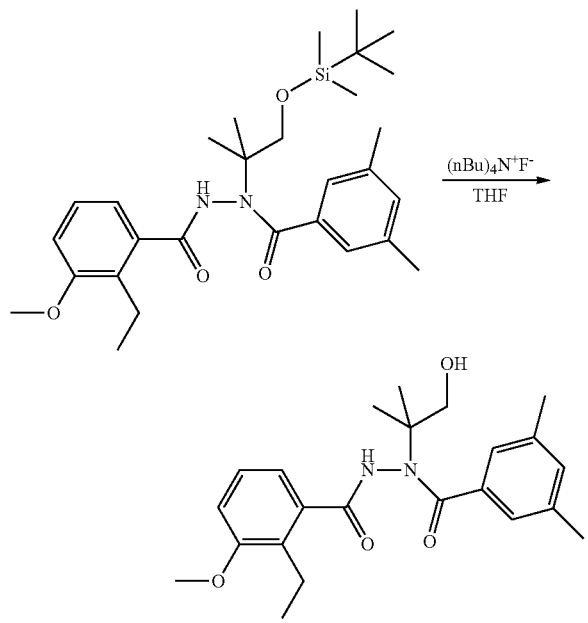

2.78 g (0.00526 mol) of 2-ethyl-3-methoxy-benzoic acid N'-[2-(tert-butyl-dimethyl-silanyloxy)-1,1-dimethyl-ethyl]-N'-(3,5-dimethyl-benzoyl)-hydrazide were dissolved in 24 mL of THF. The mixture was cooled in an ice bath and 6.0 mL (0.006 mol) of a 1 M tetrabutyl ammonium fluoride solution in THF were added. The reaction was stirred at room temperature for 5-6 hours, and then 100 mL of Et$_2$O were added and the reaction mixture was poured into ice water in a separatory funnel. The aqueous layer was further extracted twice with 25 mL of Et$_2$O and the total ether layer was dried and concentrated. TLC of the product showed a new product (Rf 0.20) below some of the starting material. The product was purified by chromatography, eluting with 40-50% ethyl acetate/hexane to yield 1.42 g of pure 3,5-dimethyl-benzoic acid N'-[1-(2-ethyl-3-methoxy-phenyl)-vinyl]-N-(2-hydroxy-1,1-dimethyl-ethyl)-hydrazide. (67% yield). TLC: Rf=0.20. $^1$H NMR (CDCl$_3$, 300 MHz) δ (ppm): 7.1-6.8 (m, 5H), 6.0 (d, 1H), 4.3 (d, 1H), 3.78 (s, 3H), 3.5 (d 1H), 2.4 (d, 1H) 2.29 (s, 6H), 2.2 (d, H), 1.56 (s, 3H), 1.45 (s, 3H), 1.00 (t, 3H).

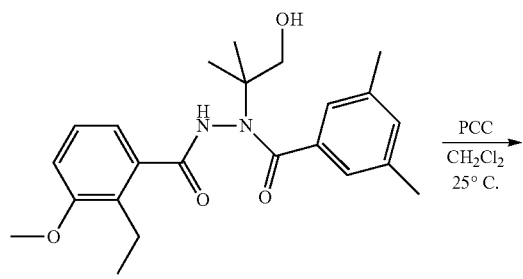

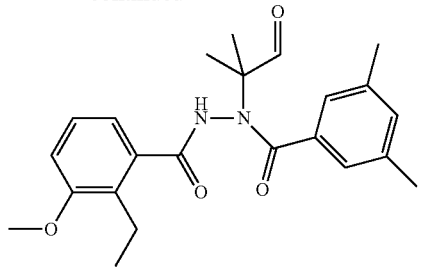

1.09 g (0.0027 mol) of 3,5-dimethyl-benzoic acid N'-[1-(2-ethyl-3-methoxy-phenyl)-vinyl]-N-(2-hydroxy-1,1-dimethyl-ethyl)-hydrazide were dissolved in 100 mL of CH$_2$Cl2 and 1.80 g (0.0082 mol) of pyridinium chlorochromate were added. The reaction mixture was refluxed for 2 hours. After cooling, the total reaction mixture was poured onto a silica chromatography column to purify the product, 3,5-dimethyl-benzoic acid N-(1,1-dimethyl-2-oxo-ethyl)-N'-[1-(2-ethyl-3-methoxy-phenyl)-vinyl]-hydrazide. A white crystalline solid (1.04 g) was eluded with 30-35% ethyl acetate/hexane. TLC indicated high purity (>95%), Rf=0.46 (1:1 ethyl acetate: hexane). $^1$H NMR (CDCl$_3$, 300 MHz) δ (ppm): 9.6 (s, 1H), 7.15 (s, 2H), 7.1 (m, 2H), 6.9 (d, 1H), 6.3 (d, 1H), 3.806 (s, 3H), 2.304 (s, 6H), 2.2-2.4 (m, 2H), 1.576 (s, 3H), 1.429 (s, 3H), 1.01 (t, 3H).

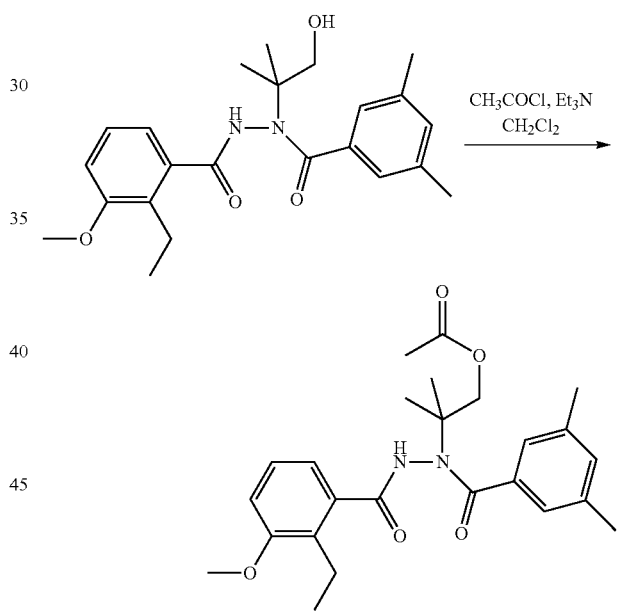

Into a 20 mL vial, was added 55 mg of 3,5-dimethyl-benzoic acid N'-[1-(2-ethyl-3-methoxy-phenyl)-vinyl]-N-(2-hydroxy-1,1-dimethyl-ethyl)-hydrazide, 2 mL of CH$_2$Cl$_2$, 200 mg of Et$_3$N. The reaction mixture was stirred and then 17 mg of acetyl chloride were added. After stirring at room temperature for 2 hours, the reaction was warmed at 40° C. for 30 min. After cooling, more CH$_2$Cl$_2$ was added, and then transferred to separatory funnel and shaken with dilute K$_2$CO$_3$. The CH$_2$Cl$_2$ layer was dried with MgSO$_4$. TLC showed a major spot at Rf 38. The product was cleaned up by chromatography by eluting with 30% ethyl acetate in hexane. This yielded about 40 mg of acetic acid 2-{N-(3,5-dimethyl-benzoyl)-N'-[1-(2-ethyl-3-methoxy-phenyl)-vinyl]-hydrazino}-2-methyl-propyl ester. $^1$H NMR (CDCl$_3$, 300 MHz) δ (ppm): 7.1-6.8 (m, 6H), 6.1 (d, 1H), 4.7-4.4 (q, 2H), 3.79 (s, 3H), 2.29 (s, 6H), 2.12 (s, 3H), 1.75 (s, 3H), 1.49 (s, 3H), 0.98 (t, 3H).

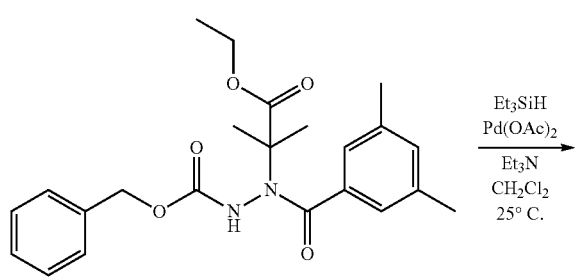

Into a flask containing 1.5 g (0.0036 mol, 80% pure) of 2-[N'-benzyloxycarbonyl-N-(3,5-dimethyl-benzoyl)-hydrazino]-2-methyl-propionic acid ethyl ester, was added 20 mL of dry CH$_2$Cl$_2$, 1.5 mL of Et$_3$N, and 1.27 g (0.010 mol) of Et$_3$SiH. While stirring, small portions of a total of 0.010 g of Pd(OAc)$_2$ was added and the reaction was stirred for 2 hours at room temperature. To the reaction mixture was added 100 mL of CH$_2$Cl$_2$ and some MgSO$_4$ to aid in the filtration/removal of the Pd product. The CH$_2$Cl$_2$ solution was shaken with saturated NH$_4$Cl, CH$_2$Cl$_2$ dried, and evaporated to yield 1.61 g of 2-[N-(3,5-dimethyl-benzoyl)-hydrazino]-2-methyl-propionic acid ethyl ester. The product was purified by chromatography, elution with 21-24% ethyl acetate in hexane. $^1$H NMR (CDCl$_3$, 300 MHz) δ (ppm): 7.045 (s 2H), 7.0 (s 1H), 4.4 (s, 2H), 2.324 (s 6H), 2.236 (s 3H), 1.487 (s, 6H).

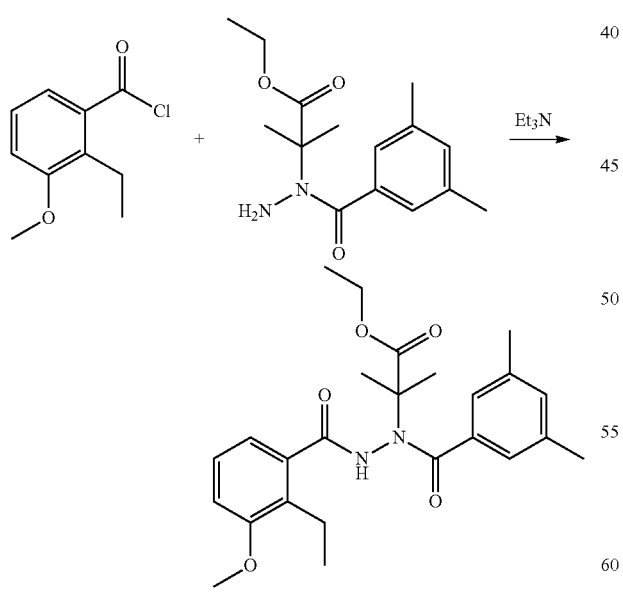

To a flask containing 1.6 g (0.0057 mol) of 2-[N-(3,5-Dimethyl-benzoyl)-hydrazino]-2-methyl-propionic acid ethyl ester in 30 mL of CH$_2$Cl$_2$ was added 3.5 g of Et$_3$N and 1.20 g (0.0060 mol) of 2-ethyl-3methoxybenzoyl chloride. The reaction mixture was refluxed for 3 hours and then evaporated to dryness. The residue was redissolved with 100 mL of CH$_2$Cl$_2$ and extracted twice with 50 mL of dilute aqueous K$_2$CO3. The CH$_2$Cl$_2$ extract was dried and evaporated to a residue, which was then triturated with 6% Et$_2$O in hexane. A white solid product, 2-[N-(3,5-dimethyl-benzoyl)-N'-(2-ethyl-3-methoxy-benzoyl)-hydrazino]-2-methyl-propionic acid ethyl ester, was filtered off and dried in a warm (50%) vacuum oven. TLC: product, Rf=0.40, starting material, Rf=0.35, 1:1 ethyl acetate:hexane. $^1$H NMR (CDCl$_3$, 300 MHz) δ (ppm): 7.70 (s 1H), 7.2-6.8 (m-5H), 6.2 (d 1H), 4.2 (q 2H), 3.801 (s 3H), 2.4 (q 2H), 2.291 (s 6H), 1.882 (s 3H), 1.557 (s 3H), 1.291 (t, 3H), 1.036 (t, 3H).

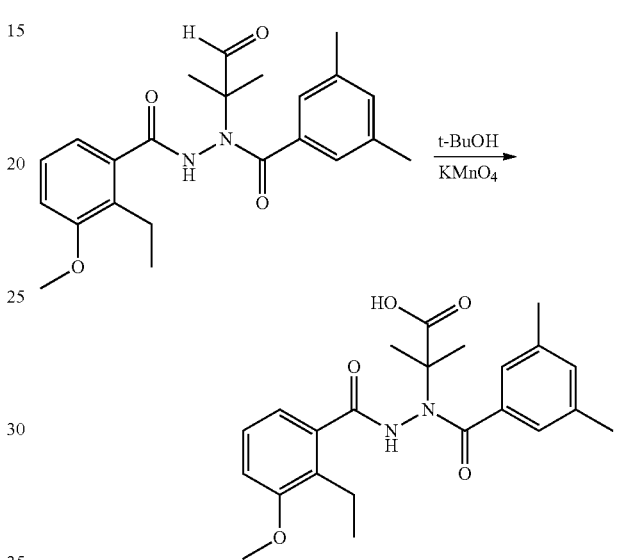

2-[N-(3,5-Dimethyl-benzoyl)-N'-(2-ethyl-3-methoxy-benzoyl)-hydrazino]-2-methyl-propionic acid was prepared by oxidation of 2-ethyl-3-methoxy-benzoic acid N'-(3,5-dimethyl-benzoyl)-N'-(1,1-dimethyl-2-oxo-ethyl)-hydrazide with KMnO$_4$. The corresponding ester could not be saponified to the acid shown, even with 40% NaOH/CH$_3$OH, or 50% aqueous NaOH+EtOH with reflux.

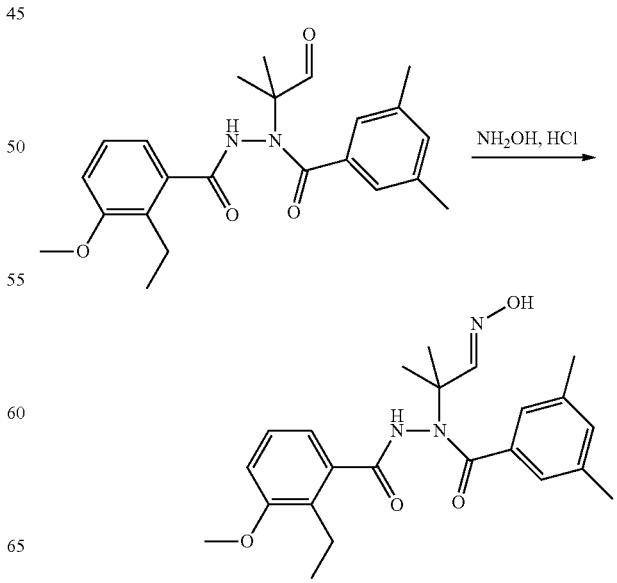

50 mg (0.000126 mol) of 2-ethyl-3-methoxy-benzoic acid N'-(3,5-dimethyl-benzoyl)-N'-(1,1-dimethyl-2-oxo-ethyl)-hydrazide was weighed into a 20 mL vial. 20 mg of hydroxylamine-HCl dissolved in 0.5 mL of CH$_3$OH was then added. 40 mg of triethylamine was added and the reaction mixture stirred at room temperature overnight. The reaction mixture was concentrated to dryness with N$_2$, re-dissolved with 5 mL of CH$_2$Cl$_2$ and 5 mL of 0.1N HCl/H$_2$O. The CH$_2$Cl$_2$ layer was separated. TLC showed the product, 2-ethyl-3-methoxy-benzoic acid N'-(3,5-dimethyl-benzoyl)-N'-(2-hydroxyimino-1,1-dimethyl-ethyl)-hydrazide, had a Rf of 0.27 (1:1 ethyl acetate:hexane) and was about 85% pure. $^1$H NMR (CDCl$_3$, 300 MHz) δ (ppm): 7.1-6.8 (m, 5H), 6.2 (d, 1H), 3.79 (s, 3H), 2.29 (s, 6H), 1.76 (s, 3H), 1.65 (s, 3H), 0.98 (t, 3H).

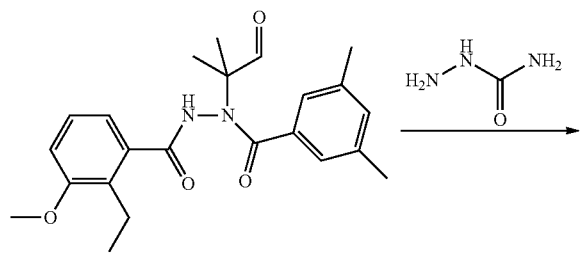

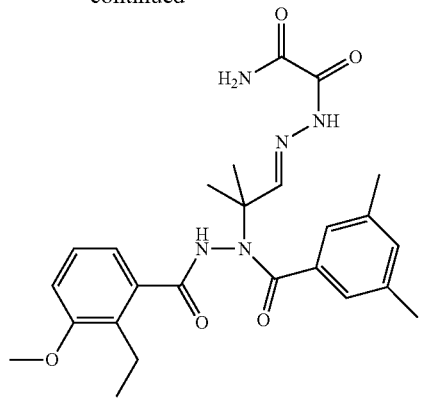

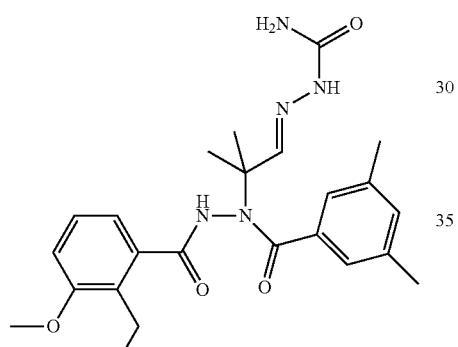

50 mg of 2-ethyl-3-methoxy-benzoic acid N'-(3,5-dimethyl-benzoyl)-N'-(1,1-dimethyl-2-oxo-ethyl)-hydrazide, 40 mg of semicarbazide, 40 mg of Et$_3$N and 2 mL of CH$_3$OH were refluxed for 2 hours, concentrated to dryness, redissolved with CH$_2$Cl$_2$ and diluted with (0.5N) HCl. The CH$_2$Cl$_2$ extract was dried and evaporated to give the semicarbazide of 2-ethyl-3-methoxy-benzoic acid N'-(3,5-dimethyl-benzoyl)-N'-(1,1-dimethyl-2-oxo-ethyl)-hydrazide. $^1$H NMR (CDCl$_3$, 300 MHz) δ (ppm): 7.4-6.8 (m, 5H), 6.2 (d, 1H), 3.767 (s, 3H), 2.203 (s, 6H), 1.717 (s, 3H), 1.474 (s, 3H), 0.913 (t, 3H).

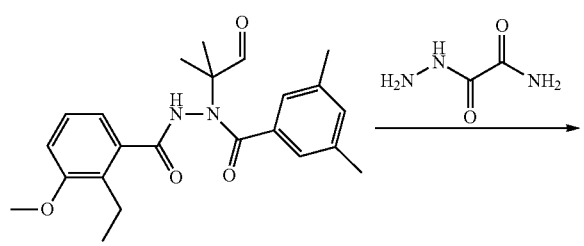

50 mg of 2-ethyl-3-methoxy-benzoic acid N'-(3,5-dimethyl-benzoyl)-N'-(1,1-dimethyl-2-oxo-ethyl)-hydrazide aldehyde, 2 mL of CH$_3$OH, 0.5 mL of a 0.5% glacial acetic acid solution with CH$_3$OH and 26 mg of oxamic hydrazide, and 40 mg of Et$_3$N were refluxed for 2 hours. The solvents were removed on an evaporator and the residue redissolved with CH$_2$Cl$_2$ and water. The CH$_2$Cl$_2$ extract was dried and evaporated. TLC showed the presence of the product, the oxamic carbazide of 2-ethyl-3-methoxy-benzoic acid N'-(3,5-dimethyl-benzoyl)-N'-(1,1-dimethyl-2-oxo-ethyl)-hydrazide, which had a Rf of 0.50 while the starting aldehyde had a Rf of 0.74 (in 100% ethyl acetate). $^1$H NMR (CDCl$_3$, 300 MHz) δ (ppm): 8.1 (s 1H), 7.1-6.8 (m, 6H), 6.1 (d, 1H), 3.667 (s, 3H), 2.3 (m, 1H), 2.19 (s, 6H), 2.00 (m, 1H), 1.581 (s, 3H), 1.511 (s, 3H), 0.802 (t, 3H).

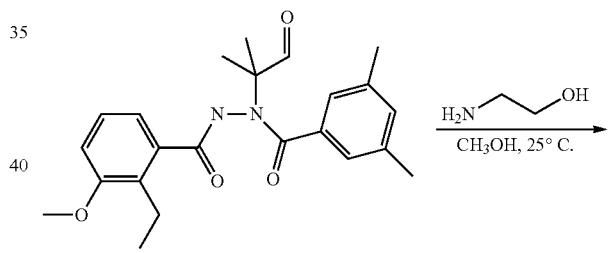

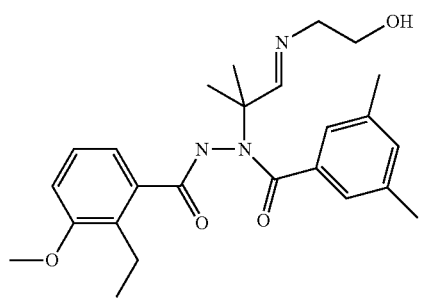

50 mL of 2-ethyl-3-methoxy-benzoic acid N'-(3,5-dimethyl-benzoyl)-N'-(1,1-dimethyl-2-oxo-ethyl)-hydrazide were added to a 20 mL flask, with 45 g of aminoethanol in 2 mL of CH$_3$OH, and then refluxed for 2 hours. After cooling, the CH$_3$OH was removed on the evaporator and the residue was chromatographed. The product 3,5-dimethyl-benzoic acid N'-[1-(2-ethyl-3-methoxy-phenyl)-vinyl]-N-(2-hydroxymethoxyimino-1,1-dimethyl-ethyl)-hydrazide was eluted with 40% ethyl acetate/hexane. $^1$H NMR (CDCl$_3$, 300 MHz) δ (ppm): 7.2-6.9 (m, 5H), 4.1 (m, 2H), 3.83 (s, 3H), 3.7 (m, 2H), 2.75 (m, 2H), 2, 338 (s, 6H), 1.36 (s, 3H), 1.21-1.87 (m, 6H).

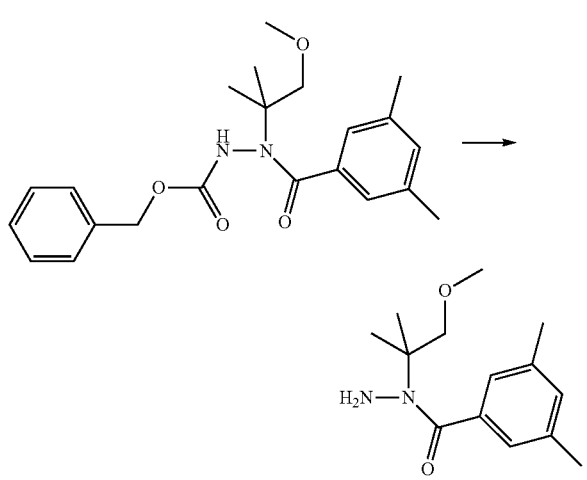

To a flask containing 0.94 g (0.002 mol) of methyl ether N'-(3,5-dimethyl-benzoyl)-N'-(2-methoxy-1,1-dimethylethyl)-hydrazinecarboxylic acid benzyl ester, was added 10 mL of $CH_2Cl_2$, 0.87 g of $Et_3SiH$, 0.10 g of palladium acetate, and 1 g of $Et_3N$. The reaction mixture was stirred at room temperature for over 10 hours. More $CH_2Cl_2$ (10-20 mL) was added, and the mixture was filtered to remove the palladium. The brown $CH_2Cl_2$ solution was treated with $MgSO_4$ and charcoal, then filtered and evaporated. The evaporation yielded 0.87 g of a red, oily solid. TLC indicated the presence of the product; Rf=0.44 in 1:1 ethyl acetate:hexane. The product was purified by chromatography, eluted with 19-20% ethyl acetate/hexane to yield 401 mg (80%) of 3,5-dimethyl-benzoic acid N-(2-methoxy-1,1-dimethyl-ethyl)-hydrazide product. $^1$H NMR ($CDCl_3$, 300 MHz) δ (ppm): 7.1 (s, 2H), 7.0 (s, 1H), 3.682 (s, 2H), 3.377 (s, 3H), 2.319 (s, 6H), 1.495 (s, 3H).

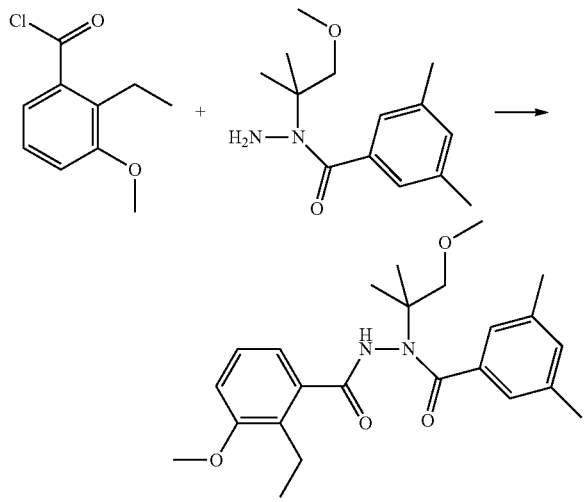

To a 20 mL vial containing 90 mg of 3,5-dimethyl-benzoic acid N-(2-methoxy-1,1-dimethyl-ethyl)-hydrazide 1462 (0.00036), was added 2 mL of $CH_2Cl_2$, 145 mg (0.00072 mol) of 2-ethyl-3-methoxybenzoyl chloride, 0.5 $K_2CO_3$ in 3 mL of $H_2O$. The reaction was stirred at room temperature overnight. The reaction mixture was transferred to separatory funnel with 10 mL of $K_2CO_3$ and 50 mL of $CH_2Cl_2$. The $CH_2Cl_2$ extract was dried and evaporated to dryness. The product,
2-ethyl-3-methoxy-benzoic acid N'-(3,5-dimethyl-benzoyl)-N'-(2-methoxy-1,1-dimethyl-ethyl)-hydrazide, was purified by chromatography, eluting with 25% ethyl acetate in hexane to yield 105 mg. TLC: Rf=0.44 (1:1 ethyl acetate:hexane). $^1$H NMR ($CDCl_3$, 300 MHz) δ (ppm): 7.8 (s, 1H), 7.1-6.8 (m, 5H), 6.2 (d, 1H), 4.0 (d, 1H), 3.84 (d, 1H), 3.77 (s, 3H), 3.387 (s, 3H), 2.27 (s, 6H), 2.4-2.1 (m, 2H), 1.728 (s, 3H), 1.503 (s, 3H) 0.98 (t 3H).

1.49 Preparation of Compound RG-101494

N-(5-ethyl-1,4-benzodioxan-6-carbonyl)-N'-(tert-butyl)-N'-(3-chloro-5-methylbenzoyl)hydrazine can be prepared in accordance with U.S. Pat. No. 5,530,028. Briefly, the product of Example 17 is treated by the method of Example 5 and then the method of Example 8. The resulting product is treated with 3-methyl-5-chlorobenzoyl chloride [(K. Knoevenagel, Chemische Berichte 28: 2045 (1895); Slootmaekers, P. J., Verbeerst, R., Bull. Soc. Chm. Belg. 77: 273-285 (1968)] according to the method of Example 9.

1.50 Preparation of Compound RG-102240

N-(3-methoxy-2-ethylbenzoyl)-N'-(3,5-dimethylbenzoyl)-N'-tert-butylhydrazine can be prepared in accordance with Example 12 of U.S. Pat. No. 5,530,028.

1.51 Preparation of Compound RG-102317

N-(5-methyl-1,4-benzodioxan-6-carbonyl)-N'-(tert-butyl)-N'-(3,5-dimethylbenzoyl)hydrazine can be prepared in accordance with Example 3 of U.S. Pat. No. 5,530,021.

1.52 Preparation of Compound RG-115092

N-(5-methyl-1,4-benzodioxan-6-carbonyl)-N'-(2-cyano-2-propyl)-N'-(3,5-dimethoxy-4-methylbenzoyl)hydrazine can be prepared by a method directly analogous to Examples 802 and 809 of U.S. Pat. No. 5,117,057 but using N-5-methyl-1,4-benzodioxan-6-carbohydrazine (for preparation see U.S. Pat. No. 5,530,021, Example 2) and 3,5-methoxy-4-methylbenzoyl chloride.

1.53 Preparation of Compound RG-115575

3,4,5-Trifluoro-benzoic acid N-tert-butyl-N'-(5-methylchroman-6-carbonyl)-hydrazide can be prepared by analogy to Example 11 of U.S. Pat. No. 5,530,021, but using 3,4,5-trifluorobenzoyl chloride.

1.54 Preparation of Compound RG-115637

5-Methyl-2,3-dihydro-benzo[1,4]dioxine-6-carboxylic acid N'-tert-butyl-N'-(3,5-dimethoxy-4-methyl-benzoyl)-hydrazide can be prepared by analogy to Example 3 of U.S. Pat. No. 5,530,021, but using 3,5-dimethoxy-4-methylbenzoyl chloride.

Example 2

Determination of Physical and Transport Properties 2.1 Determination of LC Log P (Experimental)

1000 ppm solutions for each of a set of log P standards (compounds for which log P is known experimentally; see Table 3) and for each test compound are prepared. Liquid chromatography retention times (RT) are measured for each substance using the conditions described below. A linear equation is derived relating RT to log P is developed from the data for the log P standards. The log P for the test compound is calculated from the log P/retention time equation.

| Chromatogaphic conditions: | | | |
|---|---|---|---|
| Column: | MetaChem Polaris A-18 3u 50 × 3.0 mm; part no C2001-050x030 | | |
| | time (min.) | methanol (%) | water (%) |
| Solvent Gradient: | 0.0 | 25 | 75 |
| | 7.0 | 99 | 1 |
| | 8.0 | 25 | 75 |
| Temperature: (° C.): | 30 | | |
| Detector Type: | UV or DAD (diode array detector): 200-220 nm | | |

2.2 Determination of C Log P

C log P can be calculated according to standard calculations known to those of skill in the art. Exploring QSAR: Fundamentals and Applications in Chemistry and Biology. Corwin Hansch, Albery Leo, American Chemical Society, Washington, D.C., 1995

2.3 Determination of Water Solubility

Aqueous solutions are prepared as follows in triplicate: 50 µl of a 10,000 ppm solution (2,000 µg of solid dissolved in 200 µl of methanol) of the substrate in methanol or DMSO is added to 1 mL of de-ionized water in a 2 dram or smaller vial with magnetic stirring. Stirring is continued overnight at ambient temperature. The slurry is taken up into a syringe with a luer tip. The contents are passed through a new 13 mm 0.2 ρM Acrodisc filter (tuffryn or glass fiber) into an autosampler bottle. For preparation of calibration standard solutions: dilutions of the 10,000 ppm solution were prepared at 10, 5, 1, 0.5, and 0.2 ppm. The water solubility of most diacylhydrazines falls within this concentration range. For more soluble materials, dilution of the samples into this range is preferable to increasing the calibration range because the non-linearity of the response results in less useful calibration curves. However a shift in the range of calibration standards is required for very insoluble compounds.

Chromatography of the samples was then preformed. For most diacylhydrazines the following conditions were adequate for the measurement. Other columns and gradients may be substituted as appropriate.

| Column | MetaChem Polaris A-18 3µ 50 × 3.0 mm; part no C2001-050x030 (or MetaChem Inertsil 5µ ODS3 50 mm × 2.1 mm) | | |
|---|---|---|---|
| | time (min.) | methanol (%) | water (%) |
| Solvent Gradient | 0.00 | 25 | 75 |
| | 4.50 | 99 | 1 |
| | 6.00 | 99 | 1 |
| Temperature (° C.) 30 | | | |

Analysis of the test samples is conducted as follows: Each solubility replicate is analyzed in duplicate. While any suitable analysis method is acceptable, these results were obtained by LC/MS on a Micromass Platform II in the electrospray negative ion mode using SIM (single ion monitoring). Standard curves are obtained from duplicate injections of the standards. The concentration of the substrate is determined by calculation from the equation relating concentration and response.

2.4 Determination of Cell Permeation Coefficients

The method to determine cell permeation coefficients is known to those of skill in the art. MI-QSAR: Predicting Caco-2 Cell Permeation Coefficients of Organic Molecules using Membrane-Interaction QSAR Analysis. Kulkarni, Amit; Han, Yi; Hopfinger, A. J.; Journal of Chemical Information and Computer Sciences (2002) 42: 331-342. Table 2 represents the physical and transport properties of the compounds of the present invention.

TABLE 2

Physical and Transport Properties of Compounds

| Compound | LC LogP (exp) | C logP | Exp. Water Sol. (µM) | MI-QSAR P(caco2) ×10^6 cm/sec | MI-QSAR Log BB |
|---|---|---|---|---|---|
| RG-115009 | 1.9 | 2.19 | 30.4 | NA | NA |
| RG-115613 | 2.8 | 0.82 | NA | NA | NA |
| RG-101523 | 4.35 | 4.46 | 13.4 | 9.3 | −0.63 |
| RG-101382 | 4.4 | 4.96 | NA | NA | NA |
| RG-101494 | 4.3 | 4.43 | NA | NA | NA |
| RG-102240 | 4.2 | 4.18 | 9.8 | 11.4 | −1.00 |
| RG-102317 | 3.6 | 4.21 | 10.1 | 0.13 | 0.13 |
| RG-103309 | | 5.89 | 2.9 | NA | NA |
| RG-115092 | 3.5 | 2.8 | NA | NA | NA |
| RG-115517 | 3.15 | 2.68 | 36.7 | 0.04 | 0.04 |
| RG-115575 | 4.1 | 4.22 | 21.6 | 12 | 12.0 |
| RG-115637 | 3.54 | 3.6 | 13.7 | 6.1 | 6.1 |

NA = not assayed

TABLE 3

Retention Times (RT) and logP for Diacylhydrazine standards

| Compound | RT (min.) | logP |
|---|---|---|

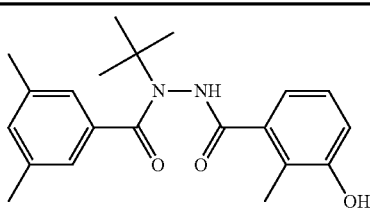

RG-102208
2.59    2.9

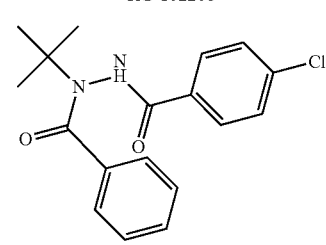

RG-100864
3.29    3.2

TABLE 3-continued

Retention Times (RT) and logP for Diacylhydrazine standards

| Compound | RT (min.) | logP |
|---|---|---|
| 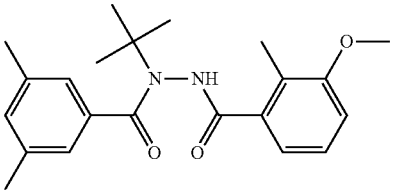 [SMILES: COc1cccc(C(=O)NN(C(=O)c2cc(C)cc(C)c2)C(C)(C)C)c1C] RG-102398 | 3.82 | 3.7 |
| 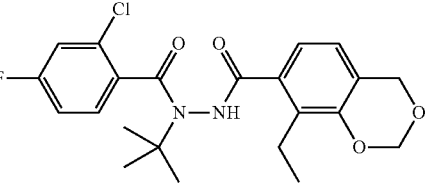 RG-115002 | 3.81 | 3.5 |
| 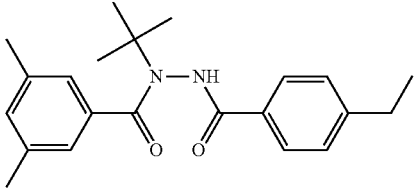 [SMILES: CCc1ccc(C(=O)NN(C(=O)c2cc(C)cc(C)c2)C(C)(C)C)cc1] RG-102125 | 4.84 | 4.2 |
| 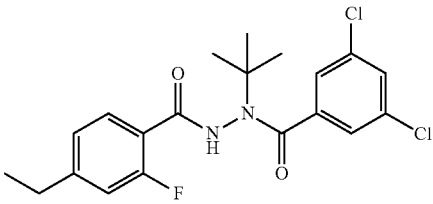 [SMILES: CCc1ccc(C(=O)NN(C(=O)c2cc(Cl)cc(Cl)c2)C(C)(C)C)c(F)c1] RG-115372 | 5.52 | 5.02 |
| 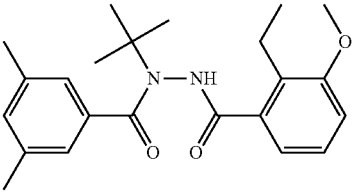 [SMILES: CCc1c(OC)cccc1C(=O)NN(C(=O)c1cc(C)cc(C)c1)C(C)(C)C] RG-102240 | 4.64 | 4.2 |

2.5 Aqueous Solubility

Equilibrium solubility was measured in pH 7.4 aqueous buffer. The buffer was prepared by adjusting the pH of a 0.07 M solution of $NaH_2PO_4$ to pH 7.4 with 10 N NaOH. The buffer had an ionic strength of 0.15. At least 1 mg of powder was combined with 1 mL of buffer to make >1 mg/mL mixture. These samples were shaken for ≥2 hours and left to stand overnight at room temperature. The samples were then filtered through a 0.45-μm Nylon syringe filter that was first saturated with the sample. The filtrate was sampled twice, consecutively. The filtrate was assayed by HPLC against standards prepared in methanol.

TABLE 4

Solubility of Compounds

| Compound | Solubility (mg/mL) pH 7.4 |
|---|---|
| RG-115280 | 0.0012 |
| RG-102125 | 0.0006 |
| RG-102398 | ≤0.0002 |
| RG-100150 | ≥1.0 |
| RG-115595 | 0.026 |
| RG-103309 | ≤0.0002 |
| RG-115555 | ≥1.0 |
| RG-115199 | 0.0064 |
| RG-115823 | 0.0003 |
| RG-101523 | 0.0010 |
| RG-102240 | 0.0007 |
| RG-102317 | 0.0043 |
| RG-115517 | 0.014 |
| RG-100021 | ≥1.0 |

2.6 Partition Coefficients

The partition coefficient, Log (D), between water-saturated 1-octanol and pH 7.4 buffer was determined for the test compounds. The buffer was prepared as described in section 2. A 12 μl aliquot of a 10 mM stock solution in DMSO was introduced to a vial containing 0.60 mL of octanol and 0.60 mL of buffer at room temperature. Testosterone was also added to a final concentration of 100 μM as an internal control. The solution was vortexed for 60 minutes and centrifuged at 10,000 rpm for 10 minutes. The organic and aqueous layers were removed. Serial dilutions of the organic layer were made with 50% methanol except for the initial dilution, which was made in 100% methanol. Serial dilutions of the aqueous layer were made in the pH 7.4 buffer. The diluted samples were then assayed by LC/MS for the compound as well as for testosterone. The Log of the ratio of peak area responses was calculated to obtain the Log (D). Typical Log D values for testosterone are from 3.0-3.3.

TABLE 5

Log (D) of Compounds

| Compound | Log(D) Octanol/pH 7.4 |
|---|---|
| RG-115280 | 3.9 |
| RG-102125 | 3.2 |
| RG-102398 | 3.5 |
| RG-100150 | −2.1 |
| RG-115595 | 2.1 |
| RG-103309 | 3.0 |
| RG-115555 | 0.0 |
| RG-115199 | 2.0 |
| RG-115823 | 3.3 |
| RG-101523 | 2.9 |
| RG-102240 | 3.4 |
| RG-102317 | 3.6 |
| RG-115517 | 2.9 |
| RG-100021 | 0.8 |

2.7 Bi-Directional Permeability, CACO-2

Caco-2 monolayers were grown to confluence on collagen-coated, microporous, polycarbonate membranes in 12-well Costar Transwell plates. Details of the plates and their certification are shown below. The permeability assay buffer was Hank's Balanced Salt Solution containing 10 mM HEPES and 15 mM glucose at a pH of 7.0±0.2. The dosing solution concentration was 10 μM in assay buffer. At each time point, 1 and 2 hours, a 200-μL aliquot was taken from the receiver chamber and replaced with fresh assay buffer. Cells were dosed on the apical side (A-to-B) or basolateral side (B-to-A) and incubated at 37° C. with 5% $CO_2$ and 90% relative humidity. Each determination was performed in duplicate. The important experimental parameters are outlined below. Permeability through a cell-free (blank) membrane was studied to determine non-specific binding and free diffusion of the compound through the device. Lucifer yellow flux was also measured for each monolayer after being subjected to the test compounds to ensure no damage was inflicted to the cell monolayers during the flux period.

All samples were assayed by LC/MS using electrospray ionization. Typical LC/MS conditions are as follows:
Liquid Chromatography
Column: Keystone Hypersil BDS C18 30×2.0 mm i.d., 3 μm, with guard column
M.P. Buffer: Ammonium Formate Buffer, pH 3.5
Aqueous Reservoir (A): 90% water, 10% buffer
Organic Reservoir (B): 90% acetonitrile, 10% buffer
Flow Rate: 300 μL/min.
Gradient Program (typically):

| Time | Grad. Curve | % A | % B | TE3 | 1E4 |
|---|---|---|---|---|---|
| −0.1 | 0 | 100 | 0 | close | |
| 1.2 | 1 | 60 | 40 | | close |
| 3.0 | 1 | 0 | 100 | | |
| 3.1 | 0 | 100 | 0 | | |
| 4 | 0 | 100 | 0 | close | |

Total run time: 4.5 min
Autosampler: 10 μL injection volume
Autosampler wash: water/acetonitrile/2-propanol::1/1/1; with 0.2% formic acid

| Mass Spectrometer (Typical Operating Conditions) | |
|---|---|
| Interface: | Electrospray ("Turbo Ionspray") |
| Mode: | Single Ion Monitoring |
| Gases: | Neb Gas = 8, Curtain Gas = 10, Turbo Ionspray Gas = 8000 mL/min. |
| TEM: | 350° C. |
| Voltages: | IS 4500, OR 25, RNG 200, Q0 −10, IQ1 −12, ST −15, RQ0 −12, DF −200, CEM (per age) |
| Method: | 4.5 minute duration. |

The apparent permeability, Papp, and percent recovery were calculated as follows:

$$Papp = (dC_r/dt) \times V_r/(A \times C_0) \quad (1)$$

$$\text{Percent Recovery} = 100 \times ((V_r \times C_r^{final}) + (V_d \times C_d^{final}))/(V_d \times C_0) \quad (2)$$

where, $dC_r/dt$ is the cumulative concentration in the receiver compartment versus time in M s$^{-1}$.

$V_r$ is the volume of the receiver compartment in cm$^3$.

$V_d$ is the volume of the donor compartment in cm$^3$.

A is the area of the cell monolayer (1.13 cm$^2$ for 12-well Transwell).

$C_0$ is the concentration of the dosing solution in M.

$C_r^{final}$ is the cumulative receiver concentration in M at the end of the incubation period.

$C_d^{final}$ is the concentration of the donor in M at the end of the incubation period.

| Plates: | TW12 | TW12 |
|---|---|---|
| Seed Date: | Jun. 11, 2002 (KW) | Jun. 18, 2002 (PSK) |
| Passage: | 62 | 61 |
| Age (days): | 27 | 22 |

| Certification | | | Acceptance Criteria |
|---|---|---|---|
| TEER Value (Ω · cm$^2$): | 506 | 504 | 450-650 Ω · cm$^2$ |
| Lucifer Yellow, Papp × 10$^{-6}$ cm/s: | 0.14 | 0.12 | <0.4 × 10$^{-6}$ cm/s |
| Atenolol, Papp × 10$^{-6}$ cm/s: | 0.20 | 0.18 | <0.5 × 10$^{-6}$ cm/s |
| Propranolol, Papp × 10$^{-6}$ cm/s: | 20 | 19 | 15-25 × 10$^{-6}$ cm/s |
| Digoxin, Papp × 10$^{-6}$ cm/s: | 1.7 | 1.8 | none |
| Digoxin, Papp × 10$^{-6}$ cm/s: | 12 | 16 | none |

| Experimental Parameters | |
|---|---|
| Dosing Concentration: | 10 μM |
| Replicates: | 2 |
| Direction: | apical-to-basolateral, basolateral-to-apical |
| Time Points: | 1 and 2 hours |

TABLE 6

Recovery and Permeability (10$^{-6}$ cm/s) of Compounds

| | Percent Recovery[C] | | | Papp[D] | Papp, A-to-B | | | Papp, B-to-A | | | Papp$^{B-A}$ | | Significant |
|---|---|---|---|---|---|---|---|---|---|---|---|---|---|
| | | | | | Rep. | Rep. | | Rep. | Rep. | | Papp$^{A-B}$ | Absorption | cant |
| Compound | Blank | A-to-B | B-to-A | Blank | 1 | 2 | Avg | 1 | 2 | Avg | Ratio[B] | Potential[A] | Efflux[B] |
| RG-115280 | 41 | 46 | 99 | 1.88 | 1.24 | 1.30 | 1.27 | 1.50 | 1.48 | 1.49 | 1.2 | High | No |
| RG-102125 | 62 | 84 | 63 | 21.9 | 25.7 | 26.3 | 26.0 | 20.7 | 19.7 | 20.2 | 0.8 | High | No |
| RG-102398 | 94 | 85 | 90 | 34.7 | 27.0 | 26.8 | 26.9 | 25.9 | 28.2 | 27.1 | 1.0 | High | No |
| RG-100150 | 117 | 102 | 107 | 36.9 | 0.19 | 0.18 | 0.18 | 0.33 | 0.34 | 0.33 | 1.8 | Low | No |
| RG-115595 | 103 | 95 | 104 | 33.2 | 19.6 | 18.9 | 19.2 | 29.8 | 31.7 | 30.7 | 1.6 | High | No |
| RG-103309 | 70 | 74 | 75 | 23.6 | 25.2 | 23.8 | 24.5 | 32.5 | 32.5 | 32.5 | 1.3 | High | No |
| RG-115555 | 110 | 98 | 106 | 35.8 | 0.18 | 0.18 | 0.18 | 1.55 | 1.67 | 1.61 | 8.9 | Low | Yes |
| RG-115199 | 82 | 85 | 87 | 23.0 | 31.1 | 30.2 | 30.6 | 31.0 | 30.9 | 30.9 | 1.0 | High | No |
| RG-115823 | 77 | 64 | 63 | 24.2 | 17.4 | 17.8 | 17.6 | 18.8 | 15.4 | 17.1 | 1.0 | High | No |
| RG-101523 | 95 | 95 | 88 | 29.4 | 24.2 | 26.6 | 25.4 | 23.6 | 25.4 | 24.5 | 1.0 | High | No |

TABLE 6-continued

Recovery and Permeability ($10^{-6}$ cm/s) of Compounds

| Compound | Percent Recovery[C] | | | Papp[D] | Papp, A-to-B | | | Papp, B-to-A | | | Papp$^{B-A}$ Papp$^{A-B}$ Ratio[B] | Absorption Potential[A] | Significant Efflux[B] |
|---|---|---|---|---|---|---|---|---|---|---|---|---|---|
| | Blank | A-to-B | B-to-A | Blank | Rep. 1 | Rep. 2 | Avg | Rep. 1 | Rep. 2 | Avg | | | |
| RG-102240 | 78 | 94 | 87 | 28.4 | 32.3 | 31.4 | 31.8 | 23.3 | 23.7 | 23.5 | 0.7 | High | No |
| RG-102317 | 87 | 91 | 86 | 27.9 | 28.6 | 27.3 | 28.0 | 21.0 | 21.2 | 21.1 | 0.8 | High | No |
| RG-115517 | 96 | 91 | 95 | 31.6 | 28.4 | 29.3 | 28.8 | 25.2 | 27.6 | 26.4 | 0.9 | High | No |
| RG-100021 | 113 | 90 | 94 | 43.0 | 0.21 | 0.22 | 0.22 | 0.91 | 0.95 | 0.93 | 4.3 | Low | No |

(A) Absorption Potential Classification:
Papp(A-to-B) ≥ $1.0 \times 10^{-6}$ cm/s High
Papp(A-to-B) > $0.5 \times 10^{-6}$ cm/s, Papp < $1.0 \times 10^{-6}$ cm/s Medium
Papp(A-to-B) < $0.5 \times 10^{-6}$ cm/s Low
(B) Efflux considered significant if:
Papp (B-to-A) ≥ $1.0 \times 10^{-6}$ cm/s and Ratio Papp(B-to-A)/Papp(A-to-B) ≥ 3.0
(C) Low recoveries caused by non-specific binding, etc. can affect the measured permeability
(D) A low rate of diffusion (<$20 \times 10^{-6}$ cm/s) through the cell-free membrane indicates a lack of free diffusion, which may affect the measured permeability.

Example 3

Biological Testing of Compounds

The ligands of the present invention are useful in various applications including gene therapy, expression of proteins of interest in host cells, production of transgenic organisms, and cell-based assays.

27-63 Assay
Gene Expression Cassette
GAL4 DBD (1-147)-CfEcR(DEF)/VP16AD-βRXREF-LmUSPEF:

The wild-type D, E, and F domains from spruce budworm *Choristoneura fumiferana* EcR ("CfEcR-DEF"; SEQ ID NO: 1) were fused to a GAL4 DNA binding domain ("Gal4DBD1-147"; SEQ ID NO: 2) and placed under the control of a phosphoglycerate kinase promoter ("PGK"; SEQ ID NO: 3). Helices 1 through 8 of the EF domains from *Homo sapiens* RXRβ ("HsRXRβ-EF"; nucleotides 1-465 of SEQ ID NO: 4) and helices 9 through 12 of the EF domains of *Locusta migratoria* Ultraspiracle Protein ("LmUSP-EF"; nucleotides 403-630 of SEQ ID NO: 5) were fused to the transactivation domain from VP16 ("VP16AD"; SEQ ID NO: 6) and placed under the control of an elongation factor-1α promoter ("EF-1α"; SEQ ID NO: 7). Five consensus GAL4 response element binding sites ("5XGAL4RE"; comprising 5 copies of a GAL4RE comprising SEQ ID NO: 8) were fused to a synthetic TATA minimal promoter (SEQ ID NO: 9) and placed upstream of the luciferase reporter gene (SEQ ID NO: 10).

Stable Cell Line

CHO cells were transiently transfected with transcription cassettes for GAL4 DBD (1-147) CJEcR(DEF) and for VP16AD βRXREF-LmUSPEF controlled by ubiquitously active cellular promoters (PGK and EF-1a, respectively) on a single plasmid. Stably transfected cells were selected by Zeocin resistance. Individually isolated CHO cell clones were transiently transfected with a GAL4 RE-luciferase reporter (pFR Luc). 27-63 clone was selected using Hygromycin.

Treatment with Ligand

Cells were trypsinized and diluted to a concentration of $2.5 \times 10^4$ cells mL. 100 µL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 M to 0.01 µM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

Z3 Assay
Stable Cell Line

Dr. F. Gage provided a population of stably transformed cells containing CVBE and 6XEcRE as described in Suhr, S. T., Gil, E. B., Senut M. C., Gage, F. H. (1998) Proc. Natl. Acad. Sci. USA 95, 7999-804. Human 293 kidney cells, also referred to as HEK-293 cells, were sequentially infected with retroviral vectors encoding first the switch construct CVBE, and subsequently the reporter construct 6XEcRE Lac Z. The switch construct contained the coding sequence for amino acids 26-546 from *Bombyx mori* EcR (BE) (Iatrou) inserted in frame and downstream of the VP16 transactivation domain (VBE). A synthetic ATG start codon was placed under the control of cytomegalovirus (CVBE) immediate early promoter and flanked by long terminal repeats (LTR). The reporter construct contained six copies of the ecdysone response element (EcRE) binding site placed upstream of LacZ and flanked on both sides with LTR sequences (6XEcRE).

Dilution cloning was used to isolate individual clones. Clones were selected using 450 ug/mL G418 and 100 ng/mL puromycin. Individual clones were evaluated based on their response in the presence and absence of test ligands. Clone Z3 was selected for screening and SAR purposes.

Human 293 kidney cells stably transformed with CVBE and 6XEcRE LacZ were maintained in Minimum Essential Medium (Mediates, 10-010-CV) containing 10% FBS (Life Technologies, 26140-087), 450 gum G418 (Mediates, 30-234-CR), and 100 gnome promising (Sigma, P-7255), at 37° C. in an atmosphere containing 5% $CO_2$ and were subculture when they reached 75% confluence.

Treatment with Ligand

Z3 cells were seeded into 96-well tissue culture plates at a concentration of $2.5 \times 10^3$ cells per well and incubated at 37° C. in 5% $CO_2$ for twenty-four hours. Stock solutions of ligands were prepared in DMSO. Ligand stock solutions were diluted 100 fold in media and 50 µL of this diluted ligand solution (33 M) was added to cells. The final concentration of DMSO was maintained at 0.03% in both controls and treatments.

Reporter Gene Assays

Reporter gene expression was evaluated 48 hours after treatment of cells, β-galactosidase activity was measured using Gal Screen™ bioluminescent reporter gene assay system from Tropix (GSY1000). Fold induction activities were calculated by dividing relative light units ("RLU") in ligand treated cells with RLU in DMSO treated cells. Luminescence was detected at room temperature using a Dynex MLX microtiter plate luminometer.

A schematic of switch construct CVBE, and the reporter construct 6XEcRE Lac Z is shown in FIG. 1. Flanking both constructs are long terminal repeats, G418 and puromycin are selectable markers, CMV is the cytomegalovirus promoter, VBE is coding sequence for amino acids 26-546 from *Bombyx mori* EcR inserted downstream of the VP16 transactivation domain, 6×EcRE is six copies of the ecdysone response element, lacZ encodes for the reporter enzyme β-galactosidase.

13B3 Assay

Gene Expression Cassette

GAL4 DBD-CfEcR(DEF)/VP16AD-MmRXRE:

The wild-type D, E, and F domains from spruce budworm *Choristoneura fumiferana* EcR ("CfEcR-DEF"; SEQ ID NO: 1) were fused to a GAL4 DNA binding domain ("Gal4DBD1-147"; SEQ ID NO: 2) and placed under the control of the SV40e promoter of pM vector (PT3119-5, Clontech, Palo Alto, Calif.). The D and E domains from *Mus Musculus* RXR ("MmRXR-DE"; SEQ ID NO: 11) were fused to the transactivation domain from VP16 ("VP16AD"; SEQ ID NO: 6) and placed under the control of the SV40e promoter of the pVP16 vector (PT3127-5, Clontech, Palo Alto, Calif.).

Stable Cell Line

CHO cells were transiently transfected with transcription cassettes for GAL4 DBD-CJEcR(DEF) and for VP16AD-MmRXRE controlled by SV40e promoters. Stably transfected cells were selected using Hygromycin. Individually isolated CHO cell clones were transiently transfected with a GALA RE-luciferase reporter (pFR-Luc, Stratagene, La Jolla, Calif.). The 13B3 clone was selected using Zeocin.

Treatment with Ligand

Cells were trypsinized and diluted to a concentration of $2.5 \times 10^4$ cells mL. 100 µL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 µM to 0.01 µM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

The results of the assays are shown in Tables 7 and 8. Each assay was conducted in two separate wells, and the two values were averaged. Fold inductions were calculated by dividing relative light units ("RLU") in ligand treated cells with RLU in DMSO treated cells. $EC_{50}$s were calculated from dose response data using a three-parameter logistic model. Relative Max FI was determined as the maximum fold induction of the tested ligand (an embodiment of the invention) observed at any concentration relative to the maximum fold induction of GS-™-E ligand (3,5-dimethyl-benzoic acid N-tert-butyl-N'-(2-ethyl-3-methoxy-benzoyl)-hydrazide) observed at any concentration.

TABLE 7

| | Biological Assay Results for Compounds: Fold Induction | | | | | |
|---|---|---|---|---|---|---|
| Compound | 13B3 Assay 3.3 uM | 13B3 Assay 33 uM | 27-63 Assay 3.3 uM | 27-63 Assay 33 uM | Z3 Assay 3.3 uM | Z3 Assay 33 uM |
| RG-100021 | | 0 | | | | 1 |
| RG-100127 | | 365 | 49 | 1239 | | 245 |
| RG-100150 | | 1 | | | | 1 |
| RG-100216 | | 8037 | 53 | 1312 | | 398 |
| RG-100342 | | 611 | 2 | 1287 | | 427 |
| RG-100360 | 1111 | 745 | 1627 | 1353 | 870 | 891 |
| RG-100394 | | 178 | | | 1339 | 11 |
| RG-100425 | | 747 | 1156 | 1099 | 1128 | 592 |
| RG-100448 | | 2 | 66 | 847 | | 423 |
| RG-100492 | | 1002 | 4 | 1378 | | 143 |
| RG-100524 | | 1211 | | | 991 | 146 |
| RG-100568 | 2 | 4122 | 615 | 2286 | 276 | 1193 |
| RG-100569 | 1710 | 329 | 884 | 841 | 754 | 457 |
| RG-100574 | | 0 | 151 | 21 | | 389 |
| RG-100603 | | 570 | | | | 453 |
| RG-100620 | | 13982 | | | 710 | 428 |
| RG-100667 | | 1191 | | | 1480 | 238 |
| RG-100690 | 1094 | 500 | 1136 | 1047 | 779 | 475 |
| RG-100691 | | 643 | 1378 | 1209 | 843 | 565 |
| RG-100694 | 3385 | 2078 | 1057 | 1004 | 1294 | 1288 |
| RG-100698 | | 434 | | | 1089 | 591 |
| RG-100699 | | 2296 | 398 | 1413 | | 415 |
| RG-100725 | | 581 | 1096 | 1050 | | 511 |
| RG-100749 | 0 | 288 | | | 874 | 145 |
| RG-100763 | | 2442 | 107 | 1609 | | 151 |
| RG-100764 | | 3814 | | | 915 | 369 |
| RG-100766 | | 391 | 931 | 1993 | 921 | 474 |
| RG-100767 | 4504 | 682 | 2097 | 2171 | 825 | 371 |
| RG-100768 | | 709 | 1738 | 1852 | 1246 | 425 |
| RG-100769 | 1014 | 386 | 1595 | 1556 | 1096 | 542 |
| RG-100778 | | 2344 | 2159 | 2312 | | 365 |
| RG-100779 | | 2979 | | | 947 | 304 |
| RG-100801 | | 16 | 1341 | 1244 | | 153 |

TABLE 7-continued

Biological Assay Results for Compounds: Fold Induction

| Compound | 13B3 Assay 3.3 uM | 13B3 Assay 33 uM | 27-63 Assay 3.3 uM | 27-63 Assay 33 uM | Z3 Assay 3.3 uM | Z3 Assay 33 uM |
|---|---|---|---|---|---|---|
| RG-100812 | | 202 | | | 1587 | 399 |
| RG-100814 | 423 | 1151 | 2441 | 2165 | 410 | 1279 |
| RG-100848 | 3391 | 578 | 1181 | 1151 | 885 | 26 |
| RG-100864 | 318 | 187 | 1 | 1184 | 63 | 840 |
| RG-100875 | 23 | 1143 | 34 | 1592 | 1006 | 1081 |
| RG-100901 | | 882 | | | 1527 | 185 |
| RG-100915 | 133 | 525 | | | 532 | 1292 |
| RG-100929 | | 359 | 1080 | 988 | | 490 |
| RG-101013 | 1084 | 406 | 927 | 988 | 1039 | 846 |
| RG-101016 | | 4693 | 308 | 1347 | | 394 |
| RG-101036 | 4582 | 908 | 1721 | 1459 | 767 | 404 |
| RG-101036 | 4582 | 908 | 1721 | 1459 | 767 | 404 |
| RG-101048 | | 701 | 19 | 1453 | | 283 |
| RG-101057 | 33 | 842 | 30 | 1008 | 632 | 930 |
| RG-101062 | | 319 | | | 1127 | 391 |
| RG-101088 | | 1400 | 6 | 1743 | | 302 |
| RG-101171 | | 8453 | 395 | 1357 | | 268 |
| RG-101178 | | 699 | | | 1200 | 431 |
| RG-101202 | 5 | 7 | | | 195 | 1 |
| RG-101218 | | 1983 | 1097 | 1223 | 886 | 398 |
| RG-101248 | | 415 | 146 | 1033 | | 375 |
| RG-101312 | | 1874 | | | 600 | 292 |
| RG-101316 | | 1280 | | | 1045 | 350 |
| RG-101340 | 675 | 879 | 1624 | 1549 | 866 | 432 |
| RG-101353 | 1347 | 718 | 3583 | 3835 | 530 | 439 |
| RG-101376 | 25656 | 7393 | | | 1293 | 415 |
| RG-101382 | 13058 | 1012 | 2704 | 2568 | 725 | 426 |
| RG-101398 | | 159 | | | 1138 | 403 |
| RG-101408 | | 326 | 2445 | 1886 | 780 | 398 |
| RG-101494 | 755 | 613 | 717 | 294 | 832 | 384 |
| RG-101509 | | 1144 | | | 1303 | 328 |
| RG-101511 | 1912 | 744 | 1421 | 1207 | 947 | 487 |
| RG-101523 | 831 | 718 | 2427 | 2745 | 704 | 596 |
| RG-101528 | 259 | 3027 | | | 748 | 1515 |
| RG-101531 | | 274 | | | 1130 | 428 |
| RG-101542 | | 439 | | | 1151 | 324 |
| RG-101585 | | 1015 | 154 | 1495 | | 330 |
| RG-101659 | 1556 | 1185 | 2283 | 1896 | 954 | 876 |
| RG-101664 | 1 | 0 | | | 6 | 1 |
| RG-101670 | 2297 | 738 | | | 1190 | 929 |
| RG-101691 | 5245 | 630 | 2249 | 2073 | 654 | 1089 |
| RG-101692 | 4180 | 170 | 1798 | 591 | 435 | 860 |
| RG-101734 | 918 | 442 | | | 987 | 951 |
| RG-101759 | 623 | 137 | | | 796 | 158 |
| RG-101774 | 987 | 526 | 1807 | 1359 | 631 | 429 |
| RG-101862 | 3279 | 293 | | | 717 | 250 |
| RG-101863 | 3187 | 207 | 1705 | 636 | 832 | 374 |
| RG-101864 | 5959 | 349 | 1807 | 1464 | 796 | 494 |
| RG-101887 | 2462 | 542 | 1142 | 1107 | 1004 | 334 |
| RG-101889 | | 378 | | | 1085 | 245 |
| RG-102021 | 4081 | | | 2951 | 417 | |
| RG-102125 | 762 | 315 | 1164 | 1043 | 359 | 473 |
| RG-102125 | 762 | 315 | 1164 | 1043 | 359 | 473 |
| RG-102317 | 2425 | 814 | 2551 | 2504 | 416 | 1501 |
| RG-102398 | 8125 | 795 | 2875 | 3181 | 535 | 1972 |
| RG-102408 | 25 | | | | 249 | |
| RG-102592 | 194 | 909 | 7 | 1265 | 746 | 574 |
| RG-103309 | 924 | 95 | 2537 | 1201 | 1155 | 591 |
| RG-103361 | 504 | 2262 | | | 171 | 244 |
| RG-103451 | 576 | 661 | 3326 | 3865 | 67 | 118 |
| RG-104074 | 544 | 5378 | | | 189 | 200 |
| RG-115006 | 4180 | 3146 | | | 415 | 1071 |
| RG-115009 | 19 | 2547 | | | 35 | 472 |
| RG-115025 | 8 | 1700 | 2288 | 2243 | 269 | 489 |
| RG-115033 | 386 | 12 | 2 | 1256 | 24 | 388 |
| RG-115038 | 4119 | 4970 | | | 600 | 321 |
| RG-115043 | 835 | 547 | | | 466 | 1588 |
| RG-115046 | | 1076 | 18 | 1069 | | 754 |
| RG-115050 | 2027 | 894 | | | 424 | 1446 |
| RG-115055 | 1356 | 1350 | 4499 | 2725 | 573 | 617 |
| RG-115064 | 2 | 415 | | | 1 | 3 |
| RG-115065 | | 880 | 859 | 1095 | | 878 |
| RG-115068 | 2828 | 1500 | | | 54 | 802 |
| RG-115077 | 932 | 199 | | | 294 | |
| RG-115085 | | 236 | 1143 | 1149 | | 627 |

TABLE 7-continued

Biological Assay Results for Compounds: Fold Induction

| Compound | 13B3 Assay 3.3 uM | 13B3 Assay 33 uM | 27-63 Assay 3.3 uM | 27-63 Assay 33 uM | Z3 Assay 3.3 uM | Z3 Assay 33 uM |
|---|---|---|---|---|---|---|
| RG-115086 | | | | | 433 | |
| RG-115088 | 542 | 1048 | | | 561 | 228 |
| RG-115092 | 2322 | 2409 | 2869 | 3106 | 351 | 302 |
| RG-115095 | | | | | | |
| RG-115102 | 1425 | 109 | 1154 | 971 | 88 | 865 |
| RG-115106 | | | | | 68 | |
| RG-115112 | | | | | 618 | |
| RG-115116 | 2 | | | | 276 | |
| RG-115118 | 979 | 769 | 1063 | 914 | 90 | 1160 |
| RG-115128 | | | | | 110 | |
| RG-115130 | 987 | 511 | 4436 | 4096 | 412 | 930 |
| RG-115143 | 1 | 2032 | 59 | 1736 | 111 | 1045 |
| RG-115162 | 755 | 320 | 1814 | 1464 | 334 | 772 |
| RG-115167 | | | | | 73 | |
| RG-115169 | 405 | | | | 443 | |
| RG-115171 | | | | | | |
| RG-115191 | 3 | | | | 386 | |
| RG-115199 | | | | | 349 | |
| RG-115199 | | | | | 349 | |
| RG-115207 | 7260 | 7959 | 1332 | 1279 | 354 | 508 |
| RG-115220 | 5 | 1143 | | | 298 | |
| RG-115223 | 8 | 3437 | 273 | 1935 | 323 | 1299 |
| RG-115229 | 599 | 709 | 2829 | 1423 | | 1032 |
| RG-115244 | 2404 | 573 | 2203 | 1847 | 283 | 816 |
| RG-115253 | | 471 | 848 | 910 | | 832 |
| RG-115256 | | | | | 647 | |
| RG-115257 | 820 | 354 | 1130 | 1320 | 297 | 691 |
| RG-115258 | 144 | 3745 | 1973 | 2212 | 382 | 1120 |
| RG-115259 | 3513 | 2981 | | | 91 | |
| RG-115260 | | 13 | | | | 526 |
| RG-115261 | | | | | 31 | |
| RG-115269 | | | | | 112 | |
| RG-115278 | 1950 | 1050 | 1250 | 906 | 158 | 1225 |
| RG-115280 | | 0 | 9 | 422 | | 376 |
| RG-115280 | | 0 | 9 | 422 | | 376 |
| RG-115297 | 1364 | 304 | 1544 | 946 | 443 | 604 |
| RG-115302 | 521 | 648 | 940 | 815 | | 404 |
| RG-115306 | | | | | 5 | |
| RG-115310 | 2 | 3044 | | | 199 | 960 |
| RG-115311 | | | | | | |
| RG-115327 | | 3785 | | | 279 | 325 |
| RG-115329 | | 5644 | | | 259 | 430 |
| RG-115330 | 1995 | 3577 | | | 633 | 432 |
| RG-115337 | 631 | 1010 | 1080 | 1053 | | 682 |
| RG-115350 | 450 | | | | 499 | |
| RG-115352 | | | | | 7 | |
| RG-115378 | 1778 | 2424 | 1493 | 1407 | 488 | 1464 |
| RG-115384 | 2753 | 2277 | 1713 | 1282 | 337 | |
| RG-115407 | 2476 | 2612 | 1611 | 1515 | 391 | 879 |
| RG-115416 | 3618 | 2737 | 2412 | 1867 | 164 | 1116 |
| RG-115422 | | | | | 204 | |
| RG-115429 | 18 | 1843 | | | 3 | 1724 |
| RG-115441 | | | | | 118 | |
| RG-115443 | | | | | | |
| RG-115480 | | | | | | |
| RG-115496 | | | | | 874 | |
| RG-115499 | 1182 | 731 | 2092 | 1536 | 173 | 641 |
| RG-115508 | 310 | 191 | 1195 | 969 | 199 | 680 |
| RG-115514 | 4009 | 515 | 1616 | 1427 | 383 | 658 |
| RG-115515 | | 1996 | | | 1306 | 420 |
| RG-115517 | 8397 | 11953 | | | 408 | |
| RG-115517 | 8397 | 11953 | | | 408 | |
| RG-115518 | 1644 | 926 | 1640 | 1126 | 232 | 803 |
| RG-115532 | 908 | 738 | | | 530 | |
| RG-115534 | | 211 | | | 168 | 249 |
| RG-115536 | 483 | | | | 488 | |
| RG-115539 | 20 | 592 | 1076 | 534 | | 339 |
| RG-115550 | 1 | 0 | | | | 21 |
| RG-115551 | | 290 | 1150 | 1068 | | 470 |
| RG-115555 | | | | | 1 | |
| RG-115557 | | | | | 426 | |
| RG-115567 | | | | | | |
| RG-115575 | 3085 | 865 | | | 282 | 785 |
| RG-115580 | | 298 | 1104 | 1031 | | 615 |
| RG-115592 | | | | | | |

TABLE 7-continued

Biological Assay Results for Compounds: Fold Induction

| Compound | 13B3 Assay 3.3 uM | 13B3 Assay 33 uM | 27-63 Assay 3.3 uM | 27-63 Assay 33 uM | Z3 Assay 3.3 uM | Z3 Assay 33 uM |
|---|---|---|---|---|---|---|
| RG-115595 | 6 | 1381 | | | 44 | 1067 |
| RG-115595 | 6 | 1381 | | | 44 | 1067 |
| RG-115609 | 558 | 4217 | | | 90 | 383 |
| RG-115611 | | | | | 745 | |
| RG-115613 | 180 | 1726 | | | 991 | 1469 |
| RG-115625 | 3 | 715 | | | 265 | 1559 |
| RG-115627 | 1291 | 10058 | | | 378 | 362 |
| RG-115637 | 1109 | 636 | 4159 | 2741 | 211 | |
| RG-115647 | 2169 | 98 | 817 | 815 | 96 | 510 |
| RG-115648 | 9 | | | | | |
| RG-115664 | 1363 | 333 | 1928 | 1768 | 209 | 620 |
| RG-115674 | 442 | | | | 319 | |
| RG-115683 | | | | | | |
| RG-115684 | | 151 | | | | 498 |
| RG-115689 | | | | | 13 | |
| RG-115690 | 930 | | | | 571 | |
| RG-115716 | 3 | 0 | | | | 66 |
| RG-115717 | 0 | 0 | | | | 9 |
| RG-115718 | 0 | 2 | | | | 0 |
| RG-115719 | 0 | 1 | | | | 271 |
| RG-115721 | 0 | 0 | | | | 2 |
| RG-115722 | 0 | 0 | | | | 1 |
| RG-115723 | 0 | 0 | | | | 17 |
| RG-115819 | | | 1970 | 2371 | 1433 | 722 |
| RG-115820 | | | 2861 | 1971 | 1413 | 701 |
| RG-115823 | | | 2093 | 1025 | 1440 | 1050 |
| RG-115824 | | | 2675 | 948 | 895 | 737 |
| RG-115829 | | | 2605 | 45 | 1441 | 319 |
| RG-115830 | | | 2287 | 353 | 1604 | 983 |
| RG-115831 | | | 2063 | 1435 | 1481 | 544 |
| RG-115832 | | | 2063 | 1435 | 1564 | 621 |
| RG-115834 | | | 1900 | 1837 | | |
| RG-115835 | | | 3 | 1895 | | |
| RG-115836 | | | 1822 | 823 | | |
| RG-115837 | | | 1474 | 1156 | | |
| RG-115840 | | | 1612 | 263 | | |
| RG-115841 | | | 1407 | 437 | | |
| RG-115842 | | | 1269 | 447 | | |
| RG-115846 | | | 1643 | 645 | | |
| RG-115847 | | | 2729 | 848 | | |
| RG-115848 | | | 1346 | 1156 | | |
| RG-115849 | | | 1 | 231 | | |
| RG-115850 | | | 1 | 23 | | |
| RG-115856 | | | | 1760 | | |
| RG-115857 | | | | 328 | | |
| RG-115858 | | | | 182 | | |
| RG-115859 | | | | 1056 | | |
| RG-115861 | | | 8 | 593 | | |
| RG-115862 | | | 1 | 243 | | |
| RG-115863 | | | 1 | 804 | | |
| RG-115864 | | | | 1255 | | |
| RG-115865 | | | | 76 | | |
| RG-115866 | | | | 3 | | |
| RG-115867 | | | | 654 | | |
| RG-115003 | 0 | 301 | | | | 1276 |
| RG-115044 | 0 | 1 | 1 | 2 | 1 | 7 |
| RG-115079 | 3 | 0 | | | 1 | 0 |
| RG-115091 | | 1 | | | | 61 |
| RG-115117 | 1 | | | 221 | 7 | |
| RG-115160 | 3 | 3 | | | 3 | 157 |
| RG-115172 | 1 | 0 | | | 1 | 216 |
| RG-115225 | 3 | 8 | | | 3 | 571 |
| RG-115358 | 1 | 584 | | | 33 | 769 |
| RG-115371 | 1 | 1092 | | | 249 | 1774 |
| RG-115408 | 1 | 0 | | | 1 | 3 |
| RG-115490 | 2 | 844 | | | 123 | 814 |
| RG-115497 | 1 | 0 | | | 1 | 20 |
| RG-115511 | 1 | 98 | 1 | 1155 | 10 | 570 |
| RG-115597 | 0 | 4667 | 2 | 2065 | | 942 |
| RG-115653 | 6 | 0 | 1 | 832 | | 666 |
| RG-115665 | 1 | 0 | 2 | 0 | 6 | 74 |
| RG-115783 | 3 | 2765 | | | | 1362 |

TABLE 8

Biological Assay Results for Compounds: EC50 Relative Max FI

| Compound | 13B3 EC50 (μM) | 13B3 assay Rel Max FI | 27-63 assay EC50 (μM) | 27-63 assay Rel Max FI | Z3 assay EC50 (μM) | Z3 assay Rel Max FI |
|---|---|---|---|---|---|---|
| RG-100127 | | | 6.704 | 0.689 | 4.677 | |
| RG-100216 | | | 6.972 | 0.685 | 1.778 | |
| RG-100342 | | | 17.694 | 0.674 | 10.233 | |
| RG-100360 | 0.588 | 0.825 | 0.615 | 0.873 | 0.257 | 1.073 |
| RG-100394 | | | | | 1.223 | |
| RG-100425 | | | 0.370 | 0.671 | 0.099 | 1.180 |
| RG-100448 | | | 5.288 | 0.609 | 2.818 | |
| RG-100492 | | | 11.757 | 0.916 | 8.128 | |
| RG-100524 | | | | | 0.263 | 1.002 |
| RG-100568 | 44.284 | 1.035 | 4.132 | 1.197 | 3.311 | 0.855 |
| RG-100569 | 0.185 | 0.773 | 0.287 | 0.720 | 0.098 | 0.835 |
| RG-100574 | | | 4.000 | 0.371 | 1.122 | |
| RG-100620 | | | | | 2.399 | 0.869 |
| RG-100667 | | | | | 0.347 | 0.890 |
| RG-100690 | 0.268 | 0.506 | 0.200 | 0.727 | 0.240 | 1.008 |
| RG-100691 | | | 0.330 | 0.863 | 0.257 | 0.945 |
| RG-100694 | 0.405 | 0.632 | 0.400 | 0.767 | 0.389 | 1.157 |
| RG-100698 | | | | | 1.000 | 1.025 |
| RG-100699 | | | 3.963 | 0.939 | 2.089 | |
| RG-100725 | | | 0.330 | 0.726 | | |
| RG-100749 | | | | | 2.692 | 0.951 |
| RG-100763 | | | 5.301 | 0.856 | 2.138 | |
| RG-100764 | | | | | 2.344 | 0.900 |
| RG-100766 | | | 3.419 | 0.944 | 0.174 | 1.194 |
| RG-100767 | 1.056 | 0.920 | 0.334 | 1.218 | 0.251 | 0.996 |
| RG-100768 | | | 0.333 | 1.039 | 0.214 | 1.129 |
| RG-100769 | 0.337 | 0.685 | 0.196 | 0.735 | 0.219 | 1.109 |
| RG-100778 | | | 0.678 | 1.342 | 0.513 | 1.000 |
| RG-100779 | | | | | 0.178 | 0.707 |
| RG-100801 | | | 2.076 | 0.936 | 0.891 | |
| RG-100812 | | | | | 0.912 | 0.954 |
| RG-100814 | 37.888 | 0.843 | 1.500 | 1.157 | 1.148 | |
| RG-100848 | 1.645 | 0.666 | 0.322 | 0.765 | 0.240 | 0.996 |
| RG-100864 | 1.155 | | 17.269 | 0.716 | 2.239 | |
| RG-100875 | 4.019 | 0.853 | 8.920 | 1.004 | 2.042 | 0.818 |
| RG-100901 | | | | | 0.316 | 0.918 |
| RG-100915 | 4.449 | 0.552 | | | 1.000 | 0.912 |
| RG-100929 | | | 1.047 | 0.770 | 0.631 | |
| RG-101013 | 2.256 | 0.539 | 2.140 | 0.606 | 1.479 | 0.720 |
| RG-101016 | | | 4.201 | 0.703 | 1.995 | |
| RG-101036 | 0.223 | 0.545 | 0.177 | 0.724 | 0.054 | 1.049 |
| RG-101036 | 0.223 | 0.545 | 0.177 | 0.724 | 0.054 | 1.049 |
| RG-101048 | | | 8.415 | 0.708 | 19.055 | |
| RG-101057 | 4.970 | 0.569 | 6.617 | 0.648 | 4.467 | 0.697 |
| RG-101062 | | | | | 2.570 | 0.992 |
| RG-101088 | | | 9.947 | 1.159 | 4.074 | |
| RG-101171 | | | 4.019 | 0.877 | 3.236 | |
| RG-101178 | | | | | 1.318 | 0.887 |
| RG-101202 | 0.369 | 0.007 | | | 1.738 | |
| RG-101218 | | | 0.128 | 0.645 | 0.316 | 0.998 |
| RG-101248 | | | 5.036 | 0.790 | 1.445 | |
| RG-101312 | | | | | 5.623 | 0.955 |
| RG-101316 | | | | | 1.585 | 0.896 |
| RG-101340 | 0.106 | 0.364 | 0.240 | 0.964 | 0.234 | 1.126 |
| RG-101353 | 0.675 | 1.163 | 0.266 | 1.168 | 0.107 | 1.078 |
| RG-101376 | 1.361 | 0.654 | | | 0.537 | 0.777 |
| RG-101382 | 0.588 | 0.915 | 0.306 | 1.188 | 0.066 | 0.951 |
| RG-101398 | | | | | 0.282 | 0.712 |
| RG-101408 | | | 0.336 | 1.185 | 0.148 | 1.118 |
| RG-101494 | 0.148 | 0.822 | 0.036 | 0.916 | 0.079 | 1.093 |
| RG-101509 | | | | | 1.175 | 0.882 |
| RG-101511 | 0.794 | 0.811 | 0.714 | 0.762 | 0.468 | 1.122 |
| RG-101523 | 2.374 | 0.772 | 0.165 | 0.943 | 0.242 | |
| RG-101528 | 29.303 | 1.111 | | | 1.047 | 0.923 |
| RG-101531 | | | | | 0.085 | |
| RG-101542 | | | | | 0.324 | 0.793 |
| RG-101585 | | | 5.057 | 0.893 | 4.898 | |
| RG-101659 | 0.562 | 0.867 | 0.347 | 1.009 | 0.214 | |
| RG-101664 | >50 | 0.002 | | | 21.081 | |
| RG-101670 | 0.646 | 0.874 | | | 0.468 | 0.853 |
| RG-101691 | 0.406 | 0.918 | 0.250 | 0.969 | 0.174 | 1.068 |
| RG-101692 | 0.728 | 1.004 | 0.788 | 1.008 | 0.309 | 0.975 |
| RG-101734 | | | | | 0.145 | 0.988 |
| RG-101759 | 0.877 | 0.336 | | | 0.331 | 0.639 |
| RG-101774 | 0.327 | 0.657 | 0.359 | 0.795 | 0.155 | 0.943 |

TABLE 8-continued

Biological Assay Results for Compounds: EC50 Relative Max FI

| Compound | 13B3 EC50 (μM) | 13B3 assay Rel Max FI | 27-63 assay EC50 (μM) | 27-63 assay Rel Max FI | Z3 assay EC50 (μM) | Z3 assay Rel Max FI |
|---|---|---|---|---|---|---|
| RG-101862 | 1.050 | 0.861 | | | 0.269 | 0.866 |
| RG-101863 | 0.728 | 0.837 | 1.003 | 1.043 | 0.257 | 0.953 |
| RG-101864 | 0.288 | 0.460 | 0.343 | 0.750 | 0.245 | 1.075 |
| RG-101887 | 0.861 | 0.579 | 0.351 | 0.675 | 0.257 | 0.930 |
| RG-101889 | | | | | 3.300 | |
| RG-102021 | 4.045 | 1.136 | | | 0.513 | 0.920 |
| RG-102125 | 0.479 | | 0.190 | 0.721 | 0.174 | |
| RG-102125 | 0.479 | | 0.190 | 0.721 | 0.174 | |
| RG-102240 | 0.5 | 1 | 0.288 | 1 | 0.286 | 1 |
| RG-102317 | 0.345 | | 0.102 | 0.948 | | |
| RG-102398 | 0.627 | 0.838 | 0.325 | 1.017 | 0.095 | 1.027 |
| RG-102408 | 0.091 | 0.662 | | | 0.054 | 1.114 |
| RG-102592 | 4.922 | 0.684 | 7.770 | 0.798 | 3.890 | 0.699 |
| RG-103309 | 0.146 | 1.486 | 3.024 | 0.975 | 0.078 | 0.950 |
| RG-103361 | 28.000 | 0.758 | | | 0.526 | 0.938 |
| RG-103451 | 0.208 | 0.742 | 0.314 | 0.884 | 0.083 | 1.054 |
| RG-104074 | 0.865 | 0.812 | | | 0.307 | 1.122 |
| RG-115006 | 3.496 | 0.890 | | | 0.275 | 1.031 |
| RG-115009 | 18.908 | 0.917 | | | 3.307 | 0.916 |
| RG-115025 | 39.254 | 0.186 | 2.449 | 1.523 | 0.347 | 0.385 |
| RG-115033 | 1.000 | 0.643 | 18.101 | 0.868 | 16.218 | 0.575 |
| RG-115038 | 1.743 | 1.172 | | | 0.550 | 1.064 |
| RG-115043 | 2.669 | 0.852 | | | 0.178 | 0.943 |
| RG-115046 | | | 5.657 | 0.739 | 3.548 | |
| RG-115050 | 0.762 | 0.724 | | | 0.282 | 0.808 |
| RG-115055 | 0.303 | 0.894 | 0.318 | 1.341 | 0.043 | 0.936 |
| RG-115064 | >50 | 0.000 | | | >50 | 0.031 |
| RG-115065 | | | 3.000 | 0.746 | 1.479 | |
| RG-115068 | 0.926 | 0.722 | | | 21.000 | 0.804 |
| RG-115077 | 0.847 | 1.509 | | | 0.389 | 0.911 |
| RG-115085 | | | 0.807 | 0.683 | 0.195 | |
| RG-115086 | | | | | 0.692 | 0.433 |
| RG-115088 | 1.827 | 0.709 | | | 0.501 | 0.958 |
| RG-115092 | 0.184 | 1.176 | 0.213 | 1.092 | 0.037 | 0.917 |
| RG-115102 | 0.930 | 0.546 | 0.491 | 0.667 | 0.139 | 0.858 |
| RG-115106 | | | | | 2.570 | 0.457 |
| RG-115112 | | | | | 0.309 | 0.618 |
| RG-115116 | >50 | 1.172 | | | 3.311 | 0.960 |
| RG-115118 | 0.689 | 0.530 | 0.394 | 0.612 | 0.234 | 0.969 |
| RG-115128 | | | | | 0.245 | 0.538 |
| RG-115130 | 0.512 | | 0.093 | 1.375 | 0.036 | |
| RG-115143 | >50 | 0.651 | 7.777 | 1.112 | 7.413 | 0.844 |
| RG-115162 | 0.811 | 0.630 | 0.424 | 0.653 | 0.069 | 0.988 |
| RG-115167 | | | | | 0.240 | 0.533 |
| RG-115169 | 0.497 | 0.618 | | | 0.347 | 0.956 |
| RG-115191 | >50 | 1.513 | | | 2.399 | 0.934 |
| RG-115199 | | | | | 3.467 | 0.734 |
| RG-115207 | 0.618 | 0.707 | 0.593 | 0.704 | 0.257 | 0.923 |
| RG-115220 | >50 | 0.125 | | | 0.871 | 0.591 |
| RG-115223 | >50 | 1.346 | 4.685 | 1.167 | 1.905 | 0.925 |
| RG-115229 | 2.250 | 0.418 | 1.153 | 0.735 | 0.427 | |
| RG-115244 | 0.369 | 0.663 | 0.169 | 0.785 | 0.085 | 0.959 |
| RG-115253 | | | 0.107 | 0.742 | 0.269 | |
| RG-115256 | | | | | 0.692 | 0.527 |
| RG-115257 | 0.886 | 0.742 | 0.698 | 0.663 | 0.204 | 0.885 |
| RG-115258 | 27.111 | 1.334 | 1.879 | 1.279 | 0.646 | 0.882 |
| RG-115259 | 2.704 | 0.702 | | | 0.427 | 0.617 |
| RG-115261 | | | | | 29.512 | 0.498 |
| RG-115269 | | | | | 0.437 | 0.552 |
| RG-115278 | 0.630 | 0.823 | 0.885 | 0.720 | 0.257 | 0.893 |
| RG-115280 | | | 11.000 | 0.254 | | |
| RG-115280 | | | 11.000 | 0.254 | | |
| RG-115297 | 1.361 | 0.737 | 0.330 | 0.986 | 0.066 | 0.872 |
| RG-115302 | 2.000 | 0.624 | 1.044 | 0.521 | 0.275 | |
| RG-115306 | | | | | 3.467 | 0.424 |
| RG-115310 | >50 | 0.676 | | | 2.630 | 0.781 |
| RG-115327 | | | | | 2.754 | 0.662 |
| RG-115329 | | | | | 2.570 | 0.892 |
| RG-115330 | 5.690 | 0.711 | | | 0.186 | 0.860 |
| RG-115337 | 0.621 | 0.927 | 0.363 | 0.822 | 0.095 | |
| RG-115350 | 0.795 | 0.711 | | | 0.309 | 0.935 |
| RG-115352 | | | | | 45.709 | 0.265 |
| RG-115378 | 1.762 | 0.655 | 0.758 | 0.863 | 0.324 | 0.947 |
| RG-115384 | 0.320 | 0.426 | 0.113 | 0.645 | 0.166 | 0.904 |
| RG-115407 | 7.000 | 1.048 | 1.056 | 0.932 | 0.347 | 0.906 |

TABLE 8-continued

Biological Assay Results for Compounds: EC50 Relative Max FI

| Compound | 13B3 EC50 (μM) | 13B3 assay Rel Max FI | 27-63 assay EC50 (μM) | 27-63 assay Rel Max FI | Z3 assay EC50 (μM) | Z3 assay Rel Max FI |
|---|---|---|---|---|---|---|
| RG-115416 | 0.938 | 12.104 | 0.637 | 0.721 | 0.091 | 1.869 |
| RG-115422 | | | | | 0.398 | 0.769 |
| RG-115429 | 8.676 | 1.065 | | | 9.574 | 0.880 |
| RG-115441 | | | | | 0.126 | 0.759 |
| RG-115496 | | | | | 1.175 | 0.878 |
| RG-115499 | 0.328 | 0.489 | 0.336 | 0.705 | 0.170 | 0.954 |
| RG-115508 | 0.849 | 0.805 | 1.033 | 0.719 | 0.537 | 0.787 |
| RG-115514 | 0.541 | 0.550 | 0.170 | 0.720 | 0.056 | 0.970 |
| RG-115515 | | | | | 0.617 | 0.975 |
| RG-115517 | 0.355 | 0.675 | | | 0.089 | 0.923 |
| RG-115517 | 0.355 | 0.675 | | | 0.089 | 0.923 |
| RG-115518 | 1.253 | 0.648 | 1.053 | 0.866 | 0.257 | 0.834 |
| RG-115532 | 0.518 | 0.835 | | | 0.129 | 0.933 |
| RG-115534 | | | | | 2.754 | 0.463 |
| RG-115536 | 0.781 | 0.734 | | | 0.126 | 0.950 |
| RG-115539 | 5.000 | 0.955 | 1.177 | 0.595 | 0.151 | |
| RG-115551 | | | 0.852 | 0.684 | 0.398 | |
| RG-115555 | | | | | >50 | 0.006 |
| RG-115557 | | | | | 1.698 | 0.566 |
| RG-115575 | 0.271 | 0.641 | | | 0.102 | 0.886 |
| RG-115580 | | | 0.375 | 0.760 | 0.182 | |
| RG-115595 | | | | | 5.623 | 0.686 |
| RG-115595 | | | | | 5.623 | 0.686 |
| RG-115609 | 13.782 | 0.883 | | | 1.386 | 0.625 |
| RG-115611 | | | | | 1.585 | 0.703 |
| RG-115613 | 5.937 | 0.734 | | | 0.589 | 0.964 |
| RG-115625 | 25.322 | 0.931 | | | 0.389 | 0.950 |
| RG-115627 | 0.921 | 0.854 | | | 0.813 | 0.840 |
| RG-115637 | 0.088 | 1.002 | 0.117 | 1.305 | 0.018 | 0.947 |
| RG-115647 | 0.832 | 0.662 | 0.372 | 0.505 | 0.145 | 0.923 |
| RG-115648 | | | | | 21.380 | 0.182 |
| RG-115664 | 0.323 | 0.497 | 0.359 | 0.635 | 0.126 | 0.846 |
| RG-115674 | 1.723 | 0.875 | | | 0.229 | 0.995 |
| RG-115689 | | | | | 100.000 | 0.411 |
| RG-115690 | 0.632 | 1.181 | | | 0.209 | 0.998 |
| RG-115819 | | | 0.025 | 1.045 | 0.042 | 0.915 |
| RG-115820 | | | 0.193 | 1.270 | 0.203 | 0.887 |
| RG-115823 | | | 0.011 | 1.069 | 0.020 | 0.933 |
| RG-115824 | | | 0.036 | 1.218 | 0.046 | 0.806 |
| RG-115829 | | | 0.035 | 1.264 | 0.058 | 0.937 |
| RG-115830 | | | 0.036 | 1.049 | 0.045 | 1.020 |
| RG-115831 | | | 0.096 | 1.366 | 0.102 | 0.937 |
| RG-115832 | | | 0.035 | 1.075 | 0.037 | 1.002 |
| RG-115834 | | | 1.170 | 0.733 | | |
| RG-115835 | | | 20.000 | 0.731 | | |
| RG-115836 | | | 0.098 | 0.808 | | |
| RG-115837 | | | 1.114 | 0.569 | | |
| RG-115840 | | | 0.110 | 0.776 | | |
| RG-115841 | | | 2.015 | 0.610 | | |
| RG-115842 | | | 1.196 | 0.524 | | |
| RG-115846 | | | 0.095 | 0.846 | | |
| RG-115847 | | | 1.100 | 1.120 | | |
| RG-115848 | | | 1.291 | 0.494 | | |
| RG-115849 | | | >33 | 0.007 | | |
| RG-115850 | | | >33 | 0.001 | | |
| RG-115851 | | | 0.02 | 1 | | |
| RG-115852 | | | 0.07 | 1 | | |
| RG-115856 | | | 0.003 | 0.879 | | |
| RG-115857 | | | 0.013 | 1.140 | | |
| RG-115858 | | | 0.005 | 0.915 | | |
| RG-115859 | | | 0.007 | 1.218 | | |
| RG-115861 | | | 4.308 | 0.215 | | |
| RG-115862 | | | >33 | 0.048 | | |
| RG-115863 | | | >33 | 0.154 | | |
| RG-115864 | | | 0.004 | 0.979 | | |
| RG-115865 | | | 0.010 | 1.246 | | |
| RG-115044 | >50 | 0.87 | >33 | 0.00 | >50 | 1.08 |
| RG-115079 | 0.02 | 0.20 | | | >50 | 0.02 |
| RG-115117 | >50 | 0 | | | 3.93 | 0.36 |
| RG-115160 | >50 | 0 | | | >50 | 0.21 |
| RG-115172 | >50 | 0 | | | >50 | 0.32 |
| RG-115225 | 0.58 | 0.08 | | | >50 | 0.32 |
| RG-115358 | >50 | 0.20 | | | 9.45 | 0.48 |
| RG-115371 | >50 | 1.44 | | | 3.02 | 0.76 |
| RG-115490 | >50 | 1.01 | | | 6.35 | 0.44 |

TABLE 8-continued

Biological Assay Results for Compounds: EC50 Relative Max FI

| Compound | 13B3 EC50 (μM) | 13B3 assay Rel Max FI | 27-63 assay EC50 (μM) | 27-63 assay Rel Max FI | Z3 assay EC50 (μM) | Z3 assay Rel Max FI |
|---|---|---|---|---|---|---|
| RG-115497 | >50 | 0 | | | >50 | 0.07 |
| RG-115511 | >50 | 0.07 | 12.00 | 0.74 | 38.99 | 0.66 |
| RG-115597 | | | 9.83 | 1.26 | | |
| RG-115408 | >50 | 0 | | | >50 | 0.01 |
| RG-115653 | | | 19.77 | 0.53 | | |
| RG-115665 | >50 | 0 | 5.49 | 0.01 | 12.20 | 0.09 |
| RG-115783 | ~15 | 1.42 | | | 3.05 | 0.93 |
| RG-115866 | | | 0.010 | 0.999 | | |

Example 4

Biological (In Vivo) Testing of Compounds

Applicants' ligands are useful in various applications including gene therapy, expression of proteins of interest in host cells, production of transgenic organisms, and cell-based assays. In vivo induction of a reporter enzyme with various ligands of the present invention was evaluated in a C57BL/6 mouse model system containing a gene switch.

Gene Expression Cassettes

The wild-type D, E, and F domains from spruce budworm *Choristoneura fumiferana* EcR ("CfEcR-DEF"; SEQ ID NO: 1) were mutated [V107 (gtt)→I107 (att) and Y127 (tac) →E127 (gag)] and fused to a GAL4 DNA binding domain ("Gal4DBD1-147"; SEQ ID NO: 2). Helices 1 through 8 of the EF domains from *Homo sapiens* RXRβ ("HsRXRβ-EF"; nucleotides 1-465 of SEQ ID NO: 4) and helices 9 through 12 of the EF domains of *Locusta migratoria* Ultraspiracle Protein ("LmUSP-EF"; nucleotides 403-630 of SEQ ID NO: 5) were fused to the transactivation domain from VP16 ("VP16AD"; SEQ ID NO: 6), which regulates a reporter gene human secreted alkaline phosphatase ("SEAP", SEQ ID NO: 12) that was placed under the control of a 6xGAL4 response element (SEQ ID NO: 13) and a transthyretin promoter (SEQ ID NO: 14). Each element of the gene switch was on a separate plasmid. Receptor expression was under the control of a CMV promoter (SEQ ID NO: 15). Induction was evaluated by the amount of reporter protein expressed in the presence of ligand.

Electroporation of Gene Switch

SEAP expression in serum of mice was evaluated after electroporation of the gene switch into mouse quadriceps. Mice were anesthetized with 2 μL/g of a mixture of ketamine (100 mg/mL) and xylazine (20 mg/mL). Animals were then shaved, DNA vectors injected into the muscle in a volume of 2×50 μL polyglutamic acid (12 mg/mL water), electrode conductivity gel applied, and an electrode caliber (1 cm×1 cm; model 384) was placed on hind leg. The muscle was electroporated with 200 V/cm, 8 times, for 20 msec/pulse, at 1 sec time intervals. The transverse electrical field direction was reversed after the animals received half of the pulses. Electroporation was performed with an ECM 830 electroporator from BTX Molecular Delivery Systems.

Treatment with Ligand

In some experiments mice received an intraperitoneal injection (IP) of 2.6 μmol of ligand in 50 μL of DMSO 3 days after electroporation of the gene switch. In other experiments the concentration of ligand was decrease to 26 nmol/50 μL of DMSO/mouse. SEAP expression was evaluated 2-11 days after ligand administration. In other experiments ligand was administered in rodent chow. The chow was prepared by dissolving 2 g of ligand in 20 mL of acetone and adding it to 1 kg of LabDiet 5010 autoclavable chow from Purina Mills. This was thoroughly mixed in a Hobart mixer and then mixed for an additional 15 min in a Cross Blend mixer. Animals received chow ad libitum for 1, 2, or 3 days. All values are the average from four animals. Background SEAP in sera from animals treated with vector alone without ligand addition was 0-11 ng/mL serum.

Reporter Assay

Mouse serum was obtained by centrifugation of blood acquired by retroorbital bleeding with a small glass capillary tube. SEAP quantification was determined using a Clontech Great Escape chemiluminescence kit and by comparison with the Clontech SEAP standard.

Table 9: In vivo evaluation of ligand-mediated induction of a mutated ecdysone receptor-based gene switch. SEAP expression in serum of mice was evaluated after electroporation of the gene expression cassettes into mouse quadriceps. Mice received an IP injection of 2.6 μmol of ligand 3 days after electroporation. SEAP expression was evaluated 2-11 days after ligand administration. Each dose group was composed of four animals. Percentage of GS™-E ligand induction was determined by averaging SEAP expression from four animals divided by the average SEAP expression induced with GS™-E ligand and then multiplying by 100.

Table 10: Induction of gene switch expression with low concentrations of ligand. SEAP expression in serum of mice was evaluated after electroporation of the gene expression cassettes into mouse quadriceps. Mice received an IP injection of 26 nmol of ligand or 130 nmol GS™-E ligand 3 days after electroporation. SEAP expression was evaluated 2-7 days after ligand administration. Values are the average from 4 animals.

Table 11: Induction of SEAP in C57BL/6 mice with GS™-E ligand or RG-103309 administered in rodent chow. SEAP expression in serum of mice was evaluated after electroporation of the gene expression cassettes into mouse quadriceps. Mice received GS™-E ligand or RG-103309 in their feed (2 g/kg) 3 days after electroporation. Feed was administered ad libitum for 1, 2, or 3 days. After each interval ligand-treated feed was removed and animals received untreated feed. Values are the average from 4 animals.

TABLE 9

In vivo evaluation of ligand-mediated induction of a mutated ecdysone receptor-based gene switch.

| Compound | Secreted Alkaline Phosphatase (percentage of GS ™-E ligand induction) | | |
|---|---|---|---|
|  | Day 2 | Day 3 | Day 11 |
| RG-101382 | 92 | 81 | 890 |
| RG-102317 | 112 | 116 | 61 |
| RG-101523 | 85 | 79 | 1,116 |
| RG-101494 | 136 | 138 | ND |
| RG-115613 | 2 | 1 | ND |
| RG-115575 | 74 | 78 | 69 |
| RG-115637 | 12 | 7 | 0 |
| RG-115517 | 4 | 3 | ND |
| RG-115092 | 8 | 2 | ND |
| RG-115009 | 4 | 3 | ND |
| GS ™-E ligand | 100 | 100 | 100 |
| RG-103309 | 251 | 298 | ND |
| RG-103451 | 76 | 73 | 371 |
| RG-115819 | 172 | 215 | 3,008 |
| RG-115820 | 82 | 63 | 399 |
| RG-115823 | 129 | 183 | 2,652 |
| RG-115824 | 102 | 101 | 415 |
| RG-115832 | 147 | 189 | 4,183 |
| RG-115831 | 118 | 121 | 105 |
| RG-115830 | 120 | 158 | 3,558 |
| RG-115829 | 72 | 83 | 687 |

ND - not determined.

TABLE 10

Induction of gene switch expression with low concentrations of ligand.

| Compound | Secreted Alkaline Phosphatase (ng/ml mouse sera) | | |
|---|---|---|---|
|  | Day 2 | Day 3 | Day 7 |
| GS ™-E ligand(130 nmol) | 652 | 1,780 | 139 |
| RG-103309 (26 nmol) | 3,428 | 2,800 | 143 |
| RG-115819 (26 nmol) | 5,984 | 4,096 | 453 |
| RG-115823 (26 nmol) | 3,788 | 2,705 | 373 |
| RG-115832 (26 nmol) | 2,349 | 1,807 | 149 |
| RG-115830 (26 nmol) | 6,835 | 5,339 | 590 |
| RG-115856 (26 nmol) | 2,292 | 2,350 | ND |
| RG-115857 (26 nmol) | 574 | 401 | ND |
| RG-115858 (26 nmol) | 13,661 | 11,820 | ND |
| RG-115864 (26 nmol) | 6,722 | 5,652 | ND |

ND - not determined.

TABLE 11

Induction of gene switch expression with ligands administered in rodent's feed.

| Compound (dose period) | Secreted Alkaline Phosphatase (ng/ml mouse sera) [1] | | |
|---|---|---|---|
|  | Day 2 | Day 3 | Day 7 |
| GS ™-E ligand (1 day) | 7,302 | 7,670 | 3,784 |
| GS ™-E ligand (2 day) | 13,046 | 15,831 | 8,816 |
| GS ™-E ligand (3 day) | 8,064 | 11,392 | 8,372 |
| RG-103309 (1 day) | 9,003 | 14,850 | 5,172 |
| RG-103309 (2 day) | 6,971 | 16,518 | 7,460 |
| RG-103309 (3 day) | 11,126 | 20,373 | 11,549 |

In addition, one of ordinary skill in the art is also able to predict that the ligands disclosed herein will also work to modulate gene expression in various cell types described above using gene expression systems based on group H and group B nuclear receptors.

---

What is claimed is:

1. A method of modulating the expression of a target gene in a host cell, wherein the host cell comprises:
   (i) a transactivation domain;
   (ii) a DNA-binding domain; and
   (iii) a *Choristoneura fumiferana* ecdysone receptor (EcR) ligand binding domain;
   and a gene expression cassette comprising:
   (i) a response element capable of binding to said DNA binding domain;
   (ii) a promoter that is activated by the transactivation domain; and
   (iii) said target gene;
the method comprising contacting said host cell with a compound selected from the group consisting of:
   5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide;
   5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
   5-Methyl-2,3-dihydro-benzo[1,4]dioxine-6-carboxylic acid N'-(1-tert-butyl-butyl)-N'-(3,5-dimethyl-benzoyl)-hydrazide;
   5-Methyl-2,3-dihydro-benzo[1,4]dioxine-6-carboxylic acid N'-(1-tert-butyl-butyl)-N'-(3,5-dimethoxy-4-methyl-benzoyl)-hydrazide;
   5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide;
   5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
   5-Ethyl-2,3-dihydro-benzo[1,4]dioxine-6-carboxylic acid N'-(1-tert-butyl-butyl)-N'-(3,5-dimethyl-benzoyl)-hydrazide;
   5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide;
   3,5-Dimethyl-benzoic acid N-(1-ethyl-2,2-dimethyl-propyl)-N'-(3-methoxy-2-methyl-benzoyl)-hydrazide;
   3,5-Dimethoxy-4-methyl-benzoic acid N-(1-ethyl-2,2-dimethyl-propyl)-N'-(3-methoxy-2-methyl-benzoyl)-hydrazide;
   3,5-Dimethyl-benzoic acid N-(1-tert-butyl-butyl)-N'-(3-methoxy-2-methyl-benzoyl)-hydrazide;
   3,5-Dimethoxy-4-methyl-benzoic acid N-(1-tert-butyl-butyl)-N'-(3-methoxy-2-methyl-benzoyl)-hydrazide;
   3,5-Dimethyl-benzoic acid N-(1-ethyl-2,2-dimethyl-propyl)-N'-(2-ethyl-3-methoxy-benzoyl)-hydrazide;
   3,5-Dimethoxy-4-methyl-benzoic acid N-(1-ethyl-2,2-dimethyl-propyl)-N'-(2-ethyl-3-methoxy-benzoyl)-hydrazide;
   3,5-Dimethyl-benzoic acid N-(1-tert-butyl-butyl)-N'-(2-ethyl-3-methoxy-benzoyl)-hydrazide;
   3,5-Dimethoxy-4-methyl-benzoic acid N-(1-tert-butyl-butyl)-N'-(2-ethyl-3-methoxy-benzoyl)-hydrazide;
   2-Methoxy-nicotinic acid N-(1-tert-butyl-pentyl)-N'-(4-ethyl-benzoyl)-hydrazide;
   3,5-Dimethyl-benzoic acid N-(2,2-dimethyl-1-phenyl-propyl)-N'-(4-ethyl-benzoyl)-hydrazide;
   3,5-Dimethyl-benzoic acid N-(1-tert-butyl-pentyl)-N'-(3-methoxy-2-methyl-benzoyl)-hydrazide; and
   3,5-Dimethoxy-4-methyl-benzoic acid N-(1-tert-butyl-pentyl)-N'-(3-methoxy-2-methyl-benzoyl)-hydrazide.

2. A method to modulate the expression of one or more exogenous genes in a subject, wherein the subject contains an ecdysone receptor-based inducible gene expression system, comprising administering to the subject an effective amount of a compound selected from the group consisting of:
   5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide;
   5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
   5-Methyl-2,3-dihydro-benzo[1,4]dioxine-6-carboxylic acid N'-(1-tert-butyl-butyl)-N'-(3,5-dimethyl-benzoyl)-hydrazide;
   5-Methyl-2,3-dihydro-benzo[1,4]dioxine-6-carboxylic acid N'-(1-tert-butyl-butyl)-N'-(3,5-dimethoxy-4-methyl-benzoyl)-hydrazide;
   5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide;
   5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
   5-Ethyl-2,3-dihydro-benzo[1,4]dioxine-6-carboxylic acid N'-(1-tert-butyl-butyl)-N'-(3,5-dimethyl-benzoyl)-hydrazide;
   5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide;
   3,5-Dimethyl-benzoic acid N-(1-ethyl-2,2-dimethyl-propyl)-N'-(3-methoxy-2-methyl-benzoyl)-hydrazide;
   3,5-Dimethoxy-4-methyl-benzoic acid N-(1-ethyl-2,2-dimethyl-propyl)-N'-(3-methoxy-2-methyl-benzoyl)-hydrazide;
   3,5-Dimethyl-benzoic acid N-(1-tert-butyl-butyl)-N'-(3-methoxy-2-methyl-benzoyl)-hydrazide;
   3,5-Dimethoxy-4-methyl-benzoic acid N-(1-tert-butyl-butyl)-N'-(3-methoxy-2-methyl-benzoyl)-hydrazide;
   3,5-Dimethyl-benzoic acid N-(1-ethyl-2,2-dimethyl-propyl)-N'-(2-ethyl-3-methoxy-benzoyl)-hydrazide;
   3,5-Dimethoxy-4-methyl-benzoic acid N-(1-ethyl-2,2-dimethyl-propyl)-N'-(2-ethyl-3-methoxy-benzoyl)-hydrazide;
   3,5-Dimethyl-benzoic acid N-(1-tert-butyl-butyl)-N'-(2-ethyl-3-methoxy-benzoyl)-hydrazide;
   3,5-Dimethoxy-4-methyl-benzoic acid N-(1-tert-butyl-butyl)-N'-(2-ethyl-3-methoxy-benzoyl)-hydrazide;
   2-Methoxy-nicotinic acid N-(1-tert-butyl-pentyl)-N'-(4-ethyl-benzoyl)-hydrazide;

3,5-Dimethyl-benzoic acid N-(2,2-dimethyl-1-phenyl-propyl)-N'-(4-ethyl-benzoyl)-hydrazide;

3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide, wherein the gene expression system comprises a *Choristoneura fumiferana* ecdysone receptor (EcR) ligand binding domain.

3. A method for regulating endogenous or heterologous gene expression in a transgenic subject comprising contacting a ligand with an ecdysone receptor complex within the cells of the subject, wherein the cells further contain a DNA binding sequence for the ecdysone receptor complex when in combination with the ligand and wherein formation of an ecdysone receptor complex-ligand-DNA binding sequence complex induces expression of the gene, and wherein the ligand is a compound selected from the group consisting of:

5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide;
5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
5-Methyl-2,3-dihydro-benzo[1,4]dioxine-6-carboxylic acid N'-(1-tert-butyl-butyl)-N'-(3,5-dimethyl-benzoyl)-hydrazide;
5-Methyl-2,3-dihydro-benzo[1,4]dioxine-6-carboxylic acid N'-(1-tert-butyl-butyl)-N'-(3,5-dimethoxy-4-methyl-benzoyl)-hydrazide;
5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide;
5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
5-Ethyl-2,3-dihydro-benzo[1,4]dioxine-6-carboxylic acid N'-(1-tert-butyl-butyl)-N'-(3,5-dimethyl-benzoyl)-hydrazide;
5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide;
3,5-Dimethyl-benzoic acid N-(1-ethyl-2,2-dimethyl-propyl)-N'-(3-methoxy-2-methyl-benzoyl)-hydrazide;
3,5-Dimethoxy-4-methyl-benzoic acid N-(1-ethyl-2,2-dimethyl-propyl)-N'-(3-methoxy-2-methyl-benzoyl)-hydrazide;
3,5-Dimethyl-benzoic acid N-(1-tert-butyl-butyl)-N'-(3-methoxy-2-methyl-benzoyl)-hydrazide;
3,5-Dimethoxy-4-methyl-benzoic acid N-(1-tert-butyl-butyl)-N'-(3-methoxy-2-methyl-benzoyl)-hydrazide;
3,5-Dimethyl-benzoic acid N-(1-ethyl-2,2-dimethyl-propyl)-N'-(2-ethyl-3-methoxy-benzoyl)-hydrazide;
3,5-Dimethoxy-4-methyl-benzoic acid N-(1-ethyl-2,2-dimethyl-propyl)-N'-(2-ethyl-3-methoxy-benzoyl)-hydrazide;
3,5-Dimethyl-benzoic acid N-(1-tert-butyl-butyl)-N'-(2-ethyl-3-methoxy-benzoyl)-hydrazide;
3,5-Dimethoxy-4-methyl-benzoic acid N-(1-tert-butyl-butyl)-N'-(2-ethyl-3-methoxy-benzoyl)-hydrazide;
2-Methoxy-nicotinic acid N-(1-tert-butyl-pentyl)-N'-(4-ethyl-benzoyl)-hydrazide;
3,5-Dimethyl-benzoic acid N-(2,2-dimethyl-1-phenyl-propyl)-N'-(4-ethyl-benzoyl)-hydrazide;
3,5-Dimethyl-benzoic acid N-(1-tert-butyl-pentyl)-N'-(3-methoxy-2-methyl-benzoyl)-hydrazide; and
3,5-Dimethoxy-4-methyl-benzoic acid N-(1-tert-butyl-pentyl)-N'-(3-methoxy-2-methyl-benzoyl)-hydrazide, wherein the ecdysone receptor complex comprises a *Choristoneura fumiferana* ecdysone receptor (EcR) ligand binding domain.

4. The method of claim 3, wherein the subject is a plant.

5. The method of claim 3, wherein the subject is a mammal.

6. A method of modulating the expression of a gene in a host cell comprising:

a) introducing into the host cell a gene expression modulation system comprising:
   i) a first gene expression cassette that is capable of being expressed in a host cell comprising a polynucleotide sequence that encodes a first hybrid polypeptide comprising:
      (a) a DNA-binding domain that recognizes a response element associated with a gene whose expression is to be modulated; and
      (b) an ecdysone receptor ligand binding domain;
   ii) a second gene expression cassette that is capable of being expressed in the host cell comprising a polynucleotide sequence that encodes a second hybrid polypeptide comprising:
      (a) a transactivation domain; and
      (b) a chimeric retinoid X receptor ligand binding domain; and
   iii) a third gene expression cassette that is capable of being expressed in a host cell comprising a polynucleotide sequence comprising:
      (a) a response element recognized by the DNA-binding domain of the first hybrid polypeptide;
      (b) a promoter that is activated by the transactivation domain of the second hybrid polypeptide; and
      (c) a gene whose expression is to be modulated; and
b) introducing into the host cell a compound selected from the group consisting of:

5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide;
5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
5-Methyl-2,3-dihydro-benzo[1,4]dioxine-6-carboxylic acid N'-(1-tert-butyl-butyl)-N'-(3,5-dimethyl-benzoyl)-hydrazide;
5-Methyl-2,3-dihydro-benzo[1,4]dioxine-6-carboxylic acid N'-(1-tert-butyl-butyl)-N'-(3,5-dimethoxy-4-methyl-benzoyl)-hydrazide;
5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide;
5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
5-Ethyl-2,3-dihydro-benzo[1,4]dioxine-6-carboxylic acid N'-(1-tert-butyl-butyl)-N'-(3,5-dimethyl-benzoyl)-hydrazide;
5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide;
3,5-Dimethyl-benzoic acid N-(1-ethyl-2,2-dimethyl-propyl)-N'-(3-methoxy-2-methyl-benzoyl)-hydrazide;
3,5-Dimethoxy-4-methyl-benzoic acid N-(1-ethyl-2,2-dimethyl-propyl)-N'-(3-methoxy-2-methyl-benzoyl)-hydrazide;
3,5-Dimethyl-benzoic acid N-(1-tert-butyl-butyl)-N'-(3-methoxy-2-methyl-benzoyl)-hydrazide;

3,5-Dimethoxy-4-methyl-benzoic acid N-(1-tert-butyl-butyl)-N'-(3-methoxy-2-methyl-benzoyl)-hydrazide;
3,5-Dimethyl-benzoic acid N-(1-ethyl-2,2-dimethyl-propyl)-N'-(2-ethyl-3-methoxy-benzoyl)-hydrazide;
3,5-Dimethoxy-4-methyl-benzoic acid N-(1-ethyl-2,2-dimethyl-propyl)-N'-(2-ethyl-3-methoxy-benzoyl)-hydrazide;
3,5-Dimethyl-benzoic acid N-(1-tert-butyl-butyl)-N'-(2-ethyl-3-methoxy-benzoyl)-hydrazide;
3,5-Dimethoxy-4-methyl-benzoic acid N-(1-tert-butyl-butyl)-N'-(2-ethyl-3-methoxy-benzoyl)-hydrazide;
2-Methoxy-nicotinic acid N-(1-tert-butyl-pentyl)-N'-(4-ethyl-benzoyl)-hydrazide;
3,5-Dimethyl-benzoic acid N-(2,2-dimethyl-1-phenyl-propyl)-N'-(4-ethyl-benzoyl)-hydrazide;
3,5-Dimethyl-benzoic acid N-(1-tert-butyl-pentyl)-N'-(3-methoxy-2-methyl-benzoyl)-hydrazide; and
3,5-Dimethoxy-4-methyl-benzoic acid N-(1-tert-butyl-pentyl)-N'-(3-methoxy-2-methyl-benzoyl)-hydrazide,
wherein the first hybrid polypeptide comprises a *Choristoneura fumiferana* ecdysone receptor (EcR) ligand binding domain.

7. A method for producing a polypeptide comprising:
a) selecting a cell;
b) introducing into the cell:
   1) a DNA construct comprising:
      i) an exogenous gene encoding the polypeptide; and
      ii) a response element;
   wherein the gene is under the control of the response element; and
   2) a DNA construct encoding an ecdysone receptor complex comprising:
      i) a DNA binding domain;
      ii) an ecdysone receptor ligand binding domain; and
      iii) a transactivation domain; and
c) exposing the cell to the ligand,
wherein the ligand is a compound selected from the group consisting of:
5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide;
5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
5-Methyl-2,3-dihydro-benzo[1,4]dioxine-6-carboxylic acid N'-(1-tert-butyl-butyl)-N'-(3,5-dimethyl-benzoyl)-hydrazide;
5-Methyl-2,3-dihydro-benzo[1,4]dioxine-6-carboxylic acid N'-(1-tert-butyl-butyl)-N'-(3,5-dimethoxy-4-methyl-benzoyl)-hydrazide;
5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide;
5-Ethyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide;
5-Ethyl-2,3-dihydro-benzo[1,4]dioxine-6-carboxylic acid N'-(1-tert-butyl-butyl)-N'-(3,5-dimethyl-benzoyl)-hydrazide;
5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide;
3,5-Dimethyl-benzoic acid N-(1-ethyl-2,2-dimethyl-propyl)-N'-(3-methoxy-2-methyl-benzoyl)-hydrazide;
3,5-Dimethoxy-4-methyl-benzoic acid N-(1-ethyl-2,2-dimethyl-propyl)-N'-(3-methoxy-2-methyl-benzoyl)-hydrazide;
3,5-Dimethyl-benzoic acid N-(1-tert-butyl-butyl)-N'-(3-methoxy-2-methyl-benzoyl)-hydrazide;
3,5-Dimethoxy-4-methyl-benzoic acid N-(1-tert-butyl-butyl)-N'-(3-methoxy-2-methyl-benzoyl)-hydrazide;
3,5-Dimethyl-benzoic acid N-(1-ethyl-2,2-dimethyl-propyl)-N'-(2-ethyl-3-methoxy-benzoyl)-hydrazide;
3,5-Dimethoxy-4-methyl-benzoic acid N-(1-ethyl-2,2-dimethyl-propyl)-N'-(2-ethyl-3-methoxy-benzoyl)-hydrazide;
3,5-Dimethyl-benzoic acid N-(1-tert-butyl-butyl)-N'-(2-ethyl-3-methoxy-benzoyl)-hydrazide;
3,5-Dimethoxy-4-methyl-benzoic acid N-(1-tert-butyl-butyl)-N'-(2-ethyl-3-methoxy-benzoyl)-hydrazide;
2-Methoxy-nicotinic acid N-(1-tert-butyl-pentyl)-N'-(4-ethyl-benzoyl)-hydrazide;
3,5-Dimethyl-benzoic acid N-(2,2-dimethyl-1-phenyl-propyl)-N'-(4-ethyl-benzoyl)-hydrazide;
3,5-Dimethyl-benzoic acid N-(1-tert-butyl-pentyl)-N'-(3-methoxy-2-methyl-benzoyl)-hydrazide; and
3,5-Dimethoxy-4-methyl-benzoic acid N-(1-tert-butyl-pentyl)-N'-(3-methoxy-2-methyl-benzoyl)-hydrazide,
wherein the ecdysone receptor complex comprises a *Choristoneura fumiferana* ecdysone receptor (EcR) ligand binding domain.

8. The method of claim 1 wherein the compound is selected from the group consisting of 3,5-dimethyl-benzoic acid N-(1-ethyl-2,2-dimethyl-propyl)-N'-(3-methoxy-2-methyl-benzoyl)-hydrazide and 3,5-dimethyl-benzoic acid N-(1-tert-butyl-butyl)-N'-(2-ethyl-3-methoxy-benzoyl)-hydrazide.

9. The method of claim 2 wherein the compound is selected from the group consisting of 3,5-dimethyl-benzoic acid N-(1-ethyl-2,2-dimethyl-propyl)-N'-(3-methoxy-2-methyl-benzoyl)-hydrazide and 3,5-dimethyl-benzoic acid N-(1-tert-butyl-butyl)-N'-(2-ethyl-3-methoxy-benzoyl)-hydrazide.

10. The method of claim 3 wherein the compound is selected from the group consisting of 3,5-dimethyl-benzoic acid N-(1-ethyl-2,2-dimethyl-propyl)-N'-(3-methoxy-2-methyl-benzoyl)-hydrazide and 3,5-dimethyl-benzoic acid N-(1-tert-butyl-butyl)-N'-(2-ethyl-3-methoxy-benzoyl)-hydrazide.

11. The method of claim 6 wherein the compound is selected from the group consisting of 3,5-dimethyl-benzoic acid N-(1-ethyl-2,2-dimethyl-propyl)-N'-(3-methoxy-2-methyl-benzoyl)-hydrazide and 3,5-dimethyl-benzoic acid N-(1-tert-butyl-butyl)-N'-(2-ethyl-3-methoxy-benzoyl)-hydrazide.

12. The method of claim 7 wherein the compound is selected from the group consisting of 3,5-dimethyl-benzoic acid N-(1-ethyl-2,2-dimethyl-propyl)-N'-(3-methoxy-2-methyl-benzoyl)-hydrazide and 3,5-dimethyl-benzoic acid N-(1-tert-butyl-butyl)-N'-(2-ethyl-3-methoxy-benzoyl)-hydrazide.

13. The method of claim 8 wherein the compound is 3,5-dimethyl-benzoic acid N-(1-tert-butyl-butyl)-N'-(2-ethyl-3-methoxy-benzoyl)-hydrazide.

14. The method of claim 9 wherein the compound is 3,5-dimethyl-benzoic acid N-(1-tert-butyl-butyl)-N'-(2-ethyl-3-methoxy-benzoyl)-hydrazide.

15. The method of claim 10 wherein the compound is 3,5-dimethyl-benzoic acid N-(1-tert-butyl-butyl)-N'-(2-ethyl-3-methoxy-benzoyl)-hydrazide.

16. The method of claim 11 wherein the compound is 3,5-dimethyl-benzoic acid N-(1-tert-butyl-butyl)-N'-(2-ethyl-3-methoxy-benzoyl)-hydrazide.

17. The method of claim 12 wherein the compound is 3,5-dimethyl-benzoic acid N-(1-tert-butyl-butyl)-N'-(2-ethyl-3-methoxy-benzoyl)-hydrazide.

18. The method of claim 8 wherein the compound is 3,5-dimethyl-benzoic acid N-(1-ethyl-2,2-dimethyl-propyl)-N'-(3-methoxy-2-methyl-benzoyl)-hydrazide.

19. The method of claim 9 wherein the compound is 3,5-dimethyl-benzoic acid N-(1-ethyl-2,2-dimethyl-propyl)-N'-(3-methoxy-2-methyl-benzoyl)-hydrazide.

20. The method of claim 10 wherein the compound is 3,5-dimethyl-benzoic acid N-(1-ethyl-2,2-dimethyl-propyl)-N'-(3-methoxy-2-methyl-benzoyl)-hydrazide.

21. The method of claim 11 wherein the compound is 3,5-dimethyl-benzoic acid N-(1-ethyl-2,2-dimethyl-propyl)-N'-(3-methoxy-2-methyl-benzoyl)-hydrazide.

22. The method of claim 12 wherein the compound is 3,5-dimethyl-benzoic acid N-(1-ethyl-2,2-dimethyl-propyl)-N'-(3-methoxy-2-methyl-benzoyl)-hydrazide.

23. The method of claim 1 wherein the compound is 5-methyl-2,3-dihydro-benzo[1,4]dioxine-6-carboxylic acid N'-(3,5-dimethyl-benzoyl)-N'-(1-ethyl-2,2-dimethyl-propyl)-hydrazide.

24. The method of claim 2 wherein the compound is 5-methyl-2,3-dihydro-benzo[1,4]dioxine-6-carboxylic acid N'-(3,5-dimethyl-benzoyl)-N'-(1-ethyl-2,2-dimethyl-propyl)-hydrazide.

25. The method of claim 3 wherein the compound is 5-methyl-2,3-dihydro-benzo[1,4]dioxine-6-carboxylic acid N'-(3,5-dimethyl-benzoyl)-N'-(1-ethyl-2,2-dimethyl-propyl)-hydrazide.

26. The method of claim 6 wherein the compound is 5-methyl-2,3-dihydro-benzo[1,4]dioxine-6-carboxylic acid N'-(3,5-dimethyl-benzoyl)-N'-(1-ethyl-2,2-dimethyl-propyl)-hydrazide.

27. The method of claim 7 wherein the compound is 5-methyl-2,3-dihydro-benzo[1,4]dioxine-6-carboxylic acid N'-(3,5-dimethyl-benzoyl)-N'-(1-ethyl-2,2-dimethyl-propyl)-hydrazide.

28. The method of any one of claims 1, 2, 3, 6, or 7, wherein said host cell gene expression system, gene expression modulation system, or ecdysone receptor complex comprises GAL4 DBD (1-147)-CfEcR(DEF)/VP16AD-βRXREF-LmUSPEF, CVBE and 6XEcRE Lac Z, GAL4 DBD-CfEcR(DEF)/VP16AD-MmRXRE, or GAL4 DBD (1-147)-CJEcR(DEF)/HsRXRβ-EF-LmUSPEF.

\* \* \* \* \*

SEQUENCE LISTING

<160> NUMBER OF SEQ ID NOS: 18

<210> SEQ ID NO 1
<211> LENGTH: 1054
<212> TYPE: DNA
<213> ORGANISM: Choristoneura fumiferana

<400> SEQUENCE: 1

```
cctgagtgcg tagtacccga gactcagtgc gccatgaagc ggaaagagaa gaaagcacag      60
aaggagaagg acaaactgcc tgtcagcacg acgacggtgg acgaccacat gccgcccatt     120
atgcagtgtg aacctccacc tcctgaagca gcaaggattc acgaagtggt cccaaggttt     180
ctctccgaca agctgttgga gacaaaccgg cagaaaaaca tcccccagtt gacagccaac     240
cagcagttcc ttatcgccag gctcatctgg taccaggacg ggtacgagca gccttctgat     300
gaagatttga gaggattac gcagacgtgg cagcaagcgg acgatgaaaa cgaagagtct     360
gacactccct tccgccagat cacagagatg actatcctca cggtccaact tatcgtggag     420
ttcgcgaagg gattgccagg gttcgccaag atctcgcagc ctgatcaaat tacgctgctt     480
aaggcttgct caagtgaggt aatgatgctc cgagtcgcgc gacgatacga tgcggcctca     540
gacagtgttc tgttcgcgaa caaccaagcg tacactcgcg acaactaccg caaggctggc     600
```

```
atggcctacg tcatcgagga tctactgcac ttctgccggt gcatgtactc tatggcgttg      660
gacaacatcc attacgcgct gctcacggct gtcgtcatct tttctgaccg gccaggttg       720 gagcagccgc aactggtgga agaaatccag cggtactacc tgaatacgct ccgcatctat     780
atcctgaacc agctgagcgg gtcggcgcgt cgtccgtca tatacggcaa gatcctctca      840
atcctctctg agctacgcac gctcggcatg caaaactcca acatgtgcat ctccctcaag     900
ctcaagaaca gaaagctgcc gcctttcctc gaggagatct gggatgtggc ggacatgtcg    960
cacacccaac cgccgcctat cctcgagtcc cccacgaatc tctagcccct gcgcgcacgc   1020
atcgccgatg ccgcgtccgg ccgcgctgct ctga                               1054
```

```
<210> SEQ ID NO 2
<211> LENGTH: 441
<212> TYPE: DNA
<213> ORGANISM: Saccharomyces cerevisiae

<400> SEQUENCE: 2
```

```
atgaagctac tgtcttctat cgaacaagca tgcgatattt gccgacttaa aaagctcaag      60
tgctccaaag aaaaaccgaa gtgcgccaag tgtctgaaga caactggga gtgtcgctac      120 tctcccaaaa ccaaaaggtc tccgctgact agggcacatc tgacagaagt ggaatcaagg    180
ctagaaagac tggaacagct atttctactg attttttcctc gagaagacct tgacatgatt   240
ttgaaaatgg attctttaca ggatataaaa gcattgttaa caggattatt tgtacaagat    300
aatgtgaata agatgccgt cacagataga ttggcttcag tggagactga tatgcctcta     360
acattgagac agcatagaat aagtgcgaca tcatcatcgg aagagagtag taacaaaggt    420
caaagacagt tgactgtatc g                                              441
```

```
<210> SEQ ID NO 3
<211> LENGTH: 538
<212> TYPE: DNA
<213> ORGANISM: Mus musculus

<400> SEQUENCE: 3
```

```
tcgagggccc ctgcaggtca attctaccgg gtaggggagg cgcttttccc aaggcagtct      60
ggagcatgcg ctttagcagc cccgctggca cttggcgcta cacaagtggc ctctggcctc    120
gcacacattc cacatccacc ggtagcgcca accggctccg ttctttggtg gcccttcgc     180 gccaccttct actcctcccc tagtcaggaa gttcccccccc gccccgcagc tcgcgtcgtg   240
caggacgtga caaatggaag tagcacgtct cactagtctc gtgcagatgg acagcaccgc    300
tgagcaatgg aagcgggtag gcctttgggg cagcggccaa tagcagcttt gctccttcgc    360
tttctgggct cagaggctgg gaaggggtgg gtccggggggc gggctcaggg gcgggctcag   420
gggcggggcg ggcgcgaagg tcctcccgag gcccggcatt ctcgcacgct tcaaaagcgc    480
acgtctgccg cgctgttctc ctcttcctca tctccgggcc tttcgacctg cagccaat     538
```

```
<210> SEQ ID NO 4
<211> LENGTH: 720
<212> TYPE: DNA
<213> ORGANISM: Homo sapiens

<400> SEQUENCE: 4
```

```
gcccccgagg agatgcctgt ggacaggatc ctggaggcag agcttgctgt ggaacagaag      60
agtgaccagg gcgttgaggg tcctggggga accgggggta gcggcagcag cccaaatgac    120
cctgtgacta acatctgtca ggcagctgac aaacagctat tcacgcttgt tgagtgggcg    180
```

```
aagaggatcc cacactttc ctccttgcct ctggatgatc aggtcatatt gctgcgggca      240
ggctggaatg aactcctcat tgcctccttt tcacaccgat ccattgatgt tcgagatggc     300
atcctccttg ccacaggtct tcacgtgcac cgcaactcag cccattcagc aggagtagga    360
gccatctttg atcgggtgct gacagagcta gtgtccaaaa tgcgtgacat gaggatggac    420
aagacagagc ttggctgcct gagggcaatc attctgttta atccagatgc caagggcctc    480
tccaacccta gtgaggtgga ggtcctgcgg gagaaagtgt atgcatcact ggagacctac    540
tgcaaacaga agtaccctga gcagcaggga cggtttgcca agctgctgct acgtcttcct    600
gccctccggt ccattggcct taagtgtcta gagcatctgt ttttcttcaa gctcattggt    660 gacacccca tcgacacctt cctcatggag atgcttgagg ctccccatca actggcctga    720
```

<210> SEQ ID NO 5
<211> LENGTH: 635
<212> TYPE: DNA
<213> ORGANISM: Locusta migratoria

<400> SEQUENCE: 5

```
tgcatacaga catgcctgtt gaacgcatac ttgaagctga aaaacgagtg gagtgcaaag      60
cagaaaacca agtggaatat gagctggtgg agtgggctaa acacatcccg cacttcacat    120
ccctacctct ggaggaccag gttctcctcc tcagagcagg ttggaatgaa ctgctaattg    180
cagcattttc acatcgatct gtagatgtta agatggcat agtacttgcc actggtctca    240
cagtgcatcg aaattctgcc catcaagctg gagtcggcac aatattgac agagttttga    300 cagaactggt agcaaagatg agagaaatga aatggataa aactgaactt ggctgcttgc    360
gatctgttat tcttttcaat ccagaggtga ggggtttgaa atccgcccag gaagttgaac    420
ttctacgtga aaaagtatat gccgcttttgg aagaatatac tagaacaaca catcccgatg    480
aaccaggaag atttgcaaaa cttttgcttc gtctgccttc tttacgttcc ataggcctta    540
agtgtttgga gcatttgttt ctcttcgcc ttattggaga tgttccaatt gatacgttcc    600
tgatggagat gcttgaatca ccttctgatt cataa                                635
```

<210> SEQ ID NO 6
<211> LENGTH: 271
<212> TYPE: DNA
<213> ORGANISM: herpes simplex virus 7

<400> SEQUENCE: 6

```
atgggcccta aaagaagcg taaagtcgcc ccccgaccg atgtcagcct ggggacgag         60 ctccacttag acggcgagga cgtggcgatg gcgcatgccg acgcgctaga cgatttcgat    120
ctggacatgt tggggacgg ggattccccg gggccgggat ttaccccca cgactccgcc    180 ccctacggcg ctctggatat ggccgacttc gagtttgagc agatgtttac cgatgccctt    240
ggaattgacg agtacggtgg ggaattcccg g                                      271
```

<210> SEQ ID NO 7
<211> LENGTH: 1167
<212> TYPE: DNA
<213> ORGANISM: Homo sapiens

<400> SEQUENCE: 7

```
tgaggctccg gtgcccgtca gtgggcagag cgcacatcgc ccacagtccc cgagaagttg      60
gggggagggg tcggcaattg aaccggtgcc tagagaaggt ggcgcggggt aaactggaa     120 agtgatgtcg tgtactggct ccgccttttt cccgagggtg ggggagaacc gtatataagt    180
```

-continued

```
gcagtagtcg ccgtgaacgt tcttttcgc aacgggtttg ccgccagaac acaggtaagt      240
gccgtgtgtg gttcccgcgg gcctggcctc tttacgggtt atggcccttg cgtgccttga      300
attacttcca cctggctcca gtacgtgatt cttgatcccg agctggagcc aggggcgggc      360
cttgcgcttt aggagcccct tcgcctcgtg cttgagttga ggcctggcct gggcgctggg      420
gccgccgcgt gcgaatctgg tggcaccttc gcgcctgtct cgctgctttc gataagtctc      480
tagccattta aaattttga tgacctgctg cgacgcttt ttctggcaa gatagtcttg         540 taaatgcggg ccaggatctg cacactggta tttcggtttt tgggcccgcg gccggcgacg      600
gggcccgtgc gtcccagcgc acatgttcgg cgaggcgggg cctgcgagcg cggccaccga     660
gaatcggacg ggggtagtct caagctggcc ggcctgctct ggtgcctggc ctcgcgccgc     720
cgtgtatcgc cccgccctgg gcggcaaggc tgggcccggtc ggcaccagtt gcgtgagcgg    780
aaagatggcc gcttcccggc cctgctccag ggggctcaaa atggaggacg cggcgctcgg    840
gagagcgggc gggtgagtca cccacacaaa ggaaaagggc cttccgtcc tcagccgtcg      900 cttcatgtga ctccacggag taccggcgc cgtccaggca cctcgattag ttctggagct      960
tttggagtac gtcgtcttta ggttgggggg aggggttta tgcgatggag tttccccaca     1020
ctgagtgggt ggagactgaa gttaggccag cttggcactt gatgtaattc tcgttggaat    1080 ttgcccttt tgagtttgga tcttggttca ttctcaagcc tcagacagtg gttcaaagtt      1140
tttttcttcc atttcaggtg tcgtgaa                                          1167
```

<210> SEQ ID NO 8
<211> LENGTH: 19
<212> TYPE: DNA
<213> ORGANISM: Artificial sequence
<220> FEATURE:
<223> OTHER INFORMATION: GAL4 response element

<400> SEQUENCE: 8

```
ggagtactgt cctccgagc                                                    19
```

<210> SEQ ID NO 9
<211> LENGTH: 6
<212> TYPE: DNA
<213> ORGANISM: Artificial sequence
<220> FEATURE:
<223> OTHER INFORMATION: synthetic promoter

<400> SEQUENCE: 9

```
tatata                                                                  6
```

<210> SEQ ID NO 10
<211> LENGTH: 1653
<212> TYPE: DNA
<213> ORGANISM: Artificial Sequence
<220> FEATURE:
<223> OTHER INFORMATION: luciferase gene

<400> SEQUENCE: 10

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
```

```
tcgcagccta ccgtagtgtt tgtttccaaa aaggggttgc aaaaaatttt gaacgtgcaa      420
aaaaaattac caataatcca gaaaattatt atcatggatt ctaaaacgga ttaccaggga      480
tttcagtcga tgtacacgtt cgtcacatct catctacctc ccggttttaa tgaatacgat      540
tttgtaccag agtcctttga tcgtgacaaa acaattgcac tgataatgaa ttcctctgga      600
tctactgggt tacctaaggg tgtggccctt ccgcatagaa ctgcctgcgt cagattctcg      660
catgccagag atcctatttt tggcaatcaa atcattccgg atactgcgat tttaagtgtt      720
gttccattcc atcacggttt tggaatgttt actacactcg atatttgat atgtggattt      780
cgagtcgtct taatgtatag atttgaagaa gagctgtttt tacgatccct tcaggattac      840
aaaattcaaa gtgcgttgct agtaccaacc ctattttcat tcttcgccaa aagcactctg      900
attgacaaat acgatttatc taatttacac gaaattgctt ctgggggcgc acctctttcg      960
aaagaagtcg gggaagcggt tgcaaaacgc ttccatcttc cagggatacg acaaggatat     1020
gggctcactg agactacatc agctattctg attacacccg aggggatga taaaccgggc     1080
gcggtcggta agttgttcc atttttgaa gcgaaggttg tggatctgga taccgggaaa      1140
acgctgggcg ttaatcagag aggcgaatta tgtgtcagag acctatgat tatgtccggt      1200
tatgtaaaca atccggaagc gaccaacgcc ttgattgaca aggatggatg ctacattct      1260
ggagacatag cttactggga cgaagacgaa cacttcttca tagttgaccg cttgaagtct     1320
ttaattaaat acaaaggata tcaggtgccc cccgctgaat tggaatcgat attgttacaa     1380
caccccaaca tcttcgacgc gggcgtggca ggtcttcccg acgatgacgc cggtgaactt     1440
cccgccgccg ttgttgtttt ggagcacgga agacgatga cggaaaaaga gatcgtggat      1500
tacgtcgcca gtcaagtaac aaccgcgaaa aagttgcgcg gaggagttgt gtttgtggac     1560
gaagtaccga aggtcttac cggaaaaactc gacgcaagaa aaatcagaga gatcctcata     1620
aaggccaaga agggcggaaa gtccaaattg taa                                  1653

<210> SEQ ID NO 11
<211> LENGTH: 786
<212> TYPE: DNA
<213> ORGANISM: Mus musculus

<400> SEQUENCE: 11
aagcgggaag ctgtgcagga ggagcggcag cggggcaagg accggaatga gaacgaggtg       60
gagtccacca gcagtgccaa cgaggacatg cctgtagaga agattctgga agccgagctt      120
gctgtcgagc ccaagactga gacatacgtg gaggcaaaca tggggctgaa ccccagctca      180
ccaaatgacc ctgttaccaa catctgtcaa gcagcagaca agcagctctt cactcttgtg      240
gagtgggcca gaggatcccc acactttcct gagctgcccc tagacgacca ggtcatcctg      300
ctacgggcag ctggaacgaa gctgctgatc gcctccttct cccaccgctc catagctgtg      360
aaagatggga ttctcctggc caccggcctg cacgtacacc ggaacagcgc tcacagtgct      420
ggggtgggcg ccatctttga cagggtgcta acagagctgg tgtctaagat gcgtgacatg      480
cagatggaca agacggagct gggctgcctg cgagccattg tcctgttcaa ccctgactct      540
aaggggctct caaaccctgc tgaggtggag gcgttgaggg agaaggtgta tgcgtcacta      600
gaagcgtact gcaaacacaa gtaccctgag cagccgggca ggtttgccaa gctgctgctc      660
cgcctgcctg cactgcgttc catcgggctc aagtgcctgg agcacctgtt cttcttcaag      720
ctcatcgggg acacgcccat cgacaccttc ctcatggaga tgctggaggc accacatcaa      780
gccacc                                                                 786
```

<210> SEQ ID NO 12
<211> LENGTH: 1560
<212> TYPE: DNA
<213> ORGANISM: Homo sapiens

<400> SEQUENCE: 12

```
atgctgctgc tgctgctgct gctgggcctg aggctacagc tctccctggg catcatccca      60
gttgaggagg agaacccgga cttctggaac cgcgaggcag ccgaggccct gggtgccgcc     120
aagaagctgc agcctgcaca gacagccgcc aagaacctca tcatcttcct gggcgatggg     180
atggggtgt ctacggtgac agctgccagg atcctaaaag ggcagaagaa ggacaaactg     240
gggcctgaga taccctggc catgaccgc ttcccatatg tggctctgtc caagacatac     300
aatgtagaca acatgtgcc agacagtgga gccacagcca cggcctacct gtgcggggtc     360
aagggcaact tccagaccat tggcttgagt gcagccgccc gctttaacca gtgcaacacg     420
acacgcggca acgaggtcat ctccgtgatg aatcgggcca agaaagcagg gaagtcagtg     480
ggagtggtaa ccaccacacg agtgcagcac gcctcgccag ccggcaccta cgcccacacg     540
gtgaaccgca actggtactc ggacgccgac gtgcctgcct cggcccgcca ggaggggtgc     600
caggacatcg ctacgcagct catctccaac atggacattg acgtgatcct aggtggaggc     660
cgaaagtaca tgtttcgcat gggaaccca gaccctgagt acccagatga ctacagccaa     720
ggtgggacca gctggacgg gaagaatctg gtgcaggaat ggctggcgaa cgccagggt     780
gcccggtatg tgtggaaccg cactgagctc atgcaggctt ccctggaccc gtctgtgacc     840
catctcatgg gtctctttga gcctggagac atgaaatacg agatccaccg agactccaca     900
ctggaccct cctgatgga gatgacagag gctgccctgc gcctgctgag caggaacccc     960
cgcggcttct cctcttcgt ggagggtggt cgcatcgacc atggtcatca tgaaagcagg    1020
gcttaccggg cactgactga gacgatcatg ttcgacgacg ccattgagag ggcgggccag    1080
ctcaccagcg aggaggacac gctgagcctc gtcactgccg accactccca cgtcttctcc    1140
ttcggaggct acccctgcg agggagctcc atcttcgggc tggcccctgg caaggcccgg    1200
gacaggaagg cctacacggt cctcctatac ggaaacggtc caggctatgt gctcaaggac    1260
ggcgccggc cggatgttac cgagagcgag agcgggagcc ccgagtatcg gcagcagtca    1320
gcagtgcccc tggacgaaga gacccacgca ggcgaggacg tggcggtgtt cgcgcgcggc    1380
ccgcaggcgc acctggttca cggcgtgcag gagcagacct tcatagcgca cgtcatggcc    1440
ttcgccgcct gcctggagcc ctacaccgcc tgcgacctgg cgccccgc cggcaccacc    1500
gacgccgcgc acccgggtta ctctagagtc ggggcggccg ccgcttcga gcagacatga    1560
```

<210> SEQ ID NO 13
<211> LENGTH: 117
<212> TYPE: DNA
<213> ORGANISM: Artificial
<220> FEATURE:
<223> OTHER INFORMATION: response element

<400> SEQUENCE: 13

```
gcggagtact gtcctccgag cggagtactg tcctccgagc ggagtactgt cctccgagcg      60
gagtactgtc ctccgagcgg agtactgtcc tccgagcgga gtactgtcct ccgagcg       117
```

<210> SEQ ID NO 14
<211> LENGTH: 136
<212> TYPE: DNA
<213> ORGANISM: Mus musculus -continued

```
<400> SEQUENCE: 14
cttttgttga ctaagtcaat aatcagaatc agcaggtttg gagtcagctt ggcagggatc    60
agcagcctgg gttggaagga gggggtataa aagccccttc accaggagaa gccgtcacac   120
agatccacaa gctcct                                                   136

<210> SEQ ID NO 15
<211> LENGTH: 659
<212> TYPE: DNA
<213> ORGANISM: Cytomegalovirus

<400> SEQUENCE: 15
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg accccgcccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtccg cccctattg acgtcaatga   420 cggtaaatgg cccgcctggc attatgccca gtacatgacc ttacgggact ttcctacttg   480
gcagtacatc tacgtattag tcatcgctat taccatggtg atgcggtttt ggcagtacac   540
caatgggcgt ggatagcggt ttgactcacg ggatttcca agtctccacc ccattgacgt   600
caatgggagt ttgttttggc accaaaatca acgggacttt ccaaaatgtc gtaacaact   659

<210> SEQ ID NO 16
<211> LENGTH: 17
<212> TYPE: DNA
<213> ORGANISM: Artificial sequence
<220> FEATURE:
<223> OTHER INFORMATION: Synthetic response element of the ecdysone
      receptor
<220> FEATURE:
<221> NAME/KEY: misc_feature
<222> LOCATION: (9)..(9)
<223> OTHER INFORMATION: n is a, c, g, or t

<400> SEQUENCE: 16
rrggttcant gacacyy                                                   17

<210> SEQ ID NO 17
<211> LENGTH: 13
<212> TYPE: DNA
<213> ORGANISM: Artificial sequence
<220> FEATURE:
<223> OTHER INFORMATION: Synthetic response element of the ecdysone
      receptor
<220> FEATURE:
<221> NAME/KEY: misc_feature
<222> LOCATION: (7)..(7)
<223> OTHER INFORMATION: n is a, c, g, or t

<400> SEQUENCE: 17
aggtcanagg tca                                                       13

<210> SEQ ID NO 18
<211> LENGTH: 15
<212> TYPE: DNA
<213> ORGANISM: Artificial sequence
```

-continued

```
<220> FEATURE:
<223> OTHER INFORMATION: Synthetic response element of the ecdysone
      receptor

<400> SEQUENCE: 18
gggttgaatg aattt                                                      15
```